United States Patent
Bradner et al.

(10) Patent No.: US 11,236,082 B2
(45) Date of Patent: Feb. 1, 2022

(54) EZH2 INHIBITORS AND USES THEREOF

(71) Applicant: Dana-Farber Cancer Institute, Inc., Boston, MA (US)

(72) Inventors: James E. Bradner, Weston, MA (US); Jun Qi, Sharon, MA (US); Kwok-kin Wong, Arlington, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 170 days.

(21) Appl. No.: 15/524,679

(22) PCT Filed: Nov. 6, 2015

(86) PCT No.: PCT/US2015/059622
§ 371 (c)(1),
(2) Date: May 5, 2017

(87) PCT Pub. No.: WO2016/073956
PCT Pub. Date: May 12, 2016

(65) Prior Publication Data
US 2018/0297993 A1    Oct. 18, 2018

Related U.S. Application Data

(60) Provisional application No. 62/076,410, filed on Nov. 6, 2014.

(51) Int. Cl.
*C07D 471/04*    (2006.01)
*C07D 519/00*    (2006.01)
*G01N 33/50*    (2006.01)

(52) U.S. Cl.
CPC .......... *C07D 471/04* (2013.01); *C07D 519/00* (2013.01); *G01N 33/5008* (2013.01)

(58) Field of Classification Search
CPC .................................................. C07D 471/04
See application file for complete search history.

(56) References Cited

U.S. PATENT DOCUMENTS

| | | | |
|---|---|---|---|
| 8,338,464 B2 | 12/2012 | Melnick et al. | |
| 8,410,088 B2 | 4/2013 | Kuntz et al. | |
| 8,536,179 B2 * | 9/2013 | Miller .................. | C07D 401/12 514/252.13 |
| 8,895,245 B2 | 11/2014 | Copeland et al. | |
| 9,175,331 B2 | 11/2015 | Kuntz et al. | |
| 9,562,041 B2 | 2/2017 | Burgess et al. | |
| 2008/0305113 A1 | 12/2008 | Kwon et al. | |
| 2012/0014979 A1 | 1/2012 | Dent et al. | |
| 2013/0059849 A1 * | 3/2013 | Burgess ............... | C07D 471/04 514/234.2 |

(Continued)

FOREIGN PATENT DOCUMENTS

| | | |
|---|---|---|
| WO | WO 2008/066887 A2 | 6/2008 |
| WO | WO 2010/008436 A1 | 1/2010 |

(Continued)

OTHER PUBLICATIONS

STN Chemical Database entry for 1-(2-furanylmethyl)-N-[(2-methoxyphenyl)methyl]-6-(3-pyridinyl)-1H-Pyrazolo[3,4-b]pyridine-4-carboxamide RN 1296983-00-0 Entered STN: May 19, 2011, LC STN Files: CHEMCATS.*
Online "http://web.archive.org/web/20120317091129/http://www.fchgroup.net/" dated Mar. 1, 2012, accessed Oct. 12, 2016.*
Wislicenus, J. "Adolph Strecker's Short Textbook of Organic Chemistry" 1881, Spottiswoode: London, pp. 38-39.*
Wermuth, Camille G. "Molecular Variation Based on Isosteric Replacements" in Chapter 13, The Practice of Medicinal Chemistry, Academic: 1996, pp. 203-237.*

(Continued)

*Primary Examiner* — David K O'Dell
(74) *Attorney, Agent, or Firm* — Wolf, Greenfield & Sacks, P.C.

(57) ABSTRACT

The present disclosure provides compounds of any one of Formulae (I) and (II). The compounds described herein are inhibitors of histone methyltransferases (e.g., enhancer of zeste homolog 1 (EZH1) and enhancer of zeste homolog 2 (EZH2)) and are useful in treating and/or preventing a broad range of diseases (e.g., proliferative diseases). Also provided in the present disclosure are pharmaceutical compositions, kits, methods, and uses including or using a compound described herein. Further provided in the present disclosure are methods of identifying EZH1 and/or EZH2 inhibitors.

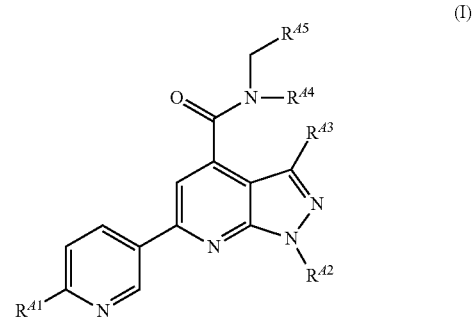

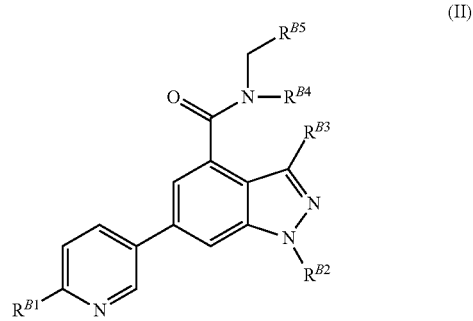

24 Claims, 67 Drawing Sheets
Specification includes a Sequence Listing.

(56) References Cited

U.S. PATENT DOCUMENTS

| | | | |
|---|---|---|---|
| 2013/0184264 A1 | 7/2013 | Bradner et al. | |
| 2013/0280332 A1 | 10/2013 | Moss et al. | |
| 2013/0317026 A1 | 11/2013 | Kuntz et al. | |
| 2015/0126522 A1 | 5/2015 | Burgess et al. | |
| 2016/0022693 A1 | 1/2016 | Kuntz et al. | |
| 2019/0000860 A1 | 1/2019 | Bradner et al. | |
| 2019/0135796 A1 | 5/2019 | Bradner et al. | |

FOREIGN PATENT DOCUMENTS

| | | | | |
|---|---|---|---|---|
| WO | WO-2011140325 A1 | * | 10/2011 | ............ A01N 43/38 |
| WO | WO 2011/140324 A1 | | 11/2011 | |
| WO | WO 2012/005805 A1 | | 1/2012 | |
| WO | WO 2012/118812 A2 | | 9/2012 | |
| WO | WO 2013/039988 A1 | | 3/2013 | |
| WO | WO 2013/049770 A2 | | 4/2013 | |
| WO | WO 2013/067296 A1 | | 5/2013 | |
| WO | WO 2013/067300 A1 | | 5/2013 | |
| WO | WO 2013/067302 A1 | | 5/2013 | |
| WO | WO 2013/138361 A1 | | 9/2013 | |
| WO | WO 2013/155464 A1 | | 10/2013 | |
| WO | WO 2013/173441 A2 | | 11/2013 | |
| WO | WO 2014/100080 A1 | | 6/2014 | |
| WO | WO 2014/100646 A1 | | 6/2014 | |
| WO | WO 2014/100665 A1 | | 6/2014 | |
| WO | WO 2014/155301 A1 | | 10/2014 | |
| WO | WO-2014155301 A1 | * | 10/2014 | ................ A61P 1/16 |
| WO | WO 2015/010049 A1 | | 1/2015 | |
| WO | WO 2015/077193 A1 | | 5/2015 | |
| WO | WO 2015/110999 A1 | | 7/2015 | |

OTHER PUBLICATIONS

STN Chemical Database entry for N-[(2,5-dimethoxyphenyl)methyl]-1-(2-furanylmethyl)-6-(3-pyridinyl)-1H-Pyrazolo[3,4-b]pyridine-4-carboxamide, RN 1296380-48-7 Entered STN: May 18, 2011, LC STN Files: CHEMCATS.*
Online: "https://www.cas.org/support/documentation/chemical-substances/faqs" Accessed Sep. 14, 2018.*
Online: "https://www.cas.org/services/knowledge/chemist-consultation" Accessed Sep. 14, 2018.*
Online "https://www.cas.org/sites/default/files/documents/chemconsultform_v0.pdf" accessed Sep. 14, 2018.*
Online "https://www.cas.org/products/chemcats/chemical-suppliers/data-submission" accessed Sep. 14, 2018.*
Fleming "Nitrile-Containing Pharmaceuticals: Efficacious Roles of the Nitrile Pharmacophore." J. Med. Chem. 2010, 53, 7902-7917.*
Shah "The role of fluorine in medicinal chemistry" Journal of Enzyme Inhibition and Medicinal Chemistry, Oct. 2007; 22(5): 527-540.*
International Search Report and Written Opinion for PCT/US15/59622, dated Mar. 30, 2016.
International Preliminary Report on Patentability for PCT/US15/59622, dated May 18, 2017.
International Search Report and Written Opinion for PCT/US2015/059551, dated Jan. 13, 2016.
International Preliminary Report on Patentability for PCT/US2015/059551, dated May 18, 2017.
Invitation to Pay Additional Fees for PCT/US17/28885, dated Jul. 10, 2017.
International Search Report and Written Opinion for PCT/US17/28885, dated Sep. 8, 2017.

[No Author Listed] "Methanesulfonyl chloride: Difference between revisions." Wikipedia Entry, Mar. 28, 2014. https://en.wikipedia.org/w/index.php?title=Methanesulfonyl_chloride&d.
[No Author Listed] PubChem CID 55504609. Create date: Jan. 25, 2012.
[No Author Listed] PubChem CID 56267130. Create date: Jan. 25, 2012.
Beguelin et al., EZH2 is required for germinal center formation and somatic EZH2 mutations promote lymphoid transformation. Cancer Cell. May 13, 2013;23(5):677-92. doi: 10.1016/j.ccr.2013.04.011.
Campbell et al., EPZ011989, A Potent, Orally-Available EZH2 Inhibitor with Robust in Vivo Activity. ACS Med Chem Lett. Mar. 4, 2015;6(5):491-5. doi: 10.1021/acsmedchemlett.5b00037. eCollection May 14, 2015.
Czermin et al., *Drosophila* enhancer of Zeste/ESC complexes have a histone H3 methyltransferase activity that marks chromosomal Polycomb sites. Cell. Oct. 18, 2002;111(2):185-96.
Flynn et al., Increased T follicular helper cells and germinal center B cells are required for cGVHD and bronchiolitis obliterans. Blood. Jun. 19, 2014;123(25):3988-98. doi: 10.1182/blood-2014-03-562231. Epub May 12, 2014.
He et al., The histone methyltransferase Ezh2 is a crucial epigenetic regulator of allogeneic T-cell responses mediating graft-versus-host disease. Blood. Dec. 12, 2013;122(25):4119-28. doi: 10.1182/blood-2013-05-505180. Epub Oct. 18, 2013.
Konze et al., An orally bioavailable chemical probe of the Lysine Methyltransferases EZH2 and EZH1. ACS Chem Biol. 2013;8(6):1324-34. doi: 10.1021/cb400133j. Epub Apr. 24, 2013.
Verma et al., Identification of Potent, Selective, Cell-Active Inhibitors of the Histone Lysine Methyltransferase EZH2. ACS Med Chem Lett. Oct. 19, 2012;3(12):1091-6. doi: 10.1021/ml3003346. eCollection Dec. 13, 2012.
Partial Supplementary European Search Report for EP 15 857 195.0, dated Apr. 16, 2018.
Partial Supplementary European Search Report for EP 15 856 340.3, dated Mar. 27, 2018.
Knutson et al., A selective inhibitor of EZH2 blocks H3K27 methylation and kills mutant lymphoma cells. Nat Chem Biol. Nov. 2012;8(11):890-6. doi: 10.1038/nchembio.1084. Epub Sep. 30, 2012.
Extended European Search Report for EP 15856340.3, dated Jul. 6, 2018.
Extended European Search Report for EP 15857195.0, dated Jul. 26, 2018.
International Preliminary Report on Patentability for PCT/US17/28885, dated Nov. 1, 2018.
Eikel et al., Liquid extraction surface analysis mass spectrometry (LESA-MS) as a novel profiling tool for drug distribution and metabolism analysis: the terfenadine example. Rapid Commun Mass Spectrom. Dec. 15, 2011;25(23):3587-96. doi: 10.1002/rcm.5274.
Haedke et al., Alkyne derivatives of isocoumarins as clickable activity-based probes for serine proteases. Bioorg Med Chem. Jan. 15, 2012;20(2):633-40. doi: 10.1016/j.bmc.2011.03.014. Epub Mar. 12, 2011.
Nguyen et al., Chiral drugs: an overview. Int J Biomed Sci. Jun. 2006;2(2):85-100.
Shaikh, The changing face of antihistamines and cardiac adverse drug reactions: a clinical perspective. J. Indian Med Assoc. 2000;98(7):397-99.
Stefan-Van Staden, Enantioanalysis of S-Ibuprofen using [5-6] fullerene-C70 and diethyl (1,2-methanofullerene C70)-71-71-dicarboxylate. R. Anal. Methods 2010;2:37-40.
Supplementary European Search Report on Patentability for EP17786731, dated Sep. 16, 2019.

* cited by examiner

| EZH2 Expression Level | | | |
|---|---|---|---|
| | N | Mean | SD |
| Tumor | 471 | 394.8 | 311.7 |
| Normal | 58 | 56.7 | 30.7 |

JQEZ23, JQEZ-23, EZ23, EZ-23, or EZ-023

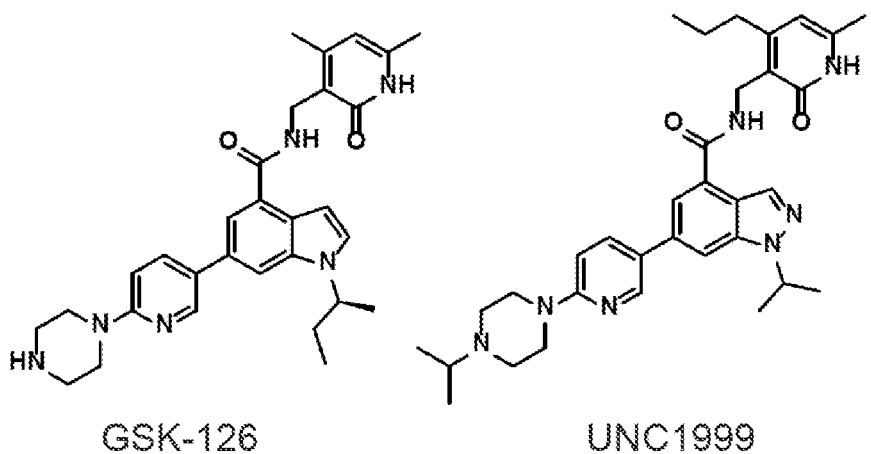
Figure 18A
| Compound | IC50 (nM) [95% CI] |
|---|---|
| JQEZ5 | 11.1 ± 2.9 |
| JQEZ23 | > 10,000 |
| GSK-126 | 7.2 ± 2.5 |
| UNC1999 | 6.4 ± 1.5 |
Figure 18B
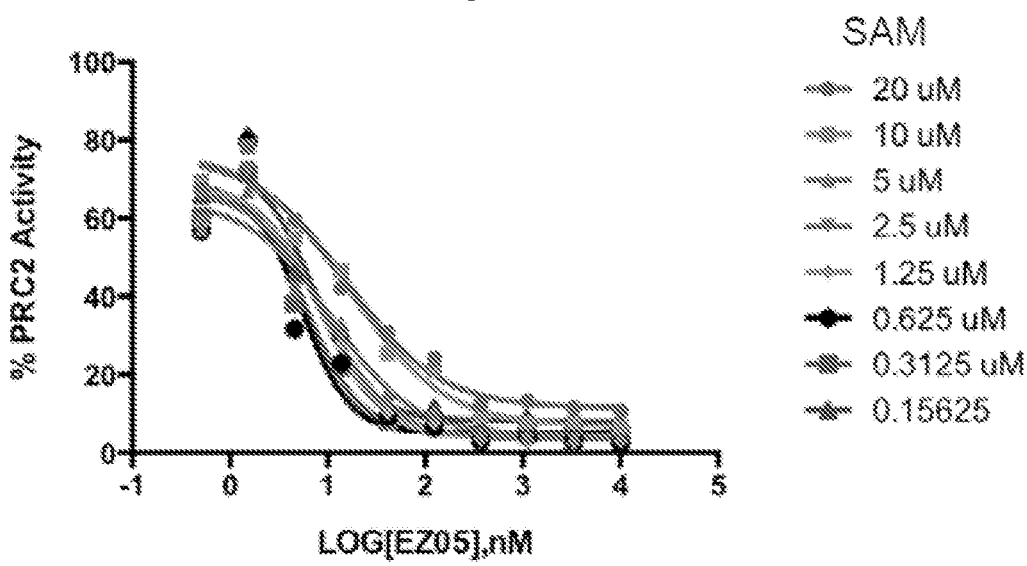
Figure 18C

| Methyltransferase: | JQEZ5 IC50 (M) | SAH IC50 (M) |
|---|---|---|
| DOT1 | 8.32E-06 | 1.41E-07 |
| EZH1 | 1.30E-06 | 2.15E-05 |
| EZH2 | 1.72E-07 | 1.52E-05 |
| G9a |  | 6.67E-06 |
| GLP |  | 3.19E-07 |
| MLL1 |  | 3.28E-06 |
| MLL2 |  | 1.79E-05 |
| MLL3 |  | 4.27E-05 |
| MLL4 |  | 1.20E-05 |
| NSD2 |  | 7.49E-06 |
| PRMT1 |  | 7.23E-07 |
| PRMT3 |  | 1.77E-06 |
| PRMT4 |  | 2.16E-07 |
| PRMT5 |  | 1.91E-07 |
| PRMT6 |  | 2.52E-07 |
| SET1b |  | 6.69E-06 |
| SET7/9 |  | 1.21E-04 |
| SET8 |  | 1.40E-04 |
| SETMAR |  | 5.61E-07 |
| SMYD2 |  | 8.24E-07 |
| SUV39H1 |  | 1.06E-04 |
| SUV39H2 |  | 2.11E-05 |

Figure 18D

Plate 1  01  02  03  04

| Plate 2 | 05 | 06 | 07 | 08 |
|---|---|---|---|---|
| A |  |  |  |  |
| B |  |  |  |  |
| C | DMSO |  |  |  |
| D |  |  |  |  |
| E |  |  |  |  |
| F |  |  |  |  |
| G |  | | DMSO |  |
| H |  |  |  |  |

Plate 3   01           02           03           04

A    Warhead

B

C

D

E

F

G           H·Cl

H

Plate 3    05        06        07        08

A

B

C  DMSO

D

E

F

G   DMSO

H

| Plate 4 | 05 | 06 | 07 | 08 |
|---|---|---|---|---|
| A |  |  |  |  |
| B |  |  |  |  |
| C | DMSO |  |  |  |
| D |  |  |  |  |
| E |  |  |  |  |
| F |  |  |  |  |
| G |  |  | DMSO |  |

| Compound | IC$_{50}$ (nM) | | Selectivity for EZH2 over EZH1 |
| --- | --- | --- | --- |
| | EZH1 | EZH2 | |
| EZH2-D | 259.3 | 42.24 | 6.1 |
| EZ29 | 1320 | 214.2 | 6.2 |
| EZ05 | 22.04 | 3.161 | 7.0 |
| UNC1999 | 13.04 | 1.863 | 7.0 |
| EZH2-16 | 20.22 | 2.676 | 7.6 |
| EZ27 | 8.63 | 1.085 | 8.0 |
| EZ23 | 21673 | 2147 | 10.1 |
| EZ25 | 15917 | 1551 | 10.3 |
| dEZH2_2 | 51.35 | 3.942 | 13.0 |
| EZH2-F | 197 | 14.98 | 13.2 |
| EZ28 | 21.03 | 1.465 | 14.4 |
| EZ21 | 33.97 | 1.901 | 17.9 |
| EZ26 | 38.94 | 2.088 | 18.6 |
| EZ24 | 9936 | 418.2 | 23.8 |
| EZ20 | 25.4 | 1.007 | 25.2 |
| GSK126 | 40.42 | 1.52 | 26.6 |
| EZ30 | 18387 | 408.2 | 45.0 |

Figure 22

H3K27me3 Quantification

|         | WT          | Y641C       | Y641F       |
|---------|-------------|-------------|-------------|
| EZH2-B  | 4418±1.11   | >50,000     | 38989±1.68  |
| EZH2-18 | 6642±1.18   | >50,000     | >50,000     |
| EZ20    | 4.613±1.11  | 65.08±1.16  | 5.155±1.1   |
| EZ21    | 4.818±1.16  | 78.43±1.22  | 4.145±1.18  |
| EZ26    | 13.05±1.15  | 414.7±1.23  | 20.53±1.19  |
| EZ27    | 2.856±1.23 | 46.91±1.19 | 2.482±1.25 |
| EZ28    | 5.691±1.2   | 201.9±1.2   | 11.45±1.21  |
| GSK126  | 1.285±1.14  | 2.467±1.17  | 0.244±1.22  |
| UNC1999 | 1.982±1.13  | 10.23±1.12  | 0.947±1.21  |
| EZH2-F  | 31.71±1.09  | 576±1.13    | 41.99±1.11  |
| EZ05    | 4.159±1.16  | 202.7±1.26  | 4.785±1.18  |
| EZH2-16 | 3.134±1.25  | 85.21±1.23  | 1.807±1.23  |

|         | Y641H       | Y641N       | Y641S       |
|---------|-------------|-------------|-------------|
| EZH2-B  | >50,000     | >50,000     | 30443±1.61  |
| EZH2-18 | >50,000     | >50,000     | >50,000     |
| EZ20    | 3.403±1.11  | 159.8±1.15  | 13.86±1.11  |
| EZ21    | 2.936±1.16  | 176.3±1.18  | 13.86±1.15  |
| EZ26    | 13.95±1.19  | 680.7±1.24  | 74.39±1.19  |
| EZ27    | 1.661±1.23 | 86.67±1.21 | 8.788±1.19 |
| EZ28    | 6.961±1.2   | 432.6±1.27  | 36.51±1.13  |
| GSK126  | 0.3511±1.22 | 2.908±1.14  | 0.9412±1.16 |
| UNC1999 | 0.7544±1.21 | 27.77±1.14  | 2.376±1.17  |
| EZH2-F  | 27.8±1.15   | 1645±1.12   | 122.8±1.07  |
| EZ05    | 3.117±1.19  | 449±1.23    | 20.95±1.17  |
| EZH2-16 | 1.339±1.29  | 201.6±1.26  | 10.27±1.23  |

Figure 24

|  | Y641C | | Y641N | |
|---|---|---|---|---|
| Pre-incubation time | 10 min | 60 min | 10 min | 60 min |
| UNC1999 | 162.10 | 126.40 | 51.78 | 33.72 |
| EZ-36 | 1747.00 | 1717.00 | 488.60 | 231.90 |
| EZ-37 | 182400.00 | 102100.00 | 586000.00 | 31820.00 |
| EZ-38 | 62650.00 | 17130.00 | 11270.00 | 6898.00 |
| EZ-41 | 10060.00 | 2827.00 | 2244.00 | 353.90 |
| EZ-35 | 312.50 | 412.00 | 107.20 | 35.58 |
| EZ-005 | 857.60 | 1314.00 | 281.50 | 187.90 |

|  | Y641S | | WT | |
|---|---|---|---|---|
| Pre-incubation time | 10 min | 60 min | 10 min | 60 min |
| UNC1999 | 26.43 | 24.18 | 27.10 | 31.20 |
| EZ-36 | 182.90 | 153.20 | 48.42 | 43.27 |
| EZ-37 | 185300.00 | 224200.00 | 415200.00 | 76780.00 |
| EZ-38 | 7070.00 | 5904.00 | 1022.00 | 785.50 |
| EZ-41 | 2871.00 | 965.50 | 1131.00 | 624.40 |
| EZ-35 | 201.60 | 219.90 | 162.10 | 160.80 |
| EZ-005 | 125.60 | 99.93 | 66.83 | 45.95 |

Acylamide-equipped EZ05 analog

| | Y641C | | Y641N | |
|---|---|---|---|---|
| Pre-incubation time | 10 min | 60 min | 10 min | 60 min |
| UNC1999 | 162.10 | 126.40 | 51.78 | 33.72 |
| EZ-41 | 10060.00 | 2827.00 | 2244.00 | 353.90 |
| EZ-005 | 857.60 | 1314.00 | 281.50 | 187.90 |

| | Y641S | | WT | |
|---|---|---|---|---|
| Pre-incubation time | 10 min | 60 min | 10 min | 60 min |
| UNC1999 | 26.43 | 24.18 | 27.10 | 31.20 |
| EZ-41 | 2871.00 | 965.50 | 1131.00 | 624.40 |
| EZ-005 | 125.60 | 99.93 | 66.83 | 45.95 |

Conditions:
50 mM Tris, pH 8.5, 5 mM DTT, 0.01% Tween-20

$IC_{50} = 40.83 \pm 1.14$
Conditions:
50 mM Tris, pH 8.5, 5 mM DTT, 0.01% Tween-20
61.5 nM PRC2
62.5 nM EZ06
[SAM] denotes the concentration of the test compound.

[CPD] denotes the concentration of the test compound.

|        | IC50(nM) - SPA | IC50(nM) - EZ06 Alpha |
|--------|----------------|------------------------|
| EZ-005 | 11.12±2.909    | 8.479±1.951            |
| EZ-23  | >10,000        | >10,000                |
| EZ-CONS| 96.34±51.62    | 54.05±12.18            |
| GSK-126| 7.235±2.518    | 4.944±0.689            |

[Cpd] denotes the concentration of the test compound.

|  | FP-IC50 (nM) | SPA-IC50 (nM) |
|---|---|---|
| EZ05 | 1.19±1.74 | 4.159±1.16 |
| EZ27 | <1.2 | 2.856±1.23 |
| UNC1999 | 6.70±1.07 | 1.982±1.13 |
| GSK126 | 16.74±1.07 | 1.285±1.14 |
| EZ23 | >3,333 | >50,000 |

Conditions:
50 mM Tris, pH 8.5, 5 mM DTT, 0.01% Tween-20
32.5 nM EZ05-FITC
43 nM PRC2-EZH2 (~170 mP, ~80% bound)

EZ05-FITC

Conditions:
50 mM Tris, pH 8.5, 5 mM DTT, 0.01% Tween-20
32.5 nM EZ05-FITC

[CPD] denotes the concentration of the test compound.

[CPD] denotes the concentration of the test compound.

| Well | IC50 (M) | HillSlope | Bottom | Span |
|---|---|---|---|---|
| EZ27 | 6.91E-09 | -0.8006 | 25.01 | 85.67 |
| EZ5 | 9.85E-09 | -0.8926 | 27.27 | 80.19 |
| EZ5 | 1.12E-08 | -0.8723 | 23.98 | 82.47 |
| EZ27 | 1.50E-08 | -1.202 | 26.74 | 81 |
| A3 | 2.63E-08 | -0.8721 | -2.481 | 106.6 |
| G9 | 2.82E-08 | -0.7247 | 15.16 | 96.26 |
| D8 | 3.10E-08 | -0.8044 | 35.39 | 71.04 |
| F3 | 3.11E-08 | -0.7159 | 18.24 | 92.57 |
| B8 | 3.83E-08 | -0.5142 | 4.454 | 109.8 |
| B12 | 3.90E-08 | -0.8006 | 3.61 | 100.9 |
| D11 | 4.08E-08 | -0.7666 | 36.91 | 68.39 |
| A7 | 4.36E-08 | -0.6769 | 5.077 | 106.1 |
| C10 | 4.43E-08 | -0.8123 | 34.35 | 74.3 |
| G8 | 5.02E-08 | -0.6506 | 21.11 | 88.04 |
| A11 | 5.18E-08 | -0.6806 | 26.59 | 85.13 |
Figure 37
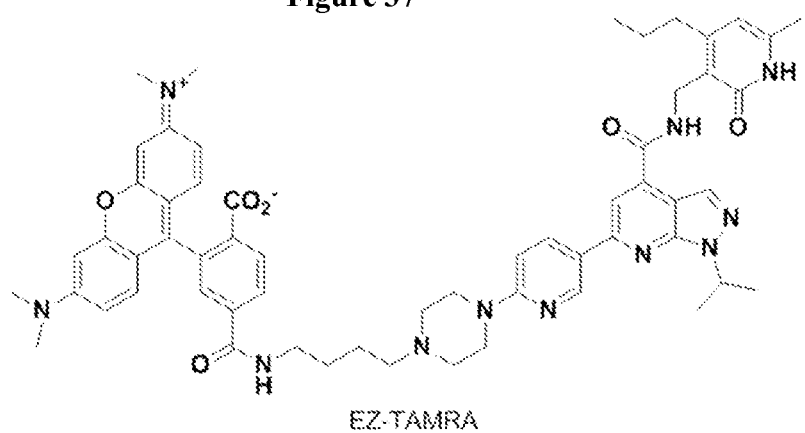
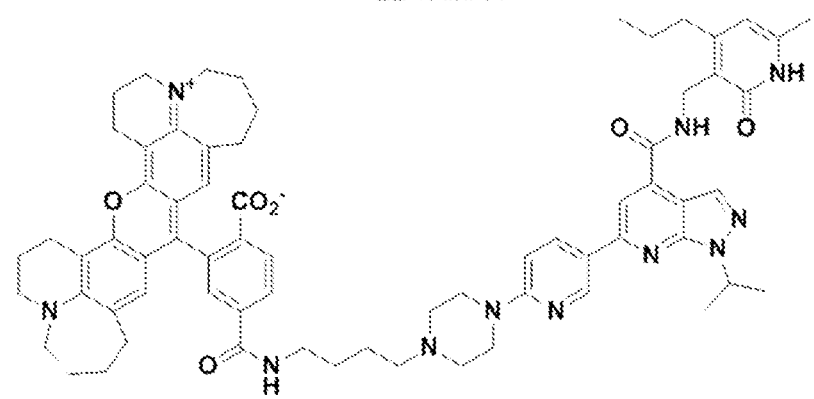
Figure 38

IC50 = 344 nM

DMSO + 5 uM TAMRA-EZ05

25 uM EZ05 + 5 uM TAMRA-EZ05

SEQUENCE LISTING

```
<160> NUMBER OF SEQ ID NOS: 4

<210> SEQ ID NO 1
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1

His His His His His His
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 2

His His His His
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 3

Leu Leu Leu Leu
1
```

```
<210> SEQ ID NO 4
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa is epsilon protonated neutral histidine

<400> SEQUENCE: 4

Arg Phe Ala Asn Xaa Ser Val
1               5
```

EZH2 INHIBITORS AND USES THEREOF

RELATED APPLICATIONS

This application is a national stage filing under 35 U.S.C. § 371 of international PCT application, PCT/US2015/059622, filed Nov. 6, 2015, which claims priority under 35 U.S.C. § 119(e) to U.S. provisional application, U.S. Ser. No. 62/076,410, filed Nov. 6, 2014, each of which is incorporated by reference herein.

GOVERNMENT SPONSORSHIP

This invention was made with government support under grant number CA128972 awarded by the National Institutes of Health. The government has certain rights in the invention.

BACKGROUND OF THE INVENTION

Chromatin structure contains important regulatory information for all DNA-based processes, such as transcription, repair, and replication. The polycomb group (PcG) and trithorax group (TrxG) protein complexes regulate chromatin structure through evolutionarily conserved mechanisms in eukaryotes for gene silencing or activation, respectively (Schuettengruber et al., 2007). Polycomb proteins assemble into at least two distinct complexes, the polycomb repressive complexes 1 and 2 (PRC1 and PRC2, respectively). Several lines of evidence suggest that PCR2 is involved in recruiting the PRC1 complex to promoters of their common target genes. A delicate balance of PcG protein levels ensures proper cell proliferation and normal tissue homeostasis while abnormal expression patterns or genomic alterations in PcG proteins can result in transcriptional dysregulation and cause various diseases including cancer (Laugesen and Helin, 2014).

Histone tails extruding from the nucleosome core are subject to multiple modifications including phosphorylation, acetylation, methylation, ubiquitination, and sumoylation. Histone modifications exert substantial influence on transcriptional regulation by modulating higher-order chromatin structures. There are two functional states of chromatin: euchromatin and heterochromatin, which are transcriptionally active and inactive, respectively. Some histone modifications, such as tri-methylation at histone 4 lysine 20 (H4K20me3), histone 3 lysine 9 (H3K9me3) or lysine 79 (H3K79me3), predominantly occur in constitutive heterochromatin domains; whereas others, such as tri-methylation at histone 3 lysine 4 (H3K4me3) and acetylation at histone 3 lysine 27 (H3K27ac), are regarded as hallmarks of actively transcribed regions in euchromatin. Tri-methylation at histone 3 lysine 27 (H3K27me3) is generally associated with transcriptional rexpression in higher eukaryotes (Cao et al., 2002; Czermin et al., 2002; Muller et al., 2002). Bivalent domains, termed by the paradoxical coexistence of repressive mark H3K27me3 and activating mark H3K4me3, keep developmental genes in a silent but poised state for activation upon differentiation (Chen and Dent, 2014).

Enhancer of zeste homolog 2 (EZH2) is core component of PRC2 that catalyzes the di- and tri-methylation at histone H3 lysine 27 (H3K27me2/3). EZH2 plays a critical role in normal development, and EZH2-deficient mice died at early stage of embryo due to the failure of implantation and gastrulation (O'Carroll et al., 2001). Somatic mutations in the SET domain of EZH2 (e.g., Y641N) resulting hyperactivity of the enzyme have been identified in a large portion of follicular and diffuse large B-cell lymphomas, implicating a driver function of EZH2 in cancer formation (Beguelin et al., 2013; Morin et al., 2010). A GEM model with conditional expression of mutant EZH2 (Y641N) was recently developed, which induced germinal center (GC) hyperplasia and accelerates lymphomagenesis in cooperation with BCL2 (Beguelin et al., 2013).

SUMMARY OF THE INVENTION

In one aspect, described herein are compounds of any one of Formulae (I) and (II), and pharmaceutically acceptable salts, solvates, hydrates, polymorphs, co-crystals, tautomers, stereoisomers, isotopically labeled derivatives, and prodrugs thereof. The compounds described herein are inhibitors of histone methyltransferases (HMTs, e.g., enhancer of zeste homolog 1 (EZH1), enhancer of zeste homolog 2 (EZH2)). The compounds are useful in treating and/or preventing diseases associated with aberrant or increased activity of an HMT, e.g., a proliferative disease, inflammatory disease, autoimmune disease, genetic disease, hematological disease, neurological disease, painful condition, psychiatric disorder, or metabolic disorder, in a subject in need thereof. The compounds are also useful in inducing apoptosis in a cell. Also provided are pharmaceutical compositions, kits, methods, and uses including a compound described herein.

In one aspect, the present disclosure provides compounds of Formula (I):

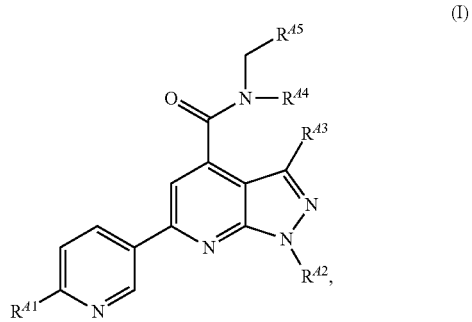

and pharmaceutically acceptable salts, solvates, hydrates, polymorphs, co-crystals, tautomers, stereoisomers, isotopically labeled derivatives, and prodrugs thereof, wherein $R^{41}$, $R^{42}$, $R^{43}$, $R^{44}$, and $R^{45}$ are defined herein.

Exemplary compounds of Formula (I) include, but are not limited to:
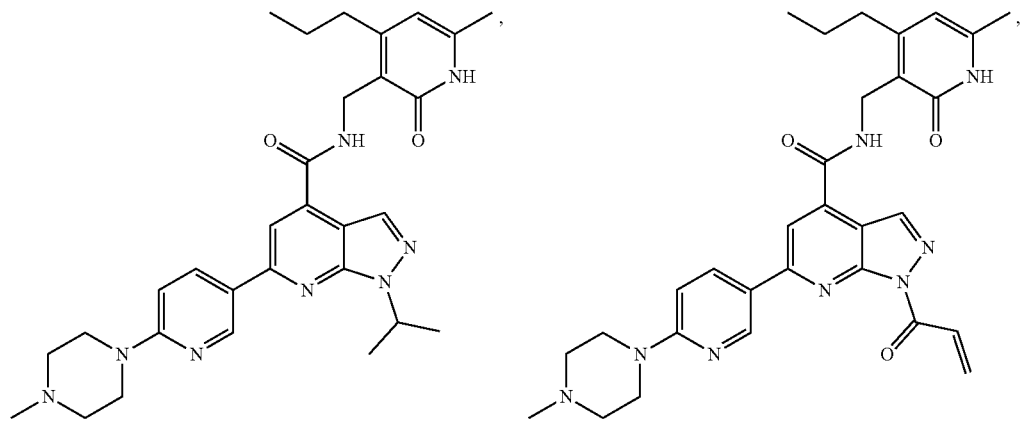
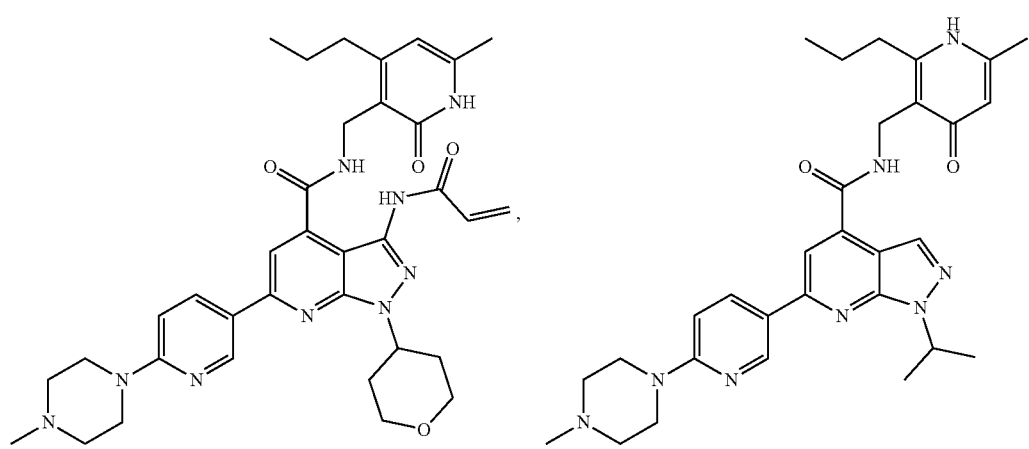
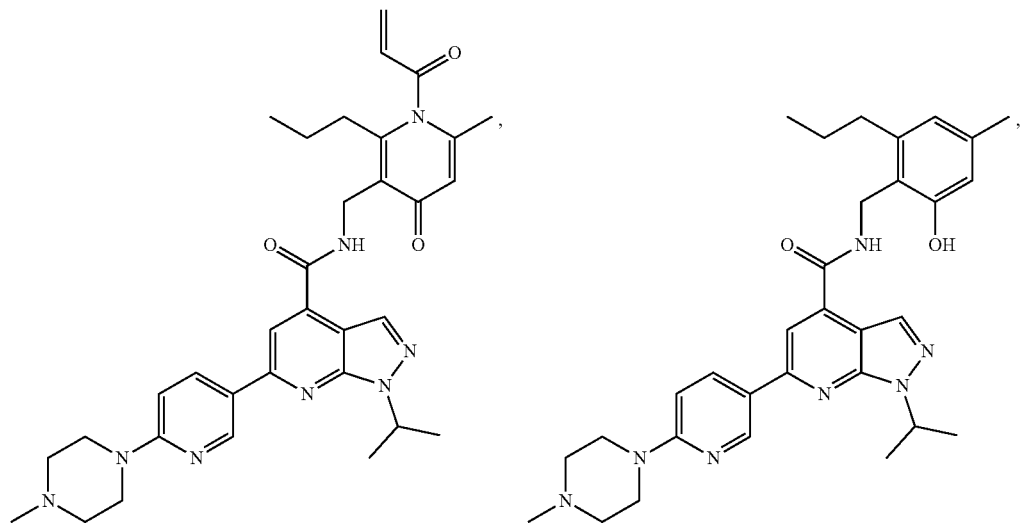

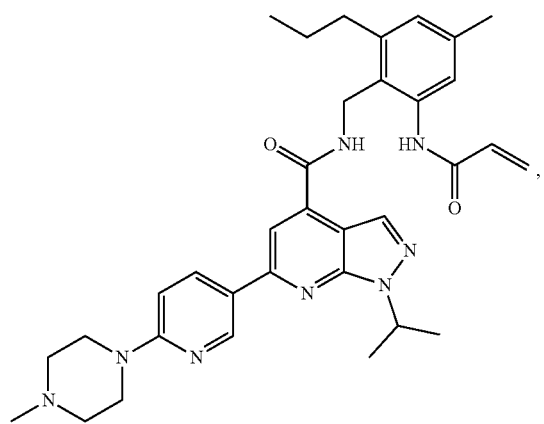
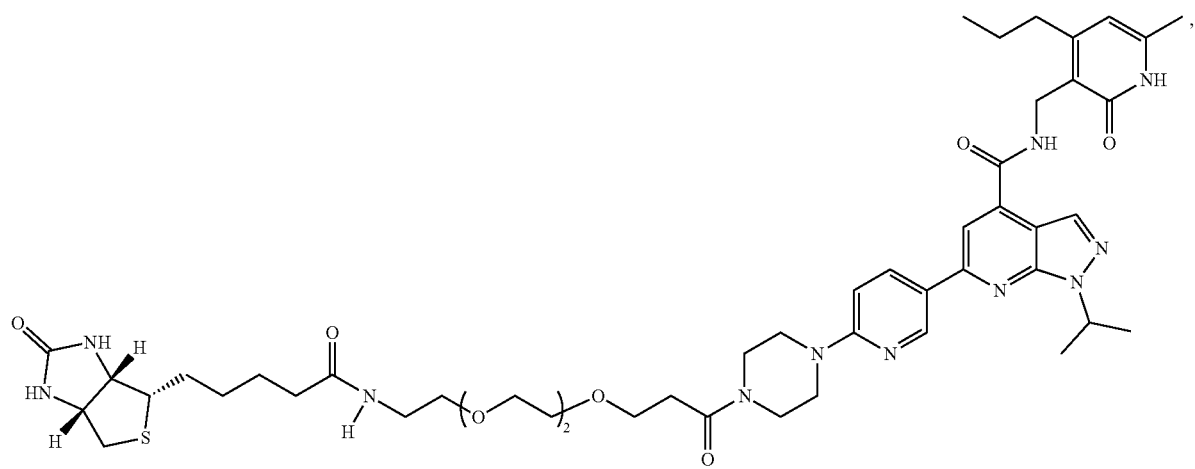
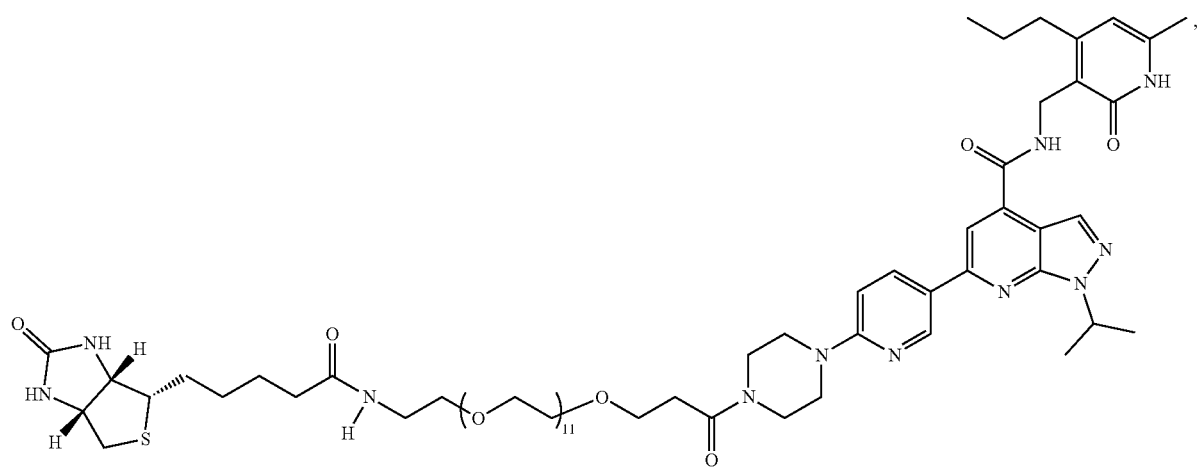

and pharmaceutically acceptable salts, solvates, hydrates, polymorphs, co-crystals, tautomers, stereoisomers, isotopically labeled derivatives, and prodrugs thereof.

In certain embodiments, the compound of Formula (I) is a compound of the formula:

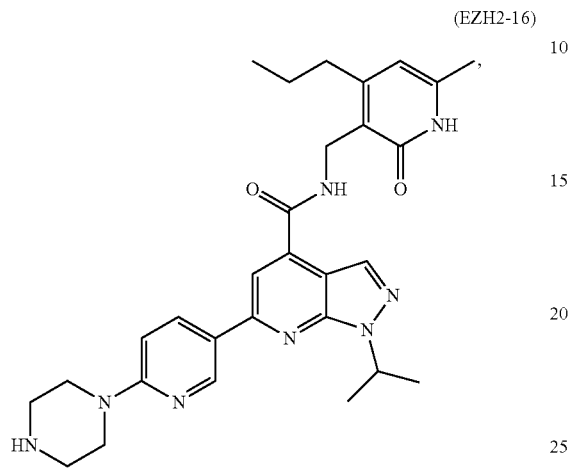

(EZH2-16)

or a pharmaceutically acceptable salt, solvate, hydrate, polymorph, co-crystal, tautomer, stereoisomer, isotopically labeled derivative, or prodrug thereof.

In certain embodiments, the compound of Formula (I) is a compound of the formula:

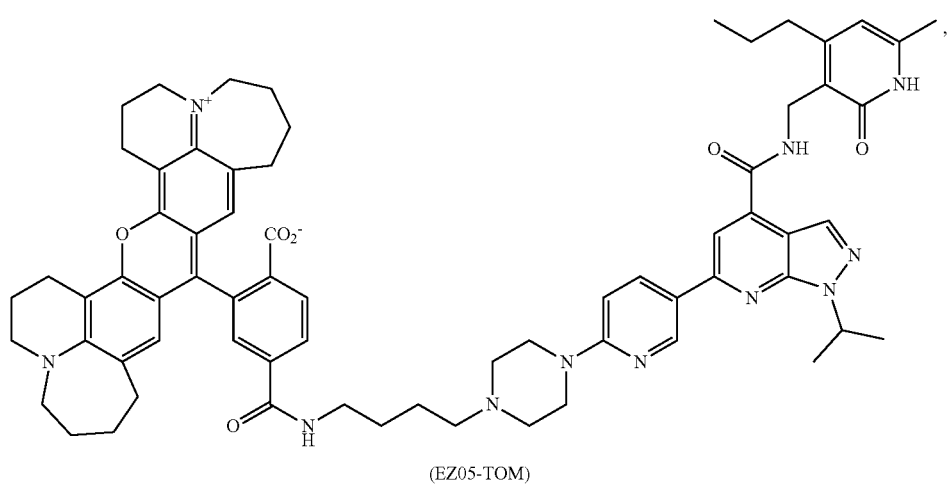

(EZ05-TOM)

-continued
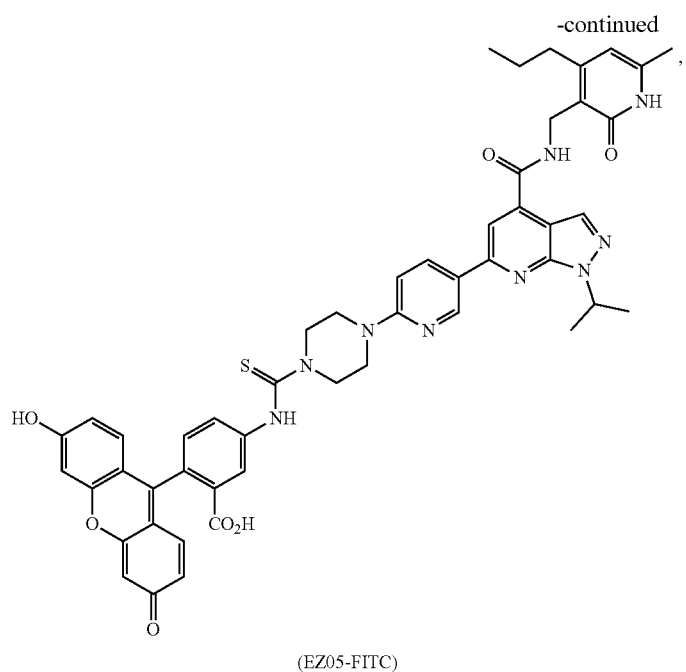
(EZ05-FITC)
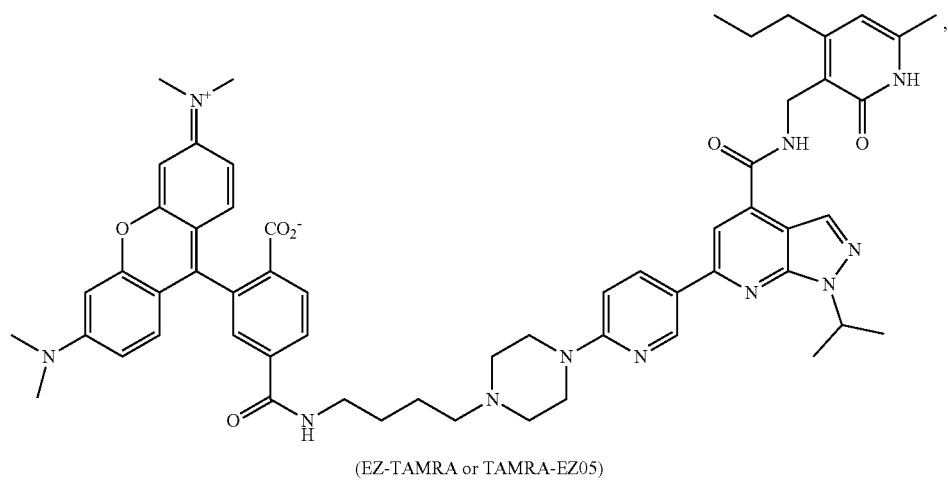
(EZ-TAMRA or TAMRA-EZ05)
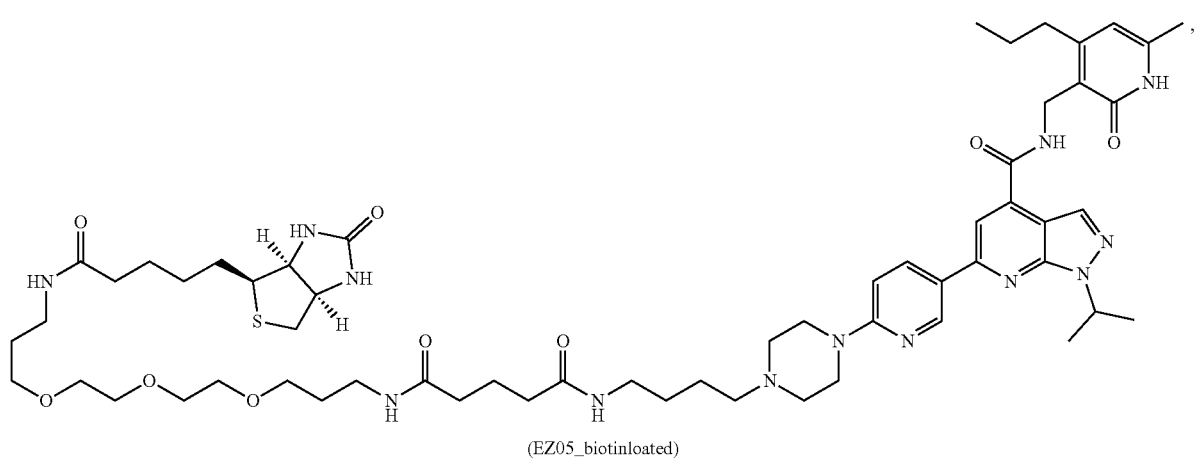 [SMILES: CCCc1cc(C)[nH]c(=O)c1CNC(=O)c1cc(-c2ccc(N3CCN(CCCCNC(=O)CCCC(=O)NCCCOCCOCCOCCCNC(=O)CCCC[C@@H]4SC[C@@H]5NC(=O)N[C@@H]54)CC3)nc2)nc2c1cnn2C(C)C]
(EZ05_biotinloated)

or a pharmaceutically acceptable salt, solvate, hydrate, polymorph, co-crystal, tautomer, stereoisomer, isotopically labeled derivative, or prodrug thereof.

In another aspect, the present disclosure provides compounds of Formula (II):

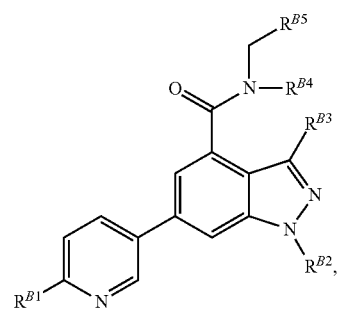
(II)

and pharmaceutically acceptable salts, solvates, hydrates, polymorphs, co-crystals, tautomers, stereoisomers, isotopically labeled derivatives, and prodrugs thereof, wherein $R^{B1}$, $R^{B2}$, $R^{B3}$, $R^{B4}$, and $R^{B5}$ are defined herein.

Exemplary compounds of Formula (II) include, but are not limited to:

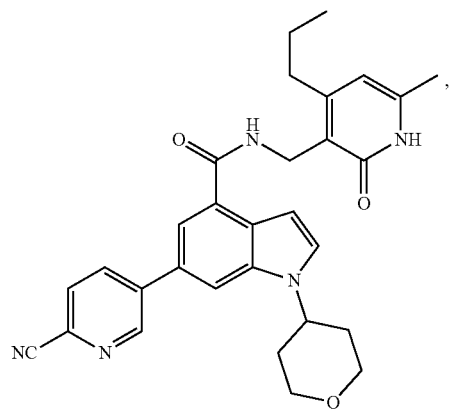

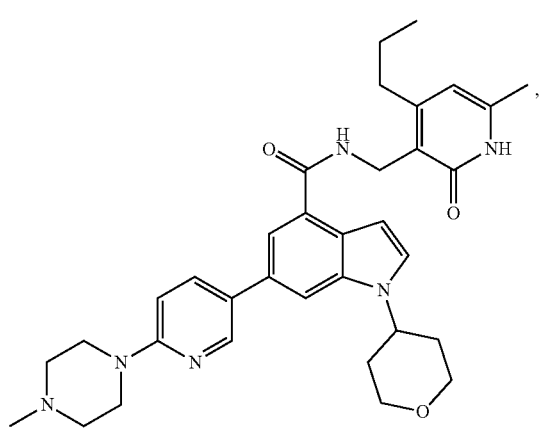

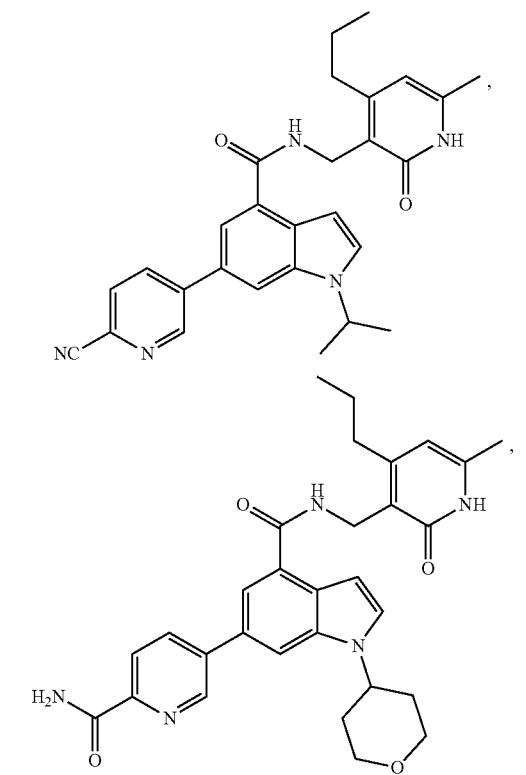

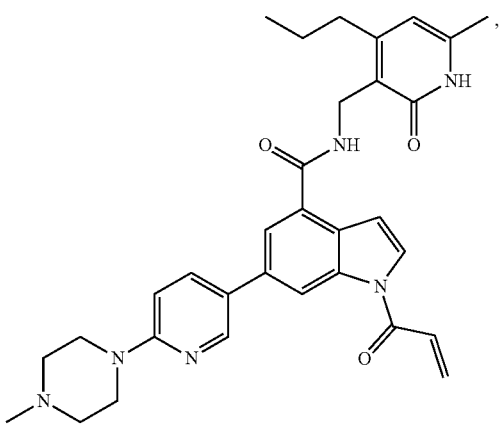

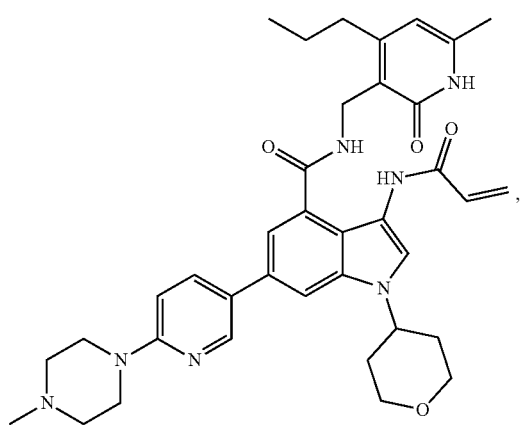

13
-continued
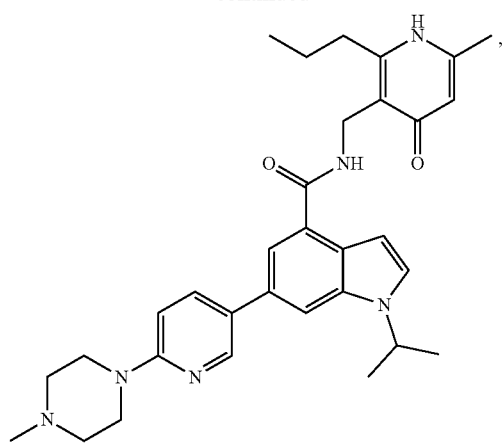
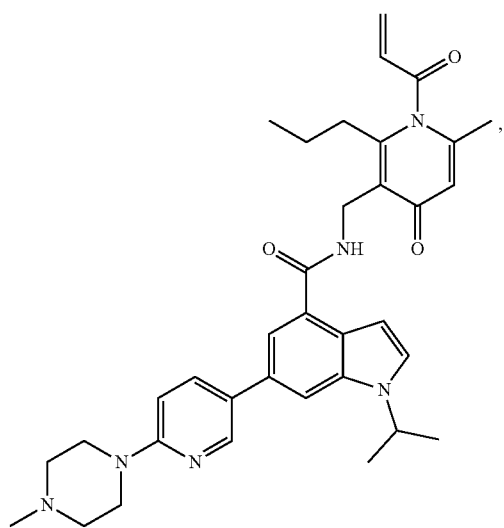
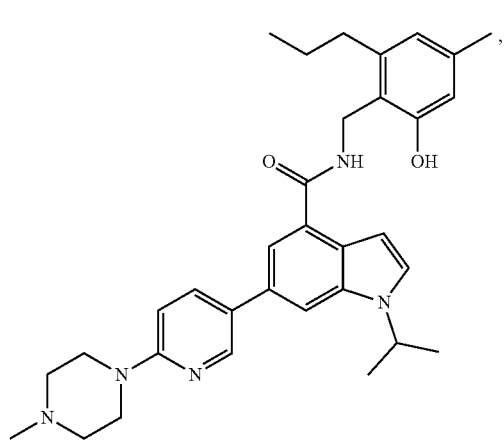
14
-continued
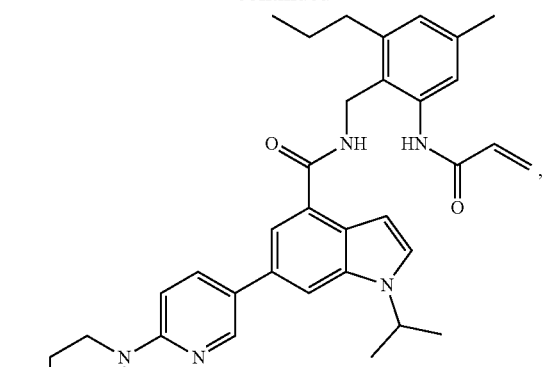
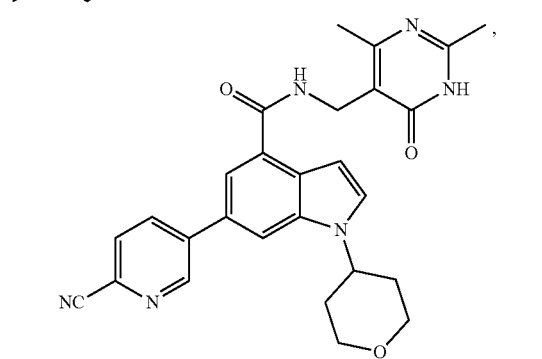
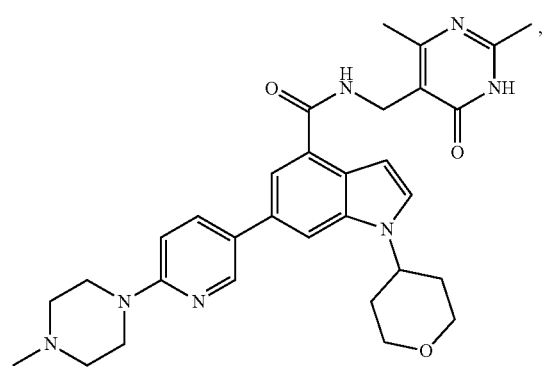
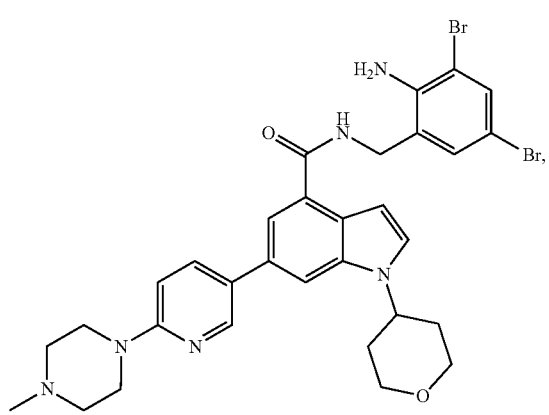 [SMILES: CN1CCN(c2ccc(-c3cc(C(=O)NCc4cc(Br)cc(Br)c4N)c4ccn(C5CCOCC5)c4c3)cn2)CC1]
and pharmaceutically acceptable salts, solvates, hydrates, polymorphs, co-crystals, tautomers, stereoisomers, isotopically labeled derivatives, and prodrugs thereof.

In certain embodiments, the compound of Formula (II) is a compound of the formula:
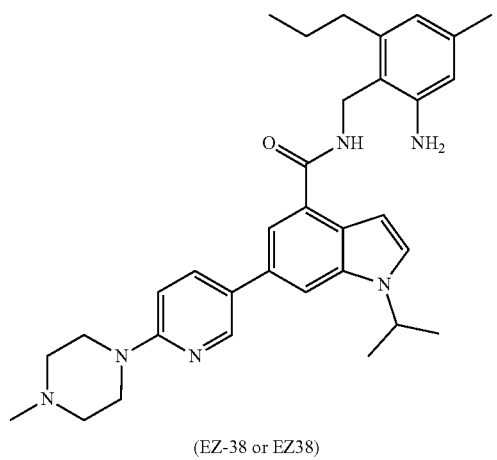
(EZ-38 or EZ38)
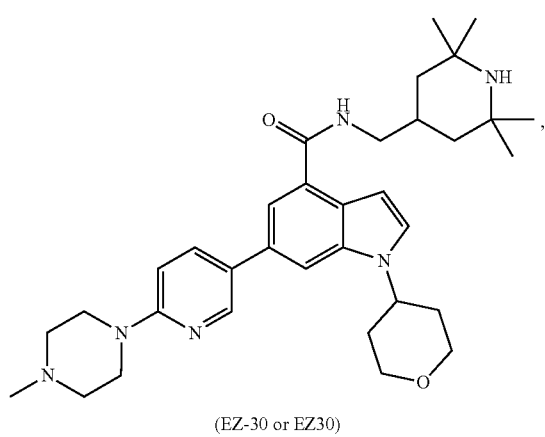
(EZ-30 or EZ30)
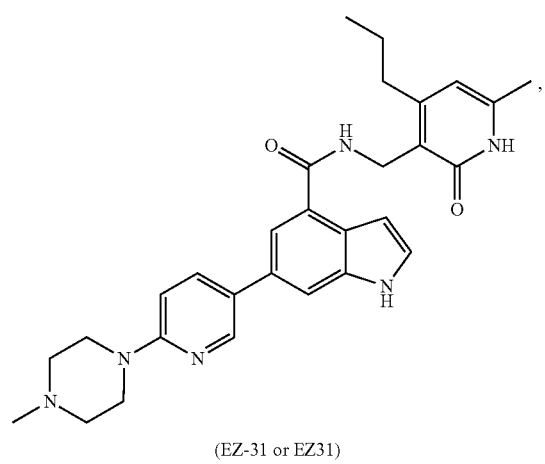
(EZ-31 or EZ31)
or a pharmaceutically acceptable salt, solvate, hydrate, polymorph, co-crystal, tautomer, stereoisomer, isotopically labeled derivative, or prodrug thereof.
In certain embodiments, the compound of Formula (II) is a compound of the formula:
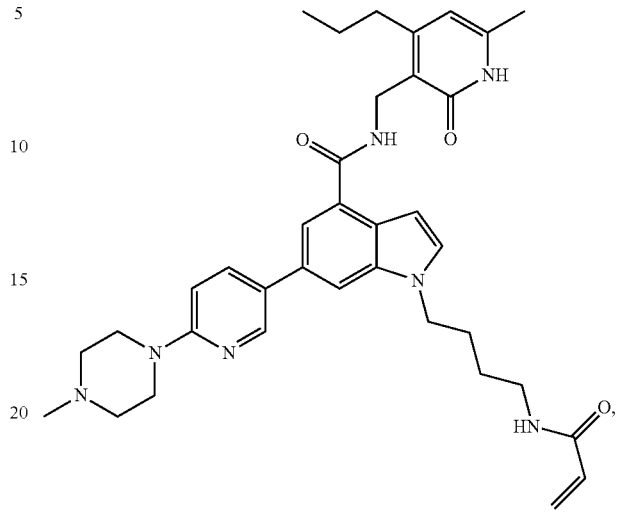
(EZ-35 or EZ35)
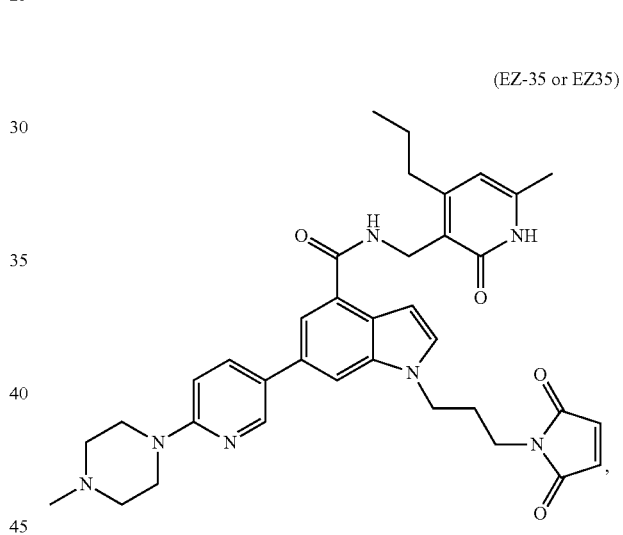
(EZ-36 or EZ36)
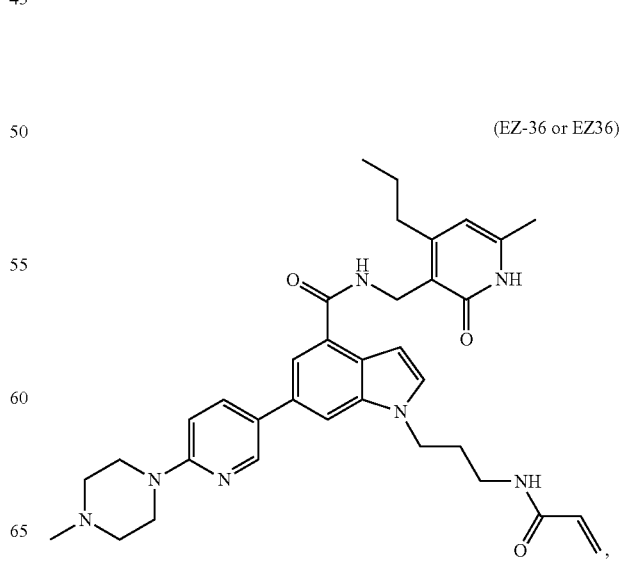

-continued

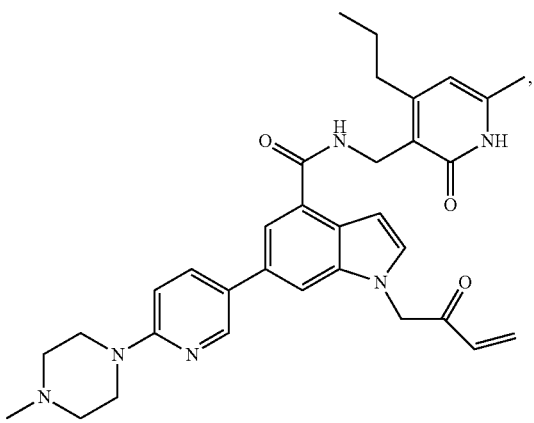

(EZ-41 or EZ41)

or a pharmaceutically acceptable salt, solvate, hydrate, polymorph, co-crystal, tautomer, stereoisomer, isotopically labeled derivative, or prodrug thereof.

In certain embodiments, the compound of Formula (II) is a compound of the formula:

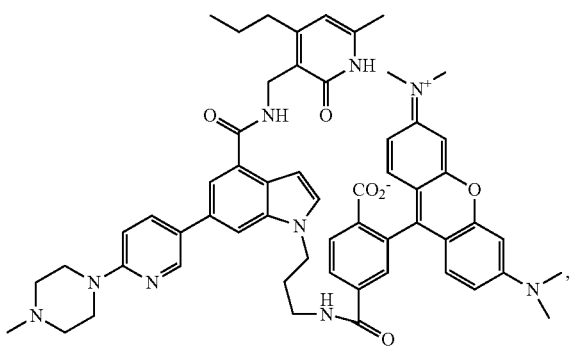

or a pharmaceutically acceptable salt, solvate, hydrate, polymorph, co-crystal, tautomer, stereoisomer, isotopically labeled derivative, or prodrug thereof.

In another aspect, described herein are pharmaceutical compositions including a compound described herein, and optionally a pharmaceutically acceptable excipient. In certain embodiments, a pharmaceutical composition described herein includes a therapeutically or prophylactically effective amount of a compound described herein. In certain embodiments, a pharmaceutical composition described herein further comprises an additional pharmaceutical agent. The pharmaceutical compositions may be useful in modulating (e.g., inhibiting) the activity of an HMT in a subject, biological sample, tissue, or cell, in treating a disease (e.g., a proliferative disease) in a subject in need thereof, or in preventing a disease in a subject in need thereof.

In certain embodiments, the disease is a disease associated with aberrant activity of an HMT. In certain embodiments, the aberrant activity of an HMT is increased activity of the HMT. In certain embodiments, the disease is a disease associated with increased activity of an HMT compared with a normal cell. In certain embodiments, the disease is a proliferative disease (e.g., cancer, benign neoplasm, pathological angiogenesis), inflammatory disease, autoimmune disease, genetic disease, hematological disease, neurological disease, painful condition, psychiatric disorder, or metabolic disorder.

In certain embodiments, the subject is a human. In certain embodiments, the subject is a non-human animal. In certain embodiments, the cell is in vitro. In certain embodiments, the cell is in vivo.

In still another aspect, described herein are kits including a container with a compound or pharmaceutical composition described herein. A kit described herein may include a single dose or multiple doses of the compound or pharmaceutical composition. The described kits may be useful in inhibiting the activity of an HMT in a subject, biological sample, tissue, or cell, in treating a disease associated with aberrant activity of an HMT in a subject in need thereof, in preventing a disease associated with aberrant activity of an HMT in a subject in need thereof, in treating a disease (e.g., proliferative disease, inflammatory disease, autoimmune disease, genetic disease, hematological disease, neurological disease, painful condition, psychiatric disorder, or metabolic disorder) in a subject in need thereof, and/or in preventing a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, a kit described herein further includes instructions for using the compound or pharmaceutical composition included in the kit.

In another aspect, the present disclosure provides methods of modulating (e.g., inhibiting) the aberrant activity of an HMT in a subject in need thereof, the methods comprising administering to the subject a therapeutically effective amount of a compound or pharmaceutical composition described herein.

In another aspect, the present disclosure provides methods of modulating (e.g., inhibiting) the activity of an HMT in a biological sample, tissue, or cell, the methods comprising contacting the biological sample, tissue, or cell with an effective amount of a compound or pharmaceutical composition described herein.

In certain embodiments, the compound being administered or used selectively inhibits the activity of a particular HMT (e.g., EZH1, EZH2, DOT1).

In another aspect, the present disclosure provides methods of inducing apoptosis in a cell, the methods comprising contacting the cell with an effective amount of a compound or pharmaceutical composition described herein.

Another aspect of the present disclosure relates to methods of treating a disease in a subject in need thereof, the methods comprising administering to the subject a therapeutically effective amount of a compound or pharmaceutical composition described herein.

In another aspect, the present disclosure provides methods of preventing a disease in a subject in need thereof, the methods comprising administering to the subject a prophylactically effective amount of a compound or pharmaceutical composition described herein.

Another aspect of the present disclosure relates to methods of decreasing the methylation of a histone in a subject in need thereof, the methods comprising administering to the subject an effective amount of a compound or pharmaceutical composition described herein.

Another aspect of the present disclosure relates to methods of decreasing the methylation of a histone in a biological sample, tissue, or cell, the methods comprising contacting the biological sample, tissue, or cell with an effective amount of a compound or pharmaceutical composition described herein.

Another aspect of the present disclosure relates to methods of modulating (e.g., down-regulating or up-regulating)

the expression of a gene in a subject in need thereof, the methods comprising administering to the subject an effective amount of a compound or pharmaceutical composition described herein.

Another aspect of the present disclosure relates to methods of modulating (e.g., down-regulating or up-regulating) the expression of a gene in a biological sample, tissue, or cell, the methods comprising contacting the biological sample, tissue, or cell with an effective amount of a compound or pharmaceutical composition described herein.

Another aspect of the disclosure relates to methods of screening a library of compounds to identify a compound that is useful in a method described herein.

Another aspect of the disclosure relates to methods of identifying EZH1 and/or EZH2 inhibitors.

In yet another aspect, the present disclosure provides compounds and pharmaceutical compositions described herein for use in a method of the disclosure (e.g., a method of inhibiting the aberrant activity of an HMT, a method of inducing apoptosis, a method of treating a disease (e.g., a proliferative disease), or a method of preventing a disease (e.g., a proliferative disease)).

DEFINITIONS

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=$CHCH_3$ or

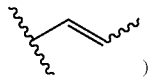
)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl").

Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —P(OR$^{cc}$)$_2$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, OC(=NR$^{ff}$)R$^{ee}$, —OC(=NR$^{ff}$)OR$^{ee}$, —C(=NR$^{aa}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, F$^-$), NO$_3$$^-$, ClO$_4$$^-$, OH$^-$, H$_2$PO$_4$$^-$, HCO$_3$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5\text{-}(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —C(=O)N$R^{bb}$SO$_2R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$OR, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2R^{aa}$) include, but are not limited to, p-toluenesulfonamide (Ts), benzenesulfonamide, 2,3,6,-trimethyl- 4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —$R^{aa}$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $X^-$, $R^{aa}$, $R^{bb}$, and $R^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein R$^{aa}$, R$^{bb}$, and R$^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

The term "leaving group" is given its ordinary meaning in the art of synthetic organic chemistry and refers to an atom or a group capable of being displaced by a nucleophile. See, for example, Smith, *March Advanced Organic Chemistry* 6th ed. (501-502). Exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein). In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —C$^A$H(C$^B$H$_2$C$^C$H$_3$)— includes one chain atom C$^A$, one hydrogen atom on C$^A$, and non-chain substituent —(C$^B$H$_2$C$^C$H$_3$). The term "C$_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —CH(C$_2$H$_5$)— is a C$_1$ hydrocarbon chain, and

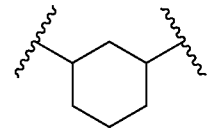 [SMILES: *C1CCCC(*)C1]

is a C$_3$ hydrocarbon chain. When a range of values is used, the meaning of the range is as described herein. For example, a C$_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH—(CH$_2$)$_2$—, —CH$_2$—C≡C—CH$_2$—, and —C≡C—CH=CH— are all examples of a unsubstituted and unsaturated hydrocarbon chain. In certain embodiments, the hydrocarbon chain is unsubstituted (e.g., —C≡C— or —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

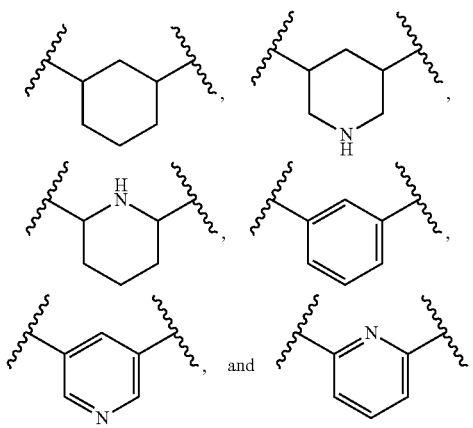

are all examples of a hydrocarbon chain. In contrast, in certain embodiments,

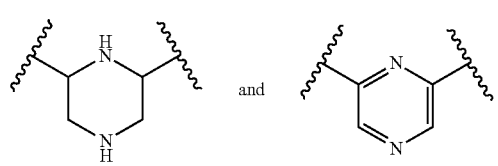 [SMILES: *C1CNCC(*)N1 ; *c1cncc(*)n1]

are not within the scope of the hydrocarbon chains described herein. When a chain atom of a C$_x$ hydrocarbon chain is replaced with a heteroatom, the resulting group is referred to as a C$_x$ hydrocarbon chain wherein a chain atom is replaced with a heteroatom, as opposed to a C$_{x-1}$ hydrocarbon chain.

For example,

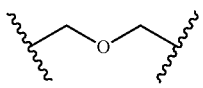

is a C$_3$ hydrocarbon chain wherein one chain atom is replaced with an oxygen atom.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5 H$_2$O)), and polyhydrates (x is a number greater than 1, e.g., dihydrates (R.2 H$_2$O) and hexahydrates (R.6 H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "small molecule drug" refers to a small molecule that has been approved by a governmental agency (e.g., FDA) for administering to a subject (e.g., human or non-human aminal), or a radical of such a small molecule.

The term "small molecule label" refers to a small molecule that is capable of being detected, or a radical of such a small molecule. Exemplary small molecule labels include, but are not limited to, biotin, radioactive isotopes, enzymes, luminescent agents, precipitating agents, fluorophores, and dyes.

The term "small molecule fluorophore" refers to a small molecule that is fluorescent, e.g., being able to re-emit light upon light excitation. Exemplary small molecule fluorophores include, but are not limited to, fluorescein, rhodamine, coumarin, cyanine, and derivatives thereof.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonuculeotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

Polynucleotides described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., *Nucl. Acids Res.*, 16, 3209, (1988), methylphosphonate oligonucleotides can be prepared by use of controlled pore glass polymer supports (Sarin et al., *Proc. Natl. Acad. Sci. U.S.A.* 85, 7448-7451, (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Any type of plasmid, cosmid, yeast artificial chromosome, or viral vector can be used to prepare the recombinant DNA construct that can be introduced directly into the tissue site.

The polynucleotides may be flanked by natural regulatory (expression control) sequences or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications, such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, isotopes (e.g., radioactive isotopes), biotin, and the like.

The term "inhibition", "inhibiting", "inhibit," or "inhibitor" refer to the ability of a compound to reduce, slow, halt or prevent activity of a particular biological process (e.g., activity of a bromodomain and/or a bromodomain-containing protein) in a cell relative to vehicle.

When a compound, pharmaceutical composition, method, use, or kit is referred to as "selectively," "specifically," or "competitively" inhibiting an HMT, the compound, pharmaceutical composition, method, use, or kit inhibits the HMT to a greater extent (e.g., not less than 2-fold, not less than 5-fold, not less than 10-fold, not less than 30-fold, not less than 100-fold, not less than 1,000-fold, or not less than 10,000-fold; and/or: not more than 2-fold, not more than 5-fold, not more than 10-fold, not more than 30-fold, not more than 100-fold, not more than 1,000-fold, or not more than 10,000-fold) than inhibiting a different HMT.

The term "aberrant activity" refers to activity deviating from normal activity. In certain embodiments, the aberrant activity is increased activity. In certain embodiments, the aberrant activity is decreased activity. The term "increased activity" refers to activity higher than normal activity. The term "decreased activity" refers to activity lower than normal activity.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount effective to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "histone" refers to highly alkaline proteins found in eukaryotic cell nuclei that package and order DNA into structural units called nucleosomes. They are the chief protein components of chromatin, acting as spools around which DNA winds, and play a role in gene regulation. In certain embodiments, the histone is histone H1 (e.g., histone H1F, histone H1H1). In certain embodiments, the histone is histone H2A (e.g., histone H2AF, histone H2A1, histone H2A2). In certain embodiments, the histone is histone H2B (e.g., histone H2BF, histone H2B1, histone H2B2). In certain embodiments, the histone is histone H3 (e.g., histone H3A1, histone H3A2, histone H3A3). In certain embodiments, the histone is histone H4 (e.g., histone H41, histone H44).

"Histone methyltransferases" or "HMTs" are histone-modifying enzymes that catalyze the transfer of one, two, or three methyl groups to lysine and/or arginine residues of histone proteins. HMTs modify histones at certain sites through methylation. Methylation of histones is of biological significance because such methylation is a principal epigenetic modification of chromatin that determines gene expression, genomic stability, stem cell maturation, cell lineage development, genetic imprinting, DNA methylation, and/or cell mitosis. In certain embodiments, an HMT described herein is a histone-lysine N-methyltransferase. In certain embodiments, an HMT described herein is a histone-arginine N-methyltransferase. In certain embodiments, an HMT described herein is EZH1. In certain embodiments, an HMT described herein is EZH2. In certain embodiments, an HMT described herein is DOT1. In certain embodiments, an HMT described herein is G9a, GLP, MLL1, MLL2, MLL3, MLL4, NSD2, PRMT1, PRMT3, PRMT4, PRMT5, PRMT6, SET1b, SET7/9, SET8, SETMAR, SMYD2, SUV39H1, or SUV39H2.

The term "enhancer of zeste homolog 1," "enhancer of zeste 2 polycomb repressive complex 1 subunit," "EZH1," "EZH1 enzyme," "histone-lysine N-methyltransferase EZH1" refers to an enzyme that is encoded by the EZH1 gene. ENSEMBL of human EZH1 gene: ENSG00000108799.

The term "enhancer of zeste homolog 2," "enhancer of zeste 2 polycomb repressive complex 2 subunit," "EZH2," "EZH2 enzyme," "histone-lysine N-methyltransferase EZH2" refers to an enzyme that is encoded by the EZH2 gene. EZH2 is a core catalytic component of the Polycomb-group (PcG) protein complex family. EZH2 is a histone methyltransferase that that catalyzes the di- and tri-methylation at histone H3 lysine 27 (H3K27me2/3), thereby silencing gene expression. The catalytic site of EZH2 is present within a SET domain, a highly conserved sequence motif that is found in several chromatin-associated proteins. EZH2 plays a critical role in normal development and EZH2 deficient mice die at early stage of embryo due to the failure of implantation and gastrulation. EZH2 is known to associate with the embryonic ectoderm development protein, the VAV1 oncoprotein, and the X-linked nuclear protein (XNP). EZH2 may also play a role in the hematopoietic and central nervous systems. ENSEMBL of human EZH2 gene: ENSG00000106462.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, dexpression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, malignant melanoma, manic dexpression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., Stedman's Medical Dictionary, 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as Plasmodium, chemical injuries from, e.g., lead poisoning, and hypersplenism. In certain embodiments, a hematological disease is a hematological malignancy. The term "hematological malignancy" refers to tumors that affect blood, bone marrow, and/or lymph nodes. Exemplary hematological malignancies include, but are not limited to, leukemia, such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt lymphoma, Waldenström's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosus, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, including, but not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawl symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the Diagnostic and Statistical Manual of Mental Disorders—Fourth Edition (DSM-IV), published by the American Psychiatric Association, Washington D.C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., dexpression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

BRIEF DESCRIPTION OF THE DRAWINGS

(FIG. 9A) Schematic depiction of LSL-EZH2 genetically engineered mouse model utilizing 3 different strategies to express Cre recombinase to induce EZH2 overexpression. (FIG. 9B) Kaplan-Meier lung cancer-free survival summary plot for LSL-EZH2 transgenic mice (EZH2) versus wildtype mice (WT). (FIG. 9C) Histology of wildtype lung (top) and EZH2-induced lung adenocarcinomas (bottom) Sections stained with hematoxylin and eosin. Right panels show immunostaining of Ki-67, a marker of proliferation. Scale bar represents 50 um. (FIG. 9D) Hematoxylin and eosin staining or immunostaining for EZH2, p-AKT, and p-ERK1/2 in EZH2-induced mouse lung tumors (top) and KRAS-induced mouse lung tumors (bottom). Scale bar represents 50 um. (FIG. 9E) Western blots of EZH2, AKT, p-AKT, ERK1,2 and p-ERK1,2 expression in normal, EZH2-induced tumor, and KRAS-induced tumor lung tissues from mice (top). Relative protein expression levels as quantified with ImageJ (bottom). See also FIG. 15.

(FIG. 10A) Heatmap of log 2 fold-change (LFC) gene expression in EZH2-overexpressing (OE) normal lungs, KRAS-mutant lung tumors, EGFR-mutant lung tumors, and EZH2-OE lung tumors versus corresponding normal lung tissues. The top 500 most variable genes were selected across all samples for clustering. Dark grey regions indicate downregulated genes in mutant or overexpressed tissue versus controls; light grey regions indicate upregulated genes in mutant or overexpressed tissue versus controls. (FIG. 10B) Distribution of EZH2 expression in 471 human lung adenocarcinomas (dark grey) versus 58 normal lungs (light grey) from The Cancer Genome Atlas (TCGA). Mean EZH2 expression level is 394.8 in human lung adenocarcinomas and 56.7 in normal lungs. (FIG. 10C) Box plot of ssGSEA comparing the enrichment of a MEK (left) and mTOR (right) gene sets in TCGA lung adenocarcinomas with specific driver mutations (KRAS, EGFR, unknown) or high EZH2 levels.

(FIG. 11A) Heatmap showing hierarchical clustering of H3K27ac super enhancer (SE) regions in wildtype (WT) and tumor lung tissues. Relative H3K27ac levels are indicated by intensity of color. (FIG. 11B) Heatmap showing similarity clustering of super enhancers between WT and tumor tissues. Color intensity indicates increasing similarity. (FIG. 11C) Waterfall plot showing rank-ordered change in H3K27ac signal at super enhancer-containing regions between tumor and wildtype (WT) lung. X-axis depicts the LFC in H3K27ac signal. Enhancers are ranked by LFC in signal with regions gaining the most H3K27ac in tumor at the top. Change in H3K27ac levels at super enhancers is colored by intensity of change from light to dark grey. (FIG. 11D) Box plot of RNA-seq expression in units of RPKM of genes associated with super enhancers that are gained, unchanged, or lost in tumor versus WT lung tissues. Significance of the difference between distributions was calculated using a two-tailed t test.  p<2e-4, * p<2e-6 (FIG. 11E) Scatter plot of normalized enrichment score (NES) versus false discovery rate (FDR) q-value comparing MSigDB curated gene set enrichment in tumor versus WT super enhancer associated genes. X-axis shows NES for evaluated gene sets. Y-axis shows false FDR q-value for each gene set. Gene sets upregulated in tumors have a high positive NES, while downregulated gene sets have a negative NES. Dotted line indicates significance cutoff q-value of 0.05. Dark grey dots indicate PRC2 associated signatures that are downregulated in tumors. For PRC2 signatures, n=8. (FIG. 11F) Super enhancer associated gene set enrichment analysis showing downregulation of EED targets in tumor versus WT tissues. (FIG. 11G) Heatmap of LFC in H3K27ac over H3K27me3 signals at super enhancer containing regions. Blue or dark grey regions indicate super enhancers with strong gains of H3K27me3 in tumor versus WT, while red or light grey regions indicate those with strong losses. (FIG. 11H) Dot plot of RNA-seq expression in units of $\log_{10}$ RPKM for genes proximal to super enhancer regions with a strong gain of H3K27me3 in tumor versus WT. Significance of the difference between distributions was calculated with a two-tailed t test. **p<1e-5. (FIG. 11I) Box plot of ssGSEA comparing the enrichment of our mouse H3K27me3 gene set in TCGA lung adenocarcinomas with high EZH2 levels and normal lung tissue. The H3K27me3 gene set is comprised of the 32 mouse genes proximal to SE regions with strong H3K27me3 gain in murine EZH2-overexpressing tumors See also FIG. 16.

(FIG. 12A) SDS-PAGE and Western blot analysis of human tracheobronchial epithelial (hTBE) cells expressing control (ctl) or EZH2 (oeEZH2) constructs. (FIG. 12B) Colony forming assay for hTBE cells over-expressing control (left) or EZH2 (right) constructs. (FIG. 12C) hTBE cells expressing control (ctl) or EZH2 (oeEZH2) were cultured for 10 or 20 passages in vitro before seeding on soft agar to perform a colony formation assay. Error bars represent SEM, * p<0.05,  p<0.001. (FIG. 12D) H661 (left) and H292 (right) cells expressing non-targeting control shRNA (NT) or two different shRNAs targeting EZH2 (shEZH2-A and shEZH2-B) were analyzed for Ezh2 expression by Western blotting. (FIG. 12E) Relative cell growth was measured by MTS assay in H661 cells expressing control (NT) or EZH2-targeting shRNAs. Error bars represent SEM, n=3.  p<0.001. (F-G) H661 cells infected with lentivirus containing control (NT) or shEZH2 were subcutaneously injected into the flank of nude mice. When the size of the biggest tumor reached approximately 5 mm in diameter, mice were euthanized and tumors were measured. (FIG. 12F) Quantification of relative shEZH2 tumor size as compared to shNT tumor size (mean±SEM, n=3/treatment). (FIG. 12G) H661 and H292 cells infected with lentivirus containing control (NT) or shEZH2 were subcutaneously injected into the flank of nude mice. When the size of the biggest tumor reached approximately 5 mm in diameter, mice were euthanized and tumors were documented (mean±SEM, n=3/treatment). See also FIG. 17.

(FIG. 13A) Chemical structure of negative control compound, JQEZ23. (FIG. 13B) Small molecule inhibitory activity of JQEZ5, JQEZ23, GSK-126 and UNC1999 were measured in a five-component PRC2 complex radiometric Scintillation Proximity Assay (SPA) using radiolabeled S-adenosyl methionine (SAM). (FIG. 13C) The IC50 of JQEZ5, as measured with increasing SAM concentrations to confirm its SAM competitive binding activity.

(FIG. 14A) H661 lung cancer cells were incubated with increasing concentrations of JQEZ5. Cell lysates were prepared and subjected to SDS-PAGE and analysis by Western blotting with the indicated antibodies. (FIG. 14B) Western blots of methylation levels in lung cancer cell line H661, 72 h after treatment with increasing concentrations of JQEZ23. H3 is a loading control. (FIG. 14C) Western blots of methylation levels in H661 lung cancer cell line after 48 h or 72 h of treatment with increasing concentrations of JQEZ5. H3 is a loading control. (FIG. 14D) H661 and (E) H292 lung cancer cells were incubated with increasing concentrations of JQEZ5 and relative cell growth was assessed by MTS assay. Error bars represent SD, n=3. (Figure F) Quantification of relative mouse tumor volume based on MRI. Relative tumor size was compared before and after treatment with JQEZ5 for three weeks (mean±SEM, n=2). (FIG. 14G) MRI reveals that in vivo treatment of mice with JQEZ5 causes remission of lung tumors, as indicated by the circle. H, Heart. See also FIG. 19.

(FIG. 15A) Schematic for generating EZH2 transgenic mice by Frt-mediated homologous recombination. The targeting vector carrying EZH2 cDNA and pgkATGfrt was targeted to a modified site located ~500 bp downstream of the 3' untranslated region of the ColA1 locus by co-electroporation with FLPe transient expression vector. A LOX-STOP-LOX (LSL) cassette placed between the CAG promoter and EZH2 cDNA ensures the EZH2 transgene is only expressed in the presence of Cre-mediated excision of LSL cassette. E=EcoRI; P=PstI; S=SpeI (FIG. 15B) Genotyping of mouse tail DNA with two different primer sets—P1 and P2, or P3 and P4. The target of the first primer set spans the integration site, ensuring a correct recombination. (FIG. 15C) Schematic depiction of switching on of EZH2 transgene by Cre-mediated excision of the LSL cassette. (FIG. 15D) Lungs from wildtype and Actin-Cre:LSL-Ezh2 mice were sectioned and stained for Ezh2 expression by immunohistochemistry. Scale bar represents 50 um. (FIG. 15E) Lysates were prepared from lungs of wildtype (control), Actin-Cre:LSL-Ezh2 and UBC:LSL-Ezh2 mice. UBC:LSL-Ezh2 mouse was treated with tamoxifen at 6 weeks of age and tissue was harvested two weeks later. Lysates were analyzed for Ezh2 protein expression levels by Western blotting.

(FIG. 16A) 32 mouse genes proximal to SE regions with strong H3K27me3 gain in EZH2-overexpressing tumors. (FIG. 16B) Genome-wide ene tracks of ChIP-seq signals in units of rpm/bp for H3K27ac and H3K27me3 in WT and tumor lung tissues. (FIG. 16C) Gene tracks of ChIP-seq signals in units of rpm/bp for H3K27ac and H3K27me3 at super enhancer (SE) region in WT and tumor lung tissues. (FIG. 16D) Gene tracks of ChIP-Seq signal in units of rpm/bp for H3K27ac and H3K27me3 at the Foxf1a locus in either WT or tumor lung tissues. (FIG. 16E) Gene tracks of ChIP-seq signals in units of rpm/bp for H3K27ac and H3K27me3 at the DUSP4 locus in either WT and tumor lung tissues. (FIG. 16F) Western blot analysis of lysates prepared from normal lung (N-1, N-2 and N-3) and lung tumor (T-1, T-2 and T-3) samples.

(FIG. 17A) Western blots comparing EZH2 expression levels between NSCLC cell lines H661 and H292. Actin is a loading control. (FIG. 17B) Relative cell growth of H292 cells expressing non-targeting control shRNA (NT) or two different shRNAs targeting EZH2 (shEZH2-A and shEZH2-B) was measured by MTS assay. Error bars represent S.E.M, n=3.

FIGS. 18A-18D, related to FIG. 13. Characterization of JQEZ5. (FIG. 18A) Chemical structure of reported EZH2 inhibitors, GSK-126 and UNC1999. (FIG. 18B) IC50 values of JQEZ5, the negative control compound, JQEZ23, and literature reported EZH2 inhibitors as determined in a radiometric Scintillation Proximity Assay (SPA) used to measure PRC2 activity. (FIG. 18C) JQEZ5 inhibitory activity against PRC2 was measured with increasing concentrations of S-adenosyl methionine (SAM) by SPA assay. (FIG. 18D) JQEZ5 activity was assayed against a panel of 22 methyltransferases. IC50 values for JQEZ5 and the control compound, S-adenosyl-homocysteine (SAH), are listed.

(FIG. 19B) MRI scan from animal #1 reveals that in vivo treatment with JQEZ5 causes remission of lung tumors from week 0 to week 3. (FIG. 19C) MRI scan from animal #2 reveals that in vivo treatment with JQEZ5 causes remission of lung tumors from week 0 to week 3.

FIG. 22 shows exemplary results regarding the EZH2 vs. EZH1 biochemical selectivity of select compounds described herein.

FIG. 23A: H3K27me3 (Ms) is shown in green or light grey; and Histone H3 (Rb; C-terminal Ab) is shown in red or dark grey. "uM" denotes µM. FIG. 23B shows exemplary H3K27me3 quantification results. "[CPD]" denotes the concentration of the test compound in molar.

FIG. 24 shows exemplary results of EZH2 (WT) vs. EZH2 (Y641) biochemical selectivity of select compounds described herein.

FIG. 25A shows the Z-factor values of the G401 cells and BT16 cells treated with 10 µM EZ05. FIG. 25B shows the Z-factor values of the G401 cells and BT16 cells treated with 3.3 µM EZ05. FIG. 25C shows the % viability of the G401 cells. DMSO was used as the control.

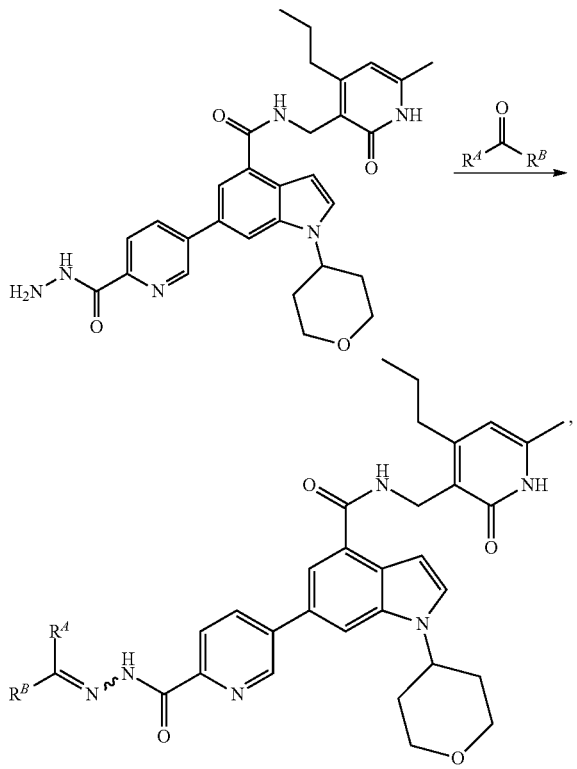

wherein

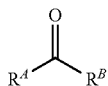

Figure 21:
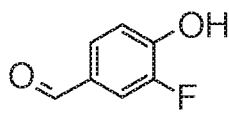
FIG. 21 shows the chemical structures of exemplary aldehydes and ketones useful for preparing the hydrazides described herein.
Figure 21:
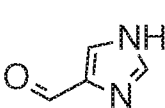
Figure 21:
Figure 21:
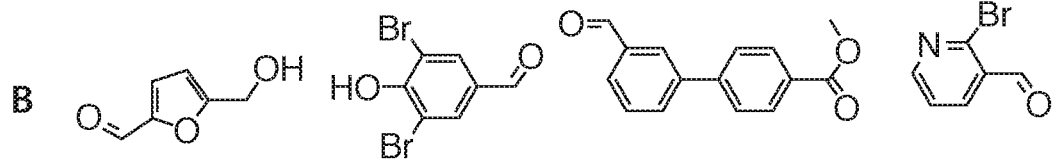
Figure 21:
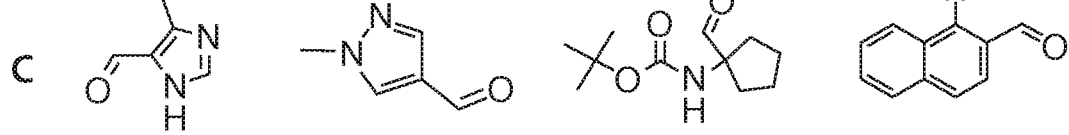
Figure 21:
Figure 21:
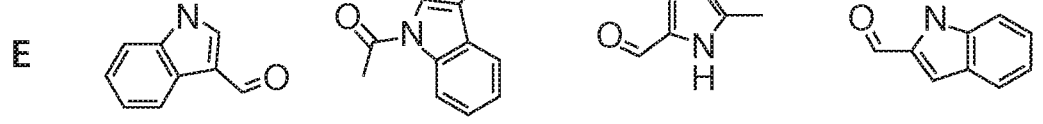
Figure 21:
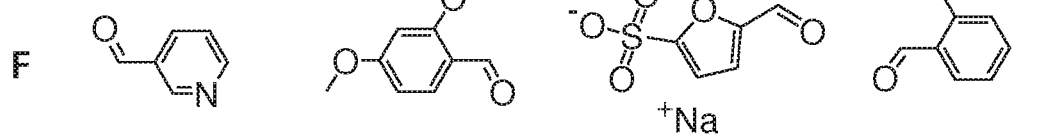
Figure 21:
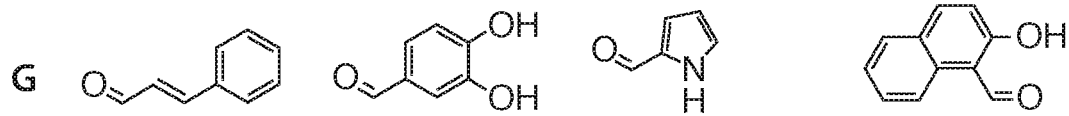
Figure 21:
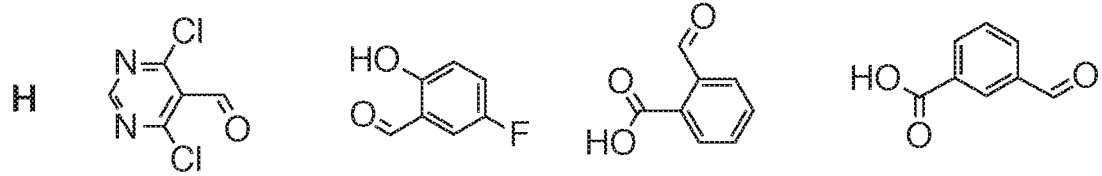
Figure 21:
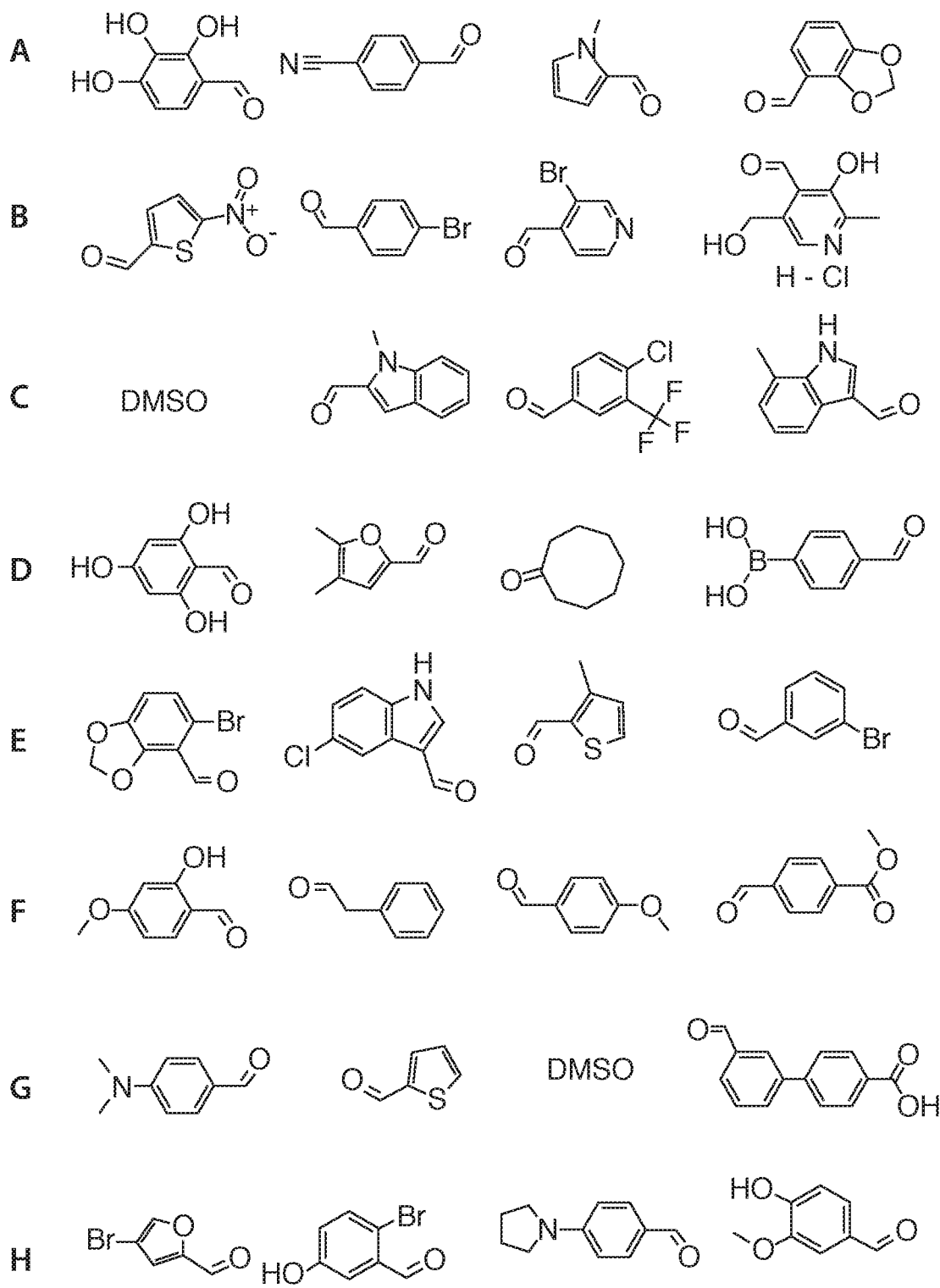
Figure 21:
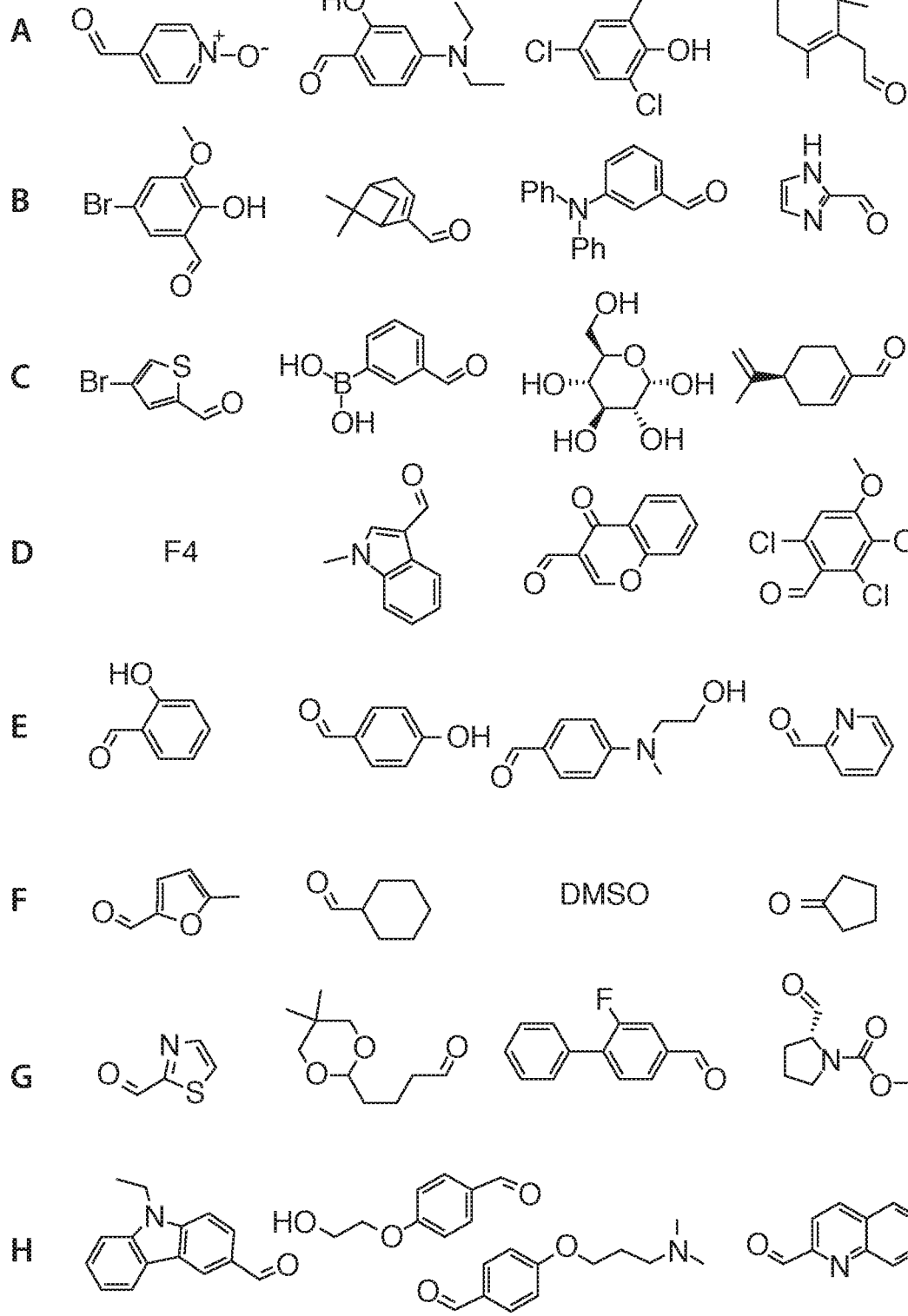
Figure 21:
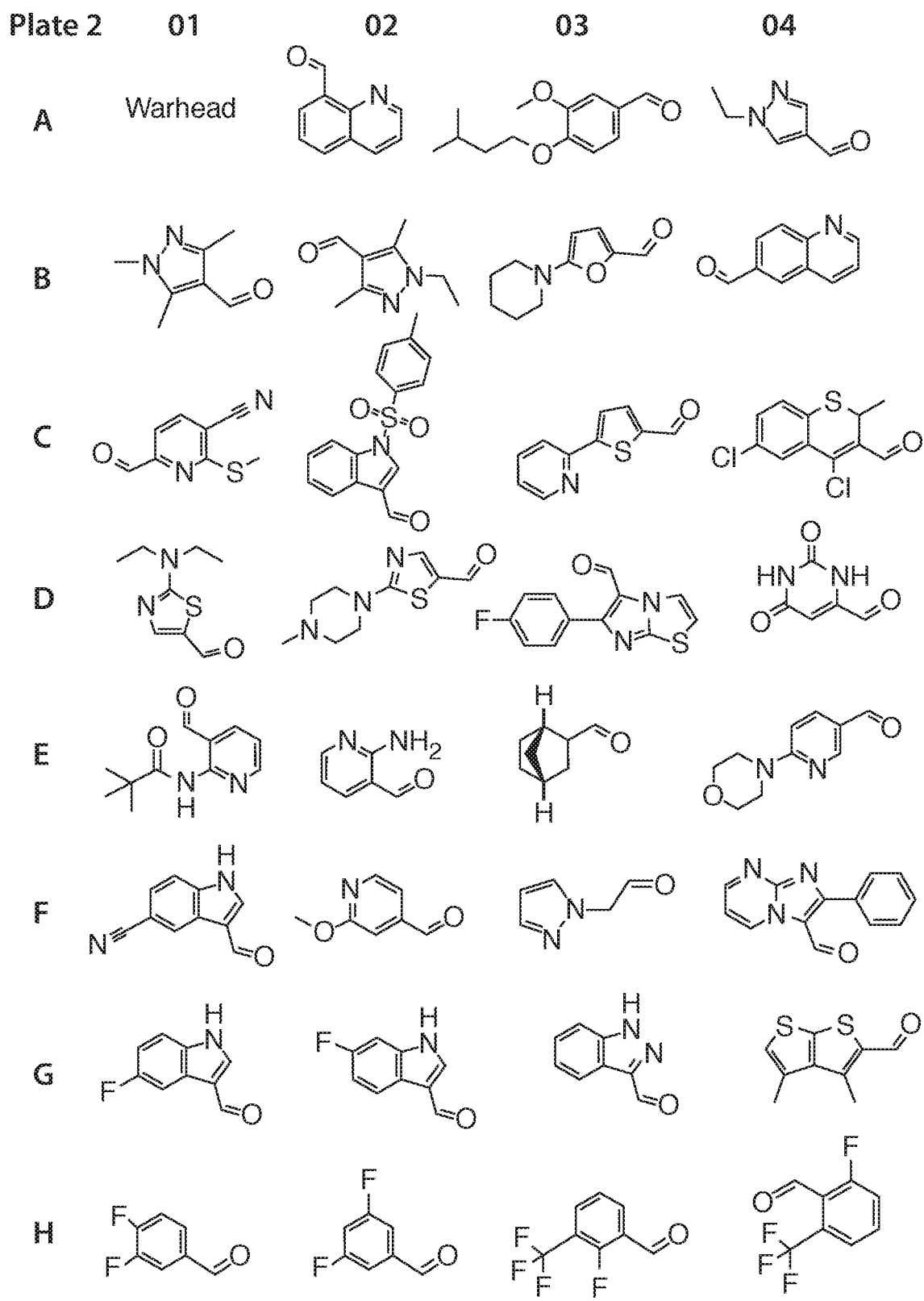
Figure 21:
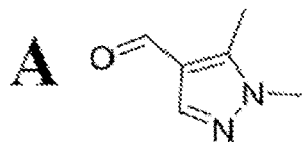
Figure 21:
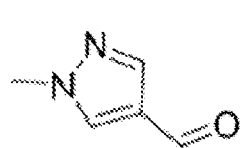
Figure 21:
Figure 21:
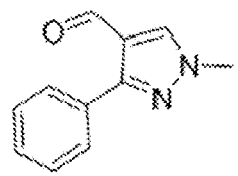
Figure 21:
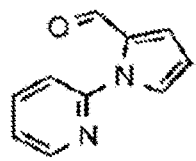
Figure 21:
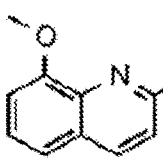
Figure 21:
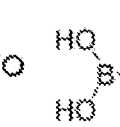
Figure 21:
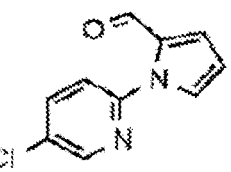
Figure 21:
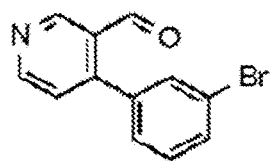
Figure 21:
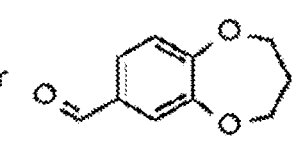
Figure 21:
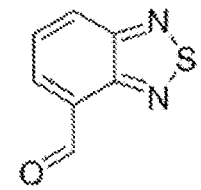
Figure 21:
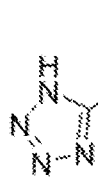
Figure 21:
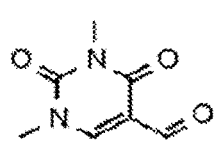
Figure 21:
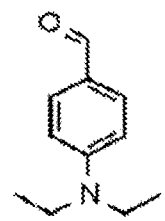
Figure 21:
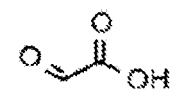
Figure 21:
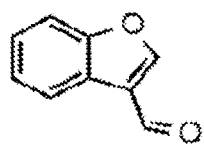
Figure 21:
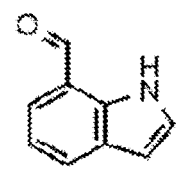
Figure 21:
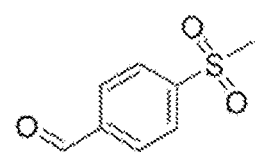
Figure 21:
Figure 21:
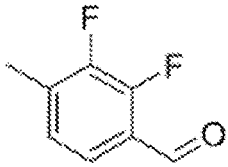
Figure 21:
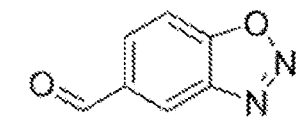
Figure 21:
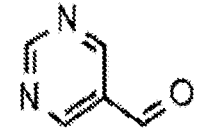
Figure 21:
Figure 21:
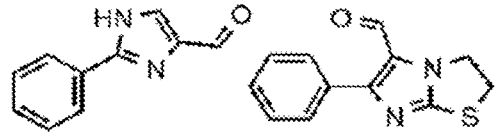
Figure 21:
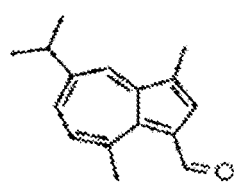
Figure 21:
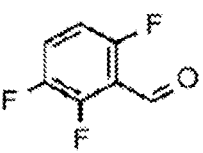
Figure 21:
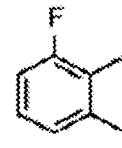
Figure 21:
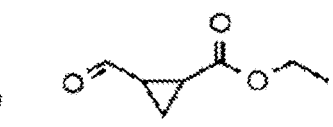
Figure 21:
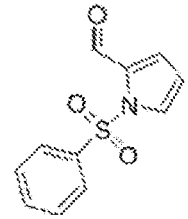
Figure 21:
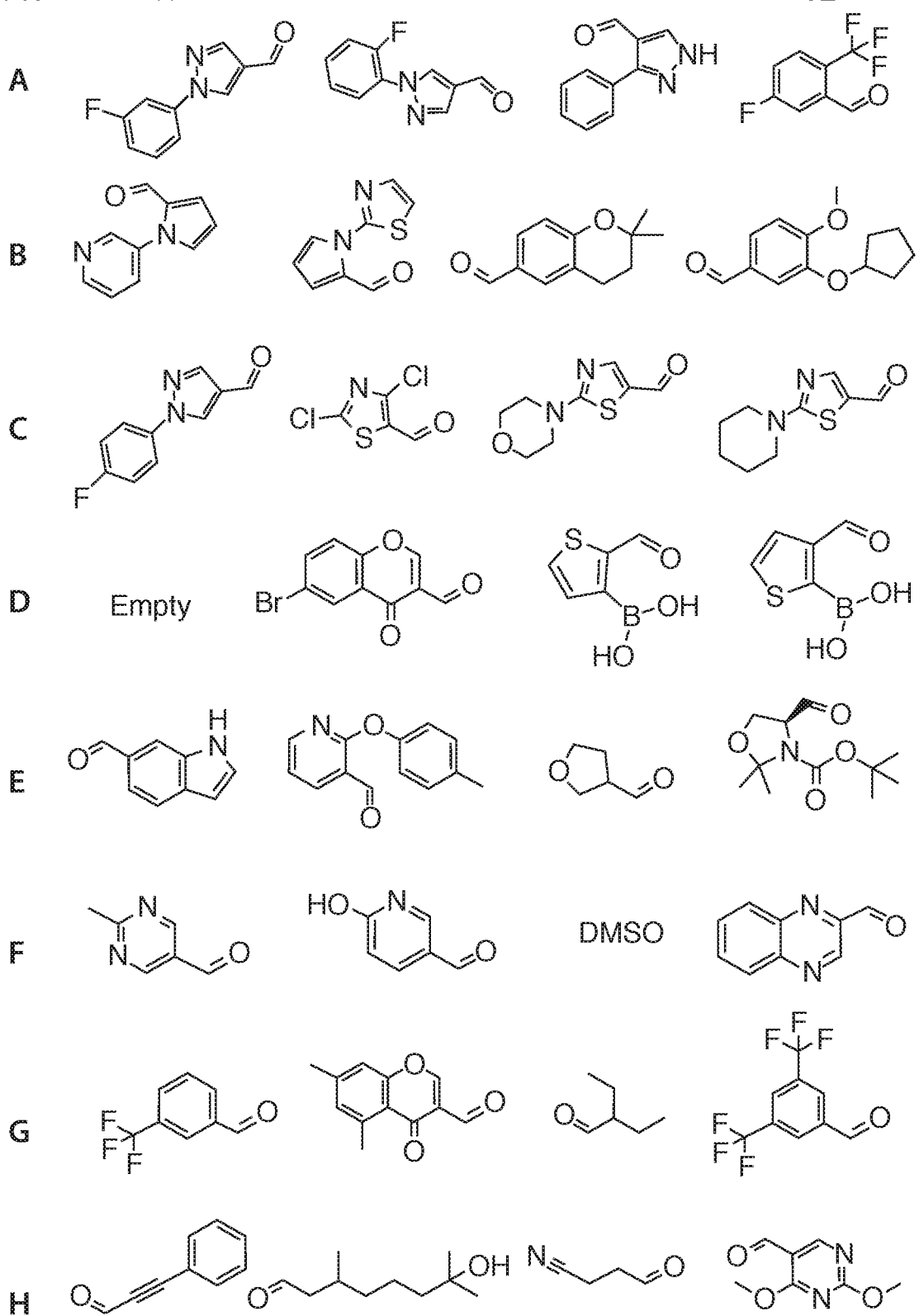
Figure 21:
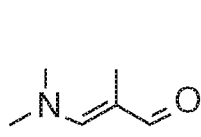
Figure 21:
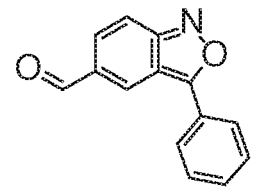
Figure 21:
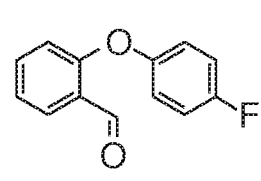
Figure 21:
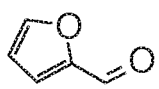
Figure 21:
Figure 21:
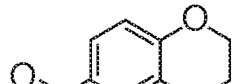
Figure 21:
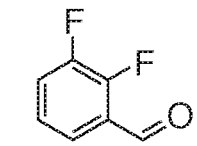
Figure 21:
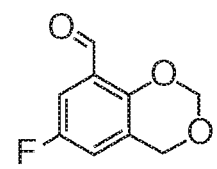
Figure 21:
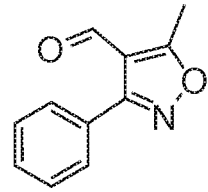
Figure 21:
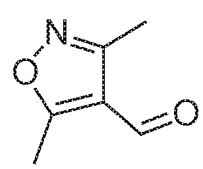
Figure 21:
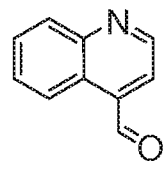
Figure 21:
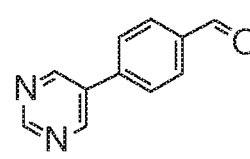
Figure 21:
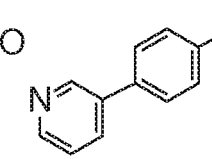
Figure 21:
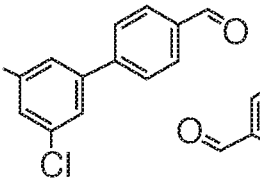
Figure 21:
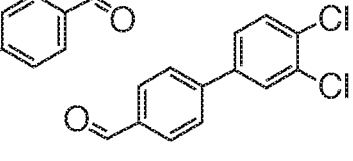
Figure 21:
Figure 21:
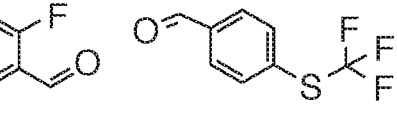
Figure 21:
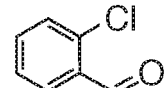
Figure 21:
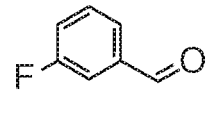
Figure 21:
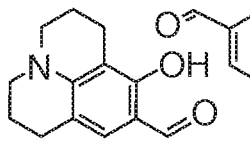
Figure 21:
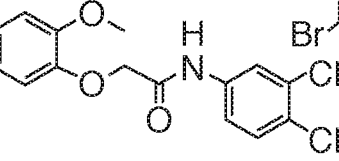
Figure 21:
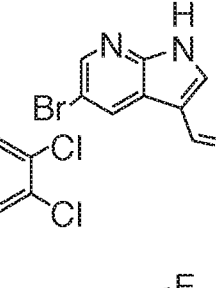
Figure 21:
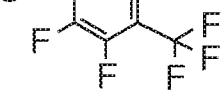
Figure 21:
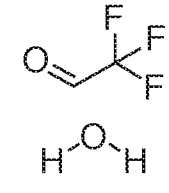
Figure 21:
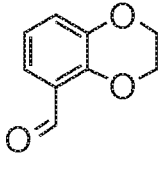
Figure 21:
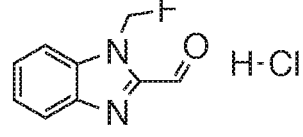
Figure 21:
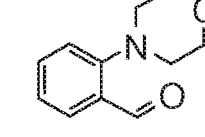
Figure 21:
Figure 21:
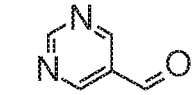
Figure 21:
Figure 21:
Figure 21:
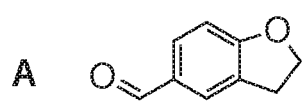
Figure 21:
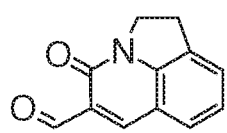
Figure 21:
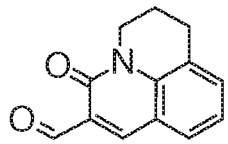
Figure 21:
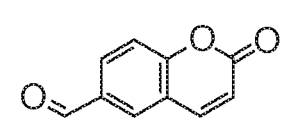
Figure 21:
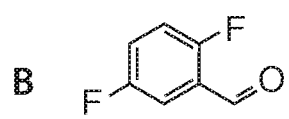
Figure 21:
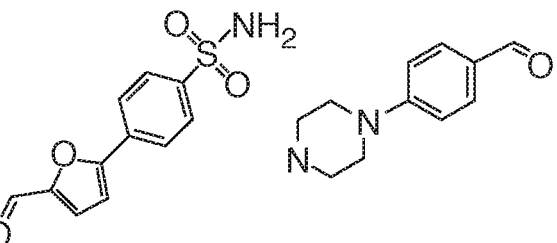
Figure 21:
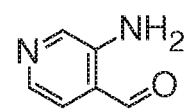
Figure 21:
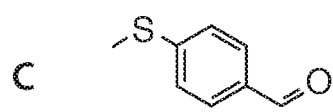
Figure 21:
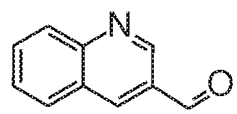
Figure 21:
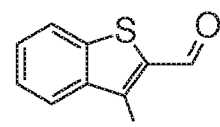
Figure 21:
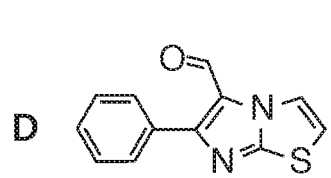
Figure 21:
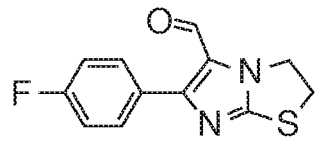
Figure 21:
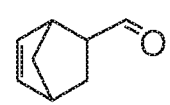
Figure 21:
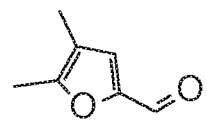
Figure 21:
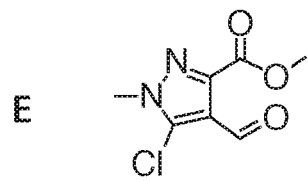
Figure 21:
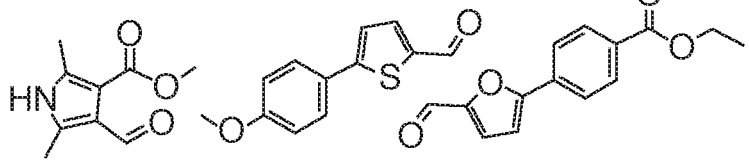
Figure 21:
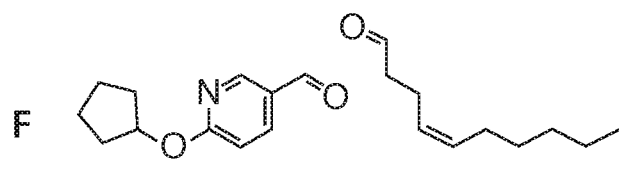
Figure 21:
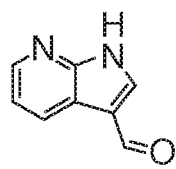
Figure 21:
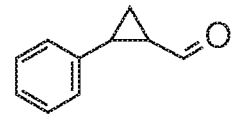
Figure 21:
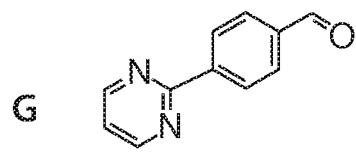
Figure 21:
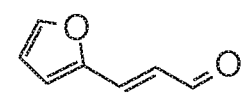
Figure 21:
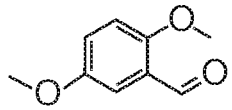
Figure 21:
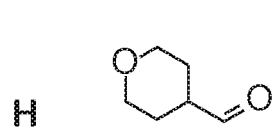
Figure 21:
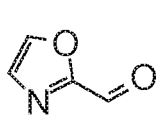
Figure 21:
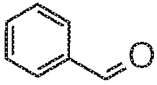
Figure 21:
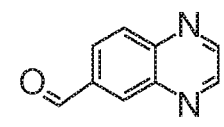
Figure 21:
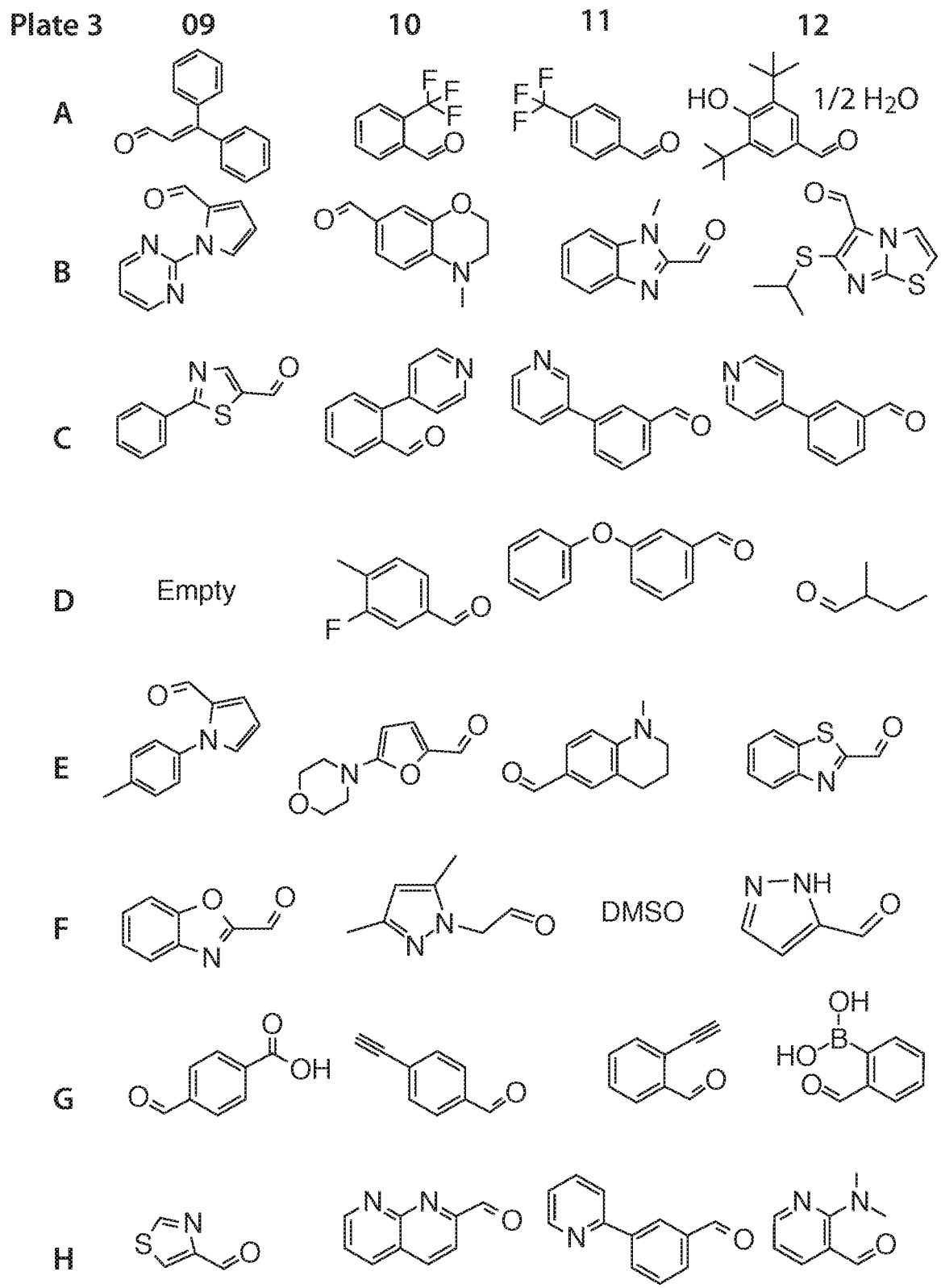
Figure 21:
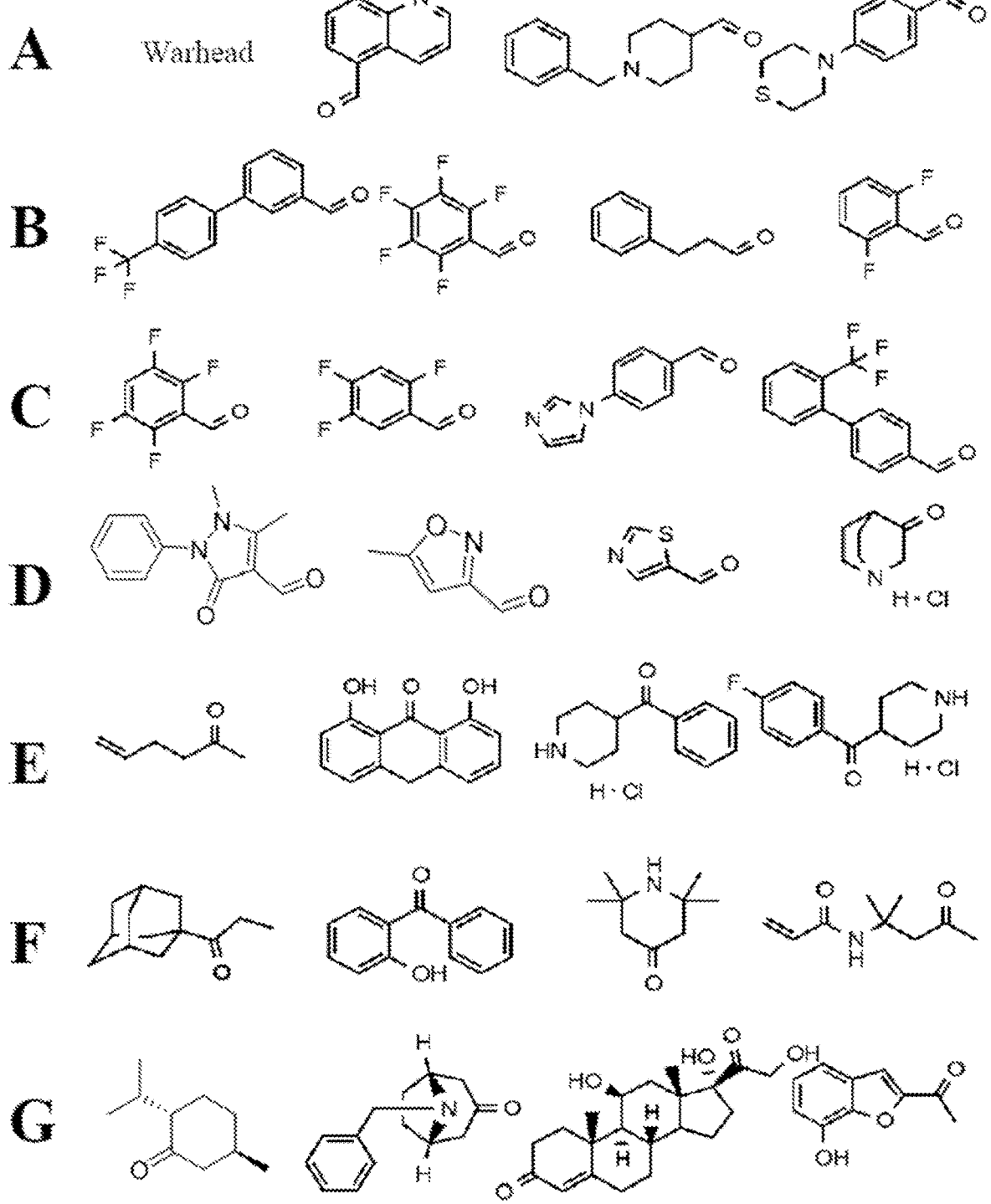
Figure 21:
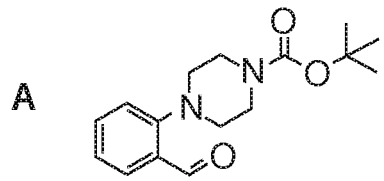
Figure 21:
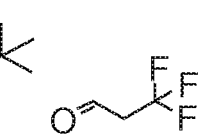
Figure 21:
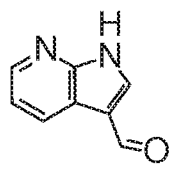
Figure 21:
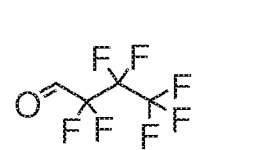
Figure 21:
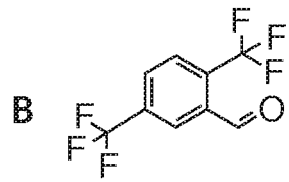
Figure 21:
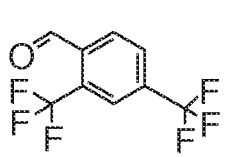
Figure 21:
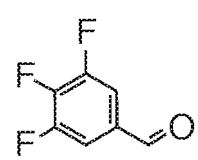
Figure 21:
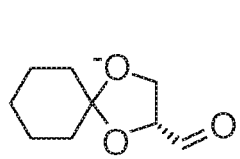
Figure 21:
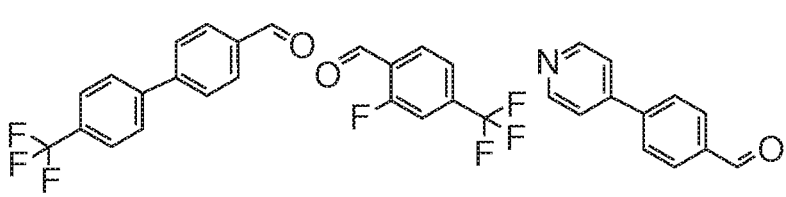
Figure 21:
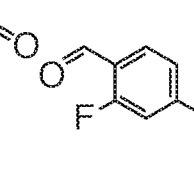
Figure 21:
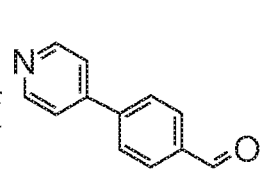
Figure 21:
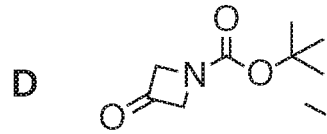
Figure 21:
Figure 21:
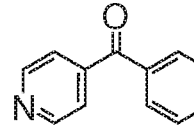
Figure 21:
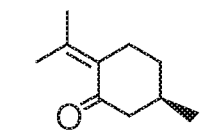
Figure 21:
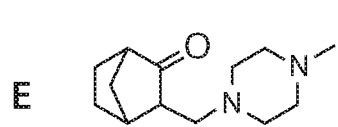
Figure 21:
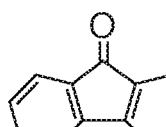
Figure 21:
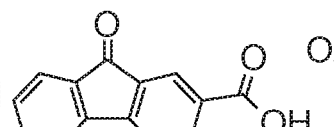
Figure 21:
Figure 21:
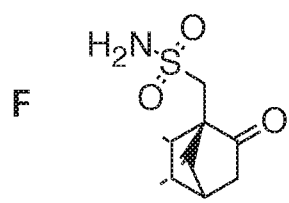
Figure 21:
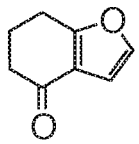
Figure 21:
Figure 21:
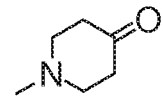
Figure 21:
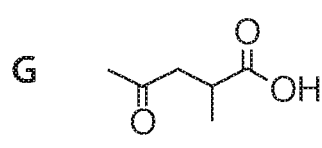
Figure 21:
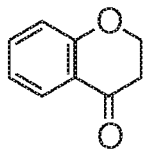
Figure 21:
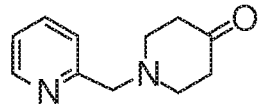
Figure 21:
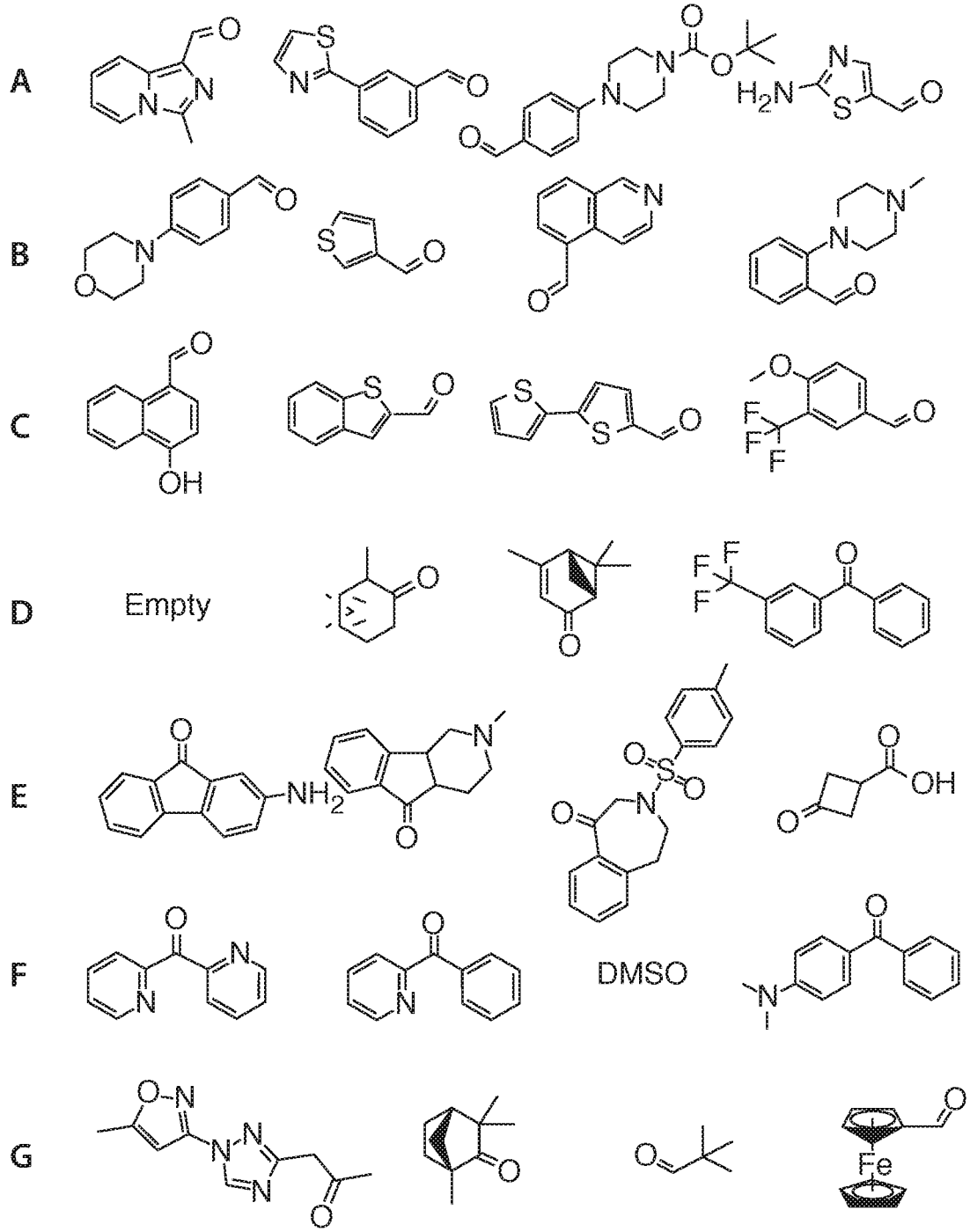
Figure 23A:
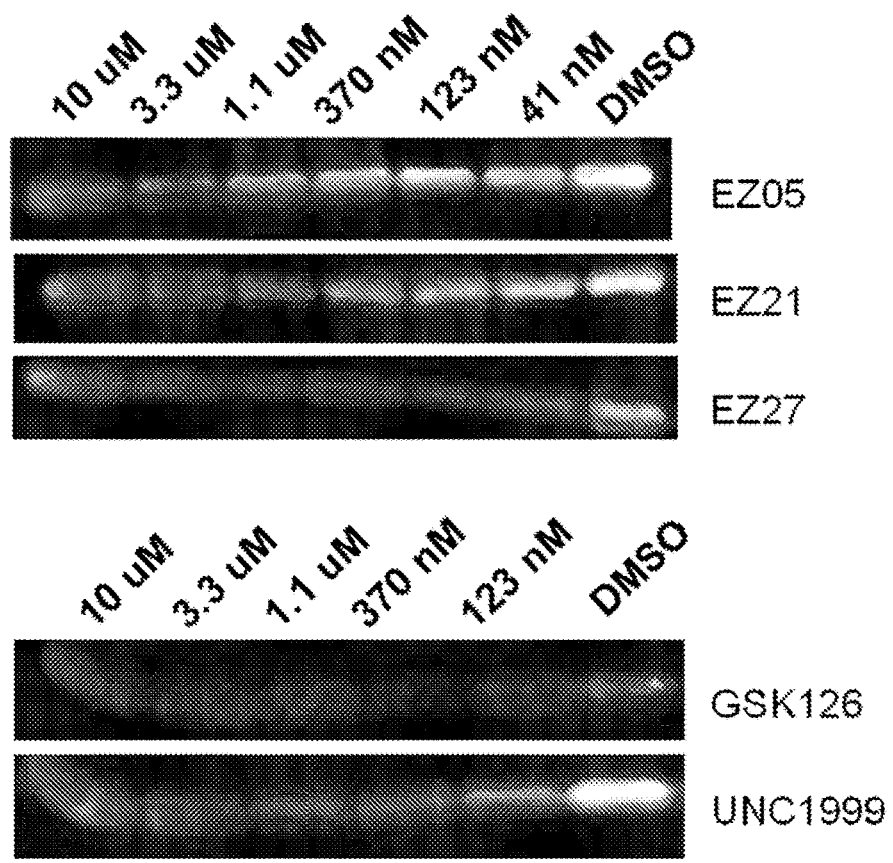
FIGS. 23A and 23B show exemplary results of two-color H3K27me3 Western blot. 293T cells were treated with any one of the test compounds at different concentrations for 3 days.
Figure 23B:
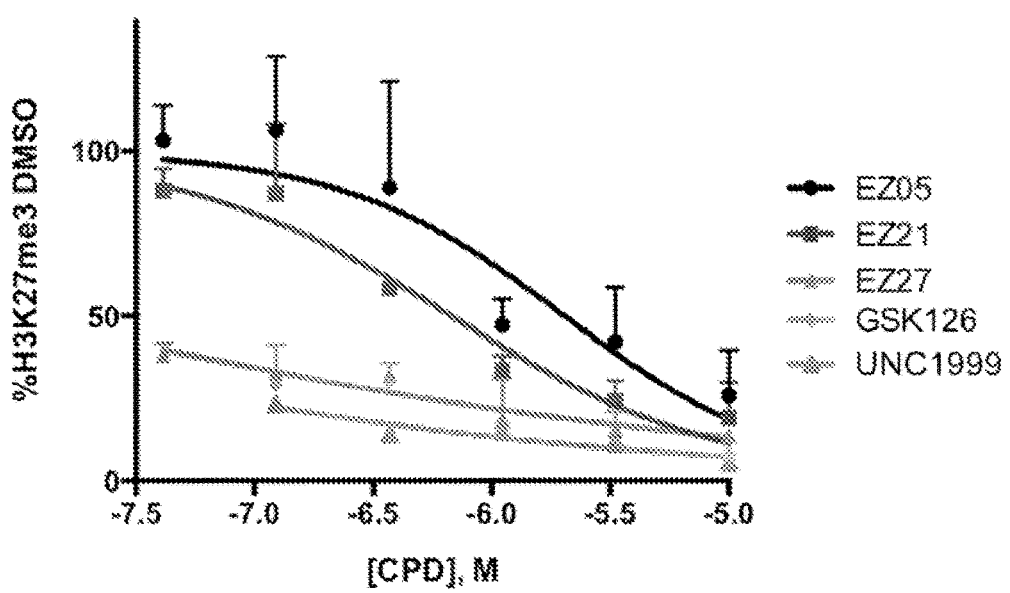
Figure 25A:
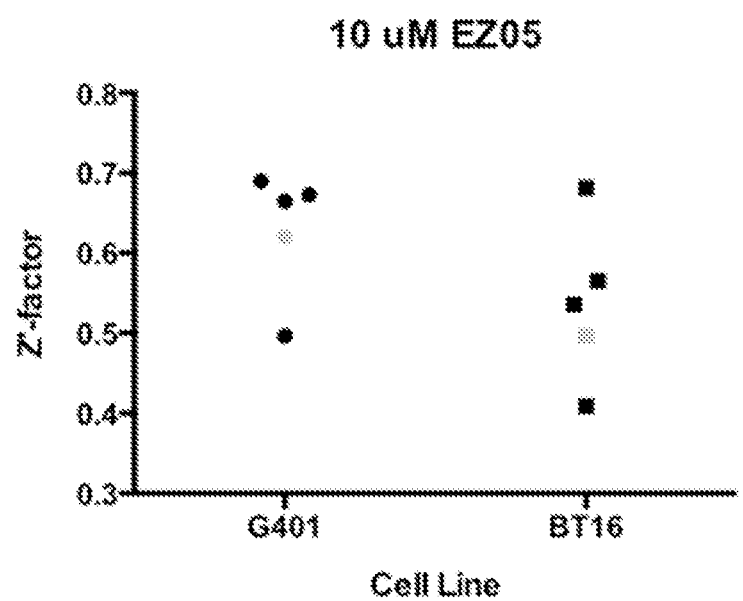
FIGS. 25A to 25C show exemplary results of a Rhabdoid viability assay. The assay was performed in a 384-well format. There were 625 G401 cells/well, and 313 BT16 cells/well. The cells were treated with any one of the test compounds for 4 days.
Figure 25B:
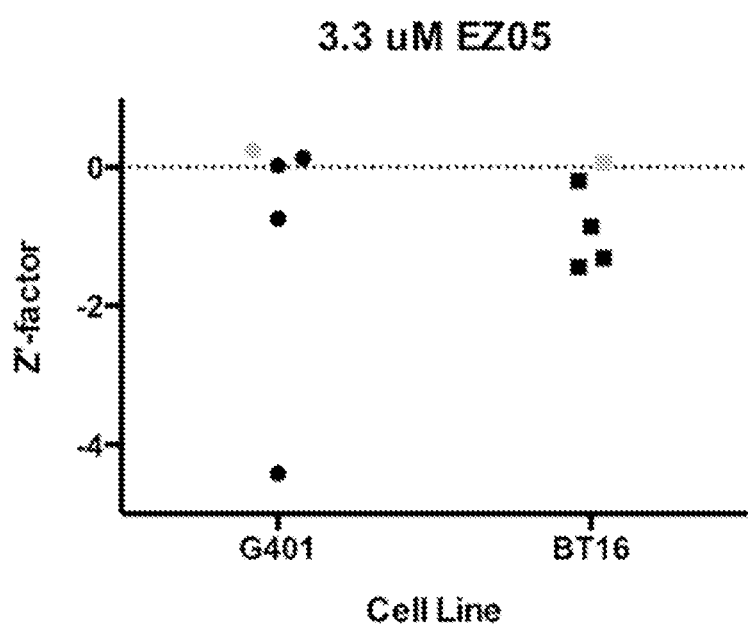
Figure 25C:
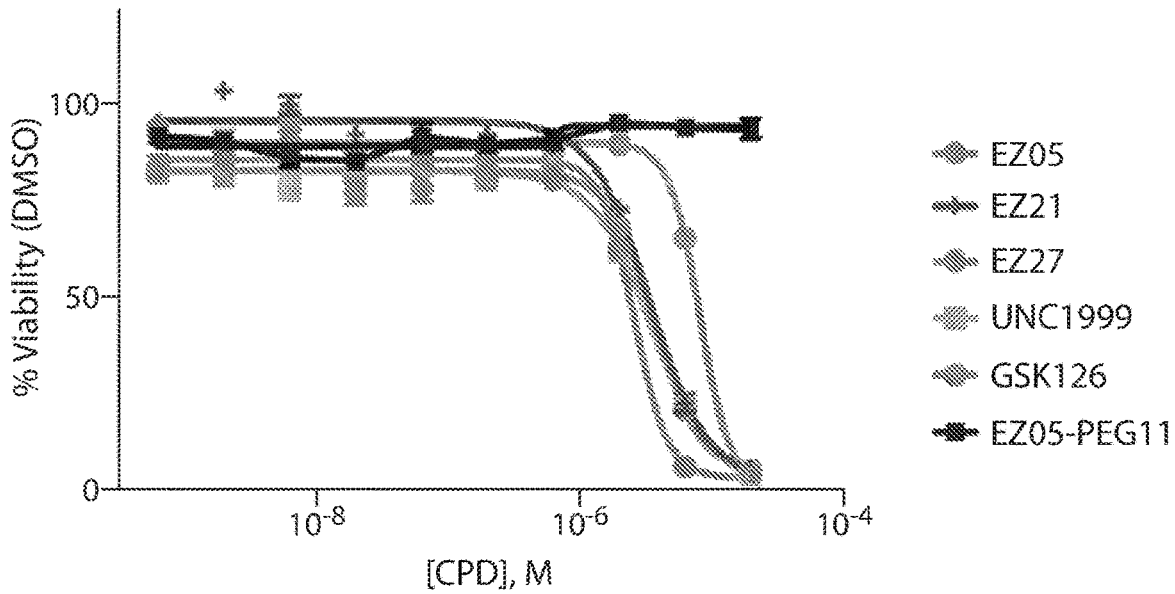
Figure 26A:
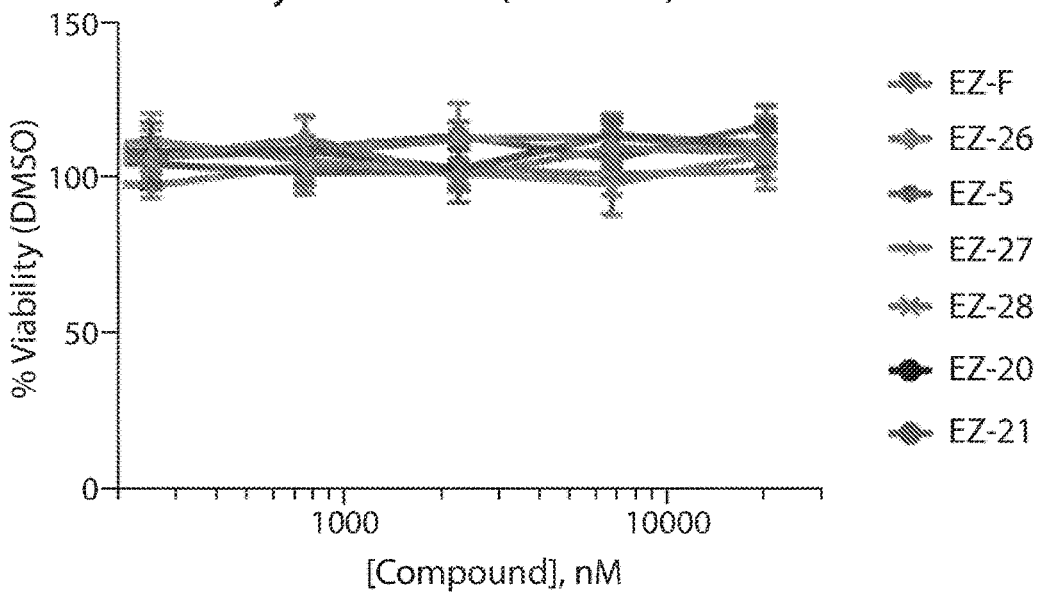
FIGS. 26A and 26B show exemplary results of the viability of DLBCL cells. OCI-LY-18 (WT EZH2) cells (FIG. 26A) and Karpas 422 (mutant EZH2) cells (FIG. 26B) were treated with any one of the test compounds at different concentrations for 6 days.
Figure 26B:
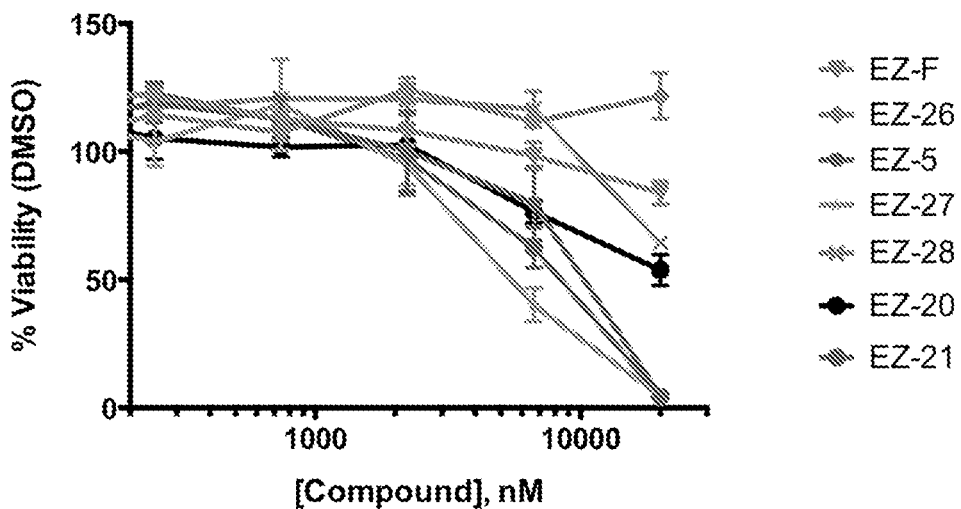
Figure 27A:
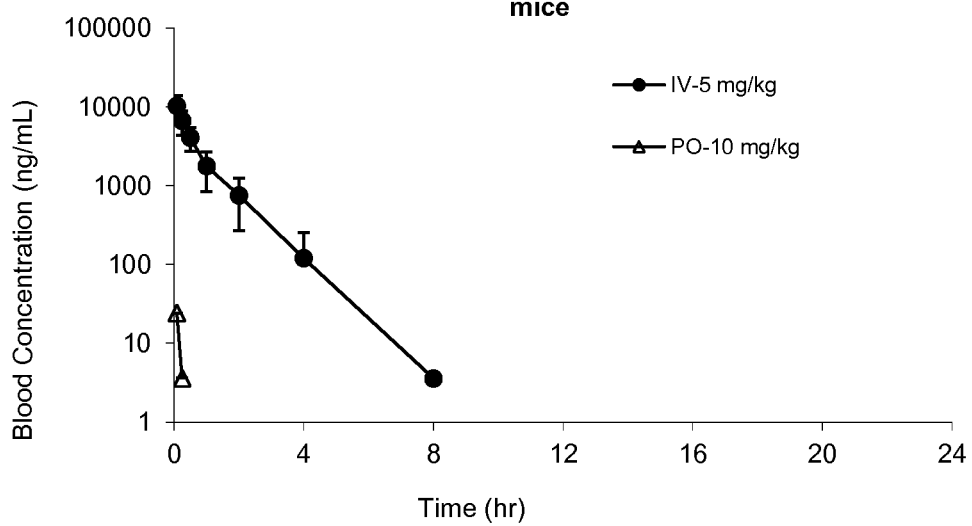
FIG. 27A shows exemplary mean whole blood concentration-time profiles of EZ26 after an IV dose at 5 mg/kg or a PO dose 10 mg/kg (N=3) in male CD1 mice.
Figure 27B:
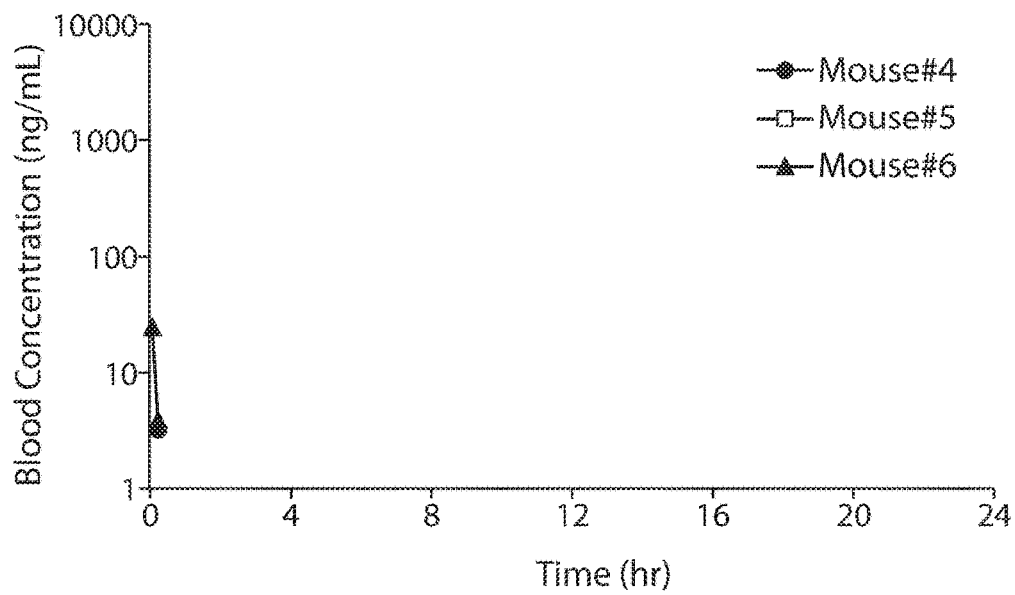
FIG. 27B shows exemplary Individual whole blood concentration-time profiles of EZ26 after a PO dose at 10 mg/kg (N=3) in male CD1 mice.
Figure 27C:
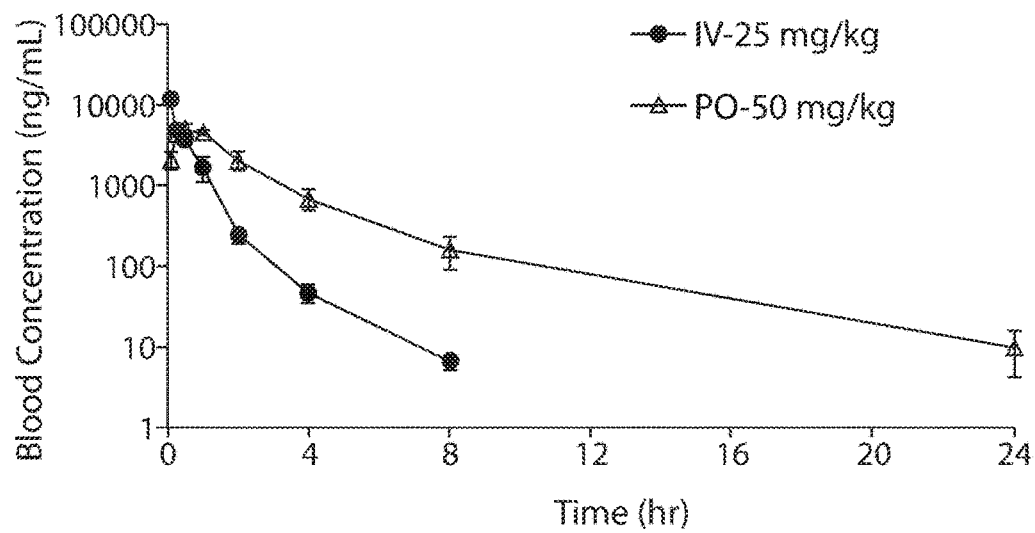
FIG. 27C shows exemplary mean whole blood concentration-time profiles of EZ27 after an IV dose at 25 mg/kg or an IP dose at 50 mg/kg (N=3) in male CD1 mice.
Figure 27D:
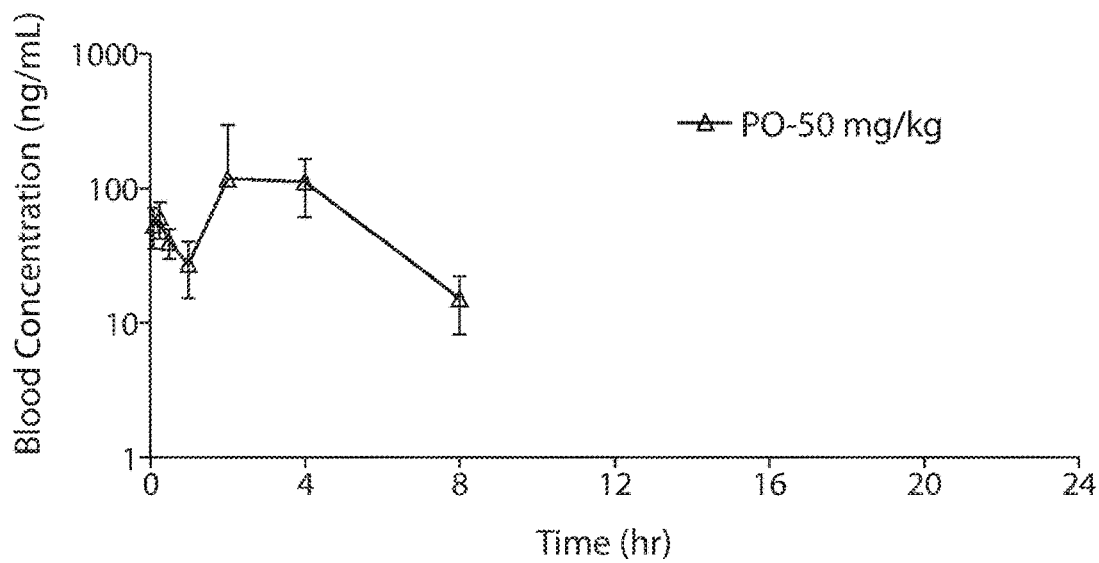
FIG. 27D shows exemplary mean whole blood concentration-time profiles of EZ27 after a PO dose at 50 mg/kg (N=3) in male CD1 mice.
Figure 27E:
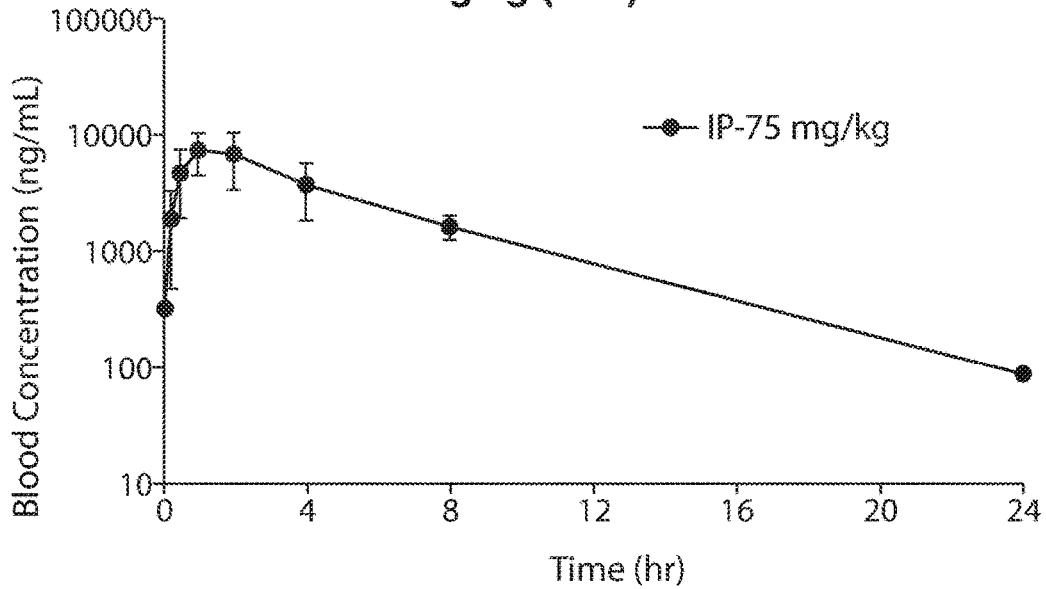
FIG. 27E shows exemplary mean whole blood concentration-time profiles of JQE5 (EZ-005) after an IP dose at 75 mg/kg (N=3) in male CD1 mice.
Figure 28A:
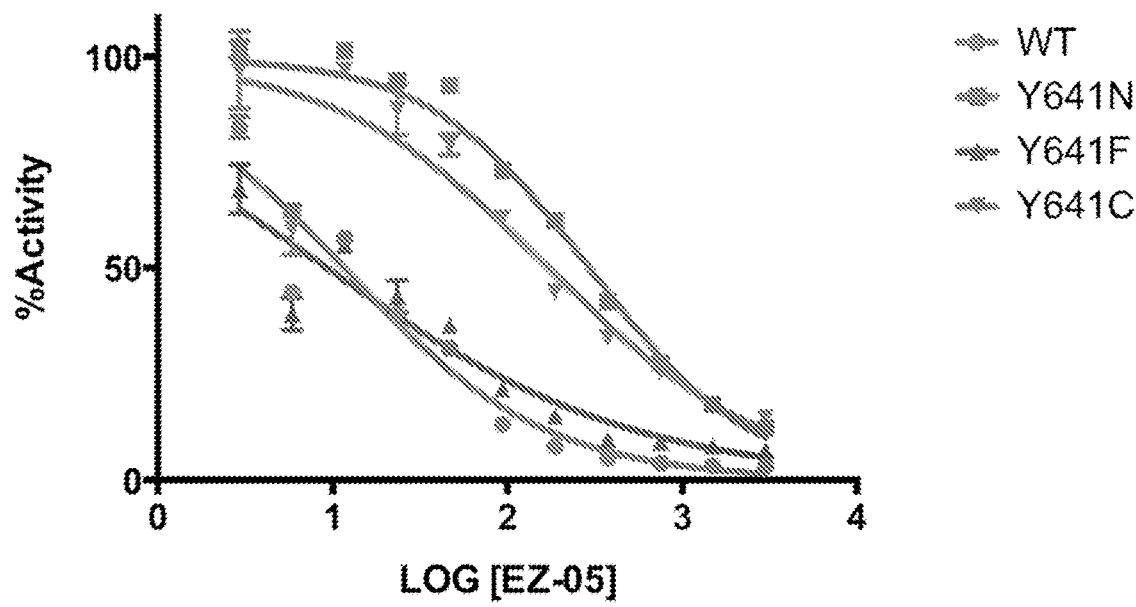
FIG. 28A shows percent activity of wild type(WT) EZH2, or EZH2 with a Y641C mutation, Y641N mutation, or Y641S mutation with varying concentrations of EZ05.
Figure 28B:
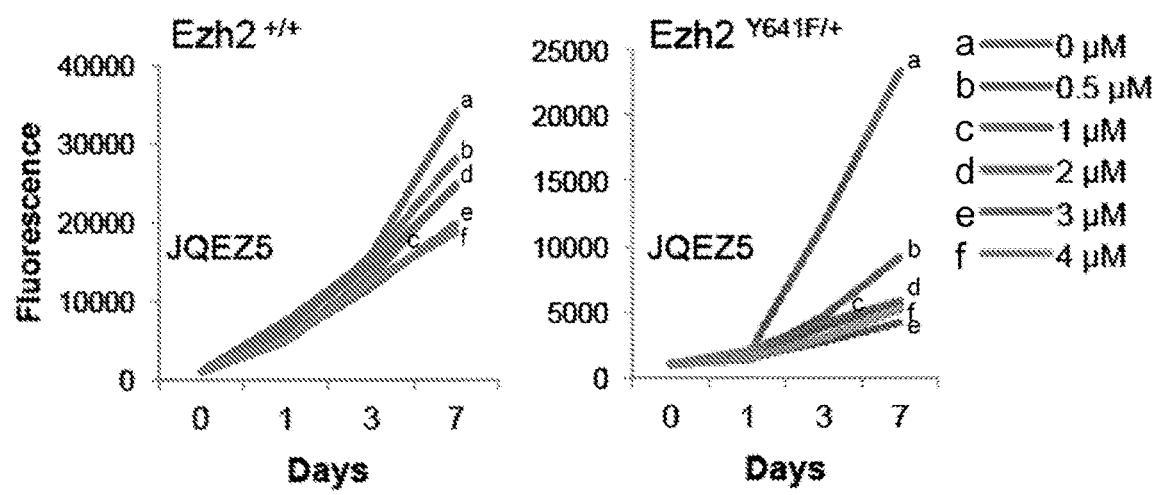
FIG. 28B shows fluorescence intensity in EZH2+/+ (WT) or Y641F/+ mutant with varying concentrations of EZ05.
Figures 29, 30A:
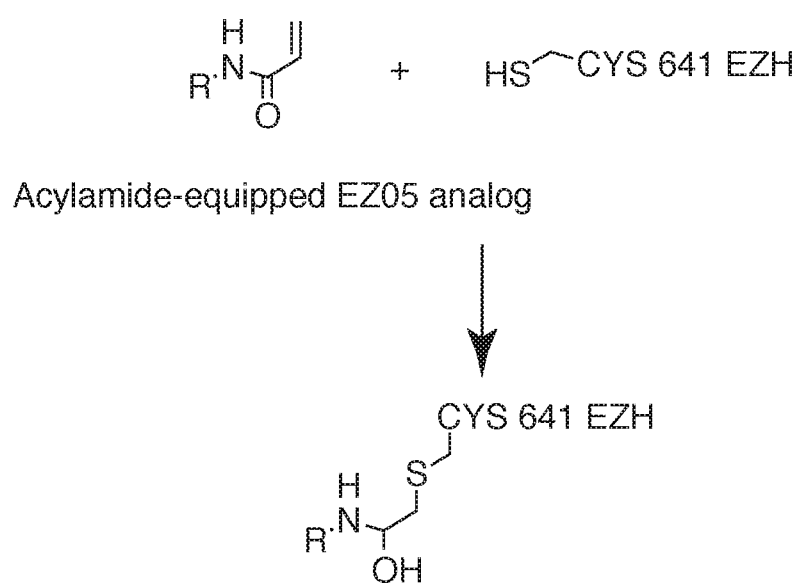
FIG. 29 shows exemplary $IC_{50}$ values (in nM) of select compounds against wild type (WT) EZH2, or EZH2 with a Y641C mutation, Y641N mutation, or Y641S mutation.
FIG. 30A shows that a compound described herein that includes a warhead, such as the depicted acylamide-equiped (covalently attached to an acylamide moiety) EZ05 analog, and Cys641 of an EZH forms a colvant bond.
Figures 30B, 30C:
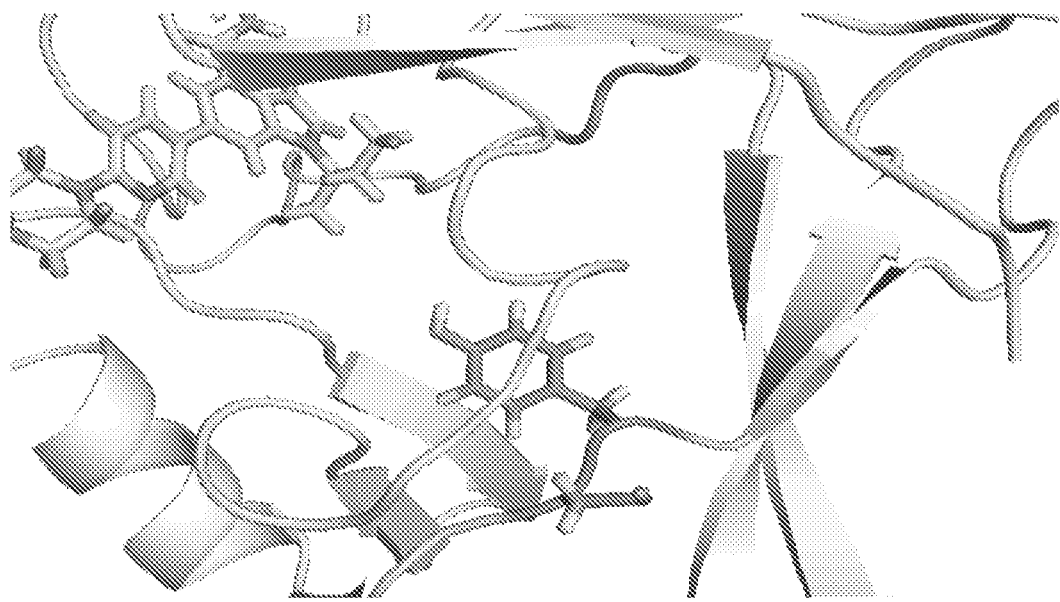
FIG. 30B shows an exemplary docking result of an enery-minimized structure of a complex of EZH and the depicted acylamide-equiped EZ05 analog.
FIG. 30C shows exemplary $IC_{50}$ values (in nM) of select compounds against wild type (WT) EZH2, or EZH2 with a Y641C mutation, Y641N mutation, or Y641S mutation

is an aldehyde or ketone shown in FIG. 21, Plate 1; "X" denotes the row number, and "#" denotes the column number.

FIG. 37 reports the calculated IC50 data for selected compounds screened in the EZH2 ligand-displacement fluorescence polarization assays. Compound "X#", wherein X is one letter, and # is one integer between 1 and 12, inclusive, denotes a compound as described in FIG. 36.

FIG. 38 depicts the structures of EZ-TAMRA and EZ-TOM.

Figure 39:
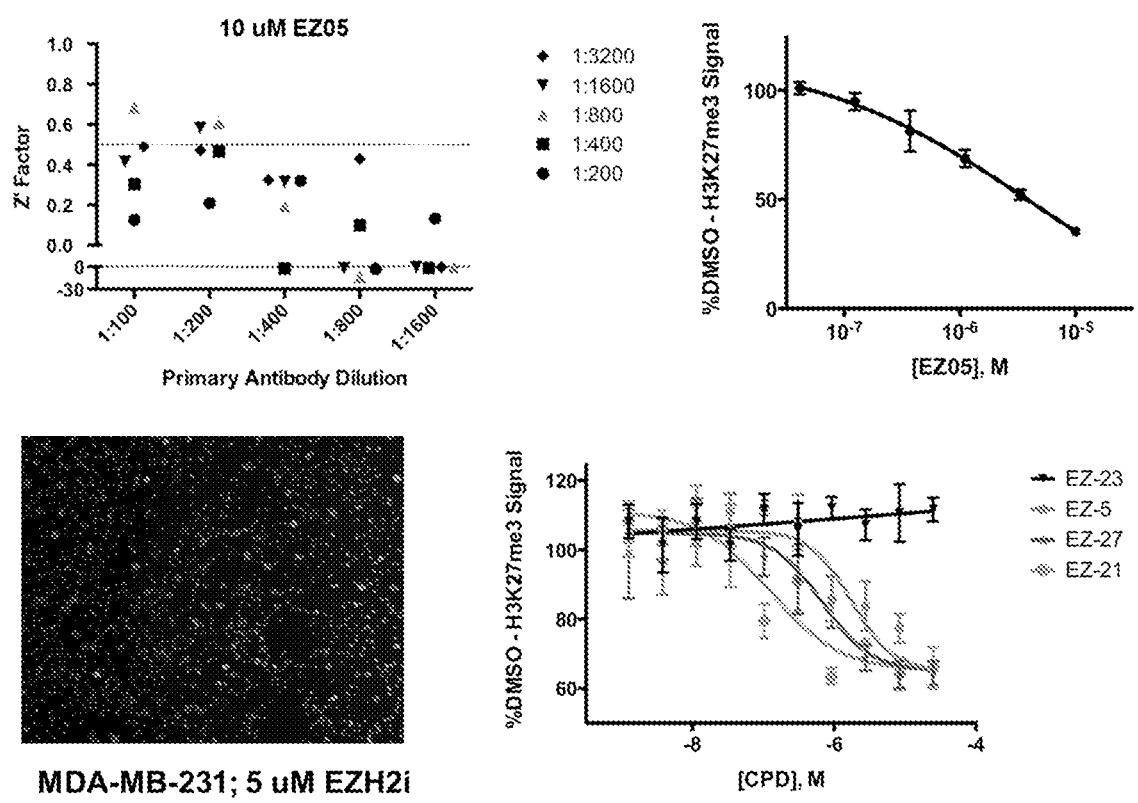

FIG. 39 depicts an intracellular EZH2 binding assay.

Figure 40:
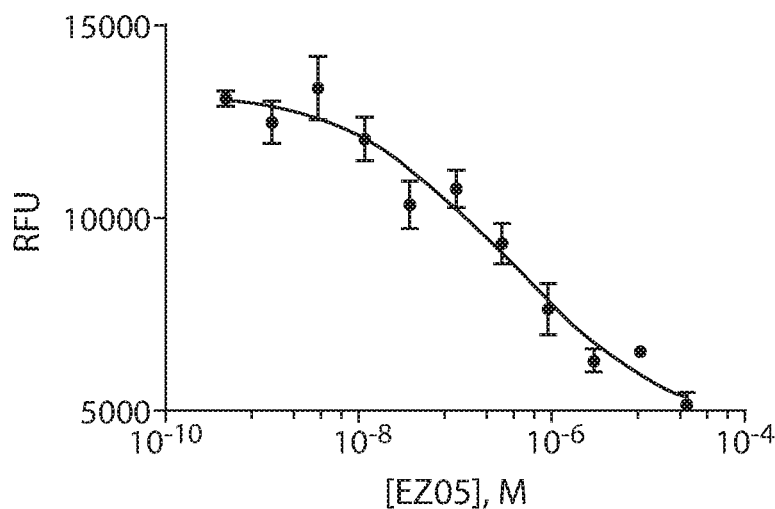
Figure 40:
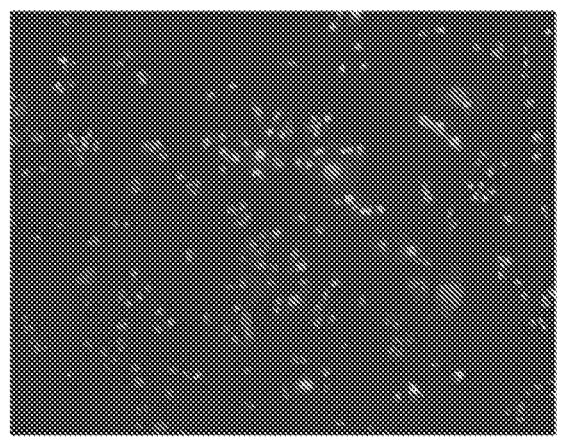
Figure 40:
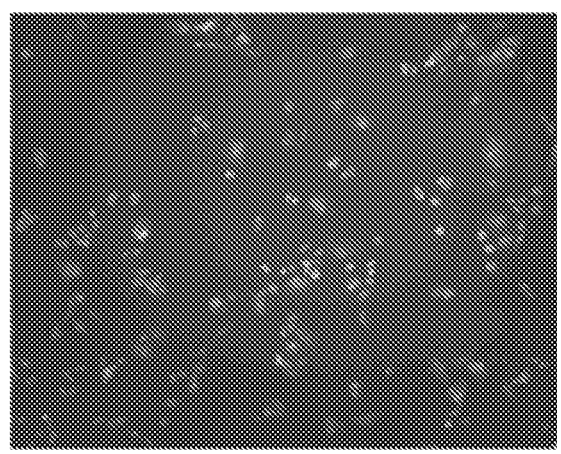

FIG. 40 depicts an intracellular competitive EZH2 binding assay.

DETAILED DESCRIPTION OF CERTAIN EMBODIMENTS OF THE INVENTION

Described herein are compounds of Formulae (I) and (II), and pharmaceutically acceptable salts, solvates, hydrates, polymorphs, co-crystals, tautomers, stereoisomers, isotopically labeled derivatives, and prodrugs thereof. The compounds described herein bind histone methyltransferases (HMTs, such as EZH1 and EZH2) and are useful in modulating (e.g., inhibiting) the activity (e.g., aberrant activity) of HMTs in a subject, biological sample, tissue, or cell. The compounds may be useful in treating or preventing a disease (e.g., proliferative disease, inflammatory disease, autoimmune disease, genetic disease, hematological disease, neurological disease, painful condition, psychiatric disorder, or metabolic disorder) in a subject in need thereof, and/or in treating or preventing a disease associated with aberrant or increased activity of an HMT in a subject. Also provided are pharmaceutical compositions, kits, and uses including a compound described herein. Further provided in the present disclosure are methods of identifying EZH1 and/or EZH2 inhibitors.

Compounds

One aspect of the present disclosure relates to the compounds described herein. The compounds described herein are inhibitors of HMTs (e.g., EZH1, EZH2, DOT1). In certain embodiments, a compound described herein is a compound of Formula (I), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I), or a pharmaceutically acceptable salt thereof. In certain embodiments, a compound described herein is a compound of Formula (II), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (II), or a pharmaceutically acceptable salt thereof.

In one aspect, the present disclosure provides compounds of Formula (I):

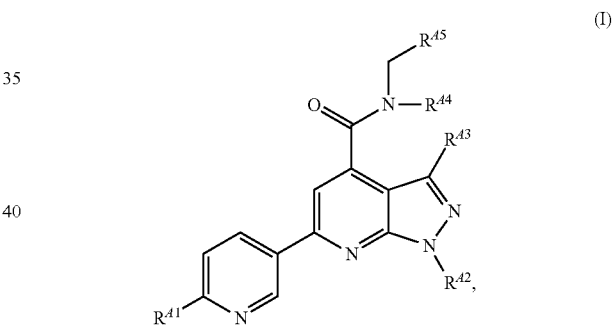

and pharmaceutically acceptable salts, solvates, hydrates, polymorphs, co-crystals, tautomers, stereoisomers, isotopically labeled derivatives, and prodrugs thereof, wherein:

$R^{A1}$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O) R$^a$, —NR$^a$C(=O)OR$^a$, —NR$^a$C(=O)N(R$^a$)$_2$, —OC(=O) R$^a$, —OC(=O)OR$^a$, —OC(=O)N(R$^a$)$_2$, a tag, or

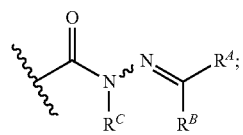

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;

$R^A$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

or $R^A$ and $R^B$ are joined to form a substituted or unsubstituted, carbocyclic ring, or a substituted or unsubstituted, heterocyclic ring;

$R^C$ is hydrogen, substituted or unsubstituted $C_{1-6}$ alkyl, or a nitrogen protecting group;

$R^{A2}$ is hydrogen, substituted or unsubstituted acyl, substituted or unsubstituted alkyl, substituted or unsubstituted carbocyclyl, substituted or unsubstituted heterocyclyl, a nitrogen protecting group, a tag, or a warhead;

$R^{A3}$ is hydrogen, halogen, substituted or unsubstituted $C_{1-6}$ alkyl, —$OR^a$, —$N(R^a)_2$, or a warhead;

$R^{A4}$ is hydrogen, substituted or unsubstituted $C_{1-6}$ alkyl, or a nitrogen protecting group; and $R^{A5}$ is of the formula:

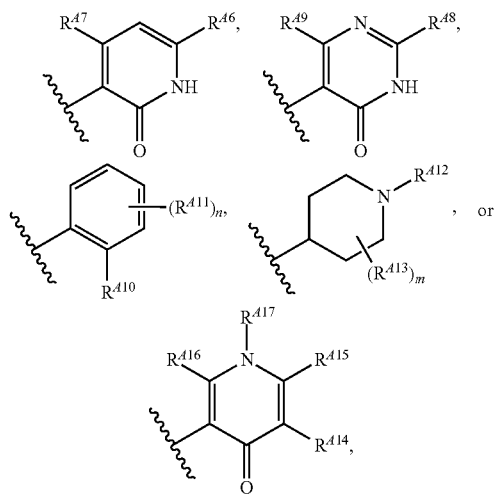

wherein:

$R^{A6}$ is hydrogen, halogen, substituted or unsubstituted $C_{1-6}$ alkyl, —$OR^a$, or —$N(R^a)_2$;

$R^{A7}$ is hydrogen, halogen, substituted or unsubstituted $C_{2-6}$ alkyl, substituted or unsubstituted, 3- to 7-membed, monocyclic carbocyclyl comprising 0, 1, or 2 double bonds in the carbocyclic ring system, —$OR^a$, or —$N(R^a)_2$;

$R^{A8}$ is hydrogen, halogen, substituted or unsubstituted $C_{1-6}$ alkyl, —$OR^a$, or —$N(R^a)_2$;

$R^{A9}$ is hydrogen, halogen, substituted or unsubstituted $C_{1-6}$ alkyl, substituted or unsubstituted, 3- to 7-membed, monocyclic carbocyclyl comprising 0, 1, or 2 double bonds in the carbocyclic ring system, —$OR^a$, or —$N(R^a)_2$;

$R^{A10}$ is —$OR^a$—$N(R^a)_2$, or a warhead;

each instance of $R^{A11}$ is independently halogen, substituted or unsubstituted $C_{1-6}$ alkyl, substituted or unsubstituted, 3- to 7-membed, monocyclic carbocyclyl comprising 0, 1, or 2 double bonds in the carbocyclic ring system, —$OR^a$, or —$N(R^a)_2$;

n is 0, 1, 2, 3, or 4;

$R^{A12}$ is hydrogen, substituted or unsubstituted $C_{1-6}$ alkyl, a nitrogen protecting group, or a warhead;

each instance of $R^{A13}$ is independently halogen, substituted or unsubstituted $C_{1-6}$ alkyl, substituted or unsubstituted, 3- to 7-membed, monocyclic carbocyclyl comprising 0, 1, or 2 double bonds in the carbocyclic ring system, —$OR^a$, or —$N(R^a)_2$;

m is 0, 1, 2, 3, 4, 5, 6, 7, 8, or 9;

$R^{A14}$ is hydrogen, halogen, substituted or unsubstituted $C_{1-6}$ alkyl, —$OR^a$, or —$N(R^a)_2$;

$R^{A15}$ is hydrogen, halogen, substituted or unsubstituted $C_{1-6}$ alkyl, —$OR^a$, or —$N(R^a)_2$;

$R^{A16}$ is hydrogen, halogen, substituted or unsubstituted $C_{2-6}$ alkyl, substituted or unsubstituted, 3- to 7-membed, monocyclic carbocyclyl comprising 0, 1, or 2 double bonds in the carbocyclic ring system, —$OR^a$, or —$N(R^a)_2$; and $R^{A17}$ is hydrogen, substituted or unsubstituted acyl, substituted or unsubstituted $C_{1-6}$ alkyl, a nitrogen protecting group, or a warhead.

In some embodiments, the EZH2 inhibitor is a compound of Formula (I):

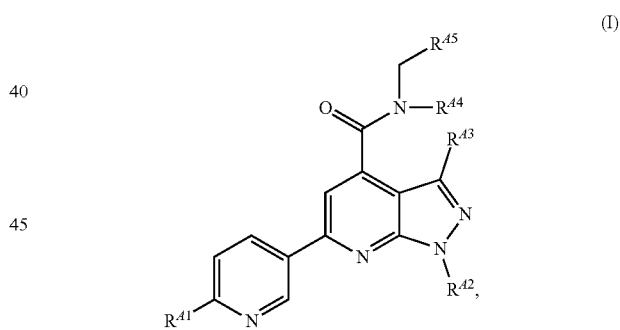

(I)

or a pharmaceutically acceptable salt, solvate, hydrate, polymorph, co-crystal, tautomer, stereoisomer, isotopic ally labeled derivative, or prodrug thereof, wherein:

$R^{A1}$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;

$R^{42}$ is hydrogen, substituted or unsubstituted acyl, substituted or unsubstituted alkyl, substituted or unsubstituted carbocyclyl, substituted or unsubstituted heterocyclyl, or a nitrogen protecting group;

$R^{43}$ is hydrogen, halogen, substituted or unsubstituted $C_{1-6}$ alkyl, —$OR^a$, or —$N(R^a)_2$;

$R^{44}$ is hydrogen, substituted or unsubstituted $C_{1-6}$ alkyl, or a nitrogen protecting group; and $R^{45}$ is of the formula:

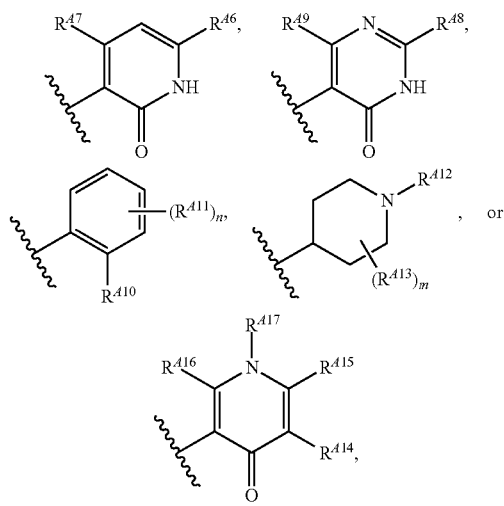

wherein:

$R^{46}$ is hydrogen, halogen, substituted or unsubstituted $C_{1-6}$ alkyl, —$OR^a$, or —$N(R^a)_2$;

$R^{47}$ is hydrogen, halogen, substituted or unsubstituted $C_{2-6}$ alkyl, substituted or unsubstituted, 3- to 7-membed, monocyclic carbocyclyl comprising 0, 1, or 2 double bonds in the carbocyclic ring system, —$OR^a$, or —$N(R^a)_2$;

$R^{48}$ is hydrogen, halogen, substituted or unsubstituted $C_{1-6}$ alkyl, —$OR^a$, or —$N(R^a)_2$;

$R^{49}$ is hydrogen, halogen, substituted or unsubstituted $C_{1-6}$ alkyl, substituted or unsubstituted, 3- to 7-membed, monocyclic carbocyclyl comprising 0, 1, or 2 double bonds in the carbocyclic ring system, —$OR^a$, or —$N(R^a)_2$;

$R^{410}$ is —$OR^a$ or —$N(R^a)_2$;

each instance of $R^{411}$ is independently halogen, substituted or unsubstituted $C_{1-6}$ alkyl, substituted or unsubstituted, 3- to 7-membed, monocyclic carbocyclyl comprising 0, 1, or 2 double bonds in the carbocyclic ring system, —$OR^a$, or —$N(R^a)_2$;

n is 0, 1, 2, 3, or 4;

$R^{412}$ is hydrogen, substituted or unsubstituted $C_{1-6}$ alkyl, or a nitrogen protecting group;

each instance of $R^{413}$ is independently halogen, substituted or unsubstituted $C_{1-6}$ alkyl, substituted or unsubstituted, 3- to 7-membed, monocyclic carbocyclyl comprising 0, 1, or 2 double bonds in the carbocyclic ring system, —$OR^a$, or —$N(R^a)_2$;

m is 0, 1, 2, 3, 4, 5, 6, 7, 8, or 9;

$R^{414}$ is hydrogen, halogen, substituted or unsubstituted $C_{1-6}$ alkyl, —$OR^a$, or —$N(R^a)_2$;

$R^{415}$ is hydrogen, halogen, substituted or unsubstituted $C_{1-6}$ alkyl, —$OR^a$, or —$N(R^a)_2$;

$R^{416}$ is hydrogen, halogen, substituted or unsubstituted $C_{2-6}$ alkyl, substituted or unsubstituted, 3- to 7-membed, monocyclic carbocyclyl comprising 0, 1, or 2 double bonds in the carbocyclic ring system, —$OR^a$, or —$N(R^a)_2$; and $R^{417}$ is hydrogen, substituted or unsubstituted acyl, substituted or unsubstituted $C_{1-6}$ alkyl, or a nitrogen protecting group.

Formula (I) includes substituent $R^{41}$ on the pyridinyl ring. In certain embodiments, $R^{41}$ is halogen (e.g., F, Cl, Br, or I). In certain embodiments, $R^{41}$ is substituted or unsubstituted alkyl (e.g., substituted or unsubstituted $C_{1-6}$ alkyl). In certain embodiments, $R^{41}$ is Me. In certain embodiments, $R^{41}$ is —$CF_3$, Bn, Et, perfluoroethyl, Pr, perfluoropropyl, Bu, or perfluorobutyl. In certain embodiments, $R^{41}$ is substituted or unsubstituted alkenyl (e.g., substituted or unsubstituted $C_{2-6}$ alkenyl). In certain embodiments, $R^{41}$ is substituted or unsubstituted alkynyl (e.g., substituted or unsubstituted $C_{1-6}$ alkynyl). In certain embodiments, $R^{41}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{41}$ is substituted or unsubstituted heterocyclyl (e.g., substituted or unsubstituted, 3- to 7-membed, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{41}$ is substituted or unsubstituted piperazinyl. In certain embodiments, $R^{41}$ is of the formula:

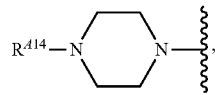

wherein R is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group. In certain embodiments, $R^{41}$ is of the formula:

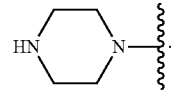

In certain embodiments, $R^{A1}$ is of the formula:

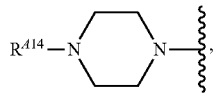

wherein $R^{A14}$ is substituted or unsubstituted $C_{1-6}$ alkyl. In certain embodiments, $R^{A1}$ is of the formula:

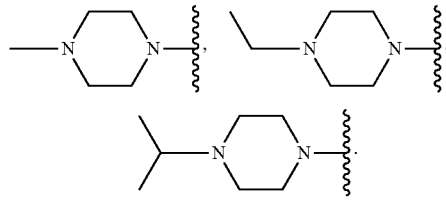

In certain embodiments, $R^{A1}$ is of the formula:

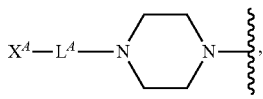

wherein $L^A$ is a bond or substituted or unsubstituted $C_{1-100}$ hydrocarbon chain, optionally wherein one or more chain atoms of the hydrocarbon chain are independently replaced with —O—, —S—, or —NR$^a$—; and $X^A$ is a small molecule, peptide, protein, or polynucleotide. In certain embodiments, $R^{A1}$ is of the formula:

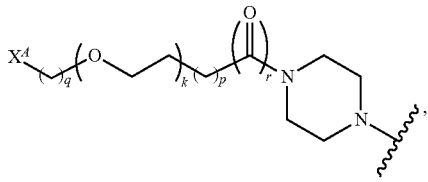

wherein r is 0 or 1, k is an integer between 0 and 11, inclusive, p is an integer between 0 and 10, inclusive, and q is an integer between 0 and 10, inclusive. In certain embodiments, k is an integer between 3 and 11, inclusive, p is 0, and q is 0, 1, 2, 3, 4, 5, or 6. In certain embodiments, $X^A$ is a small molecule. In certain embodiments, $X^A$ is a small molecule drug (e.g., 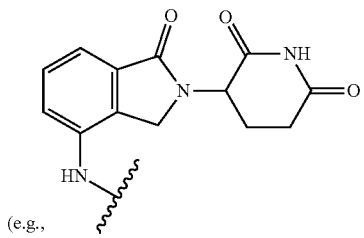, -continued

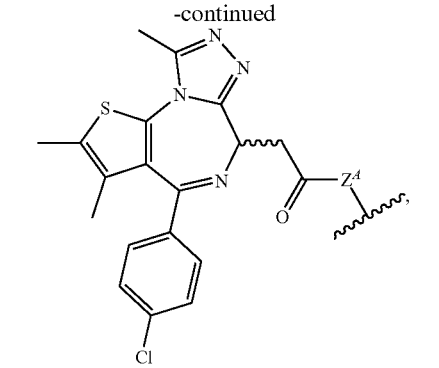

wherein $Z^A$ is —O— or —NH—, or an additional pharmaceutical agent described herein that is a small molecule). In certain embodiments, $X^A$ is a small molecule label (e.g., a biotin moiety (e.g., 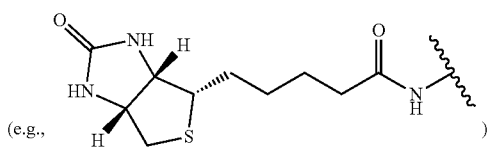 )

or a small molecule fluorophore). In certain embodiments, $R^{A1}$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, substituted or unsubstituted azepanyl, or substituted or unsubstituted diazepanyl. In certain embodiments, $R^{A1}$ is of the formula:

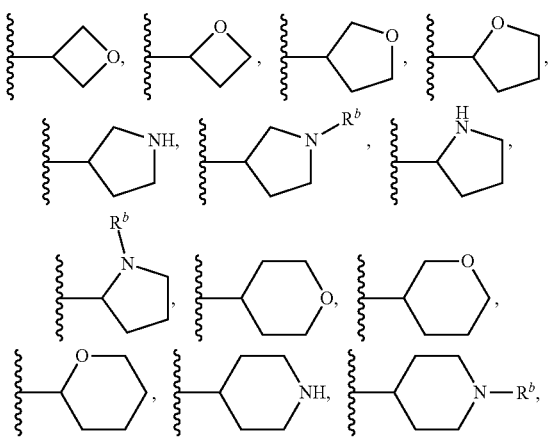

-continued

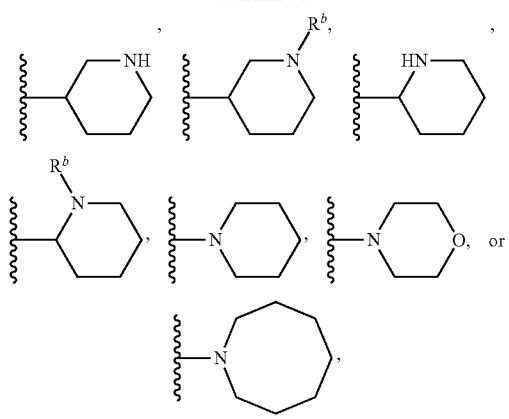

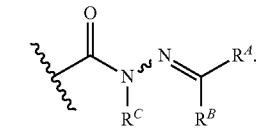

A compound described herein that includes one or more moieties

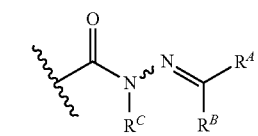

is a hydrazide.
The moiety

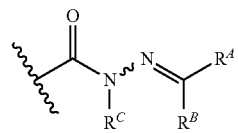

wherein each instance of $R^a$ is independently unsubstituted $C_{1-6}$ alkyl (e.g., Me)). In certain embodiments, $R^{A1}$ is substituted or unsubstituted aryl (e.g., substituted or unsubstituted, 6- to 10-membered aryl). In certain embodiments, $R^{A1}$ is substituted or unsubstituted phenyl. In certain embodiments, $R^{A1}$ is substituted or unsubstituted heteroaryl (e.g., substituted or unsubstituted, 5- to 6-membed, monocyclic heteroaryl, wherein one, two, three, or four atoms in the heteroaryl ring system are independently nitrogen, oxygen, or sulfur). In certain embodiments, $R^{A1}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, $R^{A1}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{A1}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^{A1}$ is —CN. In certain embodiments, $R^{A1}$ is —SCN or —$NO_2$. In certain embodiments, $R^{A1}$ is —$C(=NR^a)R^a$, —$C(=NR^a)OR^a$, or —$C(=NR^a)N(R^a)_2$. In certain embodiments, $R^{A1}$ is —$C(=O)R^a$ (e.g., —C(=O)(substituted or unsubstituted alkyl) or —C(=O)(substituted or unsubstituted phenyl)). In certain embodiments, $R^{A1}$ is —$C(=O)OR^a$ (e.g., —C(=O)OH, —C(=O)O(substituted or unsubstituted alkyl) (e.g., —C(=O)OMe), or —C(=O)O(substituted or unsubstituted phenyl)). In certain embodiments, $R^{A1}$ is —$C(=O)N(R^a)_2$ (e.g., —C(=O)$NH_2$, —C(=O)NH(substituted or unsubstituted alkyl), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, $R^{A1}$ is —$NR^aC(=O)R^a$ (e.g., —NHC(=O)Me). In certain embodiments, $R^{A1}$ is —$NR^aC(=O)OR^a$ or —$NR^aC(=O)N(R^a)_2$. In certain embodiments, $R^{A1}$ is —$OC(=O)R^a$, —$OC(=O)OR^a$, or —$OC(=O)N(R^a)_2$. In certain embodiments, $R^{A1}$ is substituted or unsubstituted alkyl, —$OR^a$, —$N(R^a)_2$, —$C(=O)OR^a$, or —$NR^aC(=O)R^a$. In certain embodiments, $R^{A1}$ is unsubstituted $C_{1-6}$ alkyl, —OMe, —$NH_2$, —N(Me)$_2$, —C(=O)OH, —C(=O)OMe, or —NHC(=O)Me. In certain embodiments, $R^{A1}$ is of any one of Formulae (I) and (II) includes substituents $R^A$, $R^B$, and $R^C$. In certain embodiments, $R^A$ is H. In certain embodiments, $R^A$ is substituted acyl. In certain embodiments, $R^A$ is unsubstituted acyl. In certain embodiments, $R^A$ is acetyl. In certain embodiments, $R^A$ is —$C(=O)R^C$ (e.g., —C(=O)(substituted or unsubstituted alkyl)). In certain embodiments, $R^A$ is —$C(=O)OR^C$ (e.g., —C(=O)O(substituted or unsubstituted alkyl) or —C(=O)OH). In certain embodiments, $R^A$ is —$C(=O)N(R^C)_2$, (e.g., —C(=O)$NH_2$, —C(=O)NH(substituted or unsubstituted alkyl), or —C(=O)N(substituted or unsubstituted alkyl)$_2$). In certain embodiments, $R^A$ is unsubstituted alkyl. In certain embodiments, $R^A$ is substituted alkyl. In certain embodiments, $R^A$ is unsubstituted $C_{1-6}$ alkyl. In certain embodiments, $R^A$ is substituted $C_{1-6}$ alkyl. In certain embodiments, $R^A$ is $C_{1-6}$ alkyl substituted with at least one halogen. In certain embodiments, $R^A$ is —$CH_3$. In certain embodiments, $R^A$ is substituted methyl. In certain embodiments, $R^A$ is —$CH_2F$, —$CHF_2$, or —$CF_3$. In certain embodiments, $R^A$ is Et, substituted ethyl, Pr, substituted propyl, Bu, or substituted butyl. In certain embodiments, $R^A$ is unsubstituted alkenyl. In certain embodiments, $R^A$ is substituted alkenyl. In certain embodiments, $R^A$ is unsubstituted $C_{1-6}$ alkenyl. In certain embodiments, $R^A$ is substituted $C_{1-6}$ alkenyl. In certain embodiments, $R^A$ is unsubstituted alkynyl. In certain embodiments, $R^A$ is substituted alkynyl. In certain embodiments, $R^A$ is unsubstituted $C_{1-6}$ alkynyl. In certain embodiments, $R^A$ is substituted $C_{1-6}$ alkynyl. In certain embodiments, $R^A$ is substituted carbocyclyl. In certain embodiments, $R^A$ is unsubstituted carbocyclyl. In certain embodiments, $R^A$ is saturated carbocyclyl. In certain embodiments, $R^A$ is unsaturated carbocyclyl. In certain embodiments, $R^A$ is 3- to 8-membered, monocyclic carbocyclyl, optionally including 1, 2, or 3 double bonds in the carbocyclic ring system. In certain embodiments, $R^A$ is 5- to 14-membered, bicyclic carbocyclyl, optionally including 1, 2, 3, or 4 double bonds in the carbocyclic ring system. In certain embodiments, $R^A$ is 5- to 20-membered, tricyclic carbocyclyl, optionally including 1, 2, 3, 4, or 5 double bonds in the carbocyclic ring system. In certain embodiments, $R^A$ is 5- to 26-membered, tetracyclic carbocyclyl, optionally including 1, 2, 3, 4, 5, or 6 double bonds in the carbocyclic ring system. In certain embodiments, $R^A$ is substituted heterocyclyl. In certain embodiments, $R^A$ is unsubstituted heterocyclyl. In certain embodiments, $R^A$ is saturated heterocyclyl. In certain embodiments, $R^A$ is unsaturated heterocyclyl. In certain embodiments, $R^A$ is 3- to 8-membered, monocyclic heterocyclyl, optionally including 1 or 2 double bonds in the heterocyclic ring system, wherein 1, 2, or 3 atoms in the heterocyclic ring system are independently nitrogen, oxygen, or sulfur. In certain embodiments, $R^A$ is 5- to 14-membered, bicyclic heterocyclyl, optionally including 1, 2, or 3 double bonds in the heterocyclic ring system, wherein 1, 2, 3, or 4 atoms in the heterocyclic ring system are independently nitrogen, oxygen, or sulfur. In certain embodiments, $R^A$ is 5- to 20-membered, tricyclic heterocyclyl, optionally including 1, 2, 3, or 4 double bonds in the heterocyclic ring system, wherein 1, 2, 3, 4, or 5 atoms in the heterocyclic ring system are independently nitrogen, oxygen, or sulfur. In certain embodiments, $R^A$ is substituted aryl. In certain embodiments, $R^A$ is unsubstituted aryl. In certain embodiments, $R^A$ is 6- to 14-membered aryl. In certain embodiments, $R^A$ is 6- to 10-membered aryl. In certain embodiments, $R^A$ is substituted phenyl. In certain embodiments, $R^A$ is unsubstituted phenyl. In certain embodiments, $R^A$ is substituted naphthyl. In certain embodiments, $R^A$ is unsubstituted naphthyl. In certain embodiments, $R^A$ is substituted heteroaryl. In certain embodiments, $R^A$ is unsubstituted heteroaryl. In certain embodiments, $R^A$ is 5- to 6-membered, monocyclic heteroaryl, wherein 1, 2, 3, or 4 atoms in the heteroaryl ring system are independently nitrogen, oxygen, or sulfur. In certain embodiments, $R^A$ is 8- to 10-membered, bicyclic heteroaryl, wherein 1, 2, 3, or 4 atoms in the heteroaryl ring system are independently nitrogen, oxygen, or sulfur.

In certain embodiments, $R^A$ is a moiety shown in Table 1A. In certain embodiments, $R^A$ is a moiety shown in Table 1B.

TABLE 1A

Exemplary $R^A$ moieties

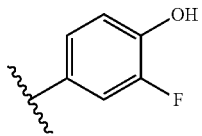 [SMILES: *c1ccc(O)c(F)c1]

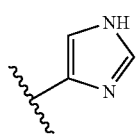 [SMILES: *c1c[nH]cn1]

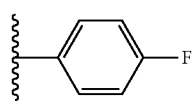

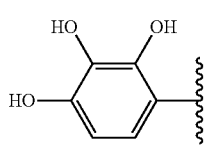 [SMILES: *c1ccc(O)c(O)c1O]

TABLE 1A-continued

Exemplary $R^A$ moieties

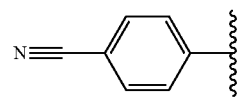

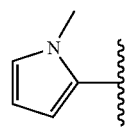

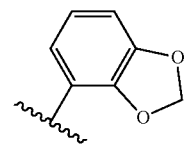 [SMILES: *c1cccc2c1OCO2]

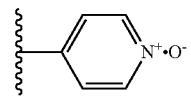

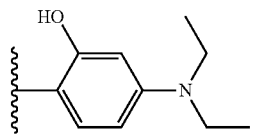 [SMILES: *c1ccc(N(CC)CC)cc1O]

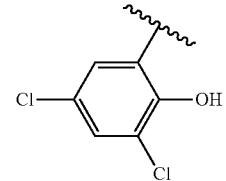 [SMILES: *c1cc(Cl)cc(Cl)c1O]

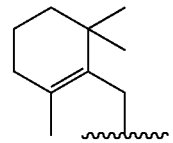 [SMILES: *CC1=C(C)CCCC1(C)C]

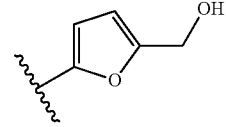 [SMILES: *c1ccc(CO)o1]

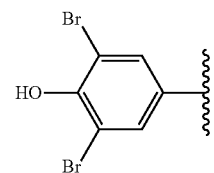

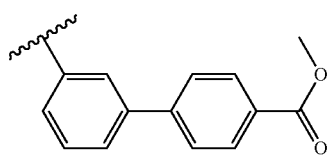 [SMILES: *c1cccc(-c2ccc(C(=O)OC)cc2)c1]

TABLE 1A-continued
Exemplary R<sup>4</sup> moieties
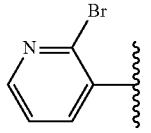 [SMILES: *c1cccnc1Br]
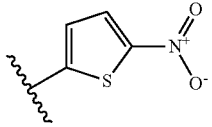 [SMILES: *c1ccc([N+](=O)[O-])s1]
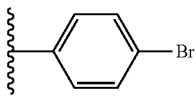
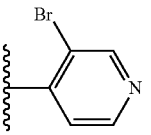 [SMILES: *c1ccncc1Br]
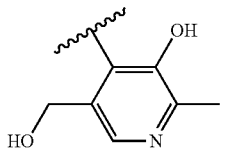 [SMILES: *c1c(CO)cnc(C)c1O]
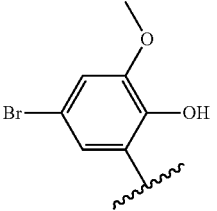 [SMILES: *c1cc(Br)cc(OC)c1O]
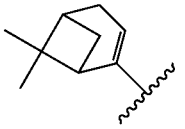 [SMILES: *C1=CCC2CC1C2(C)C]
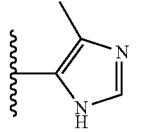 [SMILES: *c1[nH]cnc1C]
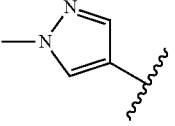 [SMILES: *c1cnn(C)c1]
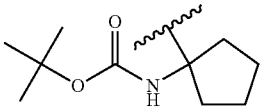 [SMILES: *C1(NC(=O)OC(C)(C)C)CCCC1]
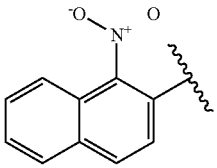
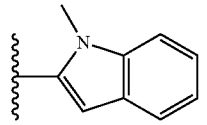 [SMILES: *c1cc2ccccc2n1C]
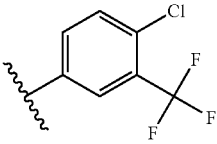 [SMILES: *c1ccc(Cl)c(C(F)(F)F)c1]
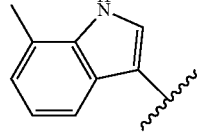
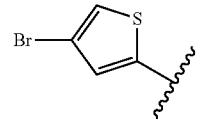 [SMILES: *c1cc(Br)cs1]
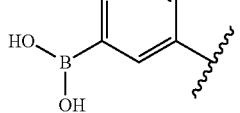
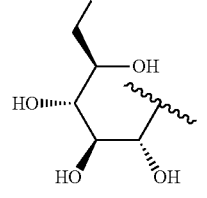
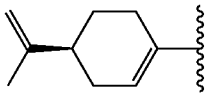 [SMILES: *C1=CC[C@@H](C(=C)C)CC1]
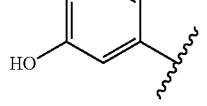
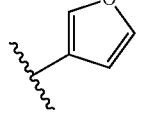

TABLE 1A-continued
Exemplary R$^A$ moieties
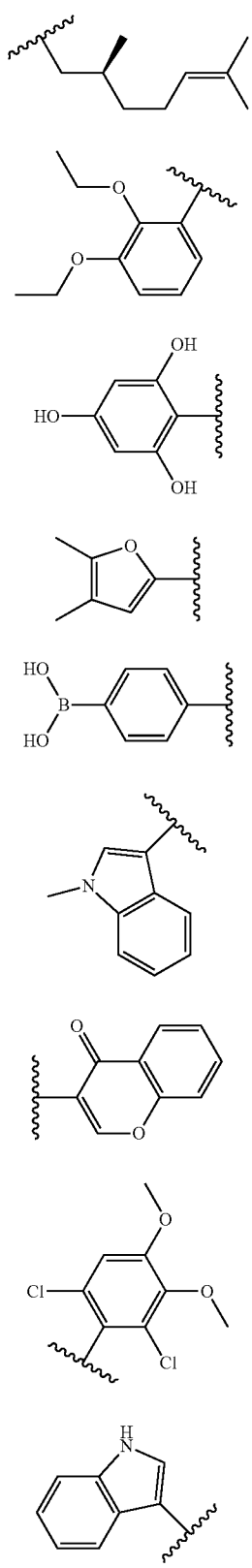
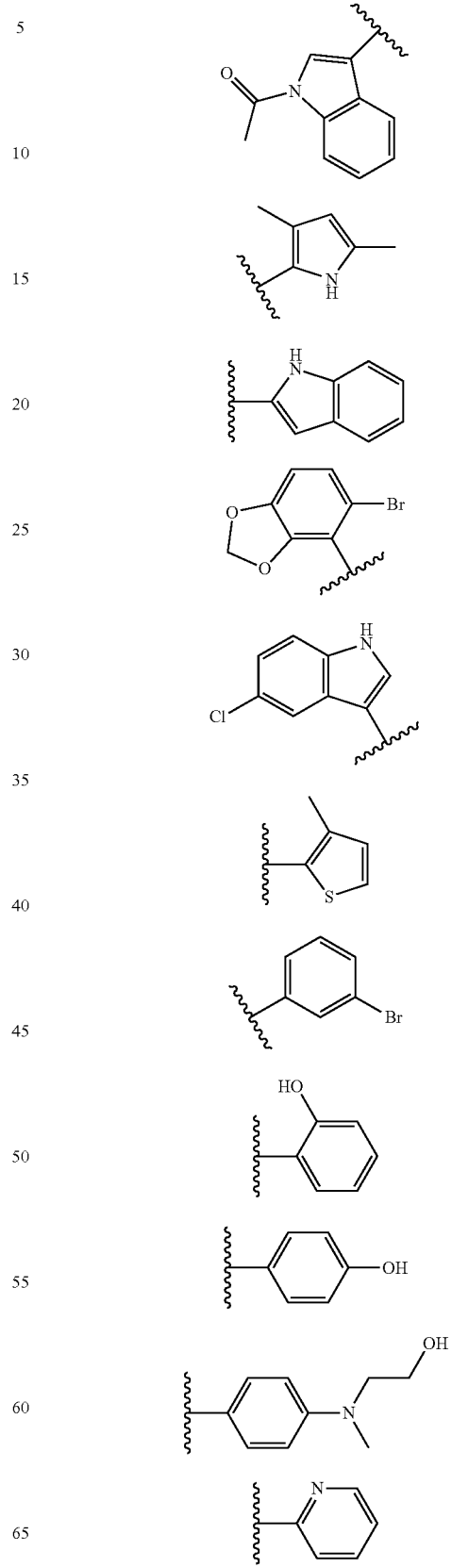

TABLE 1A-continued
Exemplary R^A moieties
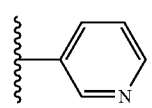 [SMILES: *c1cccnc1]
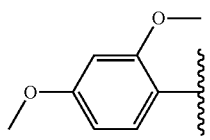 [SMILES: *c1ccc(OC)cc1OC]
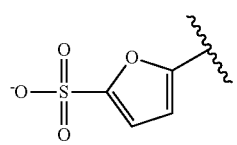
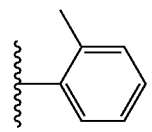
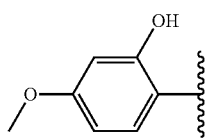 [SMILES: *c1ccc(OC)cc1O]
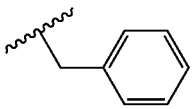
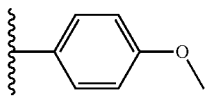
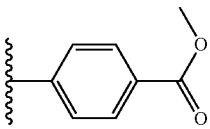
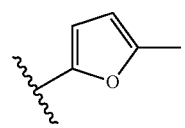 [SMILES: *c1ccc(C)o1]
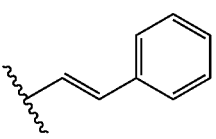 [SMILES: */C=C/c1ccccc1]
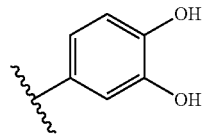 [SMILES: *c1ccc(O)c(O)c1]
TABLE 1A-continued
Exemplary R^A moieties
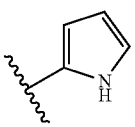 [SMILES: *c1ccc[nH]1]
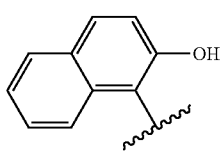 [SMILES: *c1c(O)ccc2ccccc12]
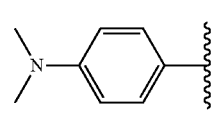 [SMILES: *c1ccc(N(C)C)cc1]
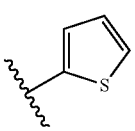 [SMILES: *c1cccs1]
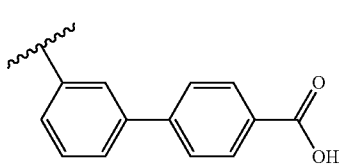 [SMILES: *c1cccc(-c2ccc(C(=O)O)cc2)c1]
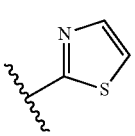 [SMILES: *c1nccs1]
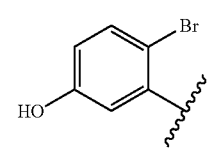 [SMILES: *c1cc(O)ccc1Br]
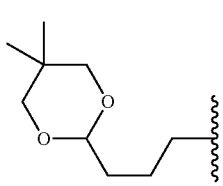 [SMILES: *CCCC1OCC(C)(C)CO1]
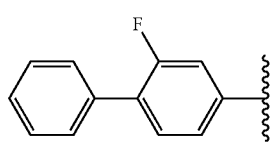 [SMILES: *c1ccc(-c2ccccc2)c(F)c1]
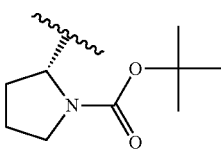 [SMILES: *[C@H]1CCCN1C(=O)OC(C)(C)C]

TABLE 1A-continued
Exemplary R^A moieties
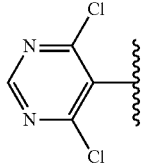 [SMILES: *c1c(Cl)ncnc1Cl]
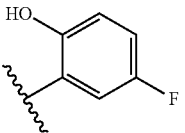
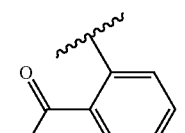
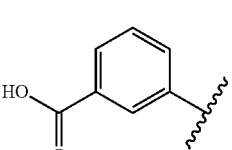
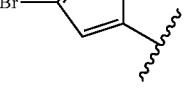
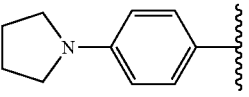 [SMILES: *c1ccc(N2CCCC2)cc1]
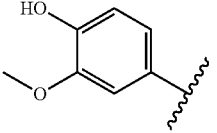 [SMILES: *c1ccc(O)c(OC)c1]
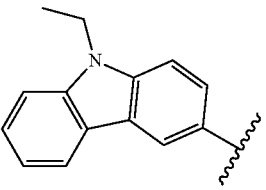 [SMILES: *c1ccc2c(c1)c1ccccc1n2CC]
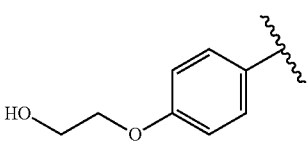 [SMILES: *c1ccc(OCCO)cc1]
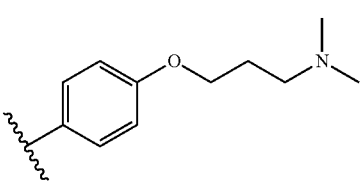 [SMILES: *c1ccc(OCCCN(C)C)cc1]
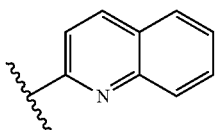 [SMILES: *c1ccc2ccccc2n1]
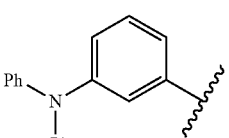
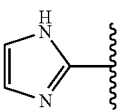
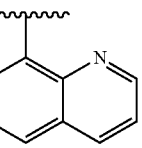
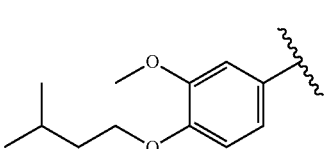
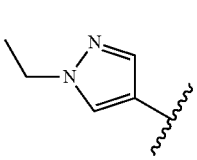 [SMILES: *c1cnn(CC)c1]
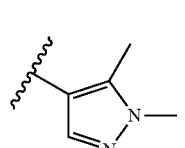
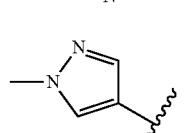
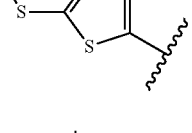
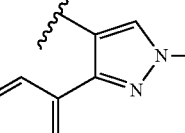

TABLE 1A-continued
Exemplary R^A moieties
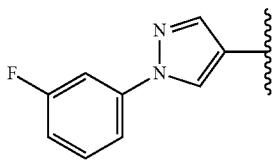 [SMILES: *c1cnn(-c2cccc(F)c2)c1]
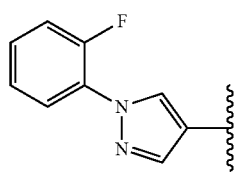 [SMILES: *c1cnn(-c2ccccc2F)c1]
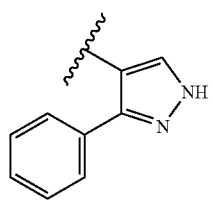 [SMILES: *c1c[nH]nc1-c1ccccc1]
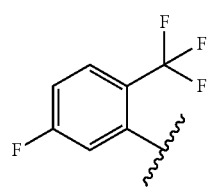 [SMILES: *c1cc(F)ccc1C(F)(F)F]
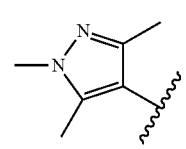
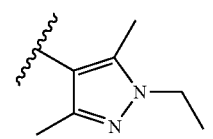 [SMILES: *c1c(C)nn(CC)c1C]
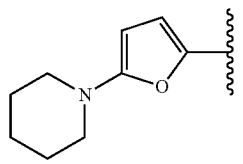 [SMILES: *c1ccc(N2CCCCC2)o1]
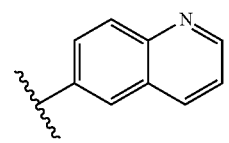 [SMILES: *c1ccc2ncccc2c1]
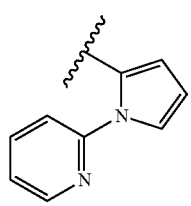 [SMILES: *c1cccn1-c1ccccn1]
TABLE 1A-continued
Exemplary R^A moieties
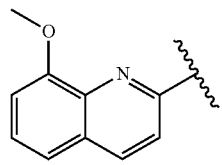 [SMILES: *c1ccc2cccc(OC)c2n1]
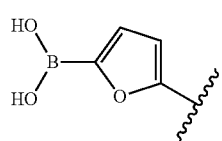 [SMILES: *c1ccc(B(O)O)o1]
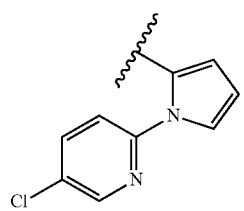 [SMILES: *c1cccn1-c1ccc(Cl)cn1]
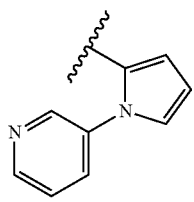 [SMILES: *c1cccn1-c1cccnc1]
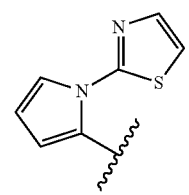 [SMILES: *c1cccn1-c1nccs1]
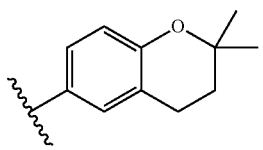 [SMILES: *c1ccc2c(c1)CCC(C)(C)O2]
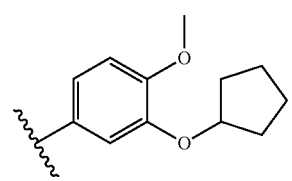 [SMILES: *c1ccc(OC)c(OC2CCCC2)c1]
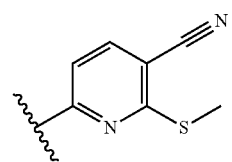 [SMILES: *c1ccc(C#N)c(SC)n1]

TABLE 1A-continued
Exemplary R[4] moieties
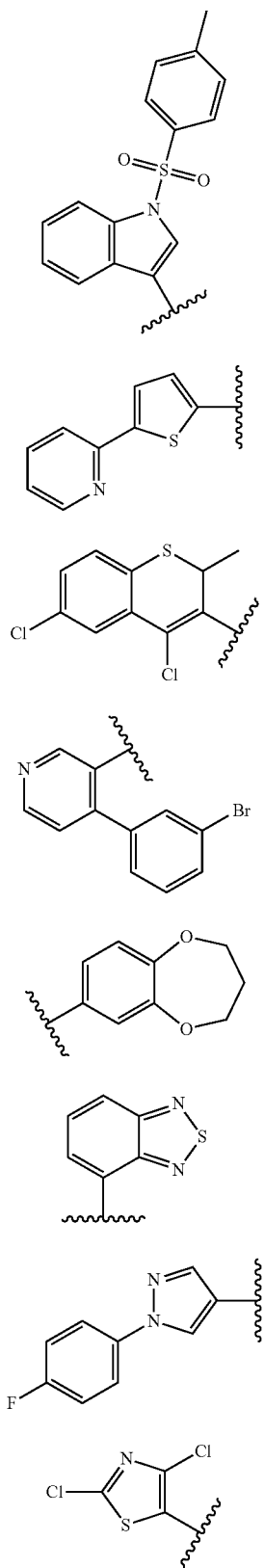
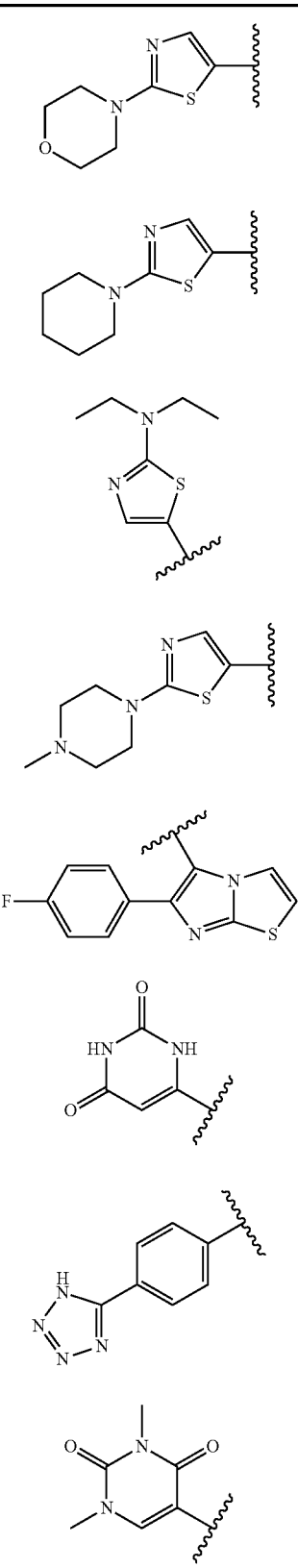

TABLE 1A-continued
Exemplary R⁴ moieties
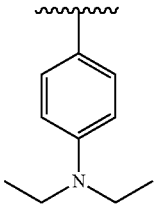
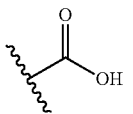 [SMILES: *C(=O)O]
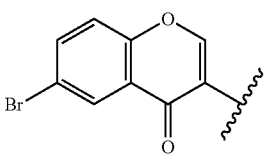 [SMILES: *c1coc2ccc(Br)cc2c1=O]
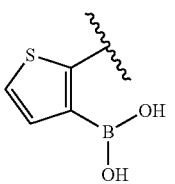 [SMILES: *c1sccc1B(O)O]
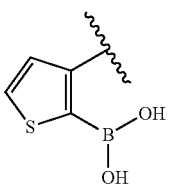 [SMILES: *c1ccsc1B(O)O]
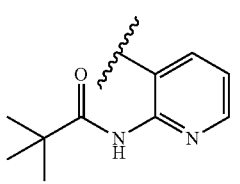 [SMILES: *c1cccnc1NC(=O)C(C)(C)C]
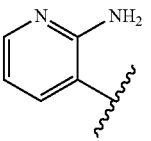 [SMILES: *c1cccnc1N]
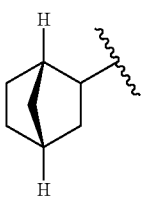 [SMILES: *C1C[C@@H]2CC[C@H]1C2]
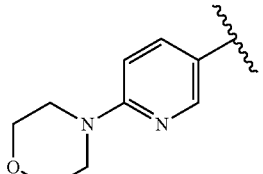
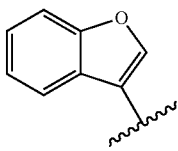 [SMILES: *c1coc2ccccc12]
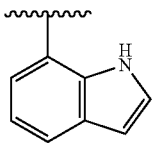 [SMILES: *c1cccc2cc[nH]c12]
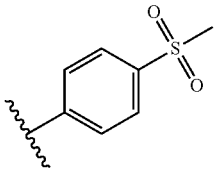 [SMILES: *c1ccc(S(C)(=O)=O)cc1]
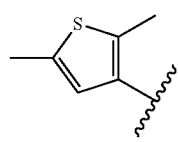 [SMILES: *c1cc(C)sc1C]
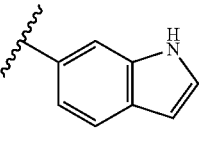 [SMILES: *c1ccc2cc[nH]c2c1]
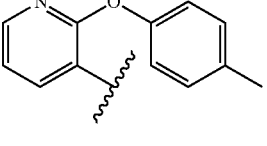
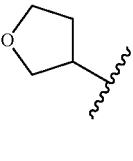 [SMILES: *C1CCOC1]
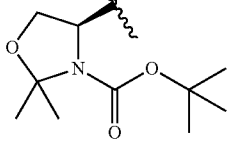

TABLE 1A-continued

Exemplary R⁴ moieties

TABLE 1A-continued
Exemplary R^A moieties
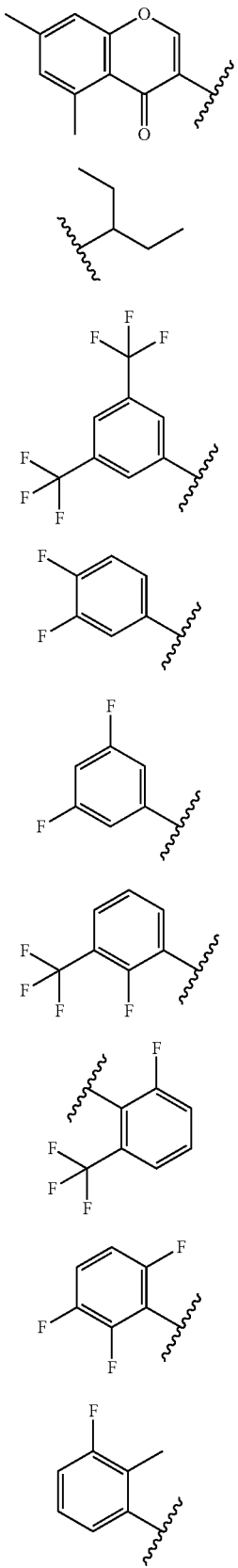
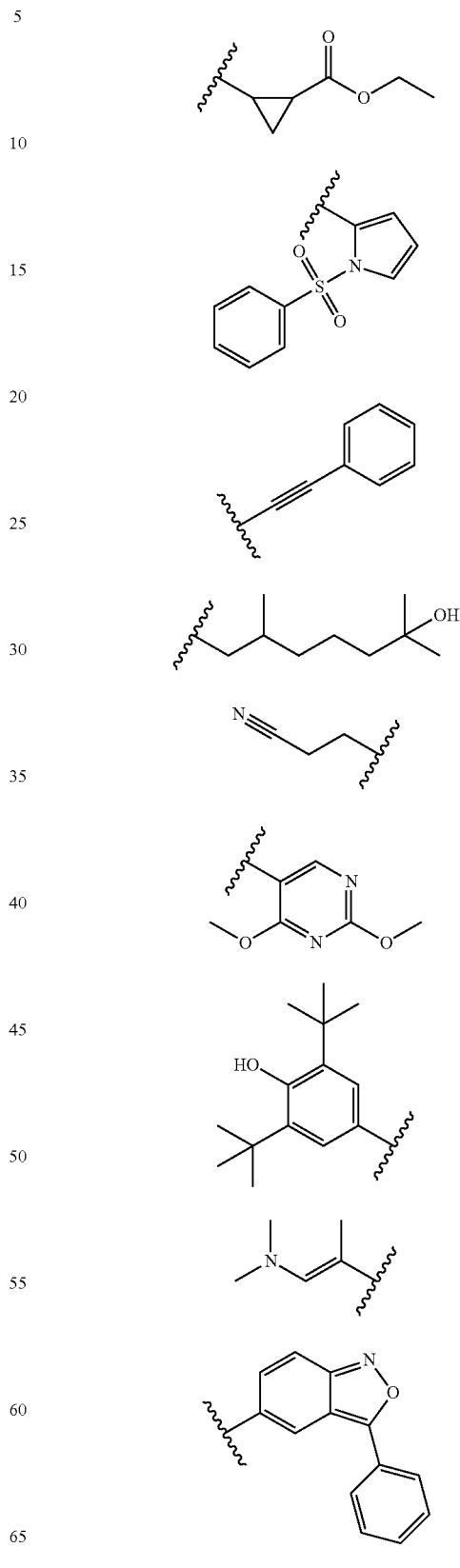

TABLE 1A-continued
Exemplary R^A moieties
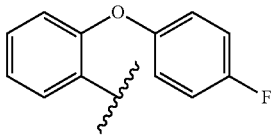 [SMILES: *c1ccccc1Oc1ccc(F)cc1]
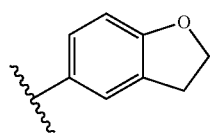 [SMILES: *c1ccc2c(c1)CCO2]
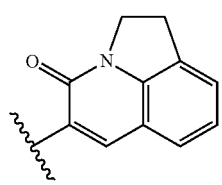 [SMILES: *c1cc2cccc3c2n(c1=O)CC3]
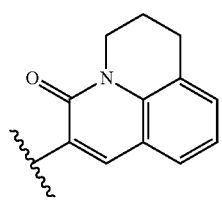 [SMILES: *c1cc2cccc3c2n(c1=O)CCC3]
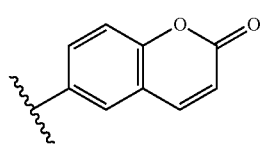 [SMILES: *c1ccc2oc(=O)ccc2c1]
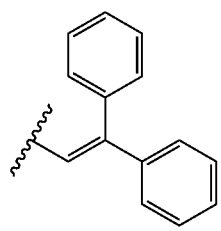 [SMILES: *C=C(c1ccccc1)c1ccccc1]
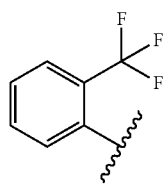 [SMILES: *c1ccccc1C(F)(F)F]
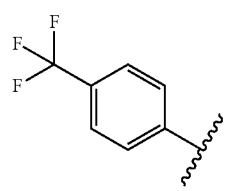 [SMILES: *c1ccc(C(F)(F)F)cc1]
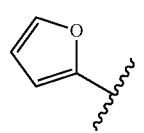 [SMILES: *c1ccco1]
TABLE 1A-continued
Exemplary R^A moieties
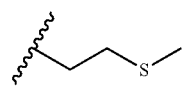 [SMILES: *CCSC]
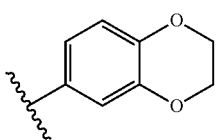 [SMILES: *c1ccc2c(c1)OCCO2]
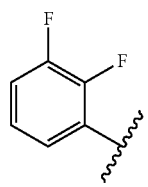 [SMILES: *c1cccc(F)c1F]
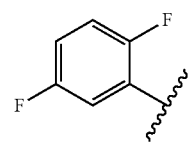
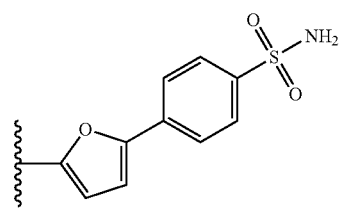 [SMILES: *c1ccc(-c2ccc(S(N)(=O)=O)cc2)o1]
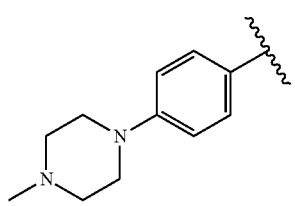 [SMILES: *c1ccc(N2CCN(C)CC2)cc1]
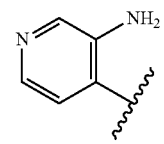 [SMILES: *c1ccncc1N]
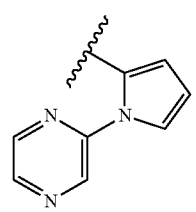 [SMILES: *c1cccn1-c1cnccn1]
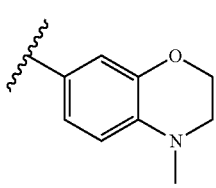 [SMILES: *c1ccc2c(c1)OCCN2C]

TABLE 1A-continued
Exemplary R^A moieties
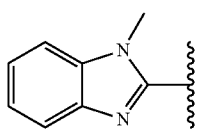 [SMILES: *c1nc2ccccc2n1C]
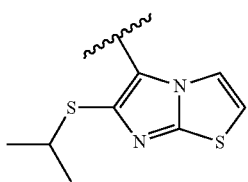 [SMILES: *c1c(SC(C)C)nc2sccn12]
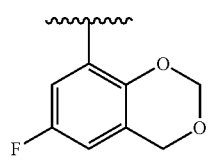
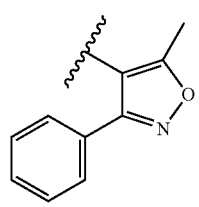 [SMILES: *c1c(-c2ccccc2)noc1C]
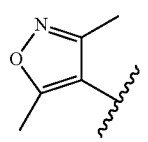 [SMILES: *c1c(C)noc1C]
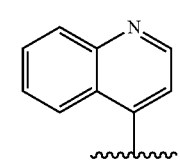 [SMILES: *c1ccnc2ccccc12]
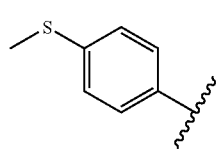 [SMILES: *c1ccc(SC)cc1]
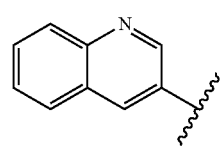 [SMILES: *c1cnc2ccccc2c1]
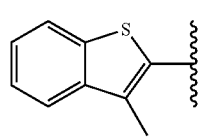 [SMILES: *c1sc2ccccc2c1C]
TABLE 1A-continued
Exemplary R^A moieties
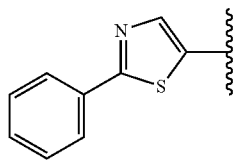 [SMILES: *c1cnc(-c2ccccc2)s1]
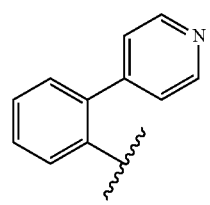 [SMILES: *c1ccccc1-c1ccncc1]
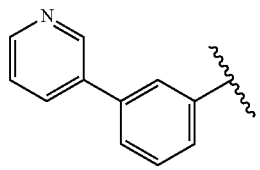 [SMILES: *c1cccc(-c2cccnc2)c1]
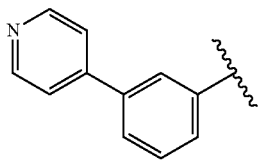 [SMILES: *c1cccc(-c2ccncc2)c1]
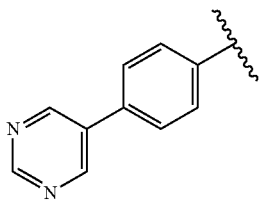 [SMILES: *c1ccc(-c2cncnc2)cc1]
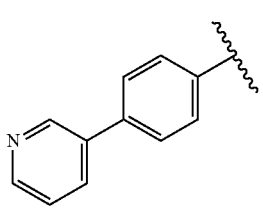 [SMILES: *c1ccc(-c2cccnc2)cc1]
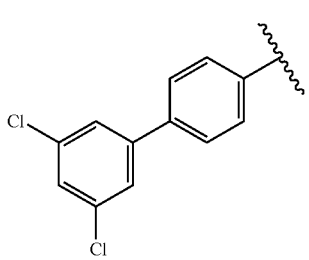 [SMILES: *c1ccc(-c2cc(Cl)cc(Cl)c2)cc1]
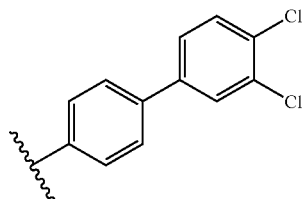 [SMILES: *c1ccc(-c2ccc(Cl)c(Cl)c2)cc1]

TABLE 1A-continued
Exemplary R^A moieties
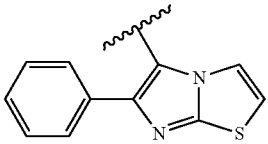 [SMILES: *c1c(-c2ccccc2)nc2sccn12]
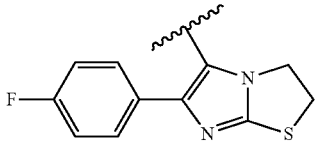 [SMILES: *c1c(-c2ccc(F)cc2)nc2n1CCS2]
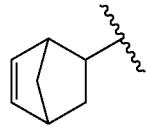 [SMILES: *C1CC2C=CC1C2]
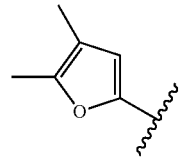 [SMILES: *c1cc(C)c(C)o1]
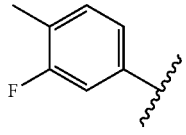 [SMILES: *c1ccc(C)c(F)c1]
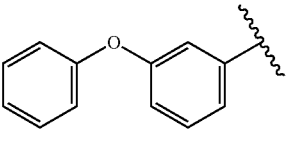 [SMILES: *c1cccc(Oc2ccccc2)c1]
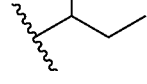
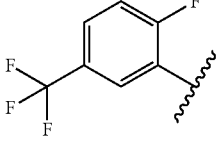
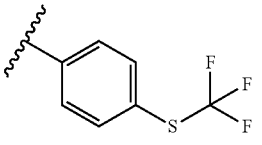 [SMILES: *c1ccc(SC(F)(F)F)cc1]
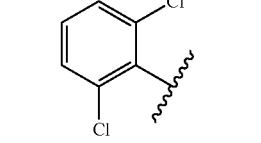
TABLE 1A-continued
Exemplary R^A moieties
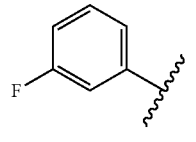 [SMILES: *c1cccc(F)c1]
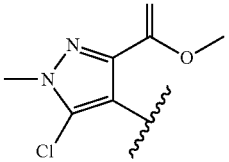
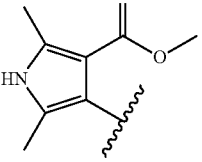
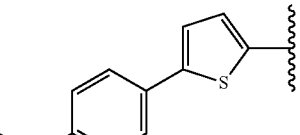
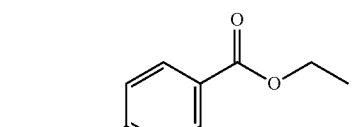
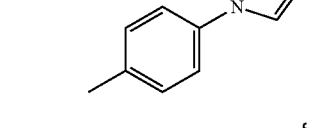
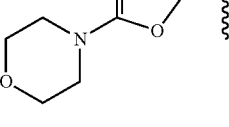
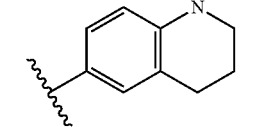
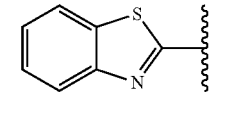 [SMILES: *c1nc2ccccc2s1]

TABLE 1A-continued
Exemplary R^A moieties
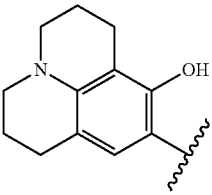 [SMILES: *c1cc2c3c(c1O)CCCN3CCC2]
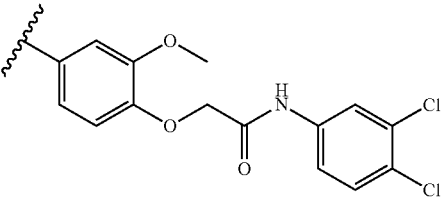 [SMILES: *c1ccc(OCC(=O)Nc2ccc(Cl)c(Cl)c2)c(OC)c1]
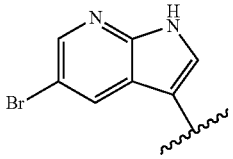 [SMILES: *c1c[nH]c2ncc(Br)cc12]
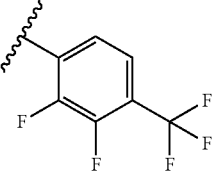 [SMILES: *c1ccc(C(F)(F)F)c(F)c1F]
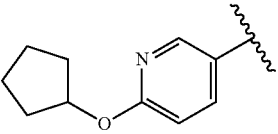 [SMILES: *c1ccc(OC2CCCC2)nc1]
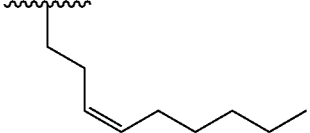 [SMILES: *CC/C=C\CCCCC]
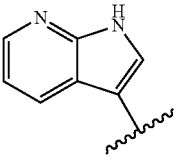 [SMILES: *c1c[nH]c2ncccc12]
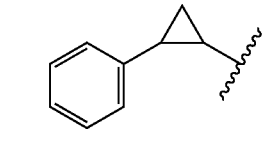 [SMILES: *C1CC1c1ccccc1]
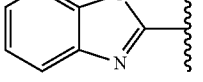
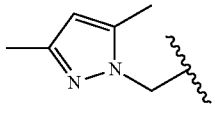
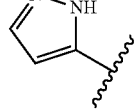
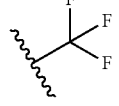
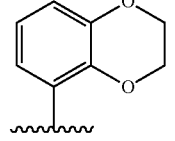
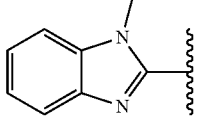
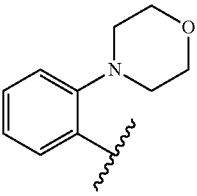
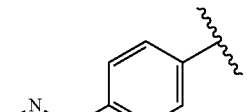
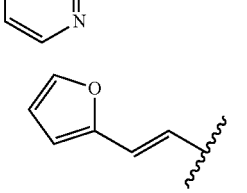
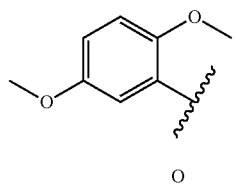
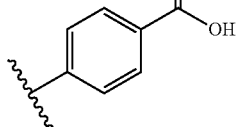

TABLE 1A-continued
Exemplary R<sup>A</sup> moieties
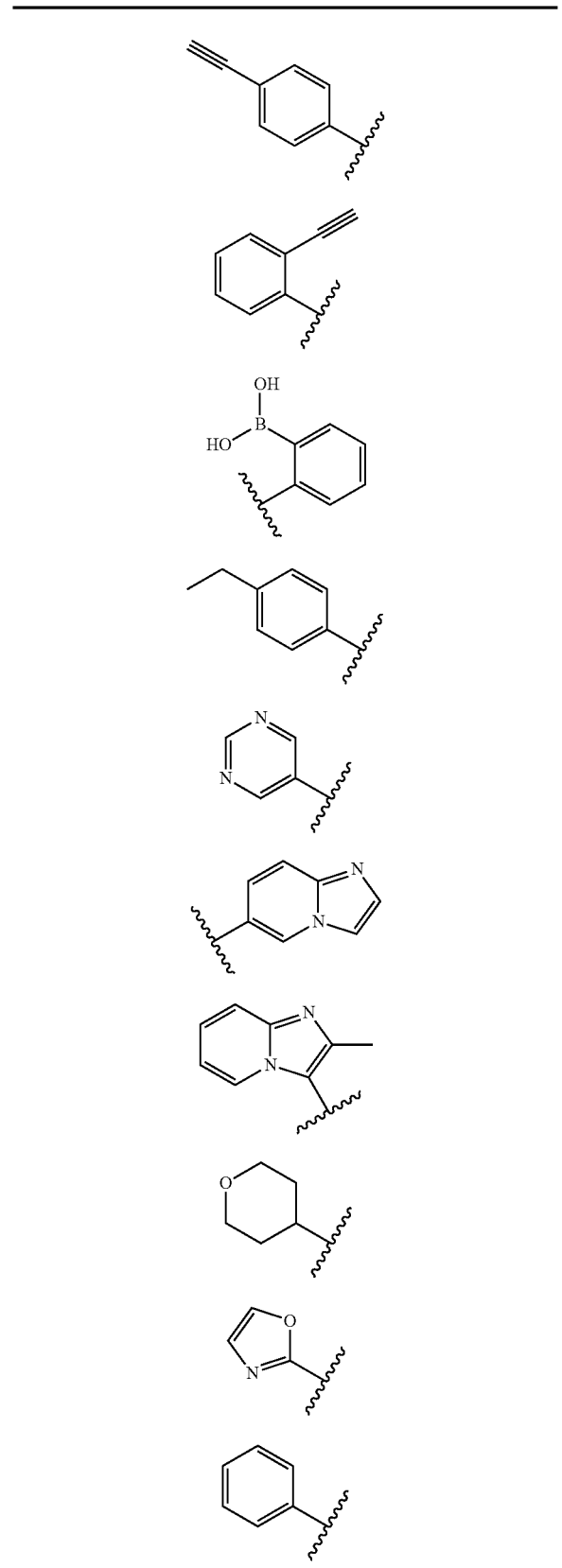
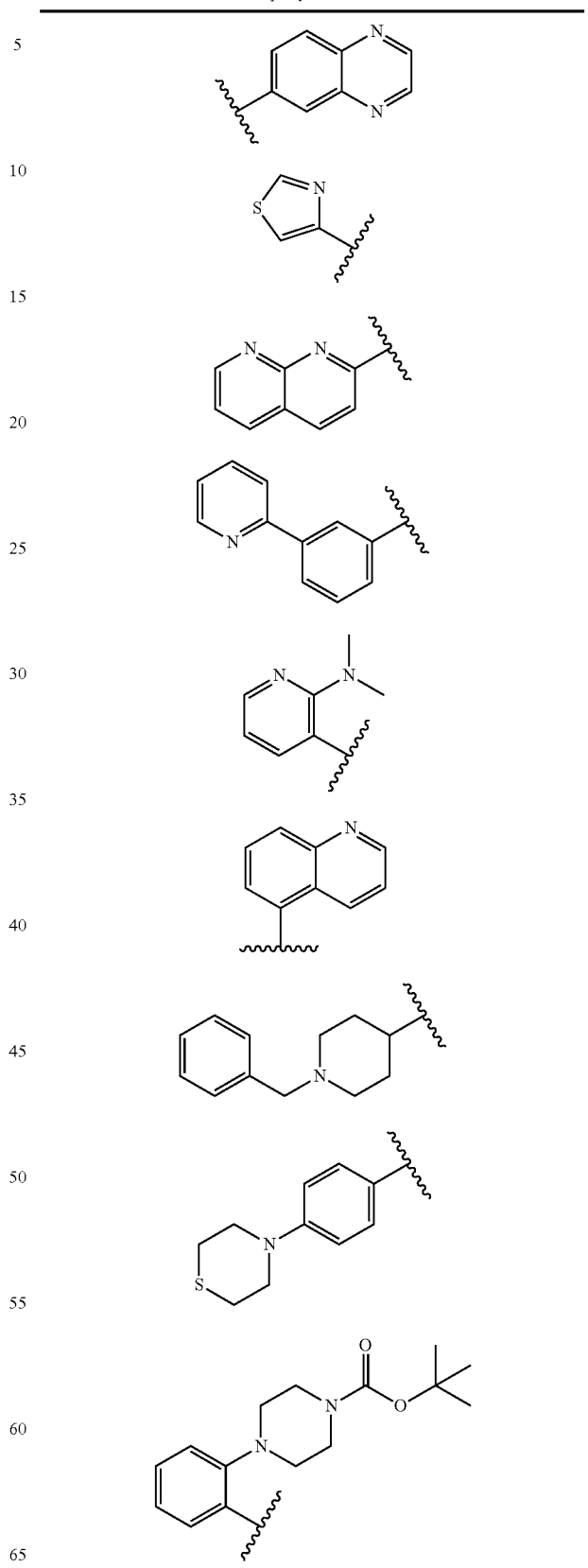

TABLE 1A-continued

Exemplary R^A moieties

TABLE 1A-continued
Exemplary R⁴ moieties
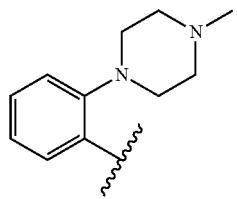 [SMILES: *c1ccccc1N1CCN(C)CC1]
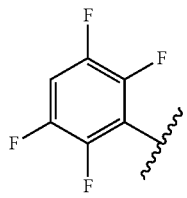 [SMILES: *c1c(F)c(F)cc(F)c1F]
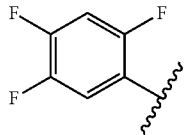 [SMILES: *c1cc(F)c(F)cc1F]
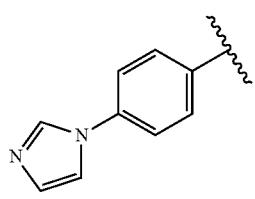 [SMILES: *c1ccc(-n2ccnc2)cc1]
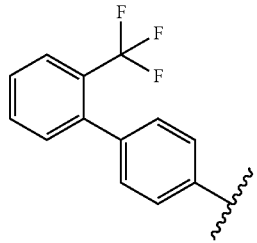 [SMILES: *c1ccc(-c2ccccc2C(F)(F)F)cc1]
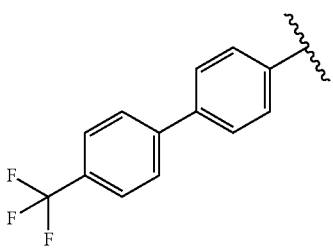 [SMILES: *c1ccc(-c2ccc(C(F)(F)F)cc2)cc1]
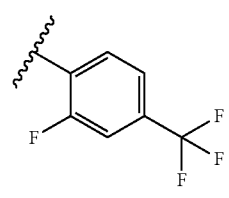 [SMILES: *c1ccc(C(F)(F)F)cc1F]
TABLE 1A-continued
Exemplary R⁴ moieties
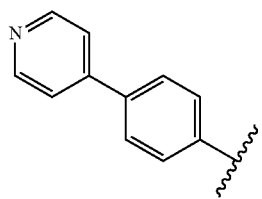 [SMILES: *c1ccc(-c2ccncc2)cc1]
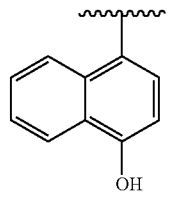 [SMILES: *c1ccc(O)c2ccccc12]
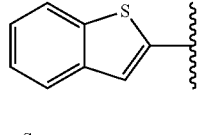
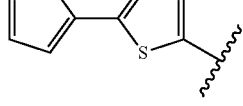
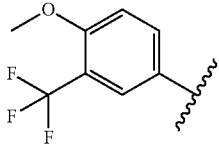 [SMILES: *c1ccc(OC)c(C(F)(F)F)c1]
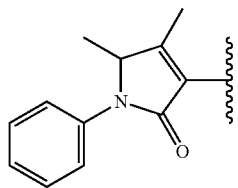 [SMILES: *C1=C(C)C(C)N(c2ccccc2)C1=O]
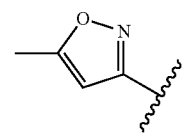 [SMILES: *c1cc(C)on1]
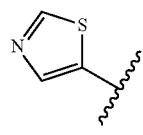
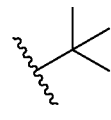

TABLE 1A-continued

Exemplary $R^A$ moieties

[ferrocene structure]

TABLE 1B

Exemplary $R^A$ and $R^B$ moieties

| $R^A$ or $R^B$ | $R^B$ or $R^A$ |
|---|---|
| adamantyl | isobutyl |
| 4-methoxyphenyl | phenyl |
| pent-4-en-1-yl | tert-butyl |
| piperidin-4-yl (HN) | phenyl |
| acrylamido-tert-butyl | isopropyl |
| pyridin-2-yl | pyridin-2-yl |
| 7-hydroxybenzofuran-2-yl | neopentyl |
| 2-methylbutanoic acid | tert-butyl |
| benzyl | pyridin-3-yl |

TABLE 1B-continued

Exemplary $R^A$ and $R^B$ moieties

| $R^A$ or $R^B$ | $R^B$ or $R^A$ |
|---|---|
| 3-(trifluoromethyl)phenyl | phenyl |
| piperidin-4-yl (NH) | 4-fluorophenyl |
| 2-hydroxyphenyl | phenyl |
| 4-(dimethylamino)phenyl | phenyl |
| steroid (11,17-dihydroxy) | 2-hydroxyethyl |
| 5-methylisoxazol-3-yl-triazolyl-ethyl | isopropyl |

An $R^A$ group may independently include one or more substituents $R^c$. In certain embodiments, all instances of $R^c$ are the same. In certain embodiments, two instances of $R^c$ are different from each other. In certain embodiments, at least one instance of $R^c$ is H. In certain embodiments, each instance of $R^c$ is H. In certain embodiments, at least one instance of $R^c$ is substituted or unsubstituted acyl (e.g., acetyl). In certain embodiments, at least one instance of $R^c$ is substituted or unsubstituted alkyl (e.g., substituted or unsubstituted $C_{1-6}$ alkyl). In certain embodiments, at least one instance of $R^c$ is —$CH_3$. In certain embodiments, at least one instance of $R^c$ is —$CF_3$, unsubstituted ethyl, perfluoroethyl, unsubstituted propyl, perfluoropropyl, unsubstituted butyl, or perfluorobutyl. In certain embodiments, at least one instance of $R^c$ is substituted or unsubstituted alkenyl (e.g., substituted or unsubstituted $C_{1-6}$ alkenyl). In certain embodiments, at least one instance of $R^c$ is substituted or unsubstituted alkynyl (e.g., substituted or unsubstituted $C_{1-6}$ alkynyl). In certain embodiments, at least one instance of $R^c$ is substituted or unsubstituted carbocyclyl (e.g., substituted or unsubstituted, 3- to 8-membered, monocyclic carbocyclyl, optionally including 1, 2, or 3 double bonds in the carbocyclic ring system; or substituted or unsubstituted, 5- to 14-membered, bicyclic carbocyclyl, optionally including 1, 2, 3, or 4 double bonds in the carbocyclic ring system). In certain embodiments, at least one instance of $R^c$ is substituted or unsubstituted heterocyclyl (e.g., substituted or unsubstituted, 3- to 8-membered, monocyclic heterocyclyl, optionally including 1 or 2 double bonds in the heterocyclic ring system, wherein 1, 2, or 3 atoms in the heterocyclic ring system are independently nitrogen, oxygen, or sulfur; or substituted or unsubstituted, 5- to 14-membered, bicyclic heterocyclyl, optionally including 1, 2, or 3 double bonds in the heterocyclic ring system, wherein 1, 2, 3, or 4 atoms in the heterocyclic ring system are independently nitrogen, oxygen, or sulfur). In certain embodiments, at least one instance of $R^c$ is substituted or unsubstituted aryl (e.g., substituted or unsubstituted, 6- to 10-membered aryl). In certain embodiments, at least one instance of $R^c$ is substituted or unsubstituted phenyl. In certain embodiments, at least one instance of $R^c$ is substituted or unsubstituted heteroaryl (e.g., substituted or unsubstituted, 5- to 6-membered, monocyclic heteroaryl, or substituted or unsubstituted, 8- to 10-membered, bicyclic heteroaryl, wherein 1, 2, 3, or 4 atoms in the heteroaryl ring system are independently nitrogen, oxygen, or sulfur). In certain embodiments, at least one instance of $R^c$ is a nitrogen protecting group (e.g., Bn, Boc, Cbz, Fmoc, trifluoroacetyl, triphenylmethyl, acetyl, or Ts) when attached to a nitrogen atom. In certain embodiments, $R^c$ is an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom. In certain embodiments, $R^c$ is a sulfur protecting group (e.g., acetamidomethyl, t-Bu, 3-nitro-2-pyridine sulfenyl, 2-pyridine-sulfenyl, or triphenylmethyl) when attached to a sulfur atom. In certain embodiments, two instances of $R^c$ are joined to form a substituted or unsubstituted heterocyclic ring (e.g., substituted or unsubstituted, 3- to 8-membered, monocyclic heterocyclic ring, optionally including 1 or 2 double bonds in the heterocyclic ring system, wherein 1, 2, or 3 atoms in the heterocyclic ring system are independently nitrogen, oxygen, or sulfur). In certain embodiments, two instances of $R^c$ are joined to form a substituted or unsubstituted heteroaryl ring (e.g., substituted or unsubstituted, 5- to 6-membered, monocyclic heteroaryl ring, wherein 1, 2, 3, or 4 atoms in the heteroaryl ring system are independently nitrogen, oxygen, or sulfur).

In certain embodiments, $R^B$ is H. In certain embodiments, $R^B$ is substituted acyl. In certain embodiments, $R^B$ is unsubstituted acyl. In certain embodiments, $R^B$ is acetyl. In certain embodiments, $R^B$ is —C(=O)$R^d$ (e.g., —C(=O)(substituted or unsubstituted alkyl)). In certain embodiments, $R^B$ is —C(=O)O$R^d$ (e.g., —C(=O)O(substituted or unsubstituted alkyl) or —C(=O)OH). In certain embodiments, $R^B$ is —C(=O)N($R^d$)$_2$, (e.g., —C(=O)NH$_2$, —C(=O)NH(substituted or unsubstituted alkyl), or —C(=O)N(substituted or unsubstituted alkyl)$_2$). In certain embodiments, $R^B$ is unsubstituted alkyl. In certain embodiments, $R^B$ is substituted alkyl. In certain embodiments, $R^B$ is unsubstituted $C_{1-6}$ alkyl. In certain embodiments, $R^B$ is substituted $C_{1-6}$ alkyl. In certain embodiments, $R^B$ is $C_{1-6}$ alkyl substituted with at least one halogen. In certain embodiments, $R^B$ is —CH$_3$. In certain embodiments, $R^B$ is substituted methyl. In certain embodiments, $R^B$ is —CH$_2$F, —CHF$_2$, or —CF$_3$. In certain embodiments, $R^B$ is ethyl. In certain embodiments, $R^B$ is propyl. In certain embodiments, $R^B$ is butyl. In certain embodiments, $R^B$ is pentyl. In certain embodiments, $R^B$ is hexyl. In certain embodiments, $R^B$ is unsubstituted alkenyl. In certain embodiments, $R^B$ is substituted alkenyl. In certain embodiments, $R^B$ is unsubstituted $C_{1-6}$ alkenyl. In certain embodiments, $R^B$ is substituted $C_{1-6}$ alkenyl. In certain embodiments, $R^B$ is unsubstituted alkynyl. In certain embodiments, $R^B$ is substituted alkynyl. In certain embodiments, $R^B$ is unsubstituted $C_{1-6}$ alkynyl. In certain embodiments, $R^B$ is substituted $C_{1-6}$ alkynyl. In certain embodiments, $R^B$ is substituted carbocyclyl. In certain embodiments, $R^B$ is unsubstituted carbocyclyl. In certain embodiments, $R^B$ is saturated carbocyclyl. In certain embodiments, $R^B$ is unsaturated carbocyclyl. In certain embodiments, $R^B$ is 3- to 8-membered, monocyclic carbocyclyl, optionally including 1, 2, or 3 double bonds in the carbocyclic ring system. In certain embodiments, $R^B$ is 5- to 14-membered, bicyclic carbocyclyl, optionally including 1, 2, 3, or 4 double bonds in the carbocyclic ring system. In certain embodiments, $R^B$ is 5- to 20-membered, tricyclic carbocyclyl, optionally including 1, 2, 3, 4, or 5 double bonds in the carbocyclic ring system. In certain embodiments, $R^B$ is 5- to 26-membered, tetracyclic carbocyclyl, optionally including 1, 2, 3, 4, 5, or 6 double bonds in the carbocyclic ring system. In certain embodiments, $R^B$ is substituted heterocyclyl. In certain embodiments, $R^B$ is unsubstituted heterocyclyl. In certain embodiments, $R^B$ is saturated heterocyclyl. In certain embodiments, $R^B$ is unsaturated heterocyclyl. In certain embodiments, $R^B$ is 3- to 8-membered, monocyclic heterocyclyl, optionally including 1 or 2 double bonds in the heterocyclic ring system, wherein 1, 2, or 3 atoms in the heterocyclic ring system are independently nitrogen, oxygen, or sulfur. In certain embodiments, $R^B$ is 5- to 14-membered, bicyclic heterocyclyl, optionally including 1, 2, or 3 double bonds in the heterocyclic ring system, wherein 1, 2, 3, or 4 atoms in the heterocyclic ring system are independently nitrogen, oxygen, or sulfur. In certain embodiments, $R^B$ is 5- to 20-membered, tricyclic heterocyclyl, optionally including 1, 2, 3, or 4 double bonds in the heterocyclic ring system, wherein 1, 2, 3, 4, or 5 atoms in the heterocyclic ring system are independently nitrogen, oxygen, or sulfur. In certain embodiments, $R^B$ is substituted aryl. In certain embodiments, $R^B$ is unsubstituted aryl. In certain embodiments, $R^B$ is 6- to 14-membered aryl. In certain embodiments, $R^B$ is 6- to 10-membered aryl. In certain embodiments, $R^B$ is substituted phenyl. In certain embodiments, $R^B$ is unsubstituted phenyl. In certain embodiments, $R^B$ is substituted naphthyl. In certain embodiments, $R^B$ is unsubstituted naphthyl. In certain embodiments, $R^B$ is substituted heteroaryl. In certain embodiments, $R^B$ is unsubstituted heteroaryl. In certain embodiments, $R^B$ is 5- to 6-membered, monocyclic heteroaryl, wherein 1, 2, 3, or 4 atoms in the heteroaryl ring system are independently nitrogen, oxygen, or sulfur. In certain embodiments, $R^B$ is 8- to 10-membered, bicyclic heteroaryl, wherein 1, 2, 3, or 4 atoms in the heteroaryl ring system are independently nitrogen, oxygen, or sulfur.

In certain embodiments, $R^B$ is a moiety shown in Table 1A. In certain embodiments, $R^B$ is a moiety shown in Table 1B.

An $R^B$ group may independently include one or more substituents $R^d$. In certain embodiments, all instances of $R^d$ are the same. In certain embodiments, two instances of $R^d$ are different from each other. In certain embodiments, at least one instance of $R^d$ is H. In certain embodiments, each instance of $R^d$ is H. In certain embodiments, at least one instance of $R^d$ is substituted or unsubstituted acyl (e.g., acetyl). In certain embodiments, at least one instance of $R^d$ is substituted or unsubstituted alkyl (e.g., substituted or unsubstituted $C_{1-6}$ alkyl). In certain embodiments, at least one instance of $R^d$ is —CH$_3$. In certain embodiments, at least one instance of $R^d$ is —$CF_3$, unsubstituted ethyl, perfluoroethyl, unsubstituted propyl, perfluoropropyl, unsubstituted butyl, or perfluorobutyl. In certain embodiments, at least one instance of $R^d$ is substituted or unsubstituted alkenyl (e.g., substituted or unsubstituted $C_{1-6}$ alkenyl). In certain embodiments, at least one instance of $R^d$ is substituted or unsubstituted alkynyl (e.g., substituted or unsubstituted $C_{1-6}$ alkynyl). In certain embodiments, at least one instance of $R^d$ is substituted or unsubstituted carbocyclyl (e.g., substituted or unsubstituted, 3- to 8-membered, monocyclic carbocyclyl, optionally including 1, 2, or 3 double bonds in the carbocyclic ring system; or substituted or unsubstituted, 5- to 14-membered, bicyclic carbocyclyl, optionally including 1, 2, 3, or 4 double bonds in the carbocyclic ring system). In certain embodiments, at least one instance of $R^d$ is substituted or unsubstituted heterocyclyl (e.g., substituted or unsubstituted, 3- to 8-membered, monocyclic heterocyclyl, optionally including 1 or 2 double bonds in the heterocyclic ring system, wherein 1, 2, or 3 atoms in the heterocyclic ring system are independently nitrogen, oxygen, or sulfur; or substituted or unsubstituted, 5- to 14-membered, bicyclic heterocyclyl, optionally including 1, 2, or 3 double bonds in the heterocyclic ring system, wherein 1, 2, 3, or 4 atoms in the heterocyclic ring system are independently nitrogen, oxygen, or sulfur). In certain embodiments, at least one instance of $R^d$ is substituted or unsubstituted aryl (e.g., substituted or unsubstituted, 6- to 10-membered aryl). In certain embodiments, at least one instance of $R^d$ is substituted or unsubstituted phenyl. In certain embodiments, at least one instance of $R^d$ is substituted or unsubstituted heteroaryl (e.g., substituted or unsubstituted, 5- to 6-membered, monocyclic heteroaryl, or substituted or unsubstituted, 8- to 10-membered, bicyclic heteroaryl, wherein 1, 2, 3, or 4 atoms in the heteroaryl ring system are independently nitrogen, oxygen, or sulfur). In certain embodiments, at least one instance of $R^d$ is a nitrogen protecting group (e.g., Bn, Boc, Cbz, Fmoc, trifluoroacetyl, triphenylmethyl, acetyl, or Ts) when attached to a nitrogen atom. In certain embodiments, $R^d$ is an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom. In certain embodiments, $R^d$ is a sulfur protecting group (e.g., acetamidomethyl, t-Bu, 3-nitro-2-pyridine sulfenyl, 2-pyridine-sulfenyl, or triphenylmethyl) when attached to a sulfur atom. In certain embodiments, two instances of $R^d$ are joined to form a substituted or unsubstituted heterocyclic ring (e.g., substituted or unsubstituted, 3- to 8-membered, monocyclic heterocyclic ring, optionally including 1 or 2 double bonds in the heterocyclic ring system, wherein 1, 2, or 3 atoms in the heterocyclic ring system are independently nitrogen, oxygen, or sulfur). In certain embodiments, two instances of $R^d$ are joined to form a substituted or unsubstituted heteroaryl ring (e.g., substituted or unsubstituted, 5- to 6-membered, monocyclic heteroaryl ring, wherein 1, 2, 3, or 4 atoms in the heteroaryl ring system are independently nitrogen, oxygen, or sulfur).

In certain embodiments, $R^A$ and $R^B$ are the same. In certain embodiments, $R^A$ and $R^B$ are different from each other. In certain embodiments, $R^A$ is a moiety shown in an entry of Table 1B, and $R^B$ is the other moiety shown in the entry.

In certain embodiments, $R^A$ and $R^B$ are joined to form a substituted or unsubstituted, saturated or unsaturated, carbocyclic ring. In certain embodiments, $R^A$ and $R^B$ are joined to form a 3- to 8-membered, monocyclic carbocyclic ring, optionally including 1, 2, or 3 double bonds in the carbocyclic ring system. In certain embodiments, $R^A$ and $R^B$ are joined to form a 5- to 14-membered, bicyclic carbocyclic ring, optionally including 1, 2, 3, or 4 double bonds in the carbocyclic ring system. In certain embodiments, $R^A$ and $R^B$ are joined to form a 5- to 20-membered, tricyclic carbocyclic ring, optionally including 1, 2, 3, 4, or 5 double bonds in the carbocyclic ring system.

In certain embodiments, $R^A$ and $R^B$ are joined to form a substituted or unsubstituted, saturated or unsaturated, heterocyclic ring. In certain embodiments, $R^A$ and $R^B$ are joined to form a 3- to 8-membered, monocyclic heterocyclic ring, optionally including 1 or 2 double bonds in the heterocyclic ring system, wherein 1, 2, or 3 atoms in the heterocyclic ring system are independently nitrogen, oxygen, or sulfur. In certain embodiments, $R^A$ and $R^B$ are joined to form a 5- to 14-membered, bicyclic heterocyclic ring, optionally including 1, 2, or 3 double bonds in the heterocyclic ring system, wherein 1, 2, 3, or 4 atoms in the heterocyclic ring system are independently nitrogen, oxygen, or sulfur. In certain embodiments, $R^A$ and $R^B$ are joined to form a 5- to 20-membered, tricyclic heterocyclic ring, optionally including 1, 2, 3, 4, or 5 double bonds in the heterocyclic ring system, wherein 1, 2, 3, 4, or 5 atoms in the heterocyclic ring system are independently nitrogen, oxygen, or sulfur.

In certain embodiments, $R^A$ and $R^B$ are joined to form a moiety shown in Table 1C.

TABLE 1C

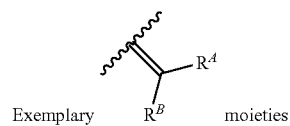

Exemplary moieties

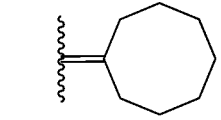 [SMILES: *=C1CCCCCCC1]

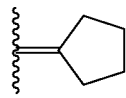 [SMILES: *=C1CCCC1]

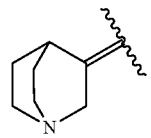

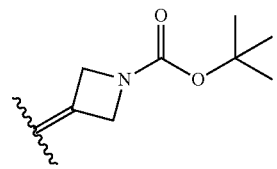 [SMILES: *=C1CN(C(=O)OC(C)(C)C)C1]

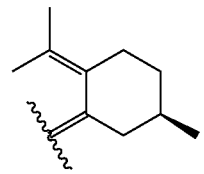 [SMILES: *=C1C[C@H](C)CCC1=C(C)C]

TABLE 1C-continued
Exemplary 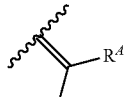 moieties
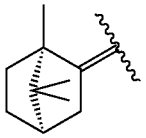 [SMILES: *=C1C[C@H]2CC[C@]1(C)C2(C)C]
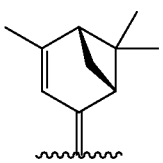
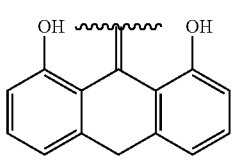 [SMILES: *=C1c2c(O)cccc2Cc2cccc(O)c21]
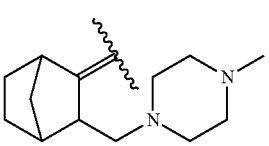 [SMILES: *=C1C2CCC(C2)C1CN1CCN(C)CC1]
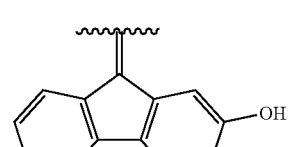
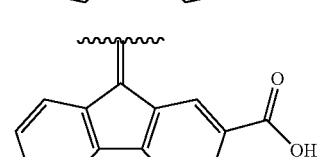
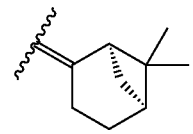 [SMILES: *=C1CC[C@H]2C[C@@H]1C2(C)C]
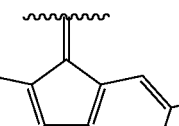
TABLE 1C-continued
Exemplary  moieties
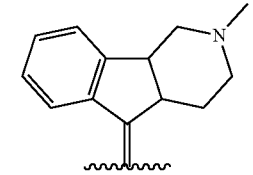 [SMILES: *=C1c2ccccc2C2CN(C)CCC12]
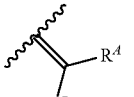
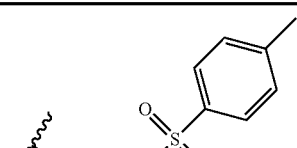
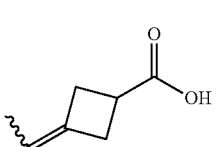
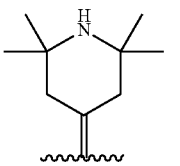
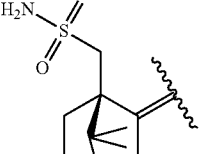
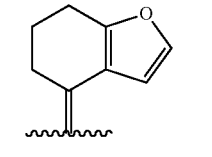 [SMILES: *=C1CCCc2occc21]
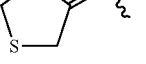
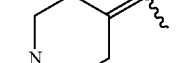

TABLE 1C-continued

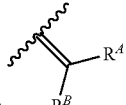

Exemplary moieties

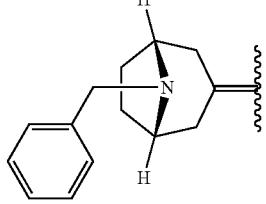

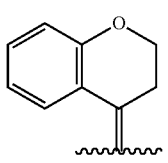 [SMILES: *=C1CCOc2ccccc21]

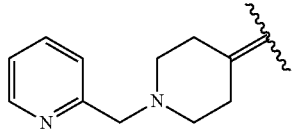 [SMILES: *=C1CCN(Cc2ccccn2)CC1]

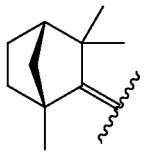 [SMILES: *=C1C(C)(C)[C@H]2CC[C@]1(C)C2]

In certain embodiments, $R^C$ is H. In certain embodiments, $R^C$ is substituted or unsubstituted $C_{1-6}$ alkyl (e.g., Me, —$CF_3$, unsubstituted ethyl, perfluoroethyl, unsubstituted propyl, perfluoropropyl, unsubstituted butyl, or perfluorobutyl). In certain embodiments, $R^C$ is Me. In certain embodiments, $R^C$ is a nitrogen protecting group (e.g., Bn, Boc, Cbz, Fmoc, trifluoroacetyl, triphenylmethyl, acetyl, or Ts).

In certain embodiments, $R^{41}$ is a tag (e.g., a biotin derivative, radiometric lable, or fluorophore). Any one of Formulae (I) and (II) may include a tag. A tag is a label. The term "label" includes any moiety that allows the compound to which it is attached to be captured, detected, or visualized. A label may be directly detectable (i.e., it does not require any further reaction or manipulation to be detectable, e.g., a fluorophore or chromophore is directly detectable) or it may be indirectly detectable (i.e., it is made detectable through reaction with or binding to another entity that is detectable, e.g., a hapten is detectable by immunostaining after reaction with an appropriate antibody comprising a reporter such as a fluorophore). Labels suitable for use in the present invention may be detectable by any of a variety of means including, but not limited to, spectroscopic, photochemical, biochemical, immunochemical, electrical, optical, or chemical means. Suitable labels include, but are not limited to, affinity tags, radiometric lables (e.g., radionuclides (such as, for example, $^{32}P$, $^{35}S$, $^{3}H$, $^{14}C$, $^{125}I$, $^{131}I$, and the like)), fluorescent dyes, phosphorescent dyes, chemiluminescent agents (such as, for example, acridinium esters, stabilized dioxetanes, and the like), spectrally resolvable inorganic fluorescent semiconductor nanocrystals (i.e., quantum dots), metal nanoparticles (e.g., gold, silver, copper, and platinum) or nanoclusters, enzymes (such as, for example, those used in an ELISA, i.e., horseradish peroxidase, beta-galactosidase, luciferase, alkaline phosphatase), colorimetric labels (such as, for example, dyes, colloidal gold, and the like), magnetic labels (such as, for example, Dynabeads™), and haptens.

In certain embodiments, the label comprises a fluorescent moiety. Numerous known fluorescent labeling moieties of a wide variety of chemical structures and physical characteristics are suitable for use in the practice of the present invention. Suitable fluorescent dyes include, but are not limited to, fluorescein and fluorescein dyes (e.g., fluorescein isothiocyanine (FITC), naphthofluorescein, 4',5'-dichloro-2', 7'-dimethoxy-fluorescein, 6-carboxyfluorescein or FAM), carbocyanine, merocyanine, styryl dyes, oxonol dyes, phycoerythrin, erythrosin, eosin, rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine or TMR), coumarin and coumarin dyes (e.g., methoxycoumarin, dialkylaminocoumarin, hydroxycoumarin and aminomethylcoumarin or AMCA), Oregon Green Dyes (e.g., Oregon Green 488, Oregon Green 500, Oregon Green 514), Texas Red, Texas Red-X, Spectrum Red™, Spectrum Green™, cyanine dyes (e.g. Cy-3™, Cy-5™, Cy-3.5™, Cy-5.5™), Alexa Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), IRDyes (e.g., IRD40, IRD 700, IRD 800), and the like. For more examples of suitable fluorescent dyes and methods for coupling fluorescent dyes to other chemical entities see, for example, *The Handbook of Fluorescent Probes and Research Products,* 9th Ed., Molecular Probes, Inc., Eugene, Oreg.

The term "luminescence" or "luminescent" means any process of light emission including fluorescence, phosphorescence, scintillation, chemiluminescence, and bioluminescence.

The term "chemiluminescence," "chemiluminescent," or "chemiluminescent substrate" refers to a chemical that produces light as a result of a chemical reaction. Commonly used chemiluminescent substrates include, but are not limited to, luminol (5-amino-2,3-dihydro-1, 4-phthalazinedione), lophine (2, 4, 5-triphenylimidazole), lucigenin (bis-N-methylacridinium), other acridinium esters, luciferin-luciferase, and thioxene derivatives. For example, in the art-recognized ECL™ detection system of Amersham, an acridinium substrate is oxidized by horse radish peroxidase to produce acridinium esters, which react with excess peroxide at an alkaline pH to produce visible chemiluminescence at 430 nm.

In certain embodiments, the label comprises an affinity tag. The term "affinity tag" includes any moiety that takes part in an interaction (e.g., antigen and antibody, enzyme and substrate, receptor and ligand) that facilitates capture and/or purification of the molecule. Examples of such affinity moieties include small chemical compounds (such as biotin and derivatives thereof), short amino acid sequences (e.g., 2 to 20 amino acids in length, 4 to 12 amino acids in length), such as the $(His)_6$ tag, $(Leu)_3$ tag, or FLAG tag. The affinity moiety may also be a fluorous tag, which is a fluorinated alkyl group (e.g., perfluoroalkyl) that allows for recovery of the molecule via its interaction with a fluorous phase (e.g., a fluorous liquid phase, a fluorous solid phase). Other affinity moieties are well known in the art.

In certain embodiments, the affinity moiety is selected from the group consisting of (His)$_6$ tag, (His)$_4$ tag, (His)$_3$ tag, (His)$_2$ tag, (Leu)$_4$ tag, (Leu)$_3$ tag, (Leu)$_2$ tag, HA tag, FLAG tag, VSV-G tag, HSV tag, V5 tag, biotin and derivatives thereof, carbohydrates, and glycans. In certain embodiments, the affinity moiety is $C_4$-$C_{20}$ perfluoroalkyl (e.g., $C_6$-$C_{12}$ perfluoroalkyl, $C_6$-$C_8$ perfluoroalkyl, $C_4$ perfluoroalkyl, $C_5$ perfluoroalkyl, $C_6$ perfluoroalkyl, $C_7$ perfluoroalkyl, $C_8$ perfluoroalkyl, $C_9$ perfluoroalkyl, $C_{10}$ perfluoroalkyl, $C_{11}$ perfluoroalkyl, $C_{12}$ perfluoroalkyl, $C_{13}$ perfluoroalkyl, $C_{14}$ perfluoroalkyl, $C_{15}$ perfluoroalkyl, $C_{16}$ perfluoroalkyl, $C_{17}$ perfluoroalkyl, $C_{18}$ perfluoralkyl, $C_{19}$ perfluoroalkyl, or $C_{20}$ perfluoroalkyl). In certain embodiments, the affinity moiety is biotin. In certain embodiments, the affinity moiety is $C_8$ perfluoralkyl.

A tag may include a divalent linker. In certain embodiments, the divalent linker is an optionally substituted $C_{1-60}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NRL$^{3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—. In certain embodiments, the divalent linker is a PEG moiety (e.g., -(PEG)$_{1-20}$-, -(PEG)$_{1-12}$-, -(PEG)$_{1-6}$-, -(PEG)$_{6-12}$-). In certain embodiments, the divalent linker is —(CH$_2$)$_{1-40}$— (e.g., —(CH$_2$)$_{1-20}$—, —(CH$_2$)$_{1-10}$—). In certain embodiments, the divalent linker is a combination of one or more PEG moieties (e.g., independently, -(PEG)$_{1-20}$-, -(PEG)$_{1-12}$-, -(PEG)$_{1-6}$-, -(PEG)$_{6-12}$-) and one or more —(CH$_2$)$_{1-40}$— moieties (e.g., independently, —(CH$_2$)$_{1-20}$—, —(CH$_2$)$_{1-10}$—), optionally wherein one or more methylene units of the PEG moieties and/or of the —(CH$_2$)$_{1-40}$— moieties are independently replaced with —C(=O)NH— or —NHC(=O)—.

Formula (I) may include one or more instances of substituent R$^a$. When Formula (I) includes two or more instances of R$^a$, any two instances of R$^a$ may be the same or different from each other. In certain embodiments, at least one instance of R$^a$ is H. In certain embodiments, each instance of R$^a$ is H. In certain embodiments, at least one instance of R$^a$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group (e.g., Bn, Boc, Cbz, Fmoc, trifluoroacetyl, triphenylmethyl, acetyl, or Ts) when attached to a nitrogen atom, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom, or two instances of R$^a$ are joined to form a substituted or unsubstituted, heterocyclic ring, or substituted or unsubstituted, heteroaryl ring.

Formula (I) includes substituent R$^{A2}$ at the 1-position of the 2,7-diazaindolyl ring. In certain embodiments, R$^A$ is H. In certain embodiments, R$^A$ is substituted or unsubstituted acyl. In certain embodiments, R$^A$ is —C(=O)R$^a$, optionally wherein R$^a$ is substituted or unsubstituted $C_{1-6}$ alkyl (e.g., Me) or substituted or unsubstituted $C_{2-6}$ alkenyl. In certain embodiments, R$^{A2}$ is —C(=O)R$^a$, wherein R$^a$ is substituted or unsubstituted vinyl. In certain embodiments, R$^{A2}$ is —C(=O)CH=CH$_2$. In certain embodiments, R$^{A2}$ is —C(=O)OR$^a$, optionally wherein R$^a$ is H, substituted or unsubstituted $C_{1-6}$ alkyl (e.g., Me), or an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, R$^{A2}$ is —C(=O)N(R$^a$)$_2$, optionally wherein each instance of R$^a$ is independently H, substituted or unsubstituted $C_{1-6}$ alkyl (e.g., Me), or a nitrogen protecting group (e.g., Bn, Boc, Cbz, Fmoc, trifluoroacetyl, triphenylmethyl, acetyl, or Ts). In certain embodiments, R$^{A2}$ is substituted or unsubstituted alkyl (e.g., substituted or unsubstituted $C_{1-6}$ alkyl). In certain embodiments, R$^{A2}$ is Me. In certain embodiments, R$^{A2}$ is Et. In certain embodiments, R$^{A2}$ is n-Pr. In certain embodiments, R$^{A2}$ is i-Pr. In certain embodiments, R$^{A2}$ is Bu (e.g., n-Bu, i-Bu, sec-Bu, or t-Bu). In certain embodiments, R$^{A2}$ is unsubstituted pentyl (e.g., unsubstituted n-pentyl, unsubstituted t-pentyl, unsubstituted neopentyl, unsubstituted isopentyl, unsubstituted sec-pentyl, or unsubstituted 3-pentyl). In certain embodiments, R$^{A2}$ is sec-Bu, t-Bu, or unsubstituted 3-pentyl. In certain embodiments, R$^{A2}$ is —CF$_3$, Bn, perfluoroethyl, perfluoropropyl, perfluorobutyl, or perfluoropentyl. In certain embodiments, R$^{A2}$ is —CH$_2$C(=O)—NH—N=C(R$^a$)$_2$. In certain embodiments, R$^A$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, R$^{A2}$ is substituted or unsubstituted cyclopropyl. In certain embodiments, R$^{A2}$ is unsubstituted cyclopropyl. In certain embodiments, R$^{A2}$ is substituted or unsubstituted cyclobutyl. In certain embodiments, R$^{A2}$ is substituted or unsubstituted cyclopentyl. In certain embodiments, R$^{A2}$ is unsubstituted cyclopropyl, unsubstituted cyclobutyl, or unsubstituted cyclopentyl. In certain embodiments, R$^{A2}$ is substituted or unsubstituted heterocyclyl (e.g., substituted or unsubstituted, 3- to 7-membed, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, R$^{A2}$ is substituted or unsubstituted tetrahydropyranyl. In certain embodiments, R$^{A2}$ is of the formula:

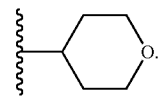

In certain embodiments, R$^{A2}$ is of the formula:

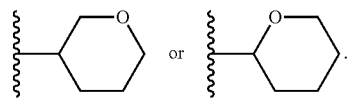

In certain embodiments, R$^{A2}$ is substituted or unsubstituted oxetanyl, substituted or unsubstituted tetrahydrofuranyl, substituted or unsubstituted pyrrolidinyl, substituted or unsubstituted piperidinyl, substituted or unsubstituted morpholinyl, or substituted or unsubstituted piperazinyl. In certain embodiments, $R^{A2}$ is of the formula:

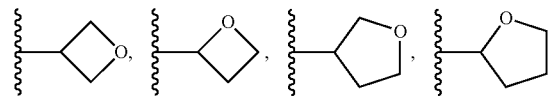

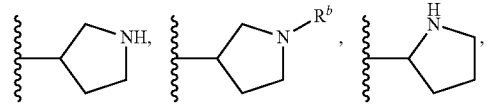

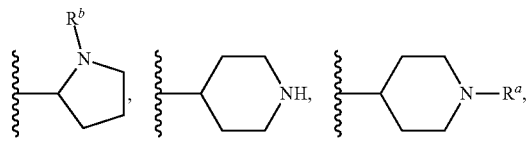

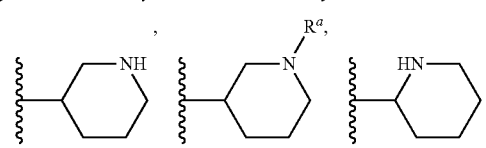

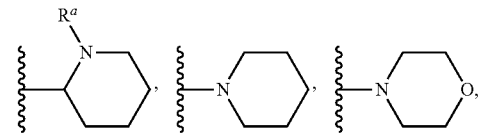

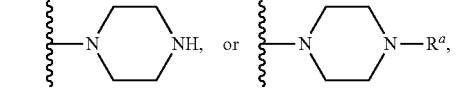

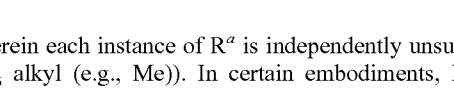

wherein each instance of $R^a$ is independently unsubstituted $C_{1-6}$ alkyl (e.g., Me)). In certain embodiments, $R^{A2}$ is a nitrogen protecting group (e.g., Bn, Boc, Cbz, Fmoc, trifluoroacetyl, triphenylmethyl, acetyl, or Ts). In certain embodiments, $R^{A2}$ is Boc. In certain embodiments, $R^{A2}$ is a warhead.

Any one of Formulae (I) and (II) may include one or more warheads, which are independently selected from the group consisting of:

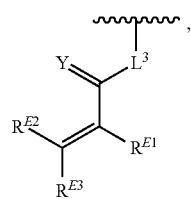 (i-1)

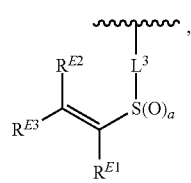 (i-2)

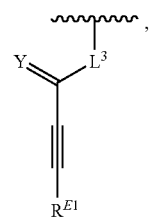 (i-3)

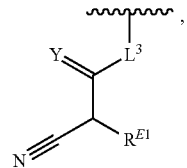 (i-4)

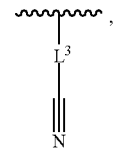 (i-5)

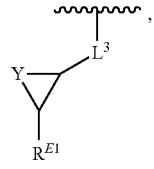 (i-6)

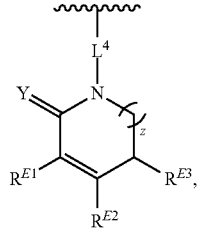 (i-7)

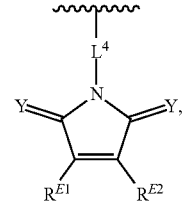 (i-8)

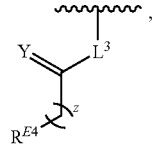 (i-9)

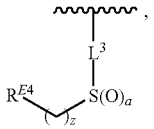 (i-10)

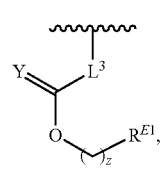 (i-11)
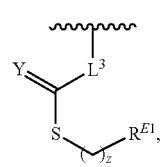 (i-12)
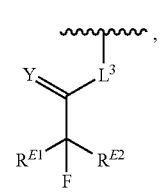 (i-13)
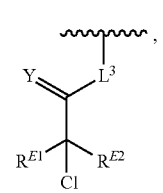 (i-14)
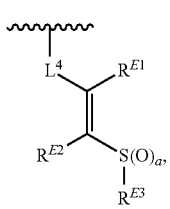 (i-15)
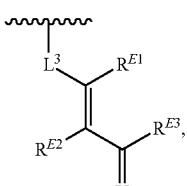 (i-16)
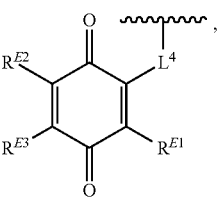 (i-17)
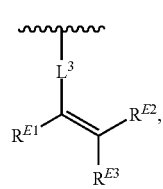 (i-18)
 (i-19)
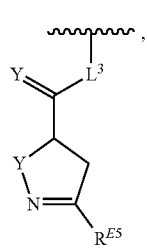 (i-20)
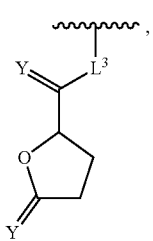 (i-21)
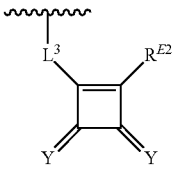 (i-22)
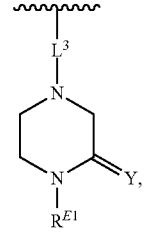 (i-23)
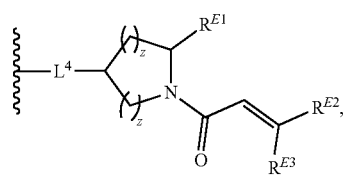 (i-24)
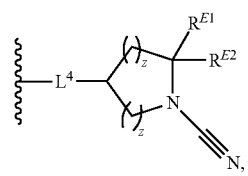 (i-25)

(i-26)
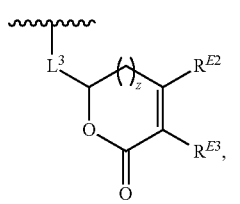

(i-27)
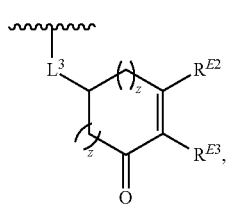

(i-28)
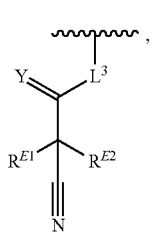

(i-29)
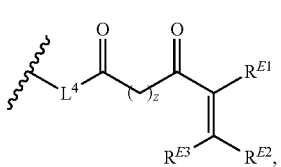

(i-30)
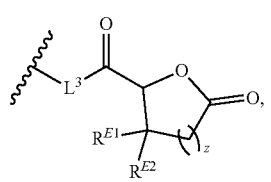

(i-31)
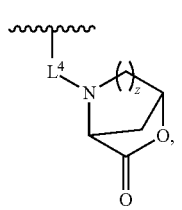

(i-32)
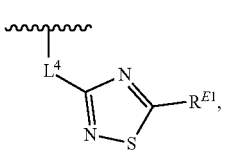

(i-33)
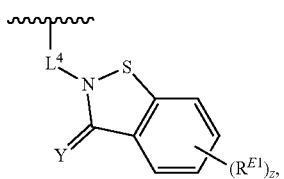

(i-34)
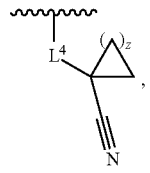

(i-35)
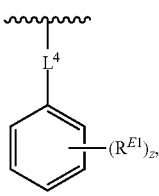

(i-36)
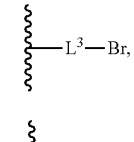

(i-37)
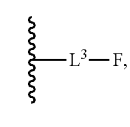

(i-38)
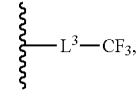

(i-39)
$\xi\text{—}L^3\text{—}CF_3$, (i-40)
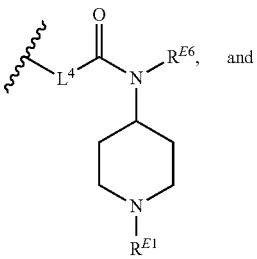

(i-41)
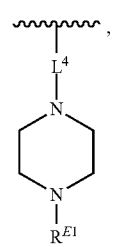

wherein:

$L^3$ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NRL$^{3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted C$_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

L$^4$ is a bond or an optionally substituted, branched or unbranched C$_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^E$, —N(R$^{EE}$)$_2$, —Si(R$^{EE}$)$_3$, or —SR$^{EE}$, wherein each occurrence of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, substituted or unsubstituted C$_{1-6}$ alkyl, or a nitrogen protecting group;

each instance of Y is independently O, S, or NR$^{E7}$, wherein R$^{E7}$ is hydrogen, substituted or unsubstituted C$_{1-6}$ alkyl, or a nitrogen protecting group;

a is 1 or 2; and each instance of z is independently 0, 1, 2, 3, 4, 5, or 6, as valency permits.

In certain embodiments, any one of Formulae (I) and (II) does not include a warhead. In certain embodiments, any one of Formulae (I) and (II) includes one warhead. In certain embodiments, any one of Formulae (I) and (II) includes two or more warheads. When Formula (I) or (II) includes two or more warheads, any two of the warheads may be the same or different from each other. In certain embodiments, at least one warhead is of Formula (i-1a):

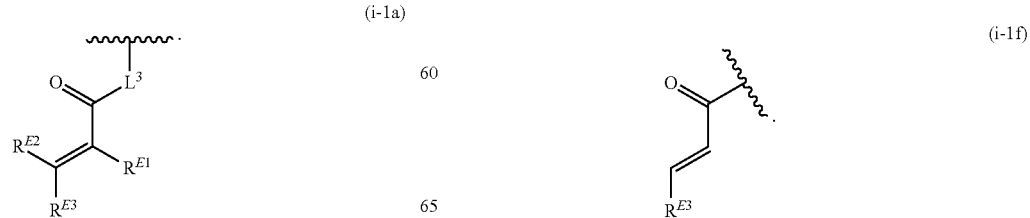

In certain embodiments, at least one warhead is of Formula (i-1b):

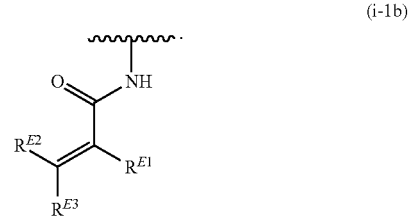

In certain embodiments, at least one warhead is of Formula (i-1c):

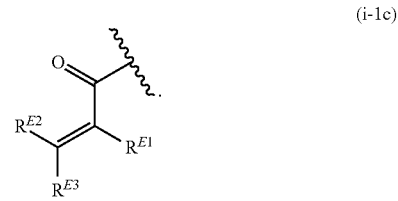

In certain embodiments, at least one warhead is of Formula (i-1d):

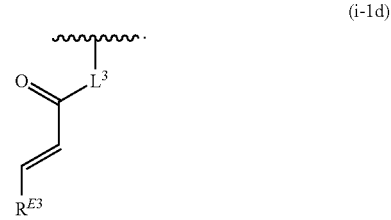

In certain embodiments, at least one warhead is of Formula (i-1e):

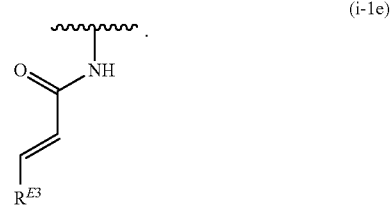

In certain embodiments, at least one warhead is of Formula (i-1f):

In certain embodiments, at least one warhead is of Formula (i-1g):

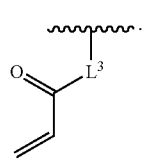

In certain embodiments, at least one warhead is

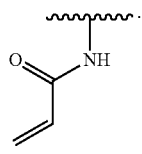

In certain embodiments, at least one warhead is

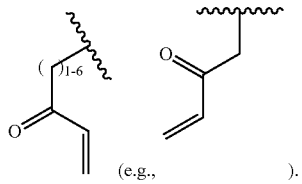

(e.g., ).

In certain embodiments, at least one warhead is

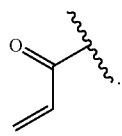

In certain embodiments, at least one warhead is

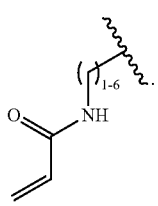

In certain embodiments, at least one warhead is of Formula (i-1h):

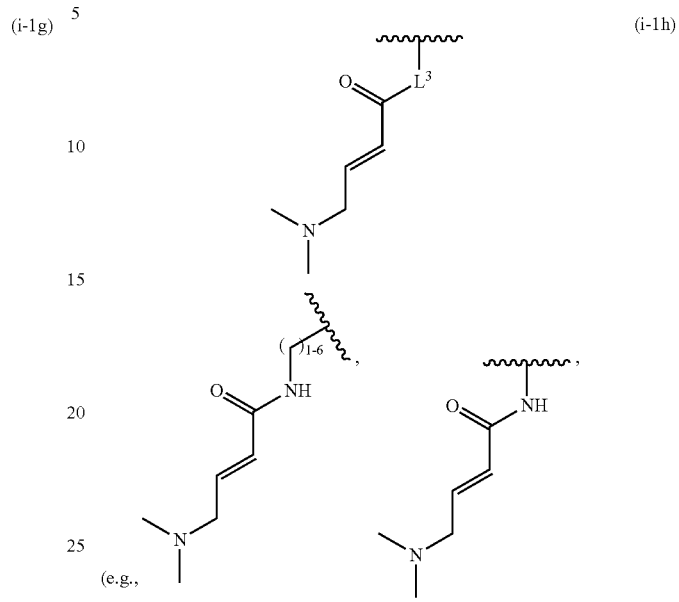

(e.g., , or

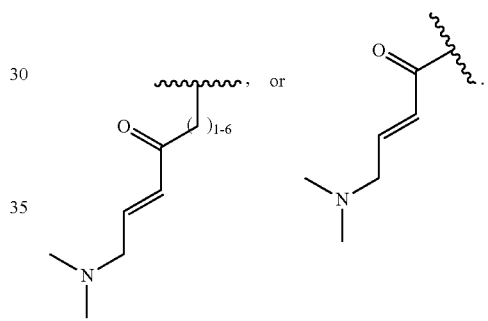

).

In certain embodiments, at least one warhead is

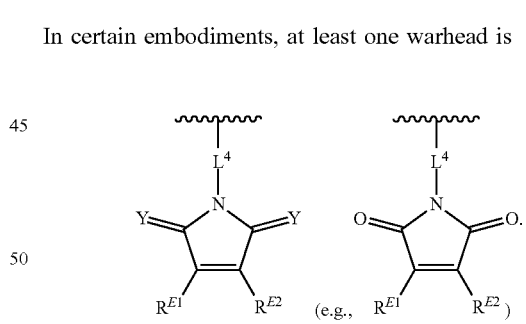

(e.g., )

In certain embodiments, at least one warhead is

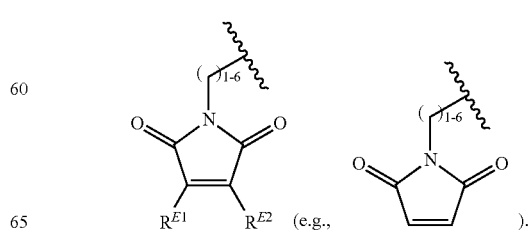

(e.g., ).

In certain embodiments, at least one warhead is

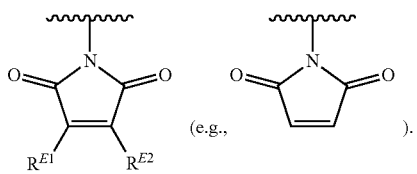

(e.g., ).

In certain embodiments, $R^{42}$ is a tag (e.g., a biotin derivative, radiometric lable, or fluorophore).

Formula (I) includes substituent $R^{43}$ at the 3-position of the 2,7-diazaindolyl ring. In certain embodiments, $R^{43}$ is H. In certain embodiments, $R^{43}$ is halogen (e.g., F, Cl, Br, or I). In certain embodiments, $R^3$ is substituted or unsubstituted $C_{1-6}$ alkyl. In certain embodiments, $R^{43}$ is Me. In certain embodiments, $R^{43}$ is —$CF_3$, Bn, Et, perfluoroethyl, Pr, perfluoropropyl, Bu, or perfluorobutyl. In certain embodiments, $R^{43}$ is —$OR^a$, optionally wherein $R^a$ is H, substituted or unsubstituted $C_{1-6}$ alkyl (e.g., Me), substituted or unsubstituted acyl, or an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, $R^{43}$ is —OC(=O)$R^a$, optionally wherein $R^a$ is H, substituted or unsubstituted $C_{1-6}$ alkyl (e.g., Me), or substituted or unsubstituted $C_{2-6}$ alkenyl (e.g., substituted or unsubstituted vinyl). In certain embodiments, $R^{43}$ is —OC(=O)CH=$CH_2$. In certain embodiments, $R^{43}$ is —$N(R^a)_2$, optionally wherein each instance of $R^a$ is independently H, substituted or unsubstituted $C_{1-6}$ alkyl (e.g., Me), substituted or unsubstituted acyl, or a nitrogen protecting group (e.g., Bn, Boc, Cbz, Fmoc, trifluoroacetyl, triphenylmethyl, acetyl, or Ts). In certain embodiments, $R^{43}$ is —$N(R^a)$C(=O)$R^a$, optionally wherein each instance of $R^a$ is independently H, substituted or unsubstituted $C_{1-6}$ alkyl (e.g., Me), or substituted or unsubstituted $C_{2-6}$ alkenyl (e.g., substituted or unsubstituted vinyl). In certain embodiments, $R^{43}$ is —NHC(=O)CH=$CH_2$. In certain embodiments, $R^{43}$ is a warhead.

Formula (I) includes substituent $R^{44}$ on a nitrogen atom. In certain embodiments, $R^{44}$ is H. In certain embodiments, $R^{44}$ is substituted or unsubstituted $C_{1-6}$ alkyl. In certain embodiments, $R^{44}$ is Me. In certain embodiments, $R^{44}$ is —$CF_3$, Bn, Et, perfluoroethyl, Pr, perfluoropropyl, Bu, or perfluorobutyl. In certain embodiments, $R^{44}$ is a nitrogen protecting group (e.g., Bn, Boc, Cbz, Fmoc, trifluoroacetyl, triphenylmethyl, acetyl, or Ts).

Formula (I) includes substituent $R^{45}$. In certain embodiments, $R^{45}$ is of the formula:

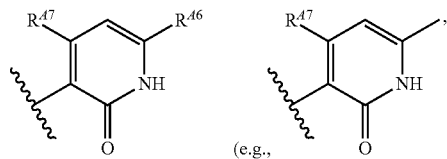

(e.g.,

Wherein $R^{47}$ is Et, Pr, or Bu). In certain embodiments, $R^{45}$ is of the formula:

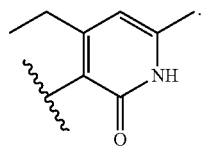 [SMILES: *c1c(CC)cc(C)[nH]c1=O]

In certain embodiments, $R^{45}$ is of the formula:

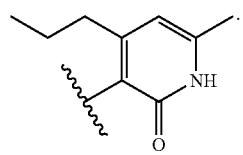 [SMILES: *c1c(CCC)cc(C)[nH]c1=O]

In certain embodiments, $R^{46}$ is H. In certain embodiments, $R^{46}$ is halogen (e.g., F, Cl, Br, or I). In certain embodiments, $R^{46}$ is substituted or unsubstituted $C_{1-6}$ alkyl. In certain embodiments, $R^{46}$ is Me. In certain embodiments, $R^{46}$ is substituted methyl (e.g., —$CF_3$ or Bn). In certain embodiments, $R^{46}$ is Et, substituted ethyl (e.g., perfluoroethyl), Pr, substituted propyl (e.g., perfluoropropyl), Bu, or substituted butyl (e.g., perfluorobutyl). In certain embodiments, $R^{46}$ is —$OR^a$ (e.g., —OH or —O(substituted or unsubstituted $C_{1-6}$ alkyl) (e.g., —OMe)). In certain embodiments, $R^{46}$ is —$N(R^a)_2$, optionally wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{46}$ is —$NH_2$, —NHMe, or —$N(Me)_2$. In certain embodiments, $R^{47}$ is H. In certain embodiments, $R^{47}$ is halogen (e.g., F, Cl, Br, or I). In certain embodiments, $R^{47}$ is substituted or unsubstituted $C_{2-6}$ alkyl. In certain embodiments, $R^{47}$ is Et. In certain embodiments, $R^{47}$ is substituted ethyl (e.g., perfluoroethyl). In certain embodiments, $R^{47}$ is n-Pr. In certain embodiments, $R^{47}$ is i-Pr. In certain embodiments, $R^{47}$ is substituted propyl (e.g., perfluoropropyl). In certain embodiments, $R^{47}$ is Bu or unsubstituted pentyl. In certain embodiments, $R^{47}$ is substituted butyl (e.g., perfluorobutyl) or substituted pentyl (e.g., perfluoropentyl). In certain embodiments, $R^{47}$ is substituted or unsubstituted, 3- to 7-membed, monocyclic carbocyclyl comprising 0, 1, or 2 double bonds in the carbocyclic ring system. In certain embodiments, $R^{47}$ is substituted or unsubstituted cyclopropyl, substituted or unsubstituted cyclobutyl, or substituted or unsubstituted cyclopentyl. In certain embodiments, $R^{47}$ is —$OR^a$ (e.g., —OH or —O(substituted or unsubstituted $C_{1-6}$ alkyl) (e.g., —OMe)). In certain embodiments, $R^{47}$ is —$N(R^a)_2$, optionally wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{47}$ is —$NH_2$, —NHMe, —NHEt, —$N(Me)_2$, or —$N(Et)_2$. In certain embodiments, $R^{47}$ is substituted or unsubstituted cyclopropyl or —$N(R^a)_2$, wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts).

In certain embodiments, $R^{A5}$ is of the formula:

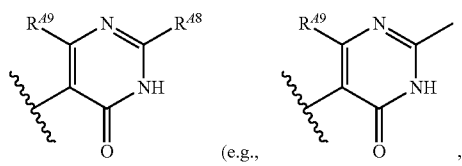

(e.g., )

wherein $R^{A9}$ is Me, Et, Pr, or Bu). The moiety of the formula:

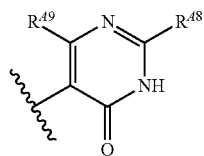

also includes its tautomeric form OH

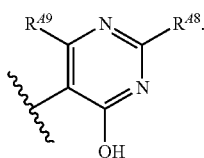

In certain embodiments, $R^{A5}$ is of the formula:

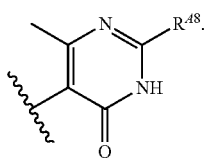

In certain embodiments, $R^{A5}$ is of the formula:

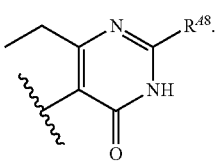

In certain embodiments, $R^{A5}$ is of the formula:

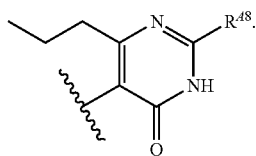

In certain embodiments, $R^{A8}$ is H. In certain embodiments, $R^{A8}$ is halogen (e.g., F, Cl, Br, or I). In certain embodiments, $R^{A8}$ is substituted or unsubstituted $C_{1-6}$ alkyl. In certain embodiments, $R^{A8}$ is Me. In certain embodiments, $R^{A8}$ is substituted methyl (e.g., —$CF_3$ or Bn). In certain embodiments, $R^{A8}$ is Et, substituted ethyl (e.g., perfluoroethyl), Pr, substituted propyl (e.g., perfluoropropyl), Bu, or substituted butyl (e.g., perfluorobutyl). In certain embodiments, $R^{A8}$ is —$OR^a$ (e.g., —OH or —O(substituted or unsubstituted $C_{1-6}$ alkyl) (e.g., —OMe)). In certain embodiments, $R^{A8}$ is —$N(R^a)_2$, optionally wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{A8}$ is —$NH_2$, —NHMe, or —$N(Me)_2$. In certain embodiments, $R^{A9}$ is H. In certain embodiments, $R^{A9}$ is halogen (e.g., F, Cl, Br, or I). In certain embodiments, $R^{A9}$ is substituted or unsubstituted $C_{1-6}$ alkyl. In certain embodiments, $R^{A9}$ is Me. In certain embodiments, $R^{A9}$ is substituted methyl (e.g., —$CF_3$ or Bn). In certain embodiments, $R^{A9}$ is Et. In certain embodiments, $R^{A9}$ is substituted ethyl (e.g., perfluoroethyl). In certain embodiments, $R^{A9}$ is n-Pr. In certain embodiments, $R^{A9}$ is i-Pr. In certain embodiments, $R^{A9}$ is substituted propyl (e.g., perfluoropropyl). In certain embodiments, $R^{A9}$ is Bu or unsubstituted pentyl. In certain embodiments, $R^{A9}$ is substituted butyl (e.g., perfluorobutyl) or substituted pentyl (e.g., perfluoropentyl). In certain embodiments, $R^{A9}$ is substituted or unsubstituted, 3- to 7-membed, monocyclic carbocyclyl comprising 0, 1, or 2 double bonds in the carbocyclic ring system. In certain embodiments, $R^{A9}$ is substituted or unsubstituted cyclopropyl, substituted or unsubstituted cyclobutyl, or substituted or unsubstituted cyclopentyl. In certain embodiments, $R^{A9}$ is —$OR^a$ (e.g., —OH or —O(substituted or unsubstituted $C_{1-6}$ alkyl) (e.g., —OMe)). In certain embodiments, $R^{A9}$ is —$N(R^a)_2$, optionally wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{A9}$ is —$NH_2$, —NHMe, —NHEt, —$N(Me)_2$, or —$N(Et)_2$. In certain embodiments, $R^{A9}$ is substituted or unsubstituted cyclopropyl, —$OR^a$, or —$N(R^a)_2$, wherein each instance of $R^a$ is independently hydrogen, substituted or unsubstituted $C_{1-6}$ alkyl, an oxygen protecting group when attached to an oxygen atom, or a nitrogen protecting group when attached to a nitrogen atom.

In certain embodiments, $R^{A5}$ is of the formula:

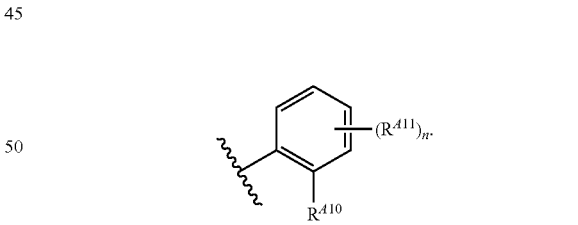

In certain embodiments, $R^{A5}$ is of the formula:

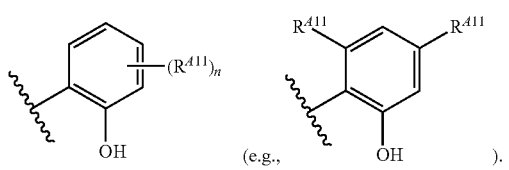

(e.g., ).

In certain embodiments, $R^{A5}$ is of the formula:

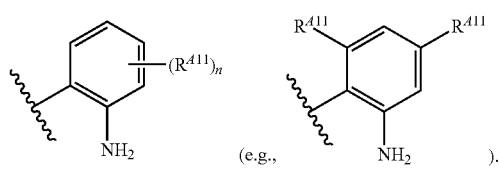

(e.g., ).

In certain embodiments, $R^{A5}$ is of the formula:

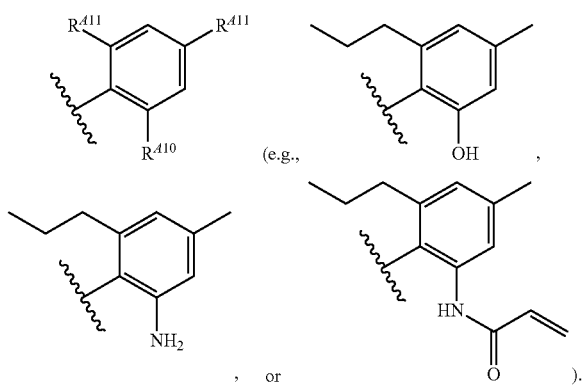

(e.g., , or ).

In certain embodiments, $R^{A5}$ is of the formula:

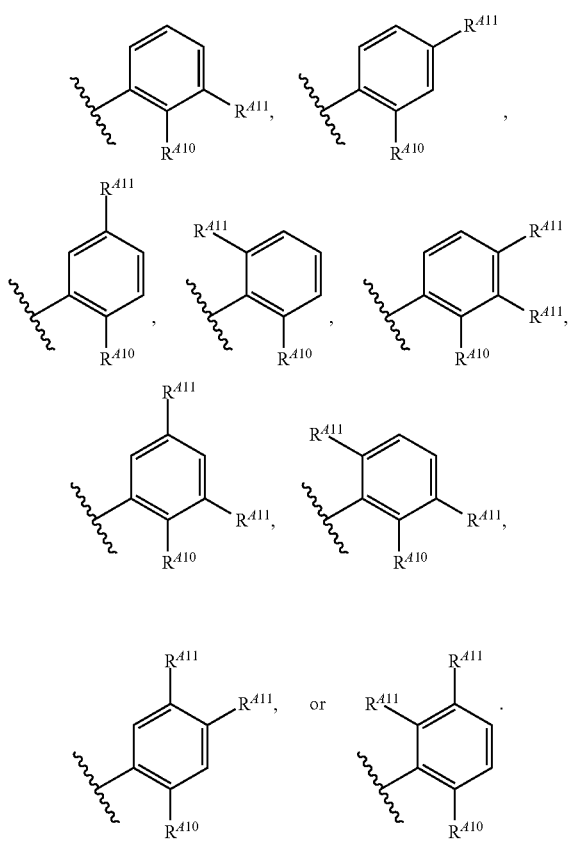

, or .

In certain embodiments, $R^{A5}$ is of the formula:

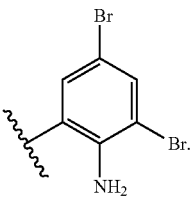 [SMILES: *c1cc(Br)cc(Br)c1N]

In certain embodiments, $R^{A10}$ is —$OR^a$ (e.g., —OH). In certain embodiments, $R^{A10}$ is —$N(R^a)_2$. In certain embodiments, $R^{A10}$ is —$NH_2$. In certain embodiments, $R^{A10}$ is —$NHR^a$, wherein $R^a$ is substituted or unsubstituted $C_{1-6}$ alkyl or a nitrogen protecting group (e.g., Bn, Boc, Cbz, Fmoc, trifluoroacetyl, triphenylmethyl, acetyl, or Ts). In certain embodiments, $R^{A10}$ is a warhead. In certain embodiments, $R^{A10}$ is —$NHC(=O)R^a$, optionally wherein $R^a$ is substituted or unsubstituted vinyl. In certain embodiments, $R^{A10}$ is —$NHC(=O)CH=CH_2$. When Formula (I) includes two or more instances of $R^{A11}$, any two instances of $R^{A11}$ may be the same or different from each other. In certain embodiments, at least one instance of $R^{A11}$ is halogen. In certain embodiments, at least one instance of $R^{A11}$ is Br. In certain embodiments, at least one instance of $R^{A11}$ is F, Cl, or I. In certain embodiments, at least one instance of $R^{A11}$ is substituted or unsubstituted $C_{1-6}$ alkyl. In certain embodiments, at least one instance of $R^{A11}$ is Me. In certain embodiments, at least one instance of $R^{A11}$ is substituted methyl (e.g., —$CF_3$ or Bn). In certain embodiments, at least one instance of $R^{A11}$ is Et. In certain embodiments, at least one instance of $R^{A11}$ is substituted ethyl (e.g., perfluoroethyl). In certain embodiments, at least one instance of $R^{A11}$ is n-Pr. In certain embodiments, at least one instance of $R^{A11}$ is i-Pr. In certain embodiments, at least one instance of $R^{A11}$ is substituted propyl (e.g., perfluoropropyl). In certain embodiments, at least one instance of $R^{A11}$ is Me, Et, or n-Pr. In certain embodiments, at least one instance of $R^{A11}$ is Bu or unsubstituted pentyl. In certain embodiments, at least one instance of $R^{A11}$ is substituted butyl (e.g., perfluorobutyl) or substituted pentyl (e.g., perfluoropentyl). In certain embodiments, at least one instance of $R^{A11}$ is substituted or unsubstituted, 3- to 7-membed, monocyclic carbocyclyl comprising 0, 1, or 2 double bonds in the carbocyclic ring system. In certain embodiments, at least one instance of $R^{A11}$ is substituted or unsubstituted cyclopropyl, substituted or unsubstituted cyclobutyl, or substituted or unsubstituted cyclopentyl. In certain embodiments, at least one instance of $R^{A11}$ is —$OR^a$ (e.g., —OH or —O(substituted or unsubstituted $C_{1-6}$ alkyl) (e.g., —OMe)). In certain embodiments, at least one instance of $R^{A11}$ is —$N(R^a)_2$, optionally wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, at least one instance of $R^{A11}$ is —$NH_2$, —NHMe, —NHEt, —$N(Me)_2$, or —$N(Et)_2$. In certain embodiments, at least one instance of $R^{A11}$ is substituted or unsubstituted $C_{1-6}$ alkyl, substituted or unsubstituted cyclopropyl, —$OR^a$, or —$N(R^a)_2$, wherein each instance of $R^a$ is independently hydrogen, substituted or unsubstituted $C_{1-6}$ alkyl, an oxygen protecting group when attached to an oxygen atom, or a nitrogen protecting group when attached to a nitrogen atom. In certain embodiments, n is 0. In certain embodiments, n is 1. In certain embodiments, n is 2. In certain embodiments, n is 3. In certain embodiments, n is 4.

In certain embodiments, $R^{A5}$ is of the formula:

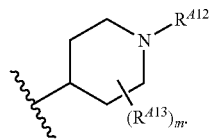

In certain embodiments, $R^{A5}$ is of the formula:

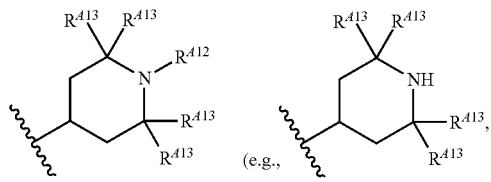

such as

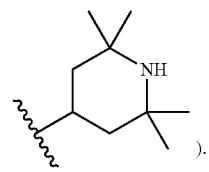 [SMILES: *C1CC(C)(C)NC(C)(C)C1]

In certain embodiments, $R^{A12}$ is H. In certain embodiments, $R^{A12}$ is substituted or unsubstituted $C_{1-6}$ alkyl. In certain embodiments, $R^{A12}$ is Me. In certain embodiments, $R^{A12}$ is —$CF_3$, Bn, Et, perfluoroethyl, Pr, perfluoropropyl, Bu, or perfluorobutyl. In certain embodiments, $R^{A12}$ is a nitrogen protecting group (e.g., Bn, Boc, Cbz, Fmoc, trifluoroacetyl, triphenylmethyl, acetyl, or Ts). In certain embodiments, $R^{A12}$ is a warhead. When Formula (I) includes two or more instances of $R^{A13}$, any two instances of $R^{A13}$ may be the same or different from each other. In certain embodiments, at least one instance of $R^{A13}$ is halogen (e.g., F, Cl, Br, or I). In certain embodiments, at least one instance of $R^{13}$ is substituted or unsubstituted $C_{1-6}$ alkyl. In certain embodiments, at least one instance of $R^{A13}$ is Me. In certain embodiments, at least one instance of $R^{A13}$ is substituted methyl (e.g., —$CF_3$ or Bn). In certain embodiments, at least one instance of $R^{A13}$ is Et. In certain embodiments, at least one instance of $R^{A13}$ is substituted ethyl (e.g., perfluoroethyl). In certain embodiments, at least one instance of $R^{A13}$ is n-Pr. In certain embodiments, at least one instance of $R^{A13}$ is i-Pr. In certain embodiments, at least one instance of $R^{A13}$ is substituted propyl (e.g., perfluoropropyl). In certain embodiments, at least one instance of $R^{A13}$ is Me, Et, or n-Pr. In certain embodiments, at least one instance of $R^{A13}$ is Bu or unsubstituted pentyl. In certain embodiments, at least one instance of $R^{A13}$ is substituted butyl (e.g., perfluorobutyl) or substituted pentyl (e.g., perfluoropentyl). In certain embodiments, at least one instance of $R^{A13}$ is substituted or unsubstituted, 3- to 7-membed, monocyclic carbocyclyl comprising 0, 1, or 2 double bonds in the carbocyclic ring system. In certain embodiments, at least one instance of $R^{A13}$ is substituted or unsubstituted cyclopropyl, substituted or unsubstituted cyclobutyl, or substituted or unsubstituted cyclopentyl. In certain embodiments, at least one instance of $R^{A13}$ is —$OR^a$ (e.g., —OH or —O(substituted or unsubstituted $C_{1-6}$ alkyl) (e.g., —OMe)). In certain embodiments, at least one instance of $R^{A13}$ is —$N(R^a)_2$, optionally wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, at least one instance of $R^{A13}$ is —$NH_2$, —NHMe, —NHEt, —$N(Me)_2$, or —$N(Et)_2$. In certain embodiments, at least one instance of $R^{A13}$ is halogen, substituted or unsubstituted cyclopropyl, —$OR^a$, or —$N(R^a)_2$, wherein each instance of $R^a$ is independently hydrogen, substituted or unsubstituted $C_{1-6}$ alkyl, an oxygen protecting group when attached to an oxygen atom, or a nitrogen protecting group when attached to a nitrogen atom. In certain embodiments, m is 0. In certain embodiments, m is 1. In certain embodiments, m is 2. In certain embodiments, m is 3, 4, 5, 6, 7, or 8. In certain embodiments, m is 9.

Formula (I) includes substituent $R^{A5}$. In certain embodiments, $R^{A5}$ is of the formula:

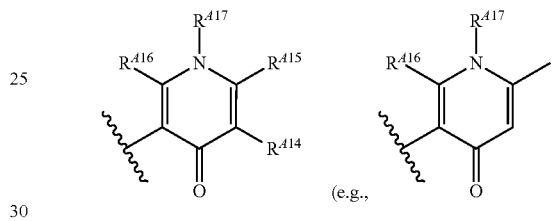

optionally wherein $R^{A16}$ is Et, Pr, or Bu). In certain embodiments, $R^{A5}$ is of the formula:

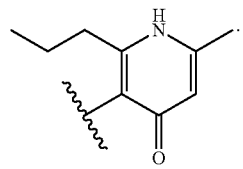 [SMILES: *c1c(CCC)[nH]c(C)cc1=O]

In certain embodiments, $R^{A5}$ is of the formula:

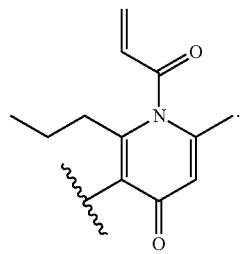 [SMILES: *c1c(CCC)n(C(=O)C=C)c(C)cc1=O]

In certain embodiments, $R^{A14}$ is H. In certain embodiments, $R^{A14}$ is halogen (e.g., F, Cl, Br, or I). In certain embodiments, $R^{A14}$ is substituted or unsubstituted $C_{1-6}$ alkyl. In certain embodiments, $R^{A14}$ is Me. In certain embodiments, $R^{A14}$ is substituted methyl (e.g., —$CF_3$ or Bn). In certain embodiments, $R^{A14}$ is Et, substituted ethyl (e.g., perfluoroethyl), Pr, substituted propyl (e.g., perfluoropropyl), Bu, or substituted butyl (e.g., perfluorobutyl). In certain embodiments, $R^{A14}$ is —$OR^a$ (e.g., —OH or —O(substituted or unsubstituted $C_{1-6}$ alkyl) (e.g., —OMe)). In certain embodiments, $R^{A14}$ is —$N(R^a)_2$, optionally wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{A14}$ is —$NH_2$, —NHMe, or —$N(Me)_2$. In certain embodiments, $R^{A15}$ is H. In certain embodiments, $R^{A15}$ is halogen (e.g., F, Cl, Br, or I). In certain embodiments, $R^{A15}$ is substituted or unsubstituted $C_{1-6}$ alkyl. In certain embodiments, $R^{A15}$ is Me. In certain embodiments, $R^{A15}$ is substituted methyl (e.g., —$CF_3$ or Bn). In certain embodiments, $R^{A15}$ is Et, substituted ethyl (e.g., perfluoroethyl), Pr, substituted propyl (e.g., perfluoropropyl), Bu, or substituted butyl (e.g., perfluorobutyl). In certain embodiments, $R^{A15}$ is —$OR^a$ (e.g., —OH or —O(substituted or unsubstituted $C_{1-6}$ alkyl) (e.g., —OMe)). In certain embodiments, $R^{A15}$ is —$N(R^a)_2$, optionally wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{A15}$ is —$NH_2$, —NHMe, or —$N(Me)_2$. In certain embodiments, $R^{A16}$ is H. In certain embodiments, $R^{A16}$ is halogen (e.g., F, Cl, Br, or I). In certain embodiments, $R^{A16}$ is substituted or unsubstituted $C_{2-6}$ alkyl. In certain embodiments, $R^{A16}$ is Et. In certain embodiments, $R^{A16}$ is substituted ethyl (e.g., perfluoroethyl). In certain embodiments, $R^{A16}$ is n-Pr. In certain embodiments, $R^{A16}$ is i-Pr. In certain embodiments, $R^{A16}$ is substituted propyl (e.g., perfluoropropyl). In certain embodiments, $R^{A16}$ is Bu or unsubstituted pentyl. In certain embodiments, $R^{A16}$ is substituted butyl (e.g., perfluorobutyl) or substituted pentyl (e.g., perfluoropentyl). In certain embodiments, $R^{A16}$ is substituted or unsubstituted, 3- to 7-membed, monocyclic carbocyclyl comprising 0, 1, or 2 double bonds in the carbocyclic ring system. In certain embodiments, $R^{A16}$ is substituted or unsubstituted cyclopropyl, substituted or unsubstituted cyclobutyl, or substituted or unsubstituted cyclopentyl. In certain embodiments, $R^{A16}$ is —$OR^a$ (e.g., —OH or —O(substituted or unsubstituted $C_{1-6}$ alkyl) (e.g., —OMe)). In certain embodiments, $R^{A16}$ is —$N(R^a)_2$, optionally wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{A16}$ is —$NH_2$, —NHMe, —NHEt, —$N(Me)_2$, or —$N(Et)_2$. In certain embodiments, $R^{A16}$ is substituted or unsubstituted cyclopropyl or —$N(R^a)_2$, wherein each instance of $R^a$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{A17}$ is H. In certain embodiments, $R^{A17}$ is substituted or unsubstituted acyl. In certain embodiments, $R^{A17}$ is —C(=O)$R^a$, optionally wherein $R^a$ is substituted or unsubstituted $C_{1-6}$ alkyl (e.g., Me) or substituted or unsubstituted $C_{2-6}$ alkenyl. In certain embodiments, $R^{A17}$ is a warhead. In certain embodiments, $R^{A17}$ is —C(=O)$R^a$, wherein $R^a$ is substituted or unsubstituted vinyl. In certain embodiments, $R^{A17}$ is —C(=O)CH=$CH_2$. In certain embodiments, $R^{A17}$ is —C(=O)$OR^a$, optionally wherein $R^a$ is H, substituted or unsubstituted $C_{1-6}$ alkyl (e.g., Me), or an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, $R^{A17}$ is —C(=O)N$(R^a)_2$, optionally wherein each instance of $R^a$ is independently H, substituted or unsubstituted $C_{1-6}$ alkyl (e.g., Me), or a nitrogen protecting group (e.g., Bn, Boc, Cbz, Fmoc, trifluoroacetyl, triphenylmethyl, acetyl, or Ts). In certain embodiments, $R^{A17}$ is substituted or unsubstituted $C_{1-6}$ alkyl. In certain embodiments, $R^{A17}$ is Me. In certain embodiments, $R^{A17}$ is —$CF_3$, Bn, Et, perfluoroethyl, Pr, perfluoropropyl, Bu, or perfluorobutyl. In certain embodiments, $R^{A17}$ is a nitrogen protecting group (e.g., Bn, Boc, Cbz, Fmoc, trifluoroacetyl, triphenylmethyl, acetyl, or Ts).

In certain embodiments, the compound of Formula (I) is of the formula:

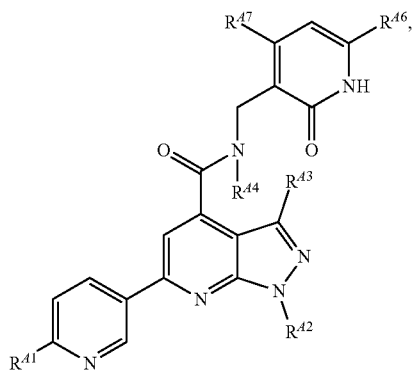

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

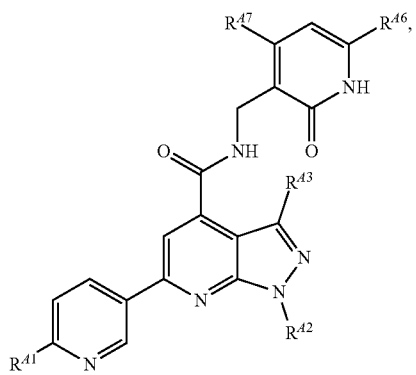

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

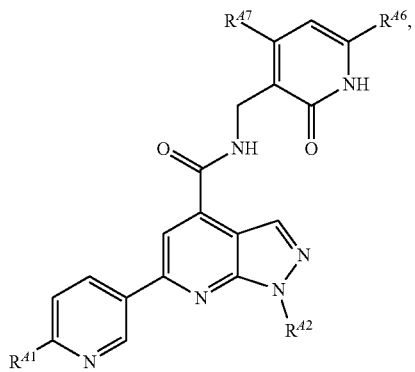

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

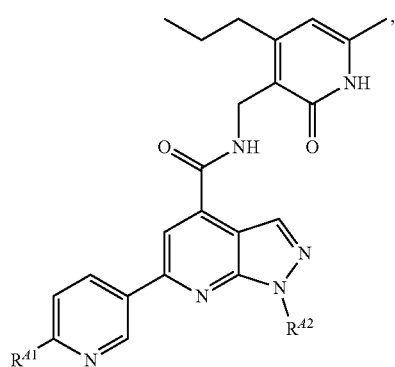

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

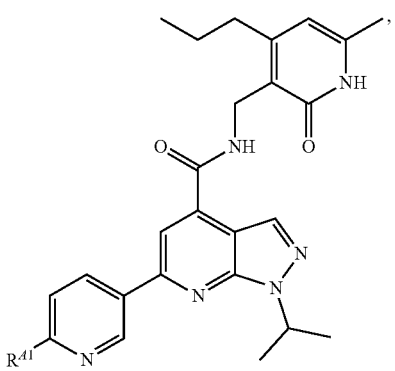

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

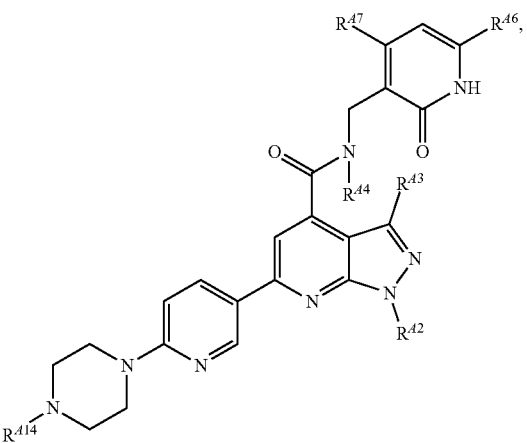

or a pharmaceutically acceptable salt, solvate, hydrate, polymorph, co-crystal, tautomer, stereoisomer, isotopically labeled derivative, or prodrug thereof, wherein R is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group.

In certain embodiments, the compound of Formula (I) is of the formula:

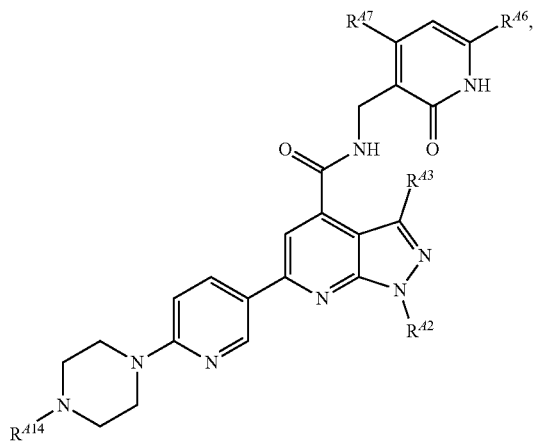

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

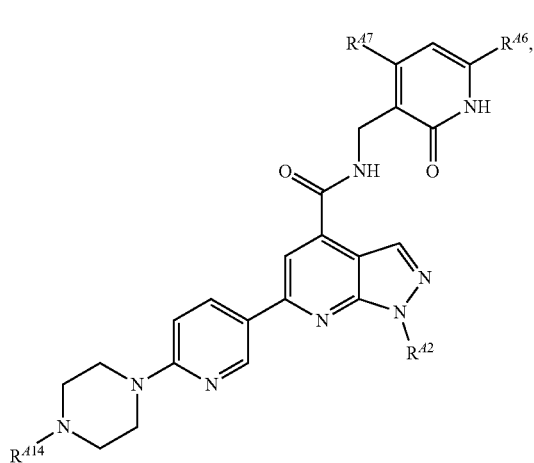

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

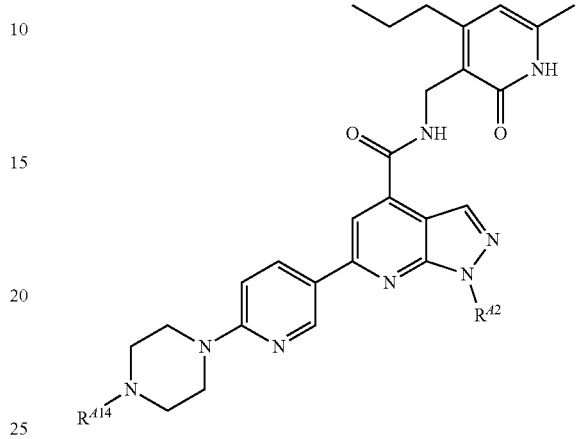

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

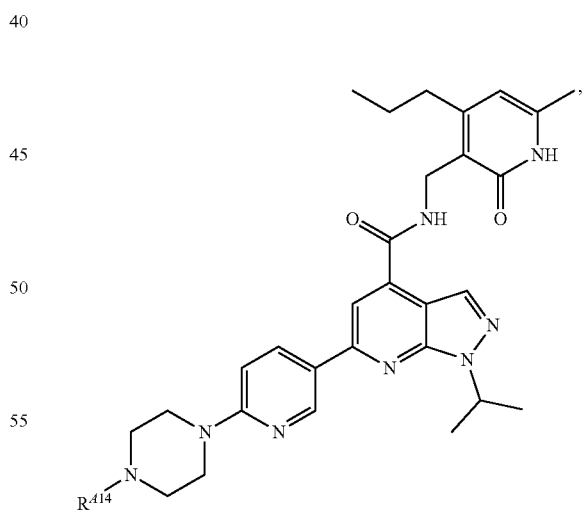

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

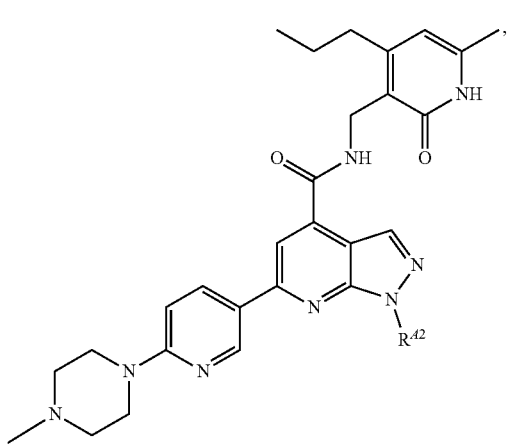

or a pharmaceutically acceptable salt, solvate, hydrate, polymorph, co-crystal, tautomer, stereoisomer, isotopically labeled derivative, or prodrug thereof, wherein $R^{A2}$ is a nitrogen protecting group (e.g., Boc).

In certain embodiments, the compound of Formula (I) is of the formula:

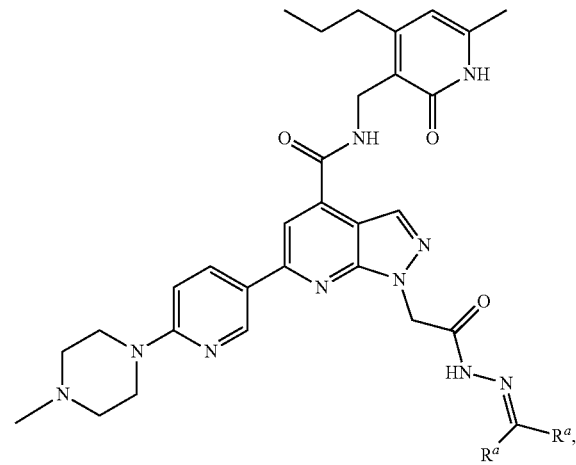

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

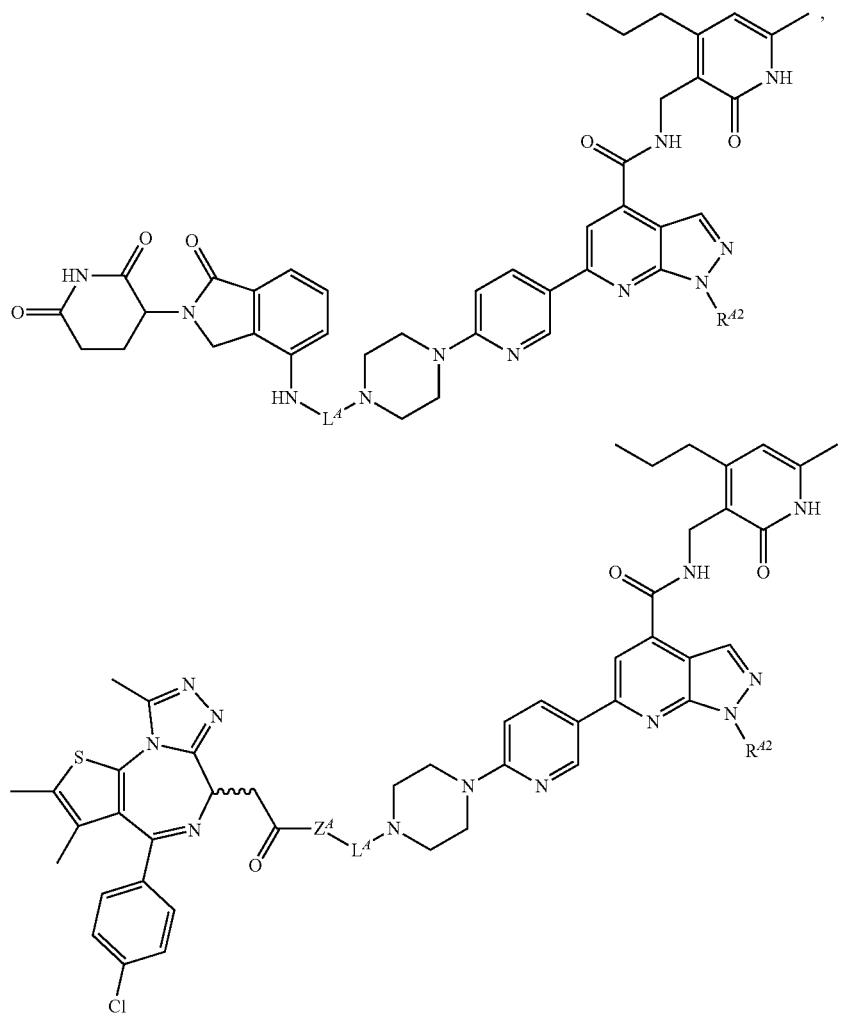

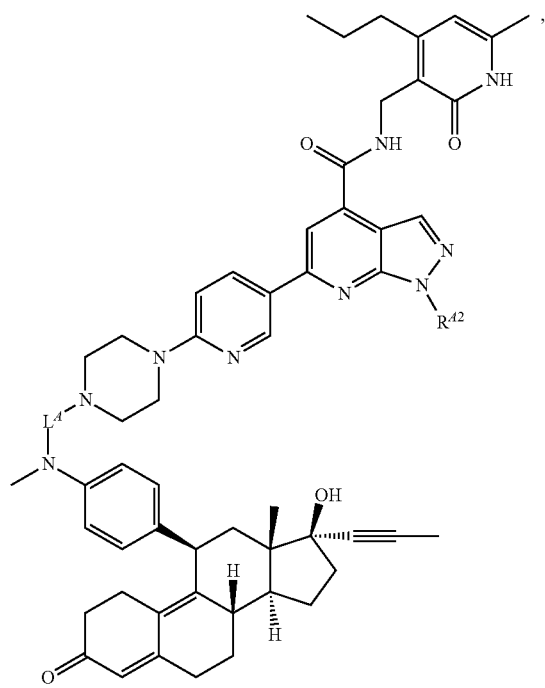
or a pharmaceutically acceptable salt, solvate, hydrate, polymorph, co-crystal, tautomer, stereoisomer, isotopically labeled derivative, or prodrug thereof, optionally wherein each instance of $R^4$ is i-Pr.
In certain embodiments, the compound of Formula (I) is of the formula:
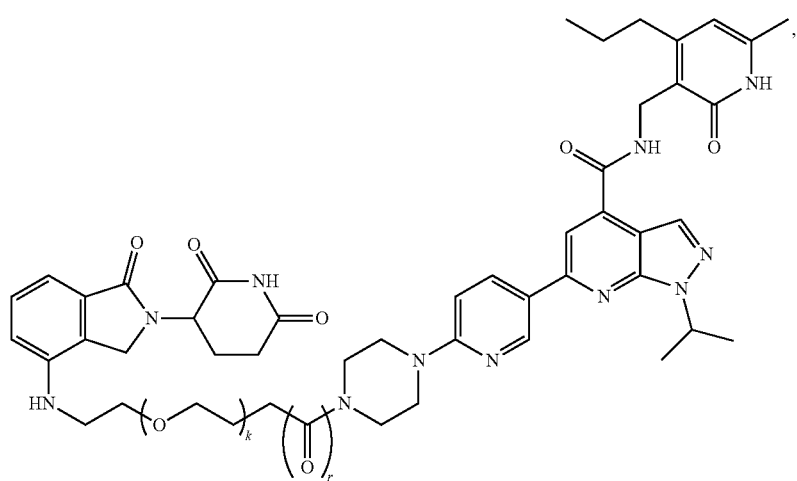

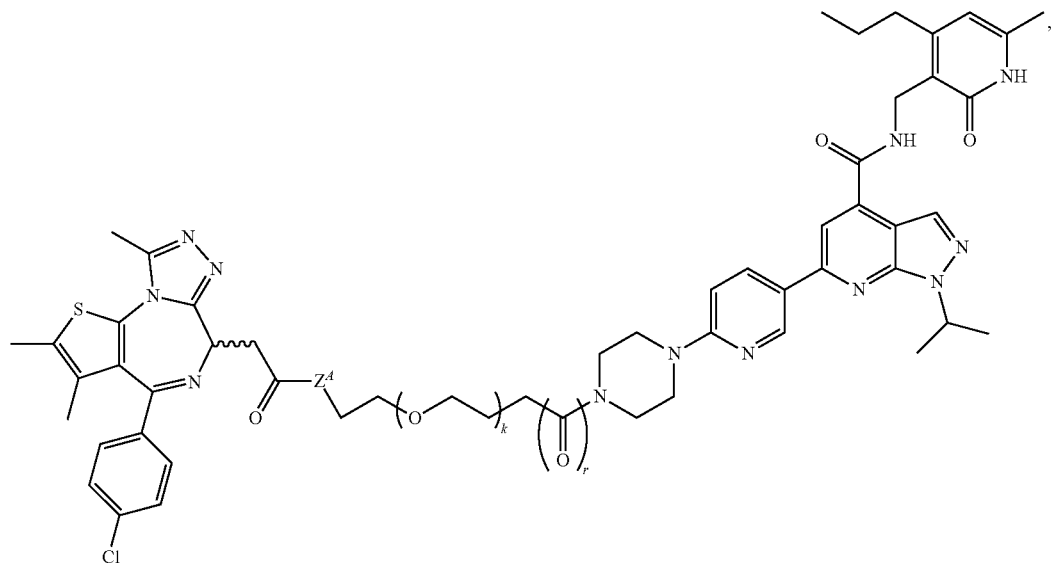
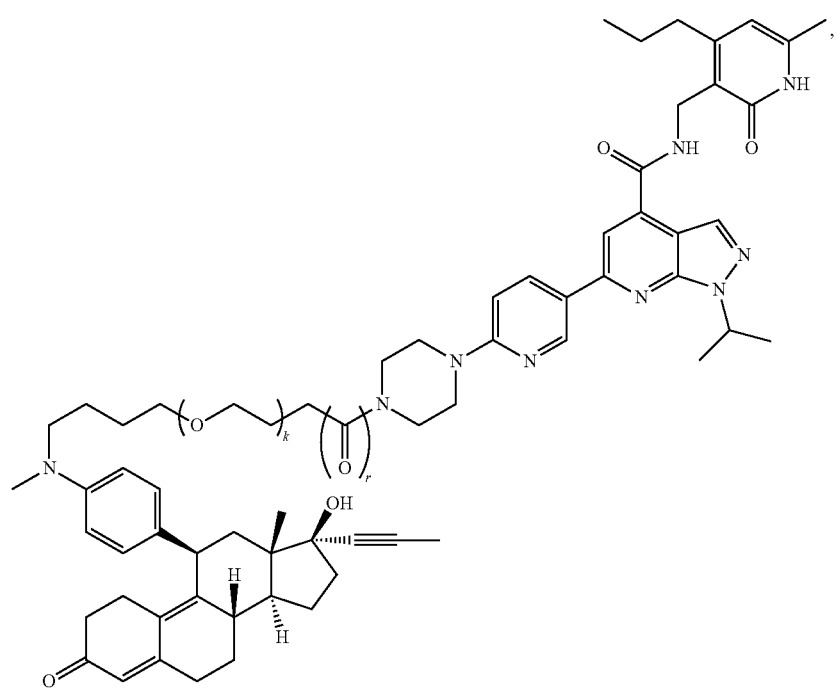

or a pharmaceutically acceptable salt, solvate, hydrate, polymorph, co-crystal, tautomer, stereoisomer, isotopically labeled derivative, or prodrug thereof, wherein each instance of k is independently an integer between 3 and 11, inclusive.

In certain embodiments, the compound of Formula (I) is of the formula:

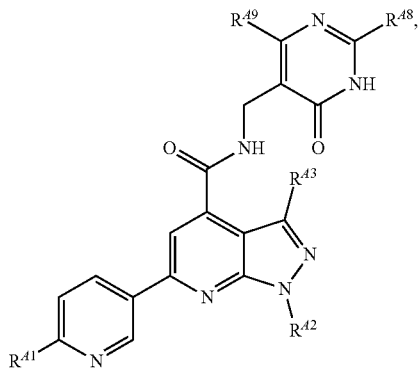

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

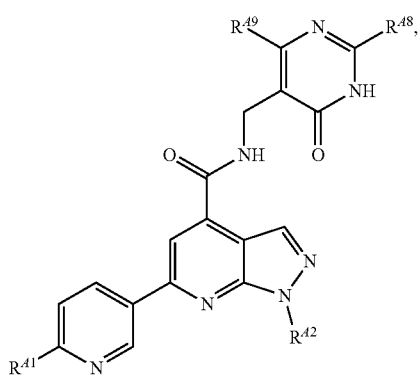

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

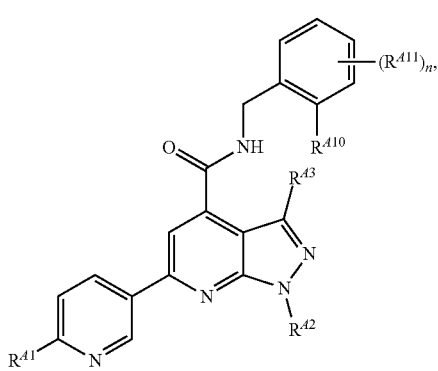

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

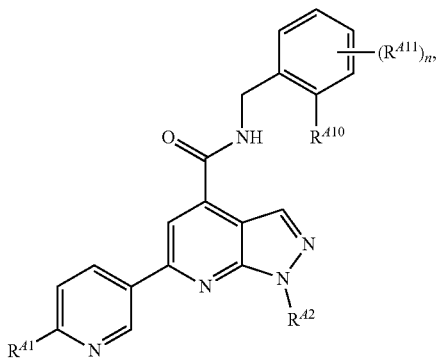

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

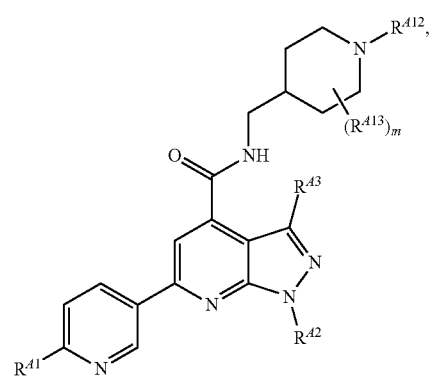

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

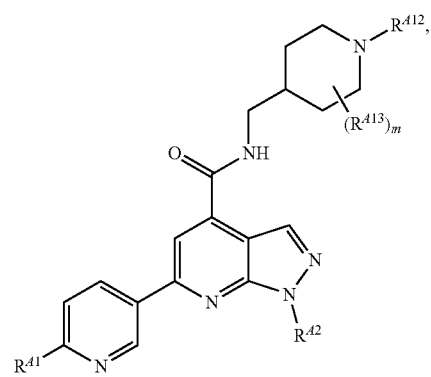

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

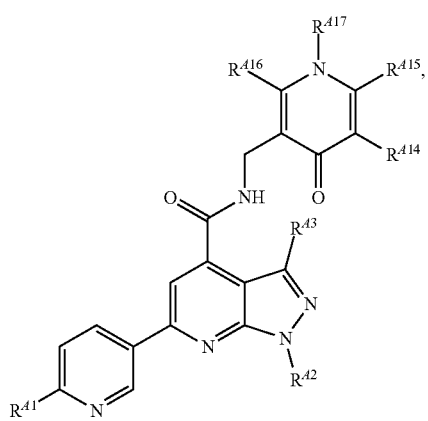

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

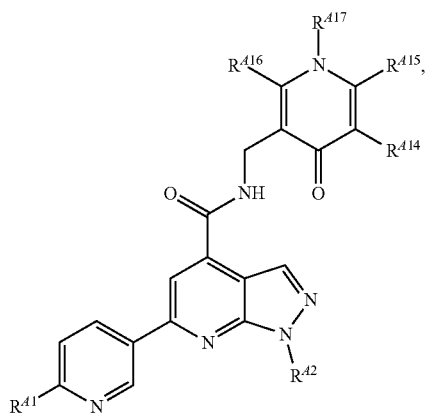

or a pharmaceutically acceptable salt, solvate, hydrate, polymorph, co-crystal, tautomer, stereoisomer, isotopically labeled derivative, or prodrug thereof.

Exemplary compounds of Formula (I) include, but are not limited to:

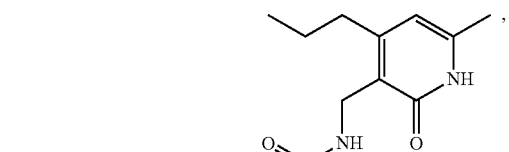

(JQEZ5, JQ-EZ-005, 5, EZ005, EZ-005, EZ05, EZ5, EZ-5, JQ5, or JQE5)

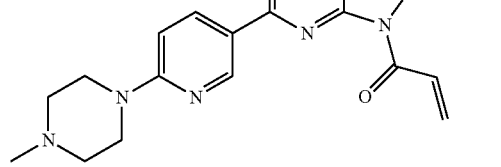

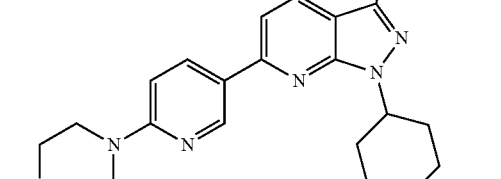

147
-continued
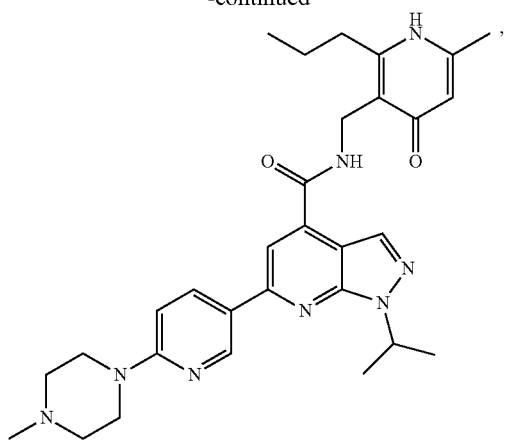
148
-continued
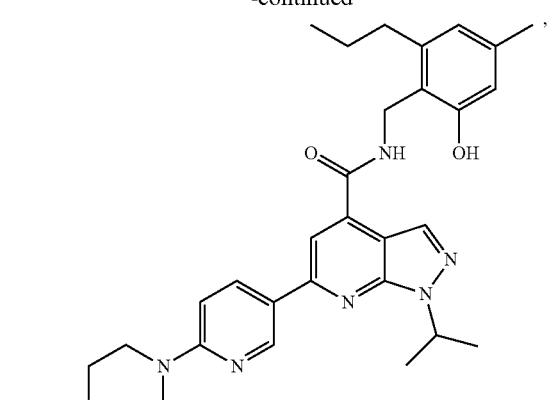
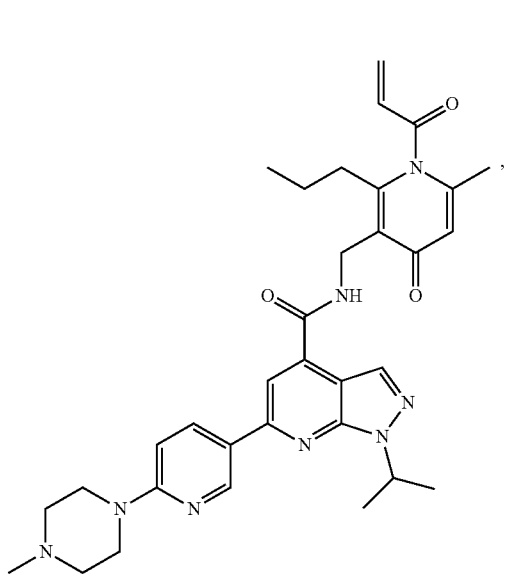
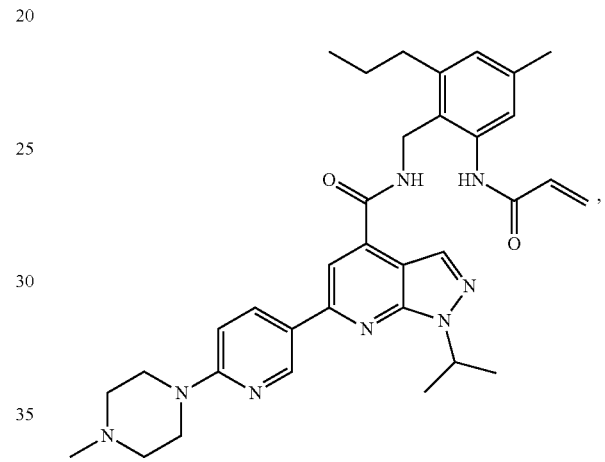
and pharmaceutically acceptable salts, solvates, hydrates, polymorphs, co-crystals, tautomers, stereoisomers, isotopically labeled derivatives, and prodrugs thereof.
Exemplary compounds of Formula (I) further include, but are not limited to:
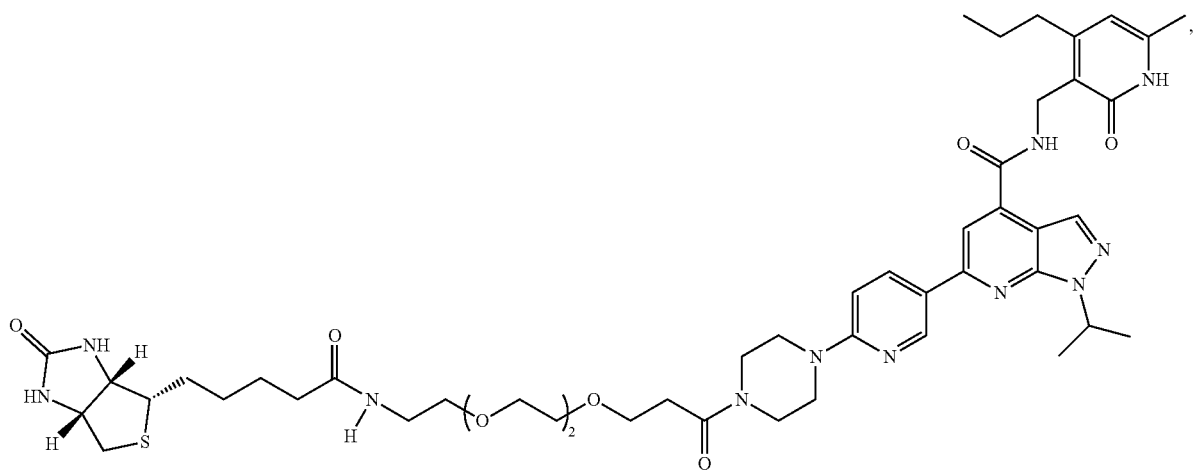
(JQEZ6, EZ-06, or EZ06)

-continued

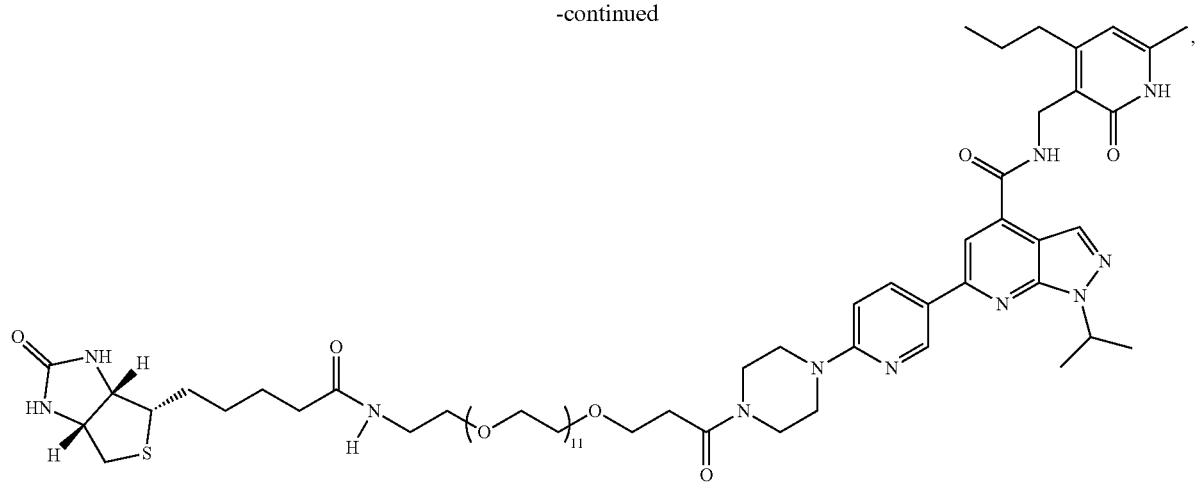

(AVC-1-018, AVC-1-013)

and pharmaceutically acceptable salts, solvates, hydrates, polymorphs, co-crystals, tautomers, stereoisomers, isotopically labeled derivatives, and prodrugs thereof.

In certain embodiments, the compound of Formula (I) is a compound of the formula:

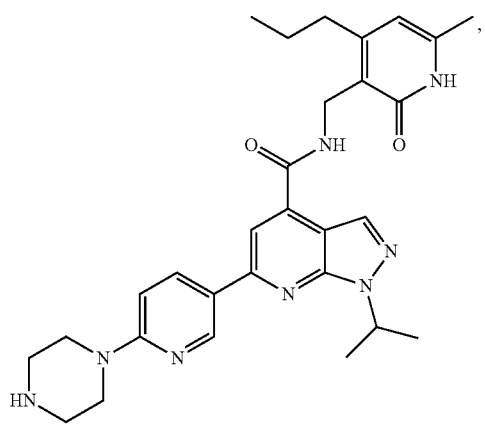

(EZH2-16, EZ-16, or EZ16)

or a pharmaceutically acceptable salt, solvate, hydrate, polymorph, co-crystal, tautomer, stereoisomer, isotopically labeled derivative, or prodrug thereof.

In certain embodiments, the compound of Formula (I) is EZ05-TOM, EZ05-FITC, EZ-TAMRA, or a pharmaceutically acceptable salt, solvate, hydrate, polymorph, co-crystal, tautomer, stereoisomer, isotopically labeled derivative, or prodrug thereof.

In certain embodiments, the compound of Formula (I) is EZ05_biotinloated, or a pharmaceutically acceptable salt, solvate, hydrate, polymorph, co-crystal, tautomer, stereoisomer, isotopically labeled derivative, or prodrug thereof.

In another aspect, the present disclosure provides compounds of Formula (II):

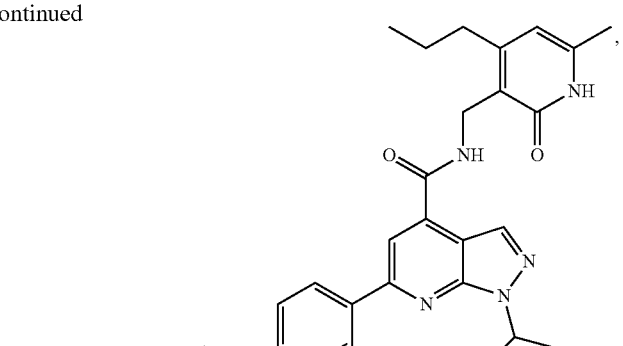

(II)

and pharmaceutically acceptable salts, solvates, hydrates, polymorphs, co-crystals, tautomers, stereoisomers, isotopically labeled derivatives, and prodrugs thereof, wherein:

$R^{B1}$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^b$, $-N(R^b)_2$, $-SR^b$, $-CN$, $-SCN$, $-C(=NR^b)R^b$, $-C(=NR^b)OR^b$, $-C(=NR^b)N(R^b)_2$, $-C(=O)R^b$, $-C(=O)OR^b$, $-C(=O)N(R^b)_2$, $-NO_2$, $-NR^bC(=O)R^b$, $-NR^bC(=O)OR^b$, $-NR^bC(=O)N(R^b)_2$, $-OC(=O)R^b$, $-OC(=O)OR^b$, $-OC(=O)N(R^b)_2$, a tag, or

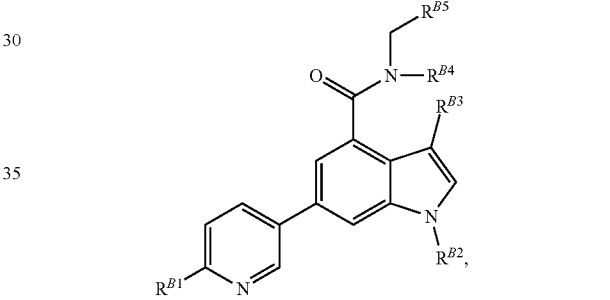

each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^b$ are joined to form a substituted or unsubstituted, heterocyclic ring, or substituted or unsubstituted, heteroaryl ring;

$R^A$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

or $R^A$ and $R^B$ are joined to form a substituted or unsubstituted, carbocyclic ring, or a substituted or unsubstituted, heterocyclic ring;

$R^C$ is hydrogen, substituted or unsubstituted $C_{1-6}$ alkyl, or a nitrogen protecting group;

$R^{B2}$ is hydrogen, substituted or unsubstituted acyl, substituted or unsubstituted alkyl, substituted or unsubstituted carbocyclyl, substituted or unsubstituted heterocyclyl, a nitrogen protecting group, a tag, or a warhead; and $R^{B3}$ is hydrogen, halogen, substituted or unsubstituted $C_{1-6}$ alkyl, —$OR^b$, —$N(R^b)_2$, or a warhead;

$R^{B4}$ is hydrogen, substituted or unsubstituted $C_{1-6}$ alkyl, or a nitrogen protecting group; and $R^{B5}$ is of the formula:

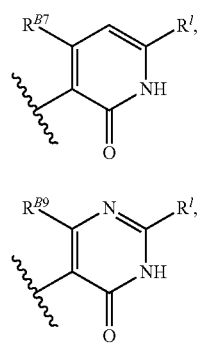

(ii-1)

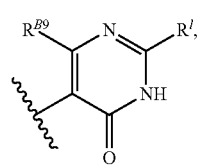

(ii-2)

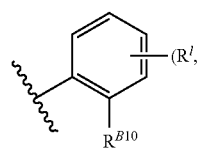

(ii-3)

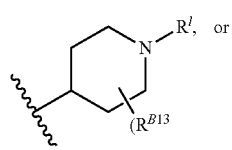

(ii-4), or

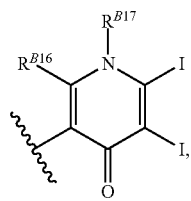

(ii-5)

wherein:
$R^{B6}$ is hydrogen, halogen, substituted or unsubstituted $C_{1-6}$ alkyl, or —$N(R^b)_2$;
$R^{B7}$ is hydrogen, halogen, substituted or unsubstituted $C_{2-6}$ alkyl, or substituted or unsubstituted, 3- to 7-membed, monocyclic carbocyclyl comprising 0, 1, or 2 double bonds in the carbocyclic ring system;
$R^{B8}$ is hydrogen, halogen, substituted or unsubstituted $C_{1-6}$ alkyl, or —$N(R^b)_2$;
$R^{B9}$ is hydrogen, halogen, substituted or unsubstituted $C_{1-6}$ alkyl, or substituted or unsubstituted, 3- to 7-membed, monocyclic carbocyclyl comprising 0, 1, or 2 double bonds in the carbocyclic ring system;
$R^{B10}$ is —$OR^b$—$N(R^b)_2$, or a warhead;
each instance of $R^{B11}$ is independently halogen, substituted or unsubstituted $C_{1-6}$ alkyl, substituted or unsubstituted, 3- to 7-membed, monocyclic carbocyclyl comprising 0, 1, or 2 double bonds in the carbocyclic ring system, or —$N(R^b)_2$;
u is 0, 1, 2, 3, or 4;
$R^{B12}$ is hydrogen, substituted or unsubstituted $C_{1-6}$ alkyl, a nitrogen protecting group, or a warhead;
each instance of $R^{B13}$ is independently halogen, substituted or unsubstituted $C_{1-6}$ alkyl, substituted or unsubstituted, 3- to 7-membed, monocyclic carbocyclyl comprising 0, 1, or 2 double bonds in the carbocyclic ring system, or —$N(R^b)_2$;
v is 0, 1, 2, 3, 4, 5, 6, 7, 8, or 9;
$R^{B14}$ is hydrogen, halogen, substituted or unsubstituted $C_{1-6}$ alkyl, —$OR^b$, or —$N(R^b)_2$;
$R^{B15}$ is hydrogen, halogen, substituted or unsubstituted $C_{1-6}$ alkyl, —$OR^b$, or —$N(R^b)_2$;
$R^{B16}$ is hydrogen, halogen, substituted or unsubstituted $C_{2-6}$ alkyl, substituted or unsubstituted, 3- to 7-membed, monocyclic carbocyclyl comprising 0, 1, or 2 double bonds in the carbocyclic ring system, —$OR^b$, or —$N(R^b)_2$; and
$R^{B17}$ is hydrogen, substituted or unsubstituted acyl, substituted or unsubstituted $C_{1-6}$ alkyl, a nitrogen protecting group, or a warhead.

In certain embodiments, the EZH2 inhibitor is a compound of Formula (II):

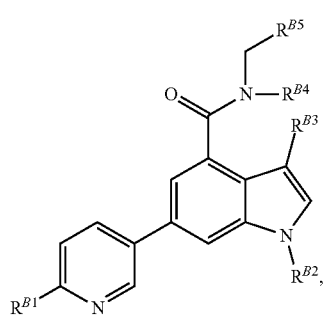

(II)

or a pharmaceutically acceptable salt, solvate, hydrate, polymorph, co-crystal, tautomer, stereoisomer, isotopically labeled derivative, or prodrug thereof, wherein:

$R^{B1}$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^b$, —$N(R^b)_2$, —$SR^b$, —CN, —SCN, —$C(=NR^b)R^b$, —$C(=NR^b)OR^b$, —$C(=NR^b)N(R^b)_2$, —$C(=O)R^b$, —$C(=O)OR^b$, —$C(=O)N(R^b)_2$, —$NO_2$, —$NR^bC(=O)R^b$, —$NR^bC(=O)OR^b$, —$NR^bC(=O)N(R^b)_2$, —$OC(=O)R^b$, —$OC(=O)OR^b$, or —$OC(=O)N(R^b)_2$;

each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^b$ are joined to form a substituted or unsubstituted, heterocyclic ring, or substituted or unsubstituted, heteroaryl ring;

$R^{B2}$ is hydrogen, substituted or unsubstituted acyl, substituted or unsubstituted alkyl, substituted or unsubstituted carbocyclyl, substituted or unsubstituted heterocyclyl, or a nitrogen protecting group;

$R^{B3}$ is hydrogen, halogen, substituted or unsubstituted $C_{1-6}$ alkyl, —$OR^b$, or —$N(R^b)_2$;

$R^{B4}$ is hydrogen, substituted or unsubstituted $C_{1-6}$ alkyl, or a nitrogen protecting group; and $R^{B5}$ is of the formula:

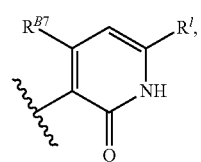 (ii-1)

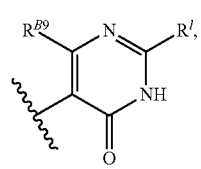 (ii-2)

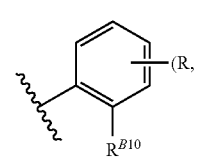 (ii-3)

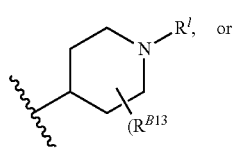 (ii-4)

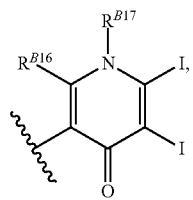 (ii-5)

wherein:

$R^{B6}$ is hydrogen, halogen, substituted or unsubstituted $C_{1-6}$ alkyl, or —$N(R^b)_2$;

$R^{B7}$ is hydrogen, halogen, substituted or unsubstituted $C_{2-6}$ alkyl, or substituted or unsubstituted, 3- to 7-membed, monocyclic carbocyclyl comprising 0, 1, or 2 double bonds in the carbocyclic ring system;

$R^{B8}$ is hydrogen, halogen, substituted or unsubstituted $C_{1-6}$ alkyl, or —$N(R^b)_2$;

$R^{B9}$ is hydrogen, halogen, substituted or unsubstituted $C_{1-6}$ alkyl, or substituted or unsubstituted, 3- to 7-membed, monocyclic carbocyclyl comprising 0, 1, or 2 double bonds in the carbocyclic ring system;

$R^{B10}$ is —$OR^b$ or —$N(R^b)_2$;

each instance of $R^{B11}$ is independently halogen, substituted or unsubstituted $C_{1-6}$ alkyl, substituted or unsubstituted, 3- to 7-membed, monocyclic carbocyclyl comprising 0, 1, or 2 double bonds in the carbocyclic ring system, or —$N(R^b)_2$;

u is 0, 1, 2, 3, or 4;

$R^{B12}$ is hydrogen, substituted or unsubstituted $C_{1-6}$ alkyl, or a nitrogen protecting group;

each instance of $R^{B13}$ is independently halogen, substituted or unsubstituted $C_{1-6}$ alkyl, substituted or unsubstituted, 3- to 7-membed, monocyclic carbocyclyl comprising 0, 1, or 2 double bonds in the carbocyclic ring system, or —$N(R^b)_2$;

v is 0, 1, 2, 3, 4, 5, 6, 7, 8, or 9;

$R^{B14}$ is hydrogen, halogen, substituted or unsubstituted $C_{1-6}$ alkyl, —$OR^b$, or —$N(R^b)_2$;

$R^{B15}$ is hydrogen, halogen, substituted or unsubstituted $C_{1-6}$ alkyl, —$OR^b$, or —$N(R^b)_2$;

$R^{B16}$ is hydrogen, halogen, substituted or unsubstituted $C_{2-6}$ alkyl, substituted or unsubstituted, 3- to 7-membed, monocyclic carbocyclyl comprising 0, 1, or 2 double bonds in the carbocyclic ring system, —$OR^b$, or —$N(R^b)_2$; and $R^{B17}$ is hydrogen, substituted or unsubstituted acyl, substituted or unsubstituted $C_{1-6}$ alkyl, or a nitrogen protecting group.

Formula (II) includes substituent $R^{B1}$ on the pyridinyl ring. In certain embodiments, $R^{B1}$ is halogen (e.g., F, Cl, Br, or I). In certain embodiments, $R^{B1}$ is substituted or unsubstituted alkyl (e.g., substituted or unsubstituted $C_{1-6}$ alkyl). In certain embodiments, $R^{B1}$ is Me. In certain embodiments, $R^{B1}$ is —$CF_3$, Bn, Et, perfluoroethyl, Pr, perfluoropropyl, Bu, or perfluorobutyl. In certain embodiments, $R^{B1}$ is substituted or unsubstituted alkenyl (e.g., substituted or unsubstituted $C_{2-6}$ alkenyl). In certain embodiments, $R^{B1}$ is substituted or unsubstituted alkynyl (e.g., substituted or unsubstituted $C_{1-6}$ alkynyl). In certain embodiments, $R^{B1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B1}$ is substituted or unsubstituted heterocyclyl (e.g., substituted or unsubstituted, 3- to 7-membed, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{B1}$ is substituted or unsubstituted piperazinyl. In certain embodiments, $R^{B1}$ is of the formula:

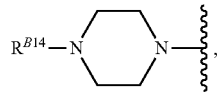

wherein $R^{B14}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group. In certain embodiments, $R^{B1}$ is of the formula:

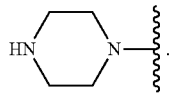

In certain embodiments, $R^{B1}$ is of the formula:

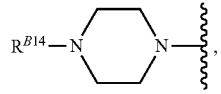

wherein $R^{B14}$ is substituted or unsubstituted $C_{1-6}$ alkyl. In certain embodiments, $R^{B1}$ is of the formula:

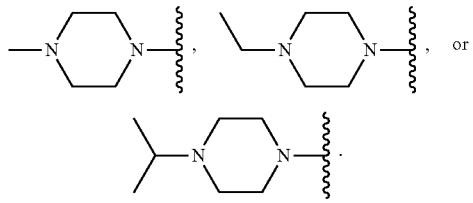

In certain embodiments, $R^{B1}$ is of the formula:

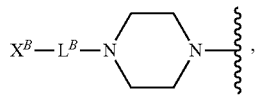

wherein $L^B$ is a bond or substituted or unsubstituted $C_{1-100}$ hydrocarbon chain, optionally wherein one or more chain atoms of the hydrocarbon chain are independently replaced with —O—, —S—, or —NR$^b$—; and $X^B$ is a small molecule, peptide, protein, or polynucleotide. In certain embodiments, $R^{B1}$ is of the formula:

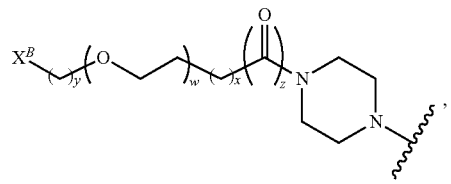

wherein z is 0 or 1, w is an integer between 0 and 11, inclusive, x is an integer between 0 and 10, inclusive, and y is an integer between 0 and 10, inclusive. In certain embodiments, w is an integer between 3 and 11, inclusive, x is 0, and y is 0, 1, 2, 3, 4, 5, or 6. In certain embodiments, $X^B$ is a small molecule. In certain embodiments, $X^B$ is a small molecule drug (e.g.,

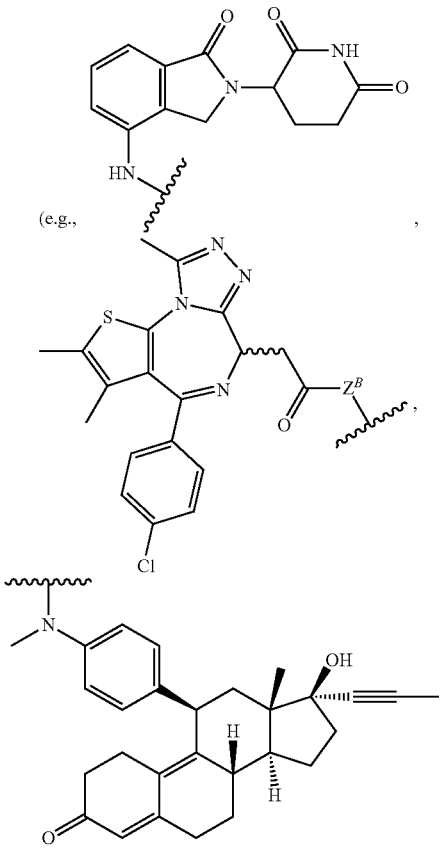

wherein $Z^B$ is —O— or —NH—, or an additional pharmaceutical agent described herein that is a small molecule). In certain embodiments, $X^B$ s a small molecule label (e.g., a biotin moiety (e.g., 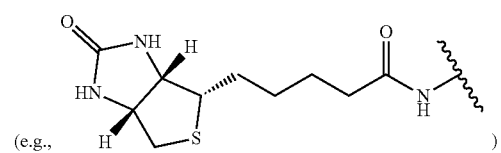 [SMILES: *NC(=O)CCCC[C@@H]1SC[C@@H]2NC(=O)N[C@@H]21] )

or a small molecule fluorophore). In certain embodiments, $R^{B1}$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, substituted or unsubstituted azepanyl, or substituted or unsubstituted diazepanyl. In certain embodiments, $R^{B1}$ is of the formula:

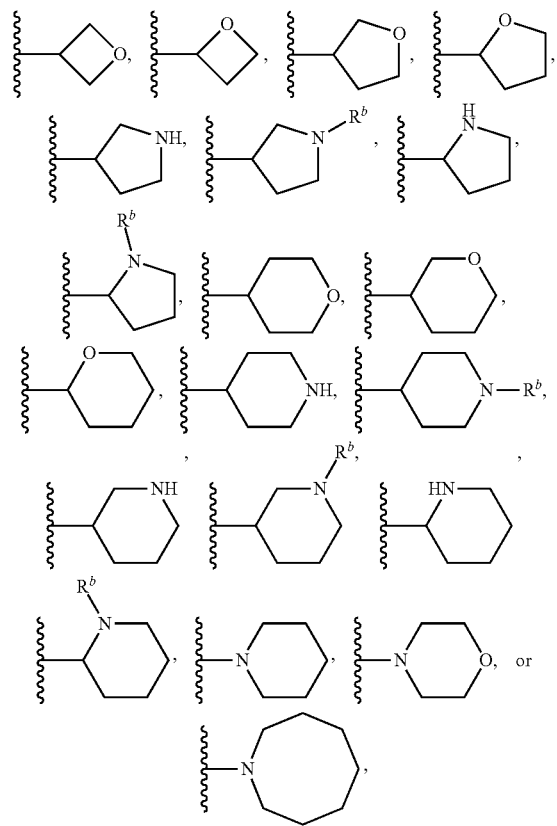

wherein each instance of $R^b$ is independently unsubstituted $C_{1-6}$ alkyl (e.g., Me)). In certain embodiments, $R^{B1}$ is substituted or unsubstituted aryl (e.g., substituted or unsubstituted, 6- to 10-membered aryl). In certain embodiments, $R^{B1}$ is substituted or unsubstituted phenyl. In certain embodiments, $R^{B1}$ is substituted or unsubstituted heteroaryl (e.g., substituted or unsubstituted, 5- to 6-membed, monocyclic heteroaryl, wherein one, two, three, or four atoms in the heteroaryl ring system are independently nitrogen, oxygen, or sulfur). In certain embodiments, $R^{B1}$ is —$OR^b$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, $R^{B1}$ is —$SR^b$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{B1}$ is —$N(R^b)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^{B1}$ is —CN. In certain embodiments, $R^{B1}$ is —SCN or —$NO_2$. In certain embodiments, $R^{B1}$ is —C(=$NR^b$)$R^b$, —C(=$NR^b$)$OR^b$, or —C(=$NR^b$)$N(R^b)_2$. In certain embodiments, $R^{B1}$ is —C(=O)$R^b$ (e.g., —C(=O)(substituted or unsubstituted alkyl) or —C(=O)(substituted or unsubstituted phenyl)). In certain embodiments, $R^{B1}$ is —C(=O)$OR^b$ (e.g., —C(=O)OH, —C(=O)O(substituted or unsubstituted alkyl) (e.g., —C(=O)OMe), or —C(=O)O(substituted or unsubstituted phenyl)). In certain embodiments, $R^{B1}$ is —C(=O)$N(R^b)_2$ (e.g., —C(=O)$NH_2$, —C(=O)NH(substituted or unsubstituted alkyl), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, $R^{B1}$ is —$NR^bC$(=O)$R^b$ (e.g., —NHC(=O)Me). In certain embodiments, $R^{B1}$ is —$NR^bC$(=O)$OR^b$ or —$NR^bC$(=O)$N(R^b)_2$. In certain embodiments, $R^{B1}$ is —OC(=O)$R^b$, —OC(=O)$OR^b$, or —OC(=O)$N(R^b)_2$. In certain embodiments, $R^{B1}$ is substituted or unsubstituted alkyl, —$OR^b$, —$N(R^b)_2$, —C(=O)$OR^b$, or —$NR^bC$(=O)$R^b$. In certain embodiments, $R^{B1}$ is unsubstituted $C_{1-6}$ alkyl, —OMe, —$NH_2$, —$N(Me)_2$, —C(=O)OH, —C(=O)OMe, or —NHC(=O)Me. In certain embodiments, $R^{B1}$ is

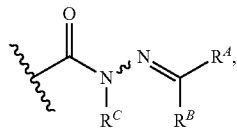

In certain embodiments, $R^{B1}$ is a tag (e.g., a biotin derivative, radiometric lable, or fluorophore).

Formula (II) may include one or more instances of substituent $R^b$. When Formula (II) includes two or more instances of $R^b$, any two instances of $R^b$ may be the same or different from each other. In certain embodiments, at least one instance of $R^b$ is H. In certain embodiments, each instance of $R^b$ is H. In certain embodiments, at least one instance of $R^b$ is substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group (e.g., Bn, Boc, Cbz, Fmoc, trifluoroacetyl, triphenylmethyl, acetyl, or Ts) when attached to a nitrogen atom, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom, or two instances of $R^b$ are joined to form a substituted or unsubstituted, heterocyclic ring, or substituted or unsubstituted, heteroaryl ring.

Formula (II) includes substituent $R^{B2}$ at the 1-position of the indolyl ring. In certain embodiments, $R^{B2}$ is H. In certain embodiments, $R^{B2}$ is substituted or unsubstituted acyl. In certain embodiments, $R^{B2}$ is —C(=O)$R^b$, optionally wherein $R^b$ is substituted or unsubstituted $C_{1-6}$ alkyl (e.g., Me) or substituted or unsubstituted $C_{2-6}$ alkenyl. In certain embodiments, $R^{B2}$ is —C(=O)$R^b$, wherein $R^b$ is substituted or unsubstituted vinyl. In certain embodiments, $R^{B2}$ is —C(=O)CH=$CH_2$. In certain embodiments, $R^{B2}$ is —C(=O)$OR^b$, optionally wherein $R^b$ is H, substituted or unsubstituted $C_{1-6}$ alkyl (e.g., Me), or an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, $R^{B2}$ is —C(=O)$N(R^b)_2$, optionally wherein each instance of $R^b$ is independently H, substituted or unsubstituted $C_{1-6}$ alkyl (e.g., Me), or a nitrogen protecting group (e.g., Bn, Boc, Cbz, Fmoc, trifluoroacetyl, triphenylmethyl, acetyl, or Ts). In certain embodiments, $R^{B2}$ is substituted or unsubstituted alkyl (e.g., substituted or unsubstituted $C_{1-6}$ alkyl). In certain embodiments, $R^{B2}$ is Me. In certain embodiments, $R^{B2}$ is Et. In certain embodiments, $R^{B2}$ is n-Pr. In certain embodiments, $R^{B2}$ is i-Pr. In certain embodiments, $R^{B2}$ is Bu (e.g., n-Bu, i-Bu, sec-Bu, or t-Bu). In certain embodiments, $R^{B2}$ is unsubstituted pentyl (e.g., unsubstituted n-pentyl, unsubstituted t-pentyl, unsubstituted neopentyl, unsubstituted isopentyl, unsubstituted sec-pentyl, or unsubstituted 3-pentyl). In certain embodiments, $R^{B2}$ is sec-Bu, t-Bu, or unsubstituted 3-pentyl. In certain embodiments, $R^{B2}$ is —$CF_3$, Bn, perfluoroethyl, perfluoropropyl, perfluorobutyl, or perfluoropentyl. In certain embodiments, $R^{B2}$ is —$CH_2C(=O)$—NH—N=$C(R^b)_2$. In certain embodiments, $R^{B2}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{B2}$ is substituted or unsubstituted cyclopropyl. In certain embodiments, $R^{B2}$ is substituted or unsubstituted cyclopropyl. In certain embodiments, $R^{B2}$ is substituted or unsubstituted cyclobutyl. In certain embodiments, $R^{B2}$ is substituted or unsubstituted cyclopentyl. In certain embodiments, $R^{B2}$ is unsubstituted cyclopropyl, unsubstituted cyclobutyl, or unsubstituted cyclopentyl. In certain embodiments, $R^{B2}$ is substituted or unsubstituted heterocyclyl (e.g., substituted or unsubstituted, 3- to 7-membed, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^{B2}$ is substituted or unsubstituted tetrahydropyranyl. In certain embodiments, $R^{B2}$ is of the formula:

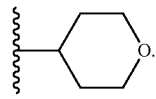

In certain embodiments, $R^{B2}$ is of the formula:

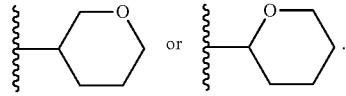

In certain embodiments, $R^{B2}$ is substituted or unsubstituted oxetanyl, substituted or unsubstituted tetrahydrofuranyl, substituted or unsubstituted pyrrolidinyl, substituted or unsubstituted piperidinyl, substituted or unsubstituted morpholinyl, or substituted or unsubstituted piperazinyl. In certain embodiments, $R^{B2}$ is of the formula:

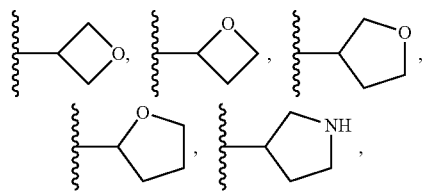

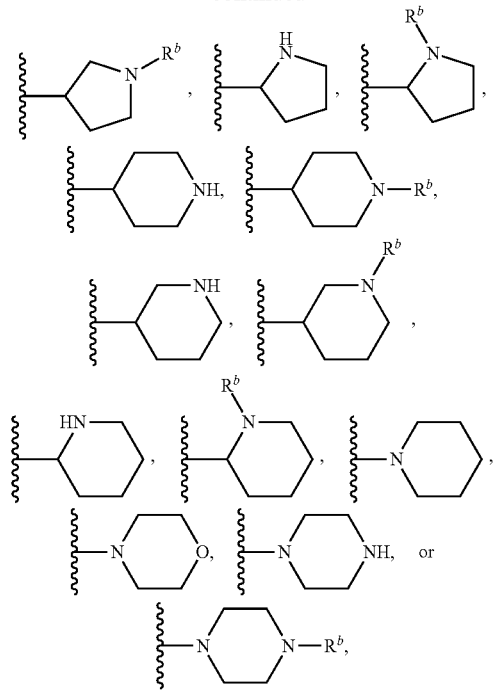

wherein each instance of $R^b$ is independently unsubstituted $C_{1-6}$ alkyl (e.g., Me)). In certain embodiments, $R^{B2}$ is a nitrogen protecting group (e.g., Bn, Boc, Cbz, Fmoc, trifluoroacetyl, triphenylmethyl, acetyl, or Ts). In certain embodiments, $R^{B2}$ is Boc. In certain embodiments, $R^{B2}$ is a warhead. In certain embodiments, $R^{B2}$ is a tag (e.g., a biotin derivative, radiometric lable, or fluorophore).

Formula (II) includes substituent $R^{B3}$ at the 3-position of the indolyl ring. In certain embodiments, $R^{B3}$ is H. In certain embodiments, $R^{B3}$ is halogen (e.g., F, Cl, Br, or I). In certain embodiments, $R^{B3}$ is substituted or unsubstituted $C_{1-6}$ alkyl. In certain embodiments, $R^{B3}$ is Me. In certain embodiments, $R^{B3}$ is —$CF_3$, Bn, Et, perfluoroethyl, Pr, perfluoropropyl, Bu, or perfluorobutyl. In certain embodiments, $R^{B3}$ is —$OR^b$, optionally wherein $R^b$ is H, substituted or unsubstituted $C_{1-6}$ alkyl (e.g., Me), substituted or unsubstituted acyl, or an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, $R^{B3}$ is —OC(=O)$R^b$, optionally wherein $R^b$ is H, substituted or unsubstituted $C_{1-6}$ alkyl (e.g., Me), or substituted or unsubstituted $C_{2-6}$ alkenyl (e.g., substituted or unsubstituted vinyl). In certain embodiments, $R^{B3}$ is —OC(=O)CH=$CH_2$. In certain embodiments, $R^{B3}$ is —$N(R^b)_2$, optionally wherein each instance of $R^b$ is independently H, substituted or unsubstituted $C_{1-6}$ alkyl (e.g., Me), substituted or unsubstituted acyl, or a nitrogen protecting group (e.g., Bn, Boc, Cbz, Fmoc, trifluoroacetyl, triphenylmethyl, acetyl, or Ts). In certain embodiments, $R^{B3}$ is —$N(R^b)C(=O)R^b$, optionally wherein each instance of $R^b$ is independently H, substituted or unsubstituted $C_{1-6}$ alkyl (e.g., Me), or substituted or unsubstituted $C_{2-6}$ alkenyl (e.g., substituted or unsubstituted vinyl). In certain embodiments, $R^{B3}$ is —NHC(=O)CH=$CH_2$. In certain embodiments, $R^{B3}$ is a warhead.

Formula (II) includes substituent $R^{B4}$ on a nitrogen atom. In certain embodiments, $R^{B4}$ is H. In certain embodiments, $R^{B4}$ is substituted or unsubstituted $C_{1-6}$ alkyl. In certain embodiments, $R^{B4}$ is Me. In certain embodiments, $R^{B4}$ is —CF$_3$, Bn, Et, perfluoroethyl, Pr, perfluoropropyl, Bu, or perfluorobutyl. In certain embodiments, R$^{B4}$ is a nitrogen protecting group (e.g., Bn, Boc, Cbz, Fmoc, trifluoroacetyl, triphenylmethyl, acetyl, or Ts).

Formula (II) includes substituent R$^{B5}$. In certain embodiments, R$^{B5}$ is of Formula (ii-1):

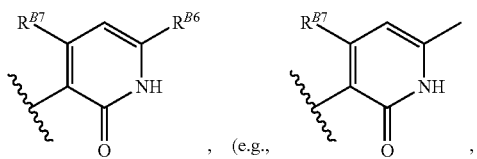

, (e.g., wherein R$^{B7}$ is Et, Pr, or Bu). In certain embodiments, R$^{B5}$ is of the formula:

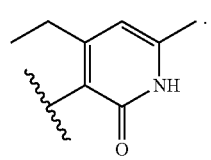 [SMILES: *c1c(CC)cc(C)[nH]c1=O]

In certain embodiments, R$^{B5}$ is of the formula:

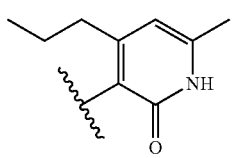

In certain embodiments, R$^{B6}$ is H. In certain embodiments, R$^{B6}$ is halogen (e.g., F, Cl, Br, or I). In certain embodiments, R$^{B6}$ is substituted or unsubstituted C$_{1-6}$ alkyl. In certain embodiments, R$^{B6}$ is Me. In certain embodiments, R$^{B6}$ is substituted methyl (e.g., —CF$_3$ or Bn). In certain embodiments, R$^{B6}$ is Et, substituted ethyl (e.g., perfluoroethyl), Pr, substituted propyl (e.g., perfluoropropyl), Bu, or substituted butyl (e.g., perfluorobutyl). In certain embodiments, R$^{B6}$ is —OR$^b$ (e.g., —OH or —O(substituted or unsubstituted C$_{1-6}$ alkyl) (e.g., —OMe)). In certain embodiments, R$^{B6}$ is —N(R$^b$)$_2$, optionally wherein each instance of R$^b$ is independently hydrogen, substituted or unsubstituted C$_{1-6}$ alkyl, or a nitrogen protecting group (e.g., Bn, Boc, Cbz, Fmoc, trifluoroacetyl, triphenylmethyl, acetyl, or Ts). In certain embodiments, R$^{B6}$ is —NH$_2$, —NHMe, or —N(Me)$_2$. In certain embodiments, R$^{B7}$ is H. In certain embodiments, R$^{B7}$ is halogen (e.g., F, Cl, Br, or I). In certain embodiments, R$^{B7}$ is substituted or unsubstituted C$_{2-6}$ alkyl. In certain embodiments, R$^{B7}$ is Et. In certain embodiments, R$^{B7}$ is substituted ethyl (e.g., perfluoroethyl). In certain embodiments, R$^{B7}$ is n-Pr. In certain embodiments, R$^{B7}$ is i-Pr. In certain embodiments, R$^{B7}$ is substituted propyl (e.g., perfluoropropyl). In certain embodiments, R$^{B7}$ is Bu or unsubstituted pentyl. In certain embodiments, R$^{B7}$ is substituted butyl (e.g., perfluorobutyl) or substituted pentyl (e.g., perfluoropentyl). In certain embodiments, R$^{B7}$ is substituted or unsubstituted, 3- to 7-membed, monocyclic carbocyclyl comprising 0, 1, or 2 double bonds in the carbocyclic ring system. In certain embodiments, R$^B$7 is substituted or unsubstituted cyclopropyl, substituted or unsubstituted cyclobutyl, or substituted or unsubstituted cyclopentyl. In certain embodiments, R$^{B7}$ is —OR$^b$ (e.g., —OH or —O(substituted or unsubstituted C$_{1-6}$ alkyl) (e.g., —OMe)). In certain embodiments, R$^{B7}$ is —N(R$^b$)$_2$, optionally wherein each instance of R$^b$ is independently hydrogen, substituted or unsubstituted C$_{1-6}$ alkyl, or a nitrogen protecting group (e.g., Bn, Boc, Cbz, Fmoc, trifluoroacetyl, triphenylmethyl, acetyl, or Ts). In certain embodiments, R$^{B7}$ is —NH$_2$, —NHMe, —NHEt, —N(Me)$_2$, or —N(Et)$_2$. In certain embodiments, R$^{B7}$ is substituted or unsubstituted cyclopropyl or —N(R$^b$)$_2$, wherein each instance of R$^b$ is independently hydrogen, substituted or unsubstituted C$_{1-6}$ alkyl, or a nitrogen protecting group (e.g., Bn, Boc, Cbz, Fmoc, trifluoroacetyl, triphenylmethyl, acetyl, or Ts).

In certain embodiments, R is of the formula:

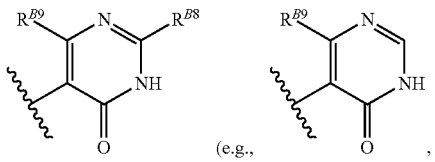

(e.g., wherein R$^{B9}$ is Me, Et, Pr, or Bu). The moiety of the formula:

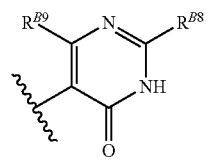

also includes its tautomeric form

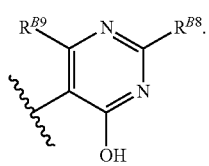

In certain embodiments, R$^{B5}$ is of the formula:

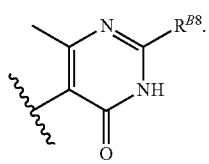

In certain embodiments, R$^{B5}$ is of the formula:

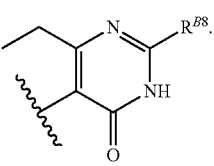

In certain embodiments, $R^{B5}$ is of the formula:

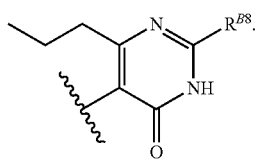

In certain embodiments, $R^{B8}$ is H. In certain embodiments, $R^{B8}$ is halogen (e.g., F, Cl, Br, or I). In certain embodiments, $R^{B}8$ is substituted or unsubstituted $C_{1-6}$ alkyl. In certain embodiments, $R^{B8}$ is Me. In certain embodiments, $R^{B8}$ is substituted methyl (e.g., —$CF_3$ or Bn). In certain embodiments, $R^{B8}$ is Et, substituted ethyl (e.g., perfluoroethyl), Pr, substituted propyl (e.g., perfluoropropyl), Bu, or substituted butyl (e.g., perfluorobutyl). In certain embodiments, $R^{B8}$ is —$OR^b$ (e.g., —OH or —O(substituted or unsubstituted $C_{1-6}$ alkyl) (e.g., —OMe)). In certain embodiments, $R^{B8}$ is —$N(R^b)_2$, optionally wherein each instance of $R^b$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{B8}$ is —$NH_2$, —NHMe, or —$N(Me)_2$. In certain embodiments, $R^{B9}$ is H. In certain embodiments, $R^{B9}$ is halogen (e.g., F, Cl, Br, or I). In certain embodiments, $R^{B9}$ is substituted or unsubstituted $C_{1-6}$ alkyl. In certain embodiments, $R^{B9}$ is Me. In certain embodiments, $R^{B9}$ is substituted methyl (e.g., —$CF_3$ or Bn). In certain embodiments, $R^{B9}$ is Et. In certain embodiments, $R^{B9}$ is substituted ethyl (e.g., perfluoroethyl). In certain embodiments, $R^{B9}$ is n-Pr. In certain embodiments, $R^{B9}$ is i-Pr. In certain embodiments, $R^{B9}$ is substituted propyl (e.g., perfluoropropyl). In certain embodiments, $R^{B9}$ is Bu or unsubstituted pentyl. In certain embodiments, $R^{B9}$ is substituted butyl (e.g., perfluorobutyl) or substituted pentyl (e.g., perfluoropentyl). In certain embodiments, $R^{B9}$ is substituted or unsubstituted, 3- to 7-membed, monocyclic carbocyclyl comprising 0, 1, or 2 double bonds in the carbocyclic ring system. In certain embodiments, $R^{B9}$ is substituted or unsubstituted cyclopropyl, substituted or unsubstituted cyclobutyl, or substituted or unsubstituted cyclopentyl. In certain embodiments, $R^{B9}$ is —$OR^b$ (e.g., —OH or —O(substituted or unsubstituted $C_{1-6}$ alkyl) (e.g., —OMe)). In certain embodiments, $R^{B9}$ is —$N(R^b)_2$, optionally wherein each instance of $R^b$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{B9}$ is —$NH_2$, —NHMe, —NHEt, —$N(Me)_2$, or —$N(Et)_2$. In certain embodiments, $R^{B9}$ is substituted or unsubstituted cyclopropyl, —$OR^b$, or —$N(R^b)_2$, wherein each instance of $R^b$ is independently hydrogen, substituted or unsubstituted $C_{1-6}$ alkyl, an oxygen protecting group when attached to an oxygen atom, or a nitrogen protecting group when attached to a nitrogen atom.

In certain embodiments, $R^{B5}$ is of the formula:

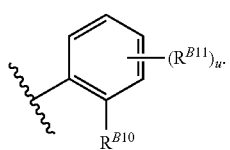

In certain embodiments, $R^{B5}$ is of the formula:

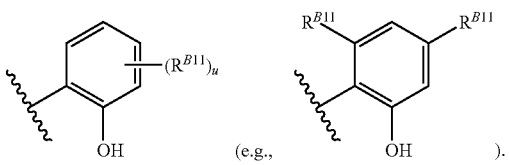

In certain embodiments, $R^{B5}$ is of the formula:

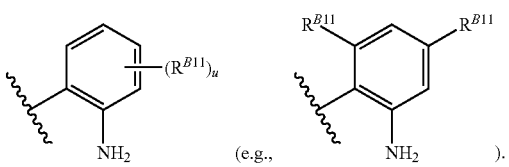

In certain embodiments, $R^{B5}$ is of the formula:

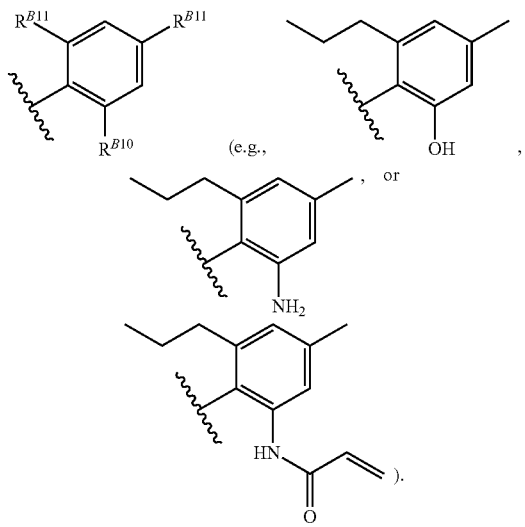

In certain embodiments, $R^{B5}$ is of the formula:

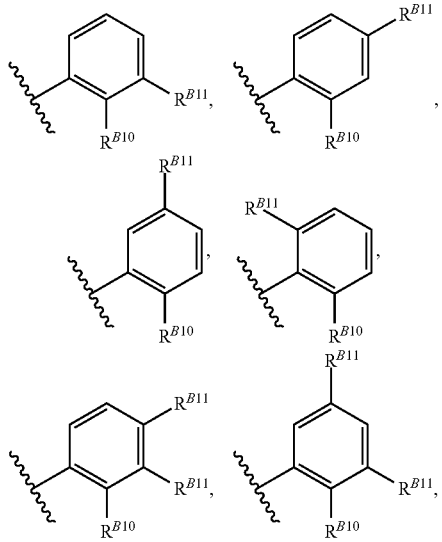

-continued

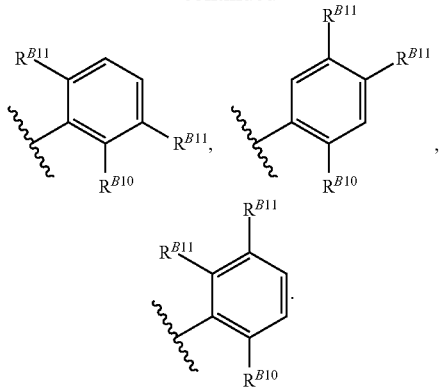

In certain embodiments, $R^{B5}$ is of the formula:

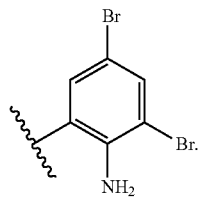 [SMILES: *c1cc(Br)cc(Br)c1N]

In certain embodiments, $R^{B10}$ is —$OR^b$ (e.g., —OH). In certain embodiments, $R^{B10}$ is —$N(R^b)_2$. In certain embodiments, $R^{B10}$ is —$NH_2$. In certain embodiments, $R^{B10}$ is —$NHR^b$, wherein $R^b$ is substituted or unsubstituted $C_{1-6}$ alkyl or a nitrogen protecting group (e.g., Bn, Boc, Cbz, Fmoc, trifluoroacetyl, triphenylmethyl, acetyl, or Ts). In certain embodiments, $R^{B10}$ is a warhead. In certain embodiments, $R^{B10}$ is —$NHC(=O)R^b$, optionally wherein $R^b$ is substituted or unsubstituted vinyl. In certain embodiments, $R^{B10}$ is —$NHC(=O)CH=CH_2$. When Formula (II) includes two or more instances of $R^{B11}$, any two instances of $R^{B11}$ may be the same or different from each other. In certain embodiments, at least one instance of $R^{B11}$ is halogen. In certain embodiments, at least one instance of $R^{B11}$ is Br. In certain embodiments, at least one instance of $R^{B11}$ is F, Cl, or I. In certain embodiments, at least one instance of $R^{B11}$ is substituted or unsubstituted $C_{1-6}$ alkyl. In certain embodiments, at least one instance of $R^{B11}$ is Me. In certain embodiments, at least one instance of $R^{B11}$ is substituted methyl (e.g., —$CF_3$ or Bn). In certain embodiments, at least one instance of $R^{B11}$ is Et. In certain embodiments, at least one instance of $R^{B11}$ is substituted ethyl (e.g., perfluoroethyl). In certain embodiments, at least one instance of $R^{B11}$ is n-Pr. In certain embodiments, at least one instance of $R^{B11}$ is i-Pr. In certain embodiments, at least one instance of $R^{B11}$ is substituted propyl (e.g., perfluoropropyl). In certain embodiments, at least one instance of $R^{B11}$ is Me, Et, or n-Pr. In certain embodiments, at least one instance of $R^{B11}$ is Bu or unsubstituted pentyl. In certain embodiments, at least one instance of $R^{B11}$ is substituted butyl (e.g., perfluorobutyl) or substituted pentyl (e.g., perfluoropentyl). In certain embodiments, at least one instance of $R^{B11}$ is substituted or unsubstituted, 3- to 7-membed, monocyclic carbocyclyl comprising 0, 1, or 2 double bonds in the carbocyclic ring system. In certain embodiments, at least one instance of $R^{B11}$ is substituted or unsubstituted cyclopropyl, substituted or unsubstituted cyclobutyl, or substituted or unsubstituted cyclopentyl. In certain embodiments, at least one instance of $R^{B11}$ is —$OR^b$ (e.g., —OH or —O(substituted or unsubstituted $C_{1-6}$ alkyl) (e.g., —OMe)). In certain embodiments, at least one instance of $R^{B11}$ is —$N(R^b)_2$, optionally wherein each instance of $R^b$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, at least one instance of $R^{B11}$ is —$NH_2$, —NHMe, —NHEt, —$N(Me)_2$, or —$N(Et)_2$. In certain embodiments, at least one instance of $R^{B11}$ is substituted or unsubstituted $C_{1-6}$ alkyl, substituted or unsubstituted cyclopropyl, —$OR^b$, or —$N(R^b)_2$, wherein each instance of $R^b$ is independently hydrogen, substituted or unsubstituted $C_{1-6}$ alkyl, an oxygen protecting group when attached to an oxygen atom, or a nitrogen protecting group when attached to a nitrogen atom. In certain embodiments, u is 0. In certain embodiments, u is 1. In certain embodiments, u is 2. In certain embodiments, u is 3. In certain embodiments, u is 4.

In certain embodiments, $R^{B5}$ is of the formula:

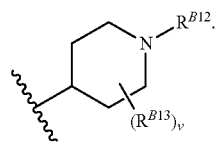

In certain embodiments, $R^{B5}$ is of the formula:

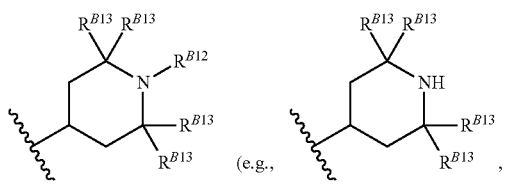

such as

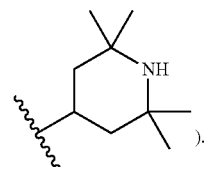 [SMILES: *C1CC(C)(C)NC(C)(C)C1]

In certain embodiments, $R^{B12}$ is H. In certain embodiments, $R^{B12}$ is substituted or unsubstituted $C_{1-6}$ alkyl. In certain embodiments, $R^{B12}$ is Me. In certain embodiments, $R^{B12}$ is —$CF_3$, Bn, Et, perfluoroethyl, Pr, perfluoropropyl, Bu, or perfluorobutyl. In certain embodiments, $R^{B12}$ is a nitrogen protecting group (e.g., Bn, Boc, Cbz, Fmoc, trifluoroacetyl, triphenylmethyl, acetyl, or Ts). In certain embodiments, $R^{B12}$ is a warhead. When Formula (II) includes two or more instances of $R^{B13}$, any two instances of $R^{B13}$ may be the same or different from each other. In certain embodiments, at least one instance of $R^{B13}$ is halogen (e.g., F, Cl, Br, or I). In certain embodiments, at least one instance of $R^{B13}$ is substituted or unsubstituted $C_{1-6}$ alkyl. In certain embodiments, at least one instance of $R^{B13}$ is Me. In certain embodiments, at least one instance of $R^{B13}$ is substituted methyl (e.g., —$CF_3$ or Bn). In certain embodiments, at least one instance of $R^{B13}$ is Et. In certain embodiments, at least one instance of $R^{B13}$ is substituted ethyl (e.g., perfluoroethyl). In certain embodiments, at least one instance of $R^{B13}$ is n-Pr. In certain embodiments, at least one instance of $R^{B13}$ is i-Pr. In certain embodiments, at least one instance of $R^{B13}$ is substituted propyl (e.g., perfluoropropyl). In certain embodiments, at least one instance of $R^{B13}$ is Me, Et, or n-Pr. In certain embodiments, at least one instance of $R^{B13}$ is Bu or unsubstituted pentyl. In certain embodiments, at least one instance of $R^{B13}$ is substituted butyl (e.g., perfluorobutyl) or substituted pentyl (e.g., perfluoropentyl). In certain embodiments, at least one instance of $R^{B13}$ is substituted or unsubstituted, 3- to 7-membed, monocyclic carbocyclyl comprising 0, 1, or 2 double bonds in the carbocyclic ring system. In certain embodiments, at least one instance of $R^{B13}$ is substituted or unsubstituted cyclopropyl, substituted or unsubstituted cyclobutyl, or substituted or unsubstituted cyclopentyl. In certain embodiments, at least one instance of $R^{B13}$ is —$OR^b$ (e.g., —OH or —O(substituted or unsubstituted $C_{1-6}$ alkyl) (e.g., —OMe)). In certain embodiments, at least one instance of $R^{B13}$ is —$N(R^b)_2$, optionally wherein each instance of $R^b$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, at least one instance of $R^{B13}$ is —$NH_2$, —NHMe, —NHEt, —$N(Me)_2$, or —$N(Et)_2$. In certain embodiments, at least one instance of $R^{B13}$ is halogen, substituted or unsubstituted cyclopropyl, —$OR^b$, or —$N(R^b)_2$, wherein each instance of $R^b$ is independently hydrogen, substituted or unsubstituted $C_{1-6}$ alkyl, an oxygen protecting group when attached to an oxygen atom, or a nitrogen protecting group when attached to a nitrogen atom. In certain embodiments, v is 0. In certain embodiments, v is 1. In certain embodiments, v is 2. In certain embodiments, v is 3, 4, 5, 6, 7, or 8. In certain embodiments, v is 9.

Formula (II) includes substituent $R^{B5}$. In certain embodiments, $R^{B5}$ is of the formula:

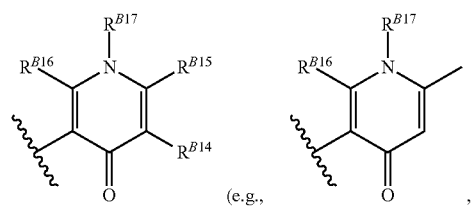

optionally wherein $R^{B16}$ is Et, Pr, or Bu). In certain embodiments, $R^{B5}$ is of the formula:

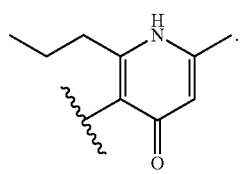

In certain embodiments, $R^{B5}$ is of the formula:

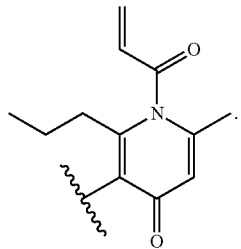 [SMILES: *c1c(CCC)n(C(=O)C=C)c(C)cc1=O]

In certain embodiments, $R^{B14}$ is H. In certain embodiments, $R^{B14}$ is halogen (e.g., F, Cl, Br, or I). In certain embodiments, $R^{B14}$ is substituted or unsubstituted $C_{1-6}$ alkyl. In certain embodiments, $R^{B14}$ is Me. In certain embodiments, $R^{B14}$ is substituted methyl (e.g., —$CF_3$ or Bn). In certain embodiments, $R^{B14}$ is Et, substituted ethyl (e.g., perfluoroethyl), Pr, substituted propyl (e.g., perfluoropropyl), Bu, or substituted butyl (e.g., perfluorobutyl). In certain embodiments, $R^{B14}$ is —$OR^b$ (e.g., —OH or —O(substituted or unsubstituted $C_{1-6}$ alkyl) (e.g., —OMe)). In certain embodiments, $R^{B14}$ is —$N(R^b)_2$, optionally wherein each instance of $R^b$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{B14}$ is —$NH_2$, —NHMe, or —$N(Me)_2$. In certain embodiments, $R^{B15}$ is H. In certain embodiments, $R^{B15}$ is halogen (e.g., F, Cl, Br, or I). In certain embodiments, $R^{B15}$ is substituted or unsubstituted $C_{1-6}$ alkyl. In certain embodiments, $R^{B15}$ is Me. In certain embodiments, $R^{B15}$ is substituted methyl (e.g., —$CF_3$ or Bn). In certain embodiments, $R^{B15}$ is Et, substituted ethyl (e.g., perfluoroethyl), Pr, substituted propyl (e.g., perfluoropropyl), Bu, or substituted butyl (e.g., perfluorobutyl). In certain embodiments, $R^{B15}$ is —$OR^b$ (e.g., —OH or —O(substituted or unsubstituted $C_{1-6}$ alkyl) (e.g., —OMe)). In certain embodiments, $R^{B15}$ is —$N(R^b)_2$, optionally wherein each instance of $R^b$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{B15}$ is —$NH_2$, —NHMe, or —$N(Me)_2$. In certain embodiments, $R^{B6}$ is H. In certain embodiments, $R^{B16}$ is halogen (e.g., F, Cl, Br, or I). In certain embodiments, $R^{B16}$ is substituted or unsubstituted $C_{2-6}$ alkyl. In certain embodiments, $R^{B16}$ is Et. In certain embodiments, $R^{B16}$ is substituted ethyl (e.g., perfluoroethyl). In certain embodiments, $R^{B16}$ is n-Pr. In certain embodiments, $R^{B16}$ is i-Pr. In certain embodiments, $R^{B16}$ is substituted propyl (e.g., perfluoropropyl). In certain embodiments, $R^{B16}$ is Bu or unsubstituted pentyl. In certain embodiments, $R^{B16}$ is substituted butyl (e.g., perfluorobutyl) or substituted pentyl (e.g., perfluoropentyl). In certain embodiments, $R^{B16}$ is substituted or unsubstituted, 3- to 7-membed, monocyclic carbocyclyl comprising 0, 1, or 2 double bonds in the carbocyclic ring system. In certain embodiments, $R^{B16}$ is substituted or unsubstituted cyclopropyl, substituted or unsubstituted cyclobutyl, or substituted or unsubstituted cyclopentyl. In certain embodiments, $R^{B16}$ is —$OR^b$ (e.g., —OH or —O(substituted or unsubstituted $C_{1-6}$ alkyl) (e.g., —OMe)). In certain embodiments, $R^{B16}$ is —$N(R^b)_2$, optionally wherein each instance of $R^b$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{B16}$ is —$NH_2$, —NHMe, —NHEt, —$N(Me)_2$, or —$N(Et)_2$. In certain embodiments, $R^{B16}$ is substituted or unsubstituted cyclopropyl or —$N(R^b)_2$, wherein each instance of $R^b$ is independently hydrogen, substituted or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, $R^{B17}$ is H. In certain embodiments, $R^{B17}$ is substituted or unsubstituted acyl. In certain embodiments, $R^{B17}$ is —C(=O)$R^b$, optionally wherein $R^b$ is substituted or unsubstituted $C_{1-6}$ alkyl (e.g., Me) or substituted or unsubstituted $C_{2-6}$ alkenyl. In certain embodiments, $R^{B17}$ is a warhead. In certain embodiments, $R^{B17}$ is —C(=O)$R^b$, wherein $R^b$ is substituted or unsubstituted vinyl. In certain embodiments, $R^{B17}$ is —C(=O)CH=$CH_2$. In certain embodiments, $R^{B17}$ is —C(=O)$OR^b$, optionally wherein $R^b$ is H, substituted or unsubstituted $C_{1-6}$ alkyl (e.g., Me), or an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, $R^{B17}$ is —C(=O)$N(R^b)_2$, optionally wherein each instance of $R^b$ is independently H, substituted or unsubstituted $C_{1-6}$ alkyl (e.g., Me), or a nitrogen protecting group (e.g., Bn, Boc, Cbz, Fmoc, trifluoroacetyl, triphenylmethyl, acetyl, or Ts). In certain embodiments, $R^{B17}$ is substituted or unsubstituted $C_{1-6}$ alkyl. In certain embodiments, $R^{B17}$ is Me. In certain embodiments, $R^{B17}$ is —$CF_3$, Bn, Et, perfluoroethyl, Pr, perfluoropropyl, Bu, or perfluorobutyl. In certain embodiments, $R^{B7}$ is a nitrogen protecting group (e.g., Bn, Boc, Cbz, Fmoc, trifluoroacetyl, triphenylmethyl, acetyl, or Ts).

In certain embodiments, the compound of Formula (II) is of the formula:

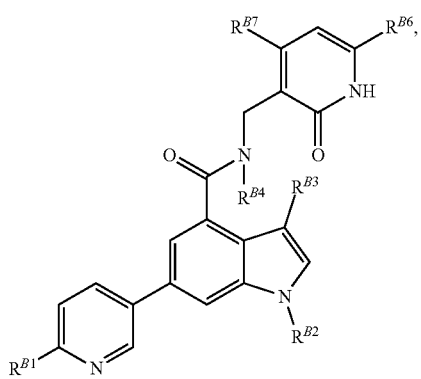

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

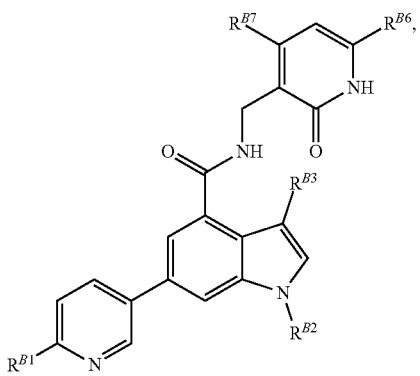

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

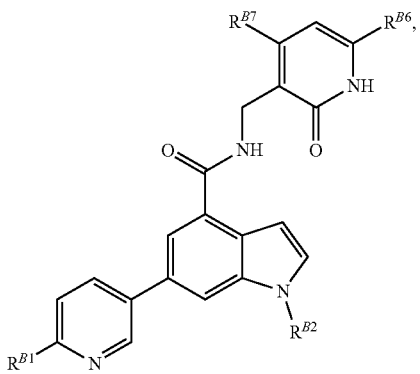

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

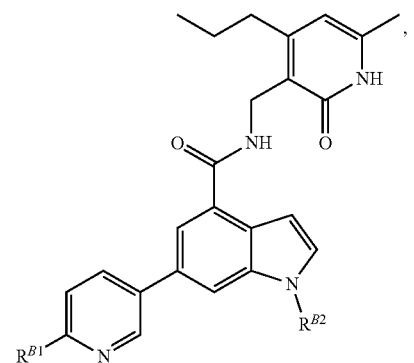

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

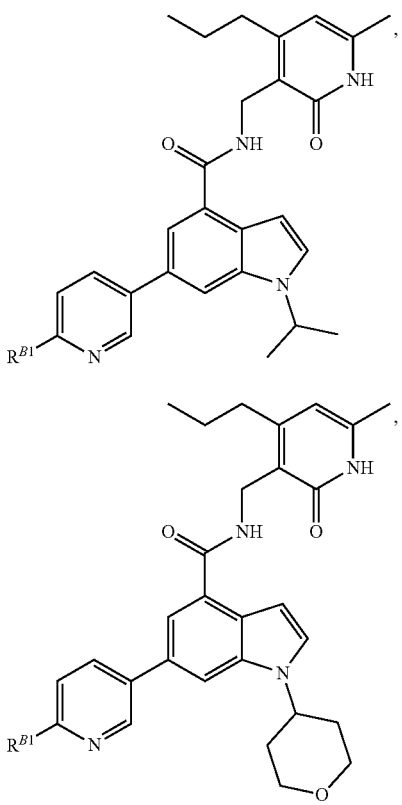

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

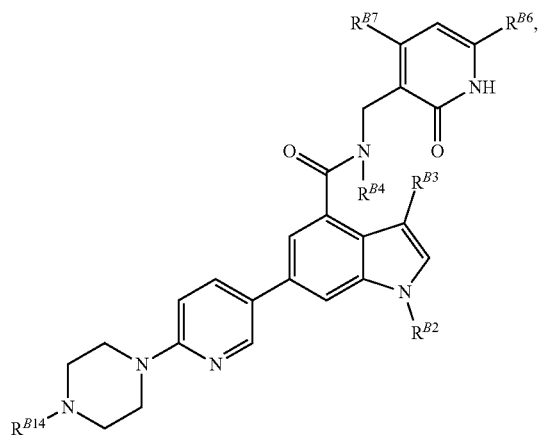

or a pharmaceutically acceptable salt, solvate, hydrate, polymorph, co-crystal, tautomer, stereoisomer, isotopically labeled derivative, or prodrug thereof, wherein $R^{B14}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group.

In certain embodiments, the compound of Formula (II) is of the formula:

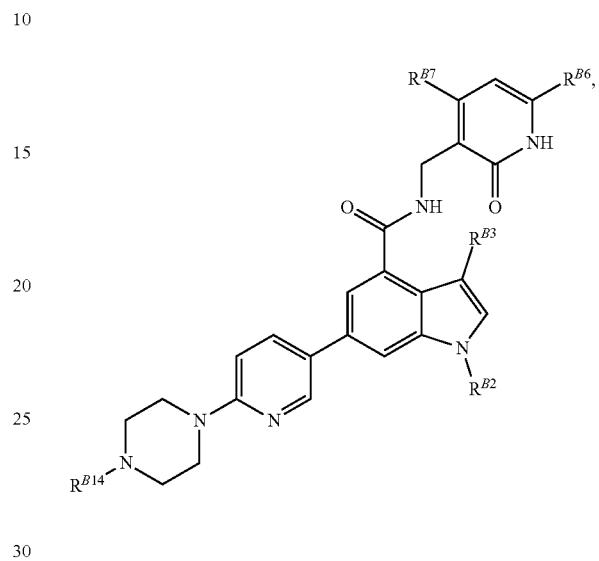

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

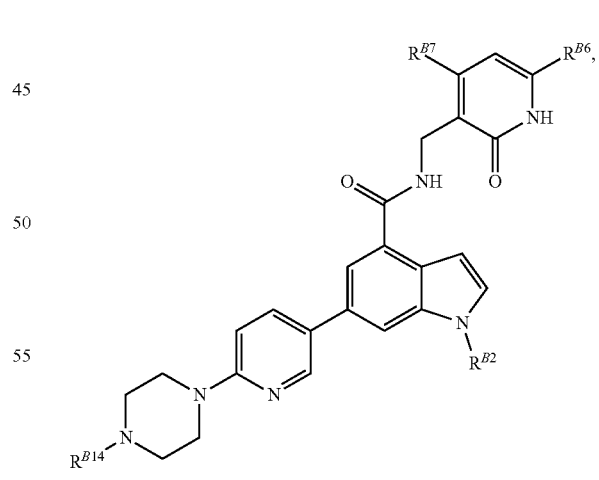

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

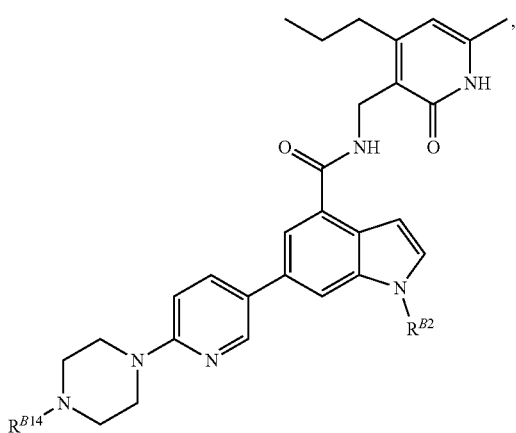

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

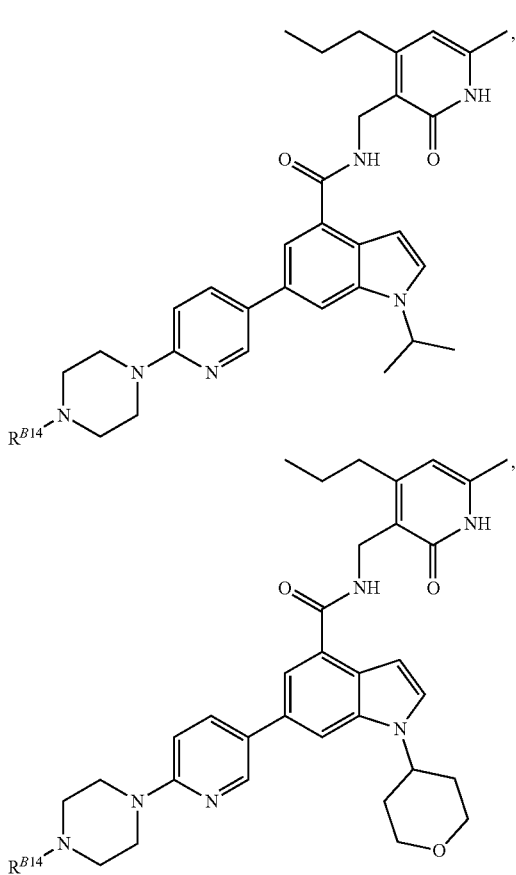

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

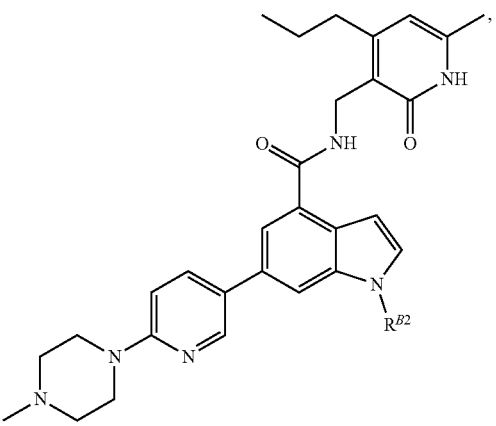

or a pharmaceutically acceptable salt, solvate, hydrate, polymorph, co-crystal, tautomer, stereoisomer, isotopically labeled derivative, or prodrug thereof, wherein $R^{B2}$ is a nitrogen protecting group (e.g., Boc).

In certain embodiments, the compound of Formula (II) is of the formula:

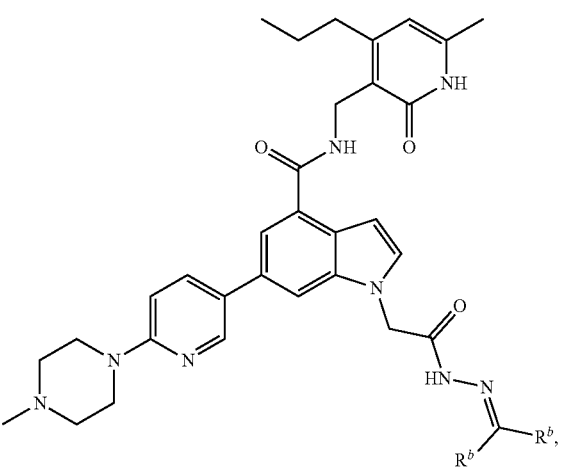

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:
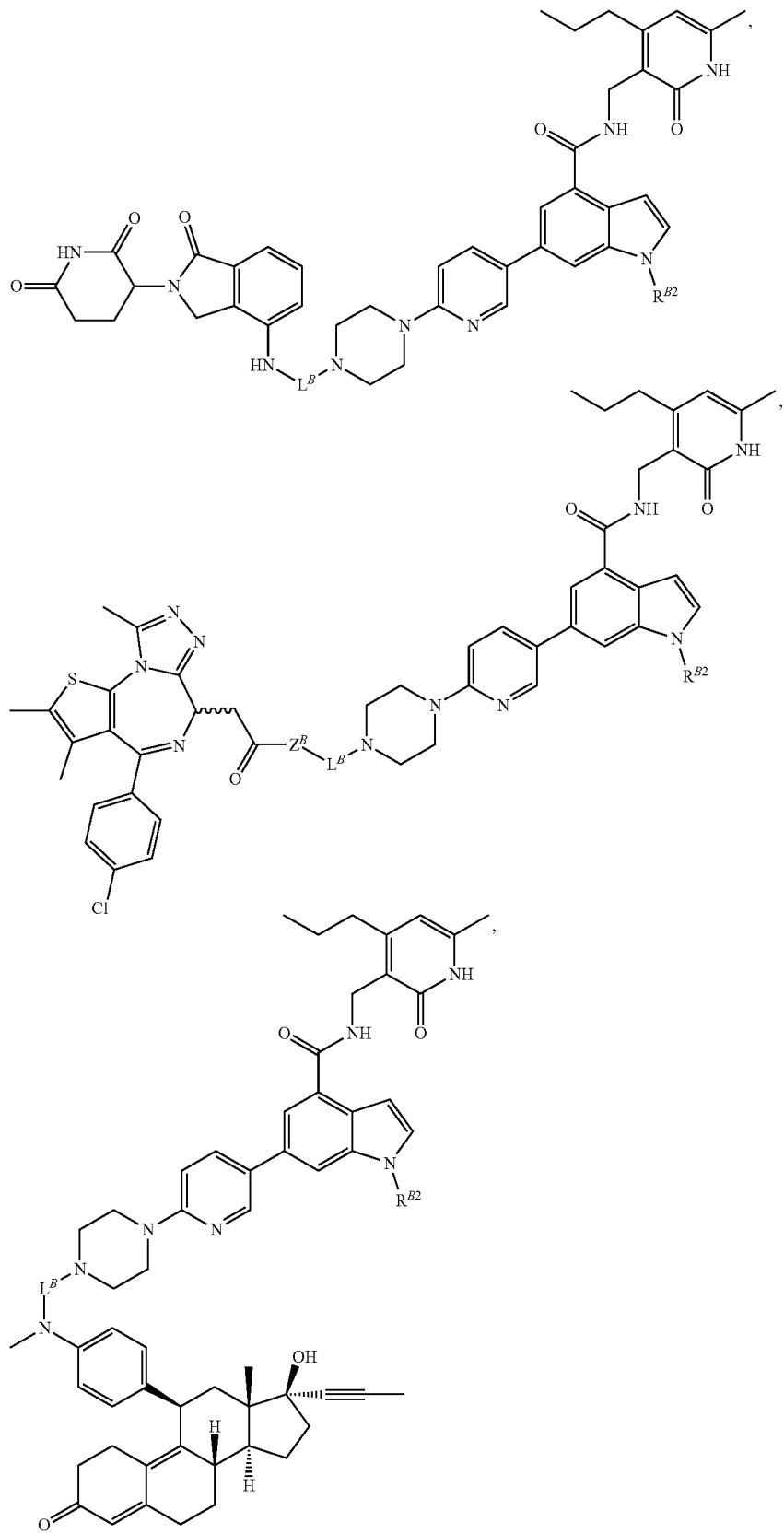

or a pharmaceutically acceptable salt, solvate, hydrate, polymorph, co-crystal, tautomer, stereoisomer, isotopically labeled derivative, or prodrug thereof, optionally wherein each instance of $R^{B2}$ is i-Pr.
In certain embodiments, the compound of Formula (II) is of the formula:
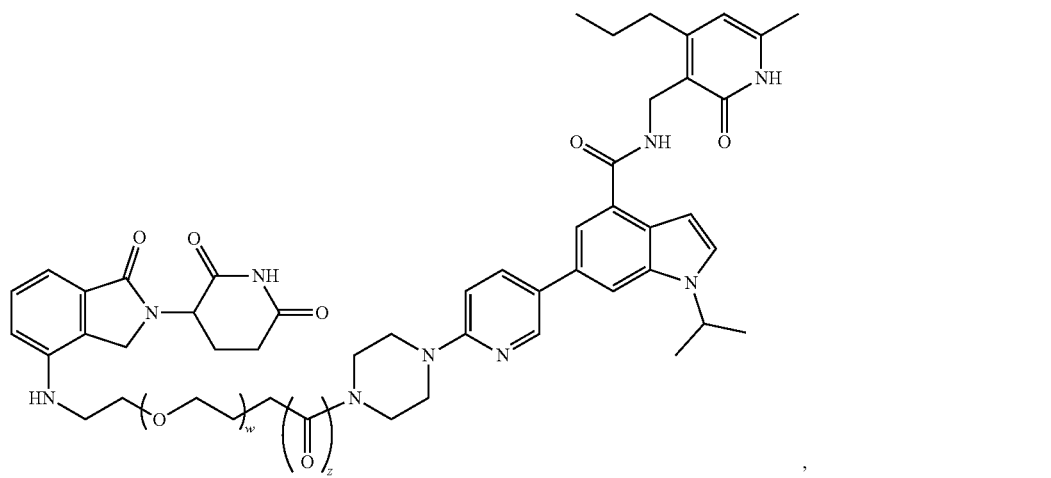
,
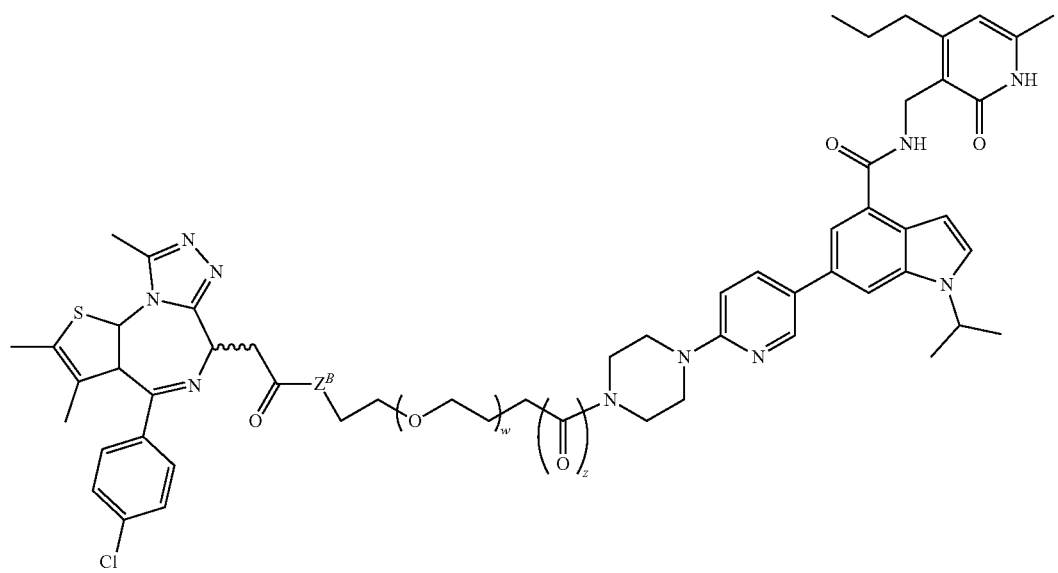
,

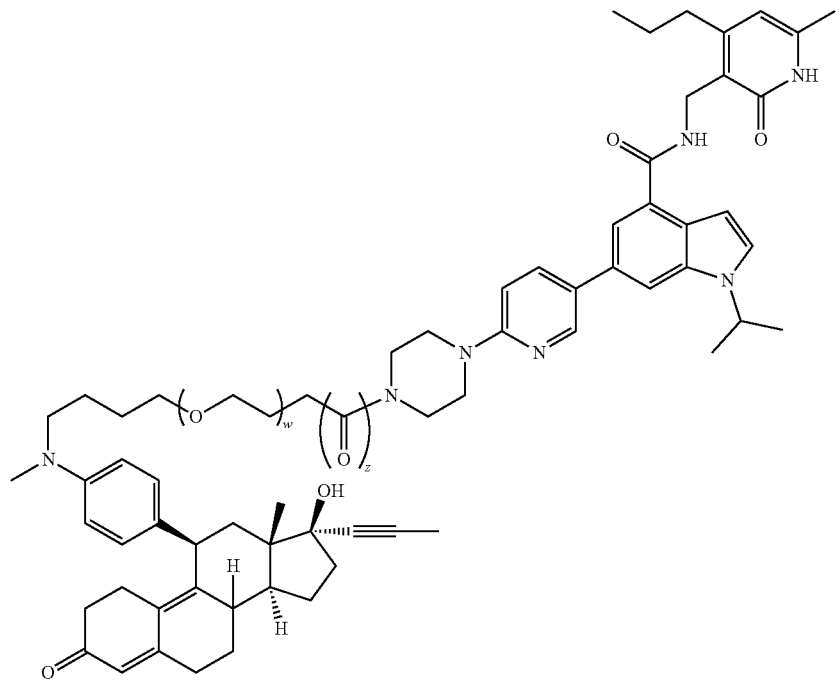

or a pharmaceutically acceptable salt, solvate, hydrate, polymorph, co-crystal, tautomer, stereoisomer, isotopically labeled derivative, or prodrug thereof, wherein each instance of w is independently an integer between 3 and 11, inclusive.

In certain embodiments, the compound of Formula (II) is of the formula:

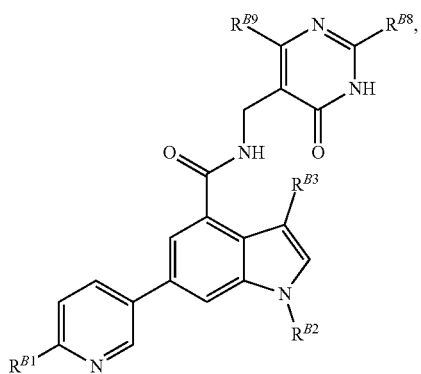

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

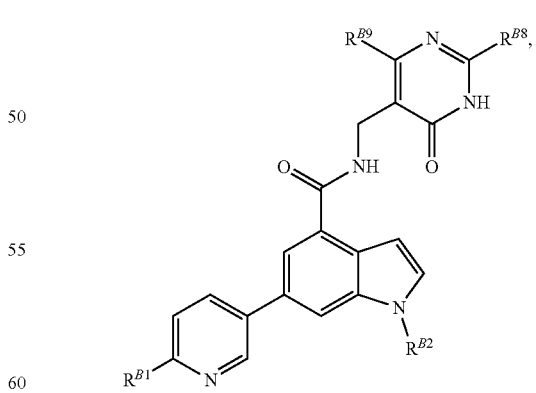

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

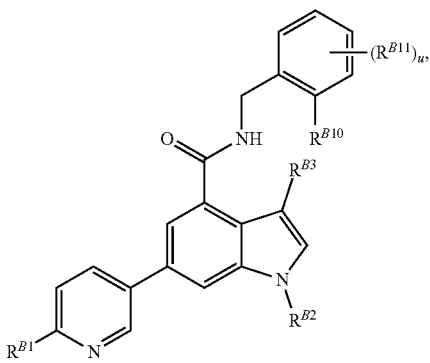

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

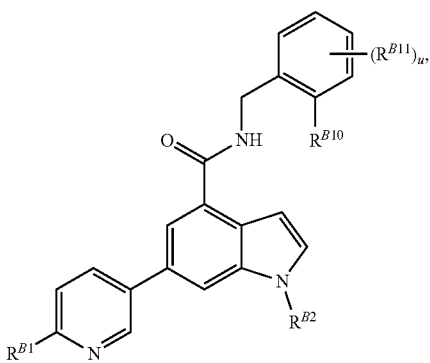

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

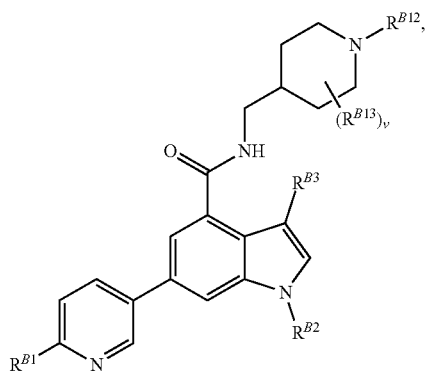

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

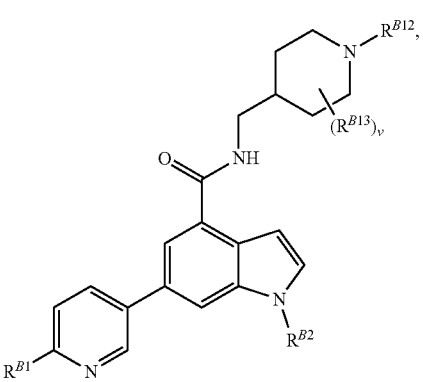

or a pharmaceutically acceptable salt, solvate, hydrate, polymorph, co-crystal, tautomer, stereoisomer, isotopically labeled derivative, or prodrug thereof.

In certain embodiments, when $R^{B2}$ is i-Pr, $R^{B3}$ is hydrogen, and $R^{B5}$ is of Formula (ii-1), then $R^{B1}$ is not Me,

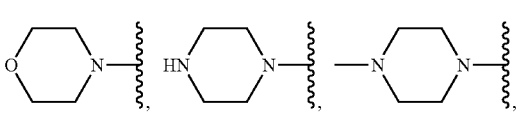

—OMe, or —NH(=O)Me. In certain embodiments, when $R^{B2}$ is unsubstituted $C_{3-5}$ alkyl, $R^{B3}$ is Me or halogen, and $R^{B5}$ is of Formula (ii-1), then $R^{B1}$ is not Me,

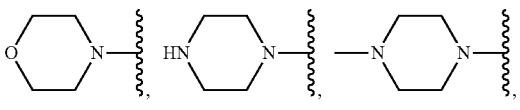

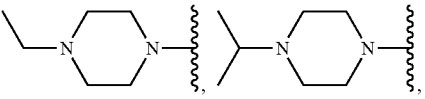

—OMe, —NH$_2$, —N(Me)$_2$, —C(=O)OH, —C(=O)OMe, or —NH(=O)Me. In certain embodiments, when $R^{B2}$ is i-Pr, $R^{B3}$ is hydrogen, and $R^{B5}$ is of Formula (ii-1), then $R^{B1}$ is not unsubstituted $C_{1-6}$ alkyl, —OR$^b$, —NH(=O)R$^b$, or unsubstituted or substituted with one unsubstituted $C_{1-6}$ alkyl, saturated, 6-membered, monocyclic heterocyclyl, wherein two atoms in the heterocyclic ring system are independently oxygen or nitrogen. In certain embodiments, when $R^{B2}$ is unsubstituted $C_{3-5}$ alkyl, $R^{B3}$ is Me or halogen, and $R^{B5}$ is of Formula (ii-1), then $R^{B1}$ is not unsubstituted $C_{1-6}$ alkyl, —OR$^b$, —N(R$^b$)$_2$, —C(=O)OR$^b$, —NH(=O) R$^b$, or unsubstituted or substituted with one unsubstituted $C_{1-6}$ alkyl, saturated, 6-membered, monocyclic heterocyclyl, wherein two atoms in the heterocyclic ring system are independently oxygen or nitrogen; wherein each instance of R$^b$ is independently H or unsubstituted $C_{1-6}$ alkyl. In certain embodiments, when $R^{B5}$ is of Formula (ii-1), then $R^{B2}$ is not unsubstituted $C_{3-5}$ alkyl. In certain embodiments, when $R^{B3}$ is hydrogen, and $R^{B5}$ is of Formula (ii-1), then $R^{B2}$ is not i-Pr. In certain embodiments, a compound of Formula (II) is not of the formula:

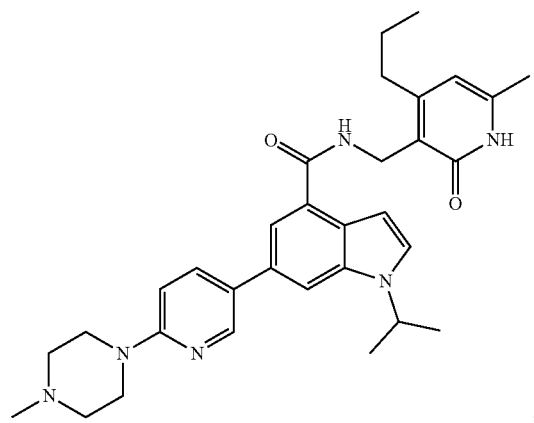

, or a pharmaceutically acceptable salt, solvate, hydrate, polymorph, co-crystal, tautomer, stereoisomer, isotopically labeled derivative, or prodrug thereof.

Exemplary compounds of Formula (II) include, but are not limited to:

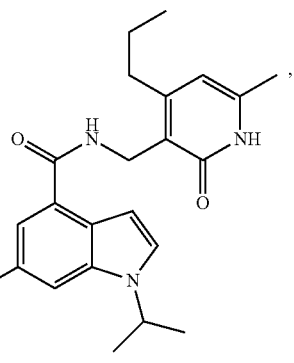

(EZ20, EZ-20, or EZ-020)

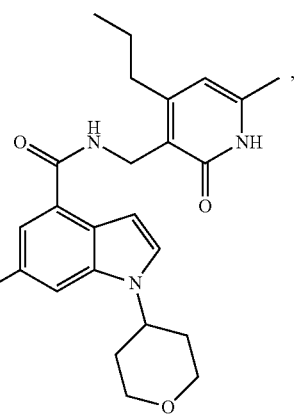

(EZ28, EZ-28, or EZ-028)

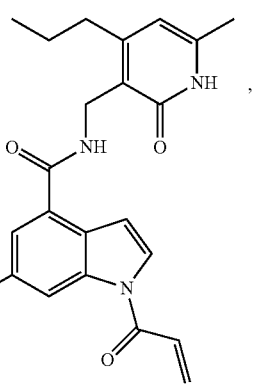

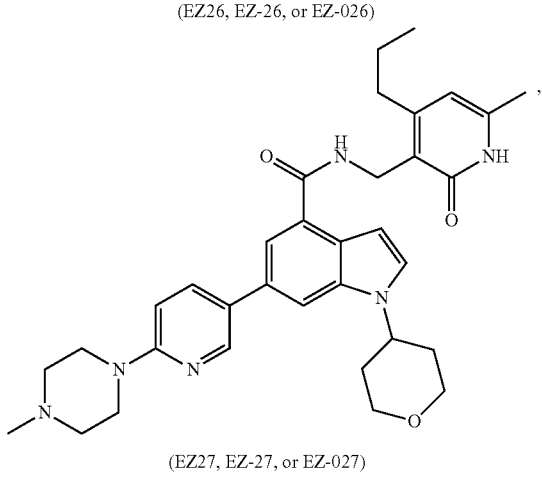

(EZ26, EZ-26, or EZ-026)

(EZ27, EZ-27, or EZ-027)

-continued
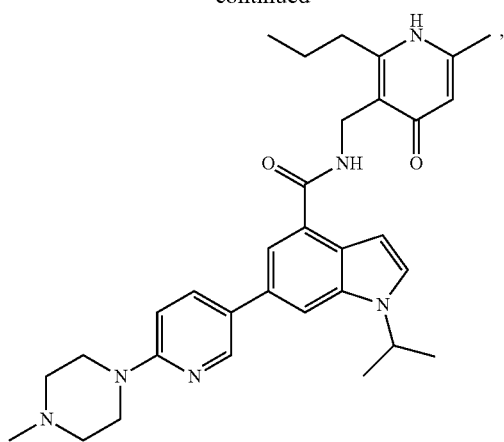
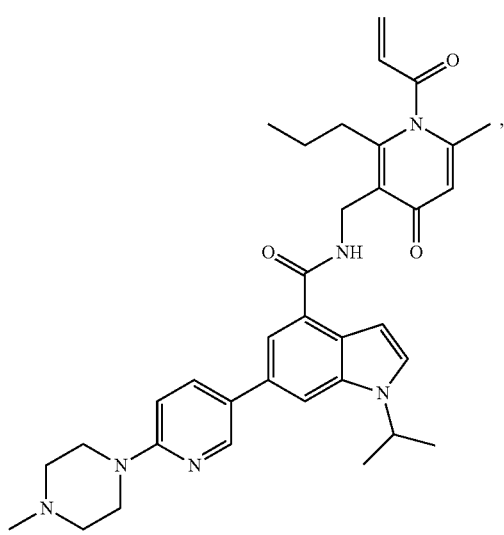
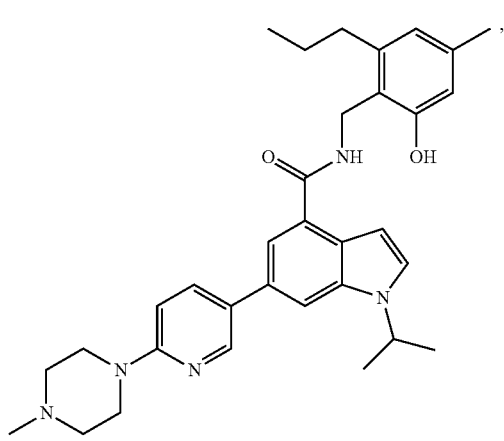
(EZ-43 or EZ43)
-continued
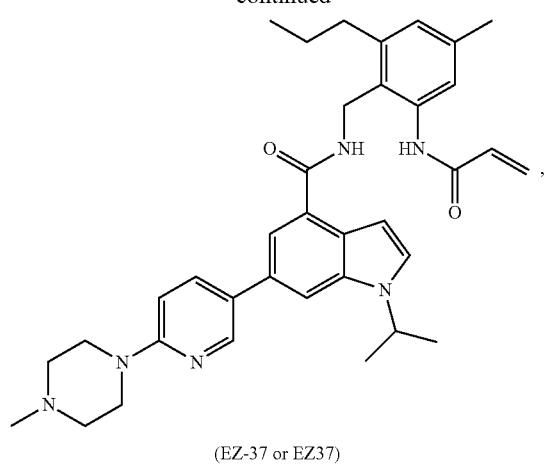
(EZ-37 or EZ37)
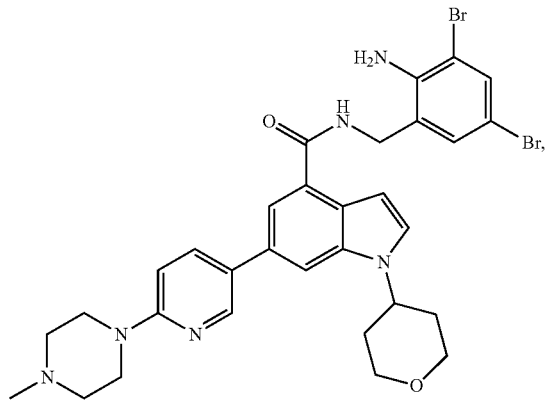
(EZ25, EZ-25, or EZ-025)
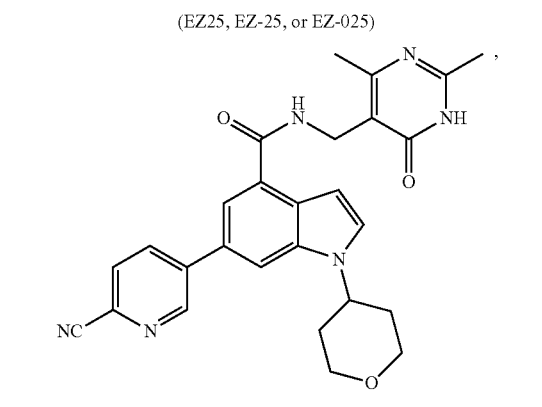
(EZ24, EZ-24, or EZ-024)
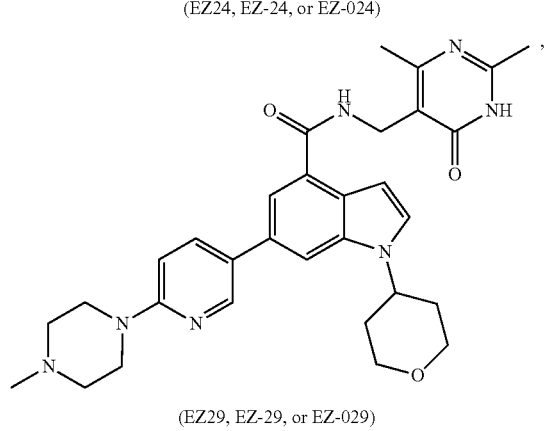
(EZ29, EZ-29, or EZ-029)

and pharmaceutically acceptable salts, solvates, hydrates, polymorphs, co-crystals, tautomers, stereoisomers, isotopically labeled derivatives, and prodrugs thereof.

Exemplary compounds of Formula (II) further include, but are not limited to:

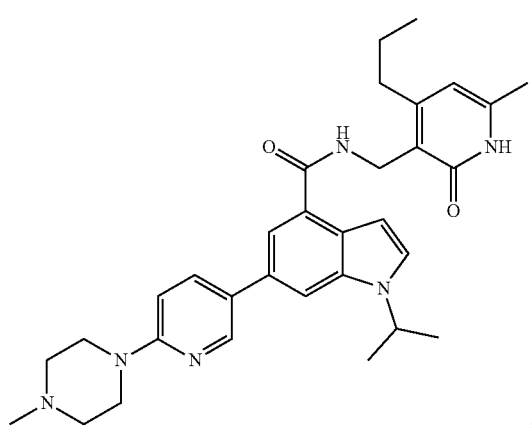

(EZ21, EZ-21, or EZ-021)

and pharmaceutically acceptable salts, solvates, hydrates, polymorphs, co-crystals, tautomers, stereoisomers, isotopically labeled derivatives, and prodrugs thereof.

In certain embodiments, the compound of Formula (II) is a compound of the formula:

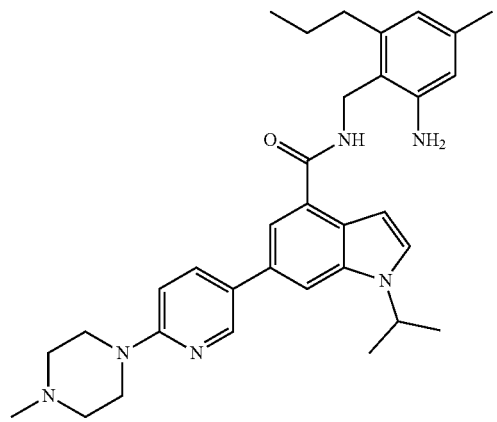

(EZ-38 or EZ38)

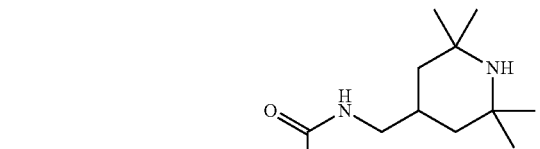

(EZ-30 or EZ30)

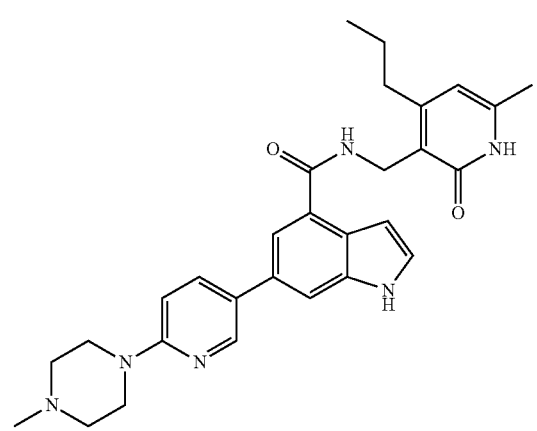

(EZ-31 or EZ31)

or a pharmaceutically acceptable salt, solvate, hydrate, polymorph, co-crystal, tautomer, stereoisomer, isotopically labeled derivative, or prodrug thereof.

In certain embodiments, the compound of Formula (II) is a compound of the formula:

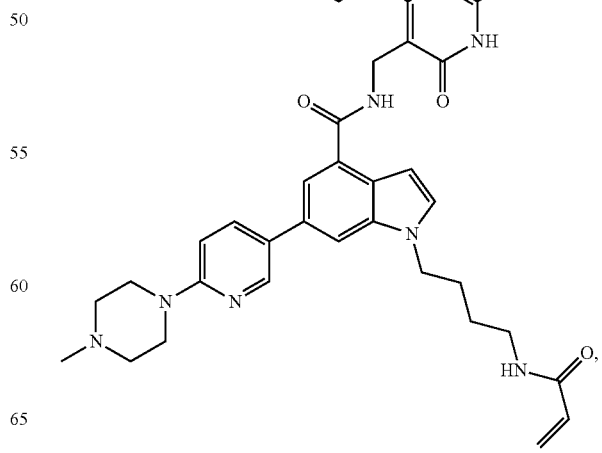

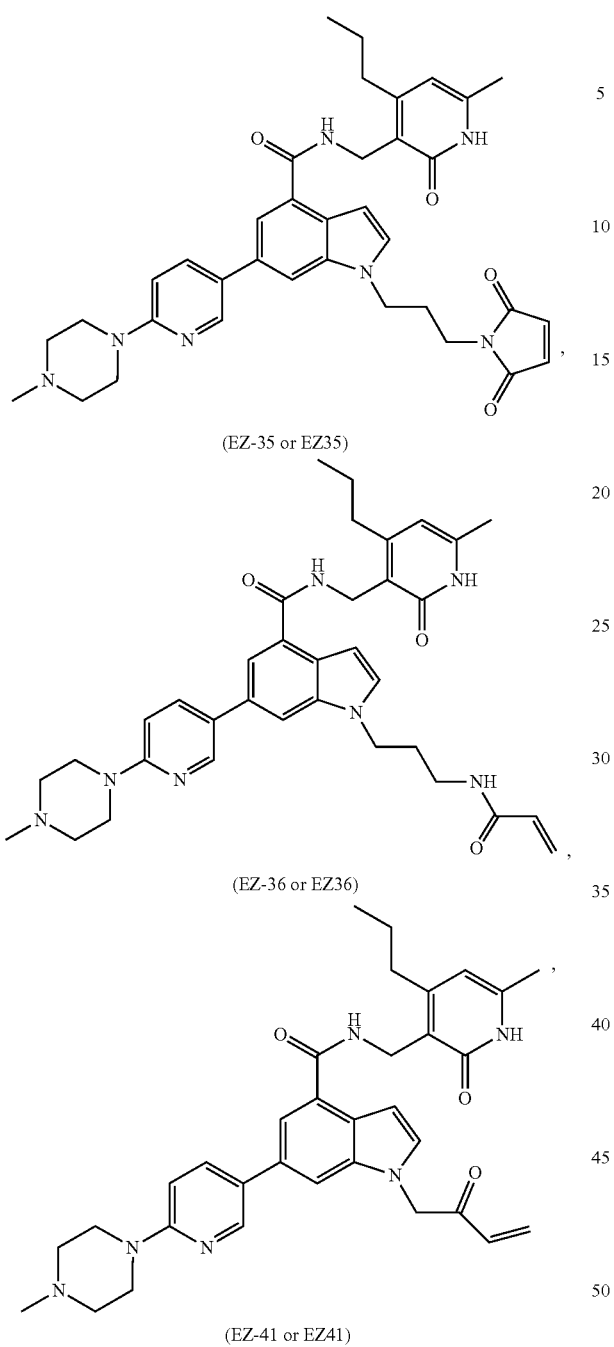

(EZ-35 or EZ35)

(EZ-36 or EZ36)

(EZ-41 or EZ41)

or a pharmaceutically acceptable salt, solvate, hydrate, polymorph, co-crystal, tautomer, stereoisomer, isotopically labeled derivative, or prodrug thereof.

In certain embodiments, a compound of Formula (I) or (II) is a reversible EZH2 inhibitor. In certain embodiments, a compound of Formula (I) or (II) that does not include a warhead is a reversible EZH2 inhibitor. In certain embodiments, a compound of Formula (I) or (II) that does not include a warhead does not form a covalent bond with EZH2.

In certain embodiments, a compound of Formula (I) or (II) is an irreversible EZH2 inhibitor. In certain embodiments, a compound of Formula (I) or (II) that includes one or more warheads is an irreversible EZH2 inhibitor. In certain embodiments, a compound of Formula (I) or (II) that includes one or more warheads forms one or more covalent bonds with EZH2 (e.g., a cysteine residue of EZH2). In certain embodiments, a compound of Formula (I) or (II) that includes one or more warheads forms one or more covalent bonds with EZH2 (e.g., a cysteine residue of EZH2) through a reaction (e.g., a Michael addition) between EZH2 and at least one of the warheads.

In certain embodiments, the irreversible EZH2 inhibitor is of the formula:

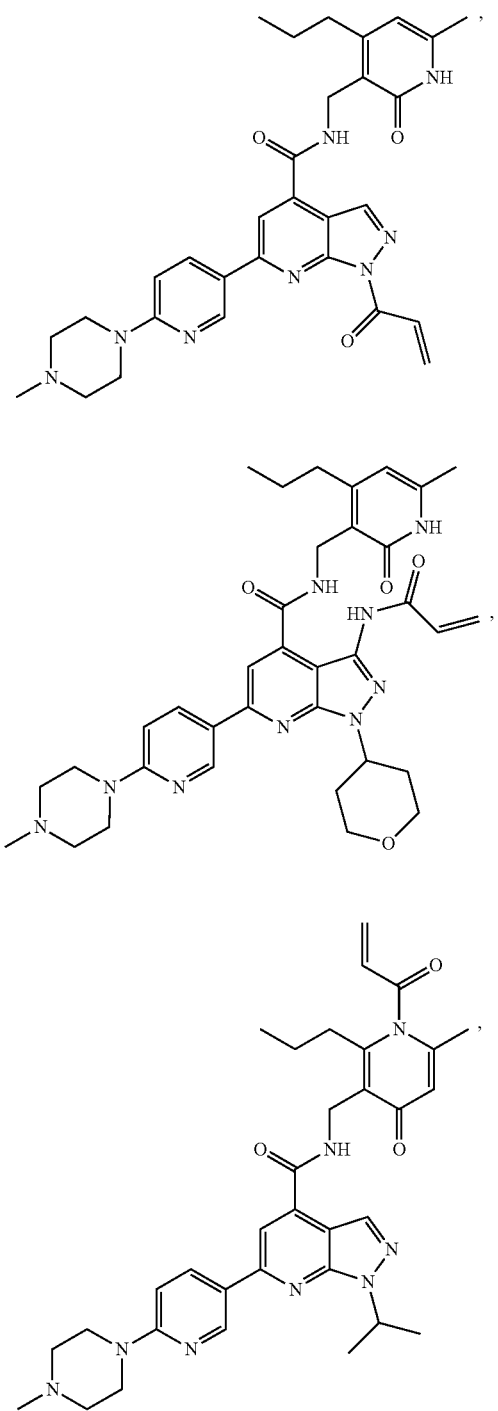

191
-continued
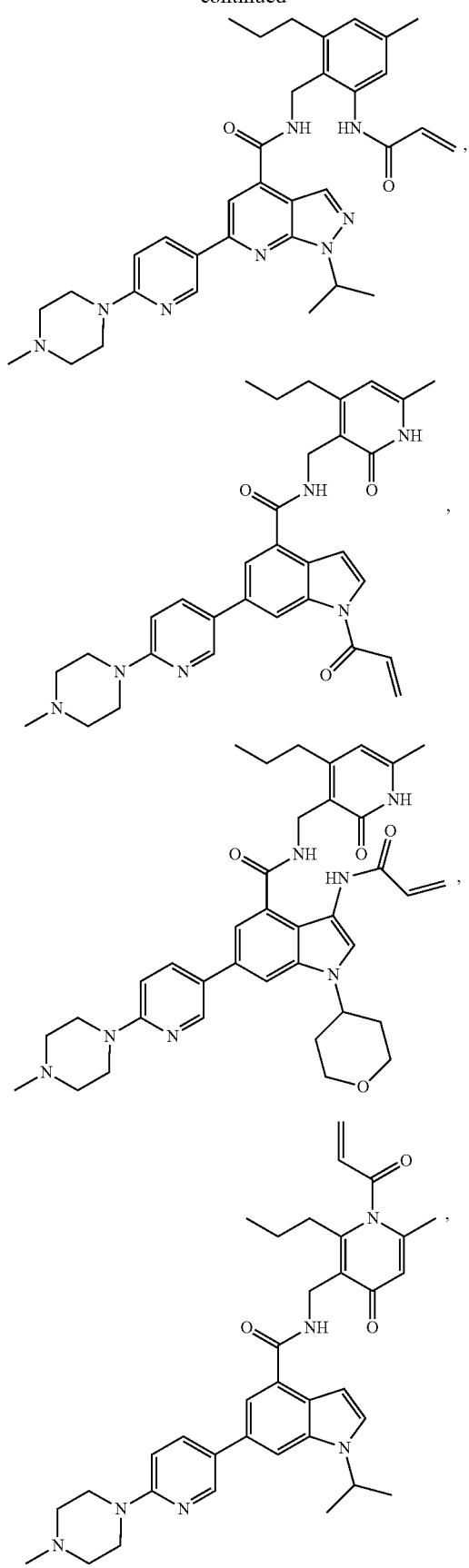
192
-continued
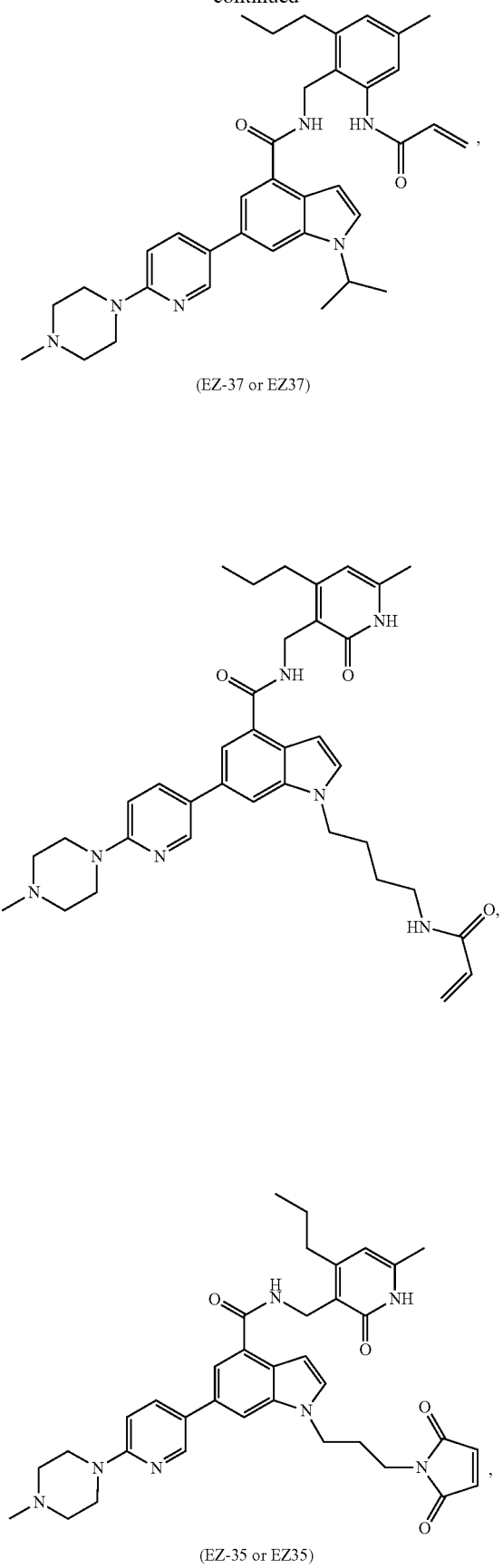
(EZ-37 or EZ37)
(EZ-35 or EZ35)

-continued

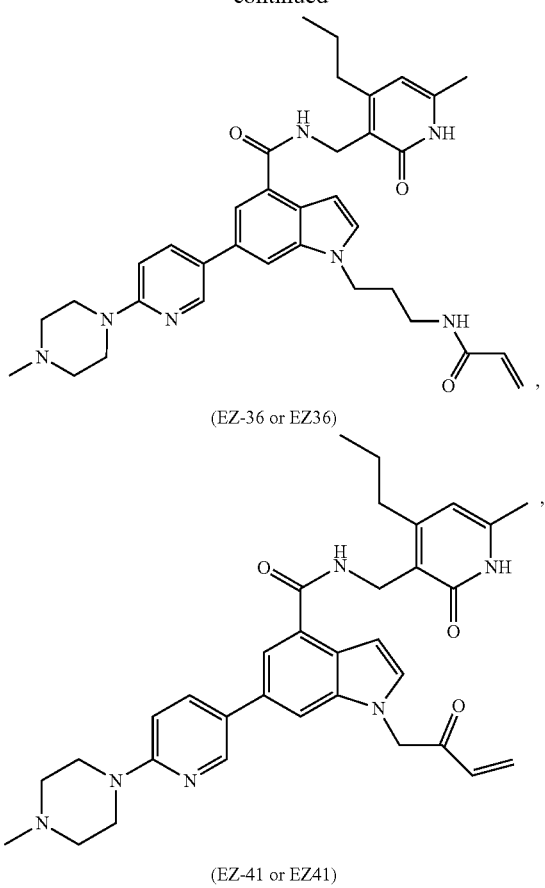

(EZ-36 or EZ36)

(EZ-41 or EZ41)

or a pharmaceutically acceptable salt, solvate, hydrate, polymorph, co-crystal, tautomer, stereoisomer, isotopically labeled derivative, or prodrug thereof. In certain embodiments, the compound of Formula (II) is a compound of the formula:

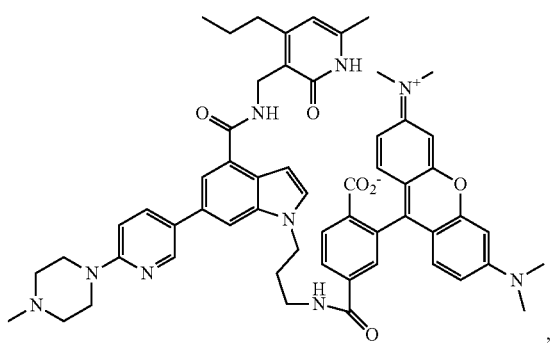

or a pharmaceutically acceptable salt, solvate, hydrate, polymorph, co-crystal, tautomer, stereoisomer, isotopically labeled derivative, or prodrug thereof.

Pharmaceutical Compositions, Kits, and Administration

The present disclosure also provides pharmaceutical compositions comprising a compound described herein and optionally a pharmaceutically acceptable excipient.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, a therapeutically effective amount is an amount effective for inhibiting the aberrant activity of an HMT (e.g., EZH1, EZH2, DOT1). In certain embodiments, a therapeutically effective amount is an amount effective for treating a disease (e.g., a disease associated with aberrant activity of an HMT (e.g., proliferative disease)). In certain embodiments, a therapeutically effective amount is an amount effective for inhibiting the aberrant activity of an HMT (e.g., EZH1, EZH2, DOT1) and treating a disease (e.g., a disease associated with aberrant activity of an HMT (e.g., proliferative disease)). In certain embodiments, a therapeutically effective amount is an amount effective for inducing apoptosis in a cell. In certain embodiments, a prophylactically effective amount is an amount effective for inhibiting the aberrant activity of an HMT (e.g., EZH1, EZH2, DOT1). In certain embodiments, a prophylactically effective amount is an amount effective for preventing or keeping a subject in need thereof in remission of a disease (e.g., a disease associated with aberrant activity of an HMT (e.g., proliferative disease)). In certain embodiments, a prophylactically effective amount is an amount effective for inhibiting the aberrant activity of an HMT (e.g., EZH1, EZH2, DOT1), and preventing or keeping a subject in need thereof in remission of a disease (e.g., a disease associated with aberrant activity of an HMT (e.g., proliferative disease)). In certain embodiments, a prophylactically effective amount is an amount effective for inducing apoptosis in a cell.

In certain embodiments, the effective amount is an amount effective for inhibiting the activity of an HMT (e.g., EZH1, EZH2, DOT1) by at least 10%, at least 20%, at least 30%, at least 40%, at least 50%, at least 60%, at least 70%, at least 80%, at least 90%, at least 95%, or at least 98%. In certain embodiments, the effective amount is an amount effective for inhibiting the activity of an HMT (e.g., EZH1, EZH2, DOT1) by not more than 10%, not more than 20%, not more than 30%, not more than 40%, not more than 50%, not more than 60%, not more than 70%, not more than 80%, not more than 90%, not more than 95%, or not more than 98%.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the cell is present in vitro. In certain embodiments, the cell is present in vivo.

Pharmaceutical compositions described herein can be prepared by any method known in the art of pharmacology. In general, such preparatory methods include bringing the compound described herein (i.e., the "active ingredient")

into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *Litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology.

They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in inhibiting the activity of an HMT in a subject, biological sample, tissue, or cell), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, inflammatory disease, autoimmune disease, genetic disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase *Erwinia chrysanthemi*), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), or a combination thereof. In certain embodiments, the additional pharmaceutical agent is a binder or inhibitor of an HMT (e.g., EZH1, EZH2, DOT1). In certain embodiments, the additional pharmaceutical agent is a protein kinase inhibitor (e.g., tyrosine protein kinase inhibitor). In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits are useful for preventing a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits are useful for inhibiting the activity (e.g., aberrant activity, such as increased activity) of an HMT in a subject, biological sample, tissue, or cell. In certain embodiments, the kits are useful for inducing apoptosis in a cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits and instructions provide for preventing a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits and instructions provide for modulating (e.g., inhibiting) the activity (e.g., aberrant activity, such as increased activity) of an HMT in a subject, biological sample, tissue, or cell. In certain embodiments, the kits and instructions provide for inducing apoptosis in a cell. A kit described herein may include one or more additional pharmaceutical agents described herein as a separate composition.

Methods of Treatment and Uses

The compounds described herein are capable of binding (e.g., reversibly binding or irreversibly binding) HMTs and modulating (e.g., reversibly modulating or irreversibly modulating) the activity of the HMTs. The present disclosure thus also provides methods of modulating (e.g., inhibiting or increasing) the activity (e.g., aberrant activity, such as increased or decreased activity) of an HMT in a subject, biological sample, tissue, or cell. The present disclosure further provides methods for the treatment of a wide range of diseases, such as diseases associated with aberrant or increased activity) of an HMT, proliferative diseases, inflammatory diseases, autoimmune diseases, genetic diseases, hematological diseases, neurological diseases, painful conditions, psychiatric disorders, and metabolic disorders in a subject in need thereof.

In another aspect, the present disclosure provides methods of modulating (e.g., inhibiting) the activity of an HMT in a subject in need thereof, the methods comprising administering to the subject an effective amount of a compound or pharmaceutical composition described herein.

In another aspect, the present disclosure provides methods of modulating (e.g., inhibiting) the activity of an HMT in a biological sample, tissue, or cell, the methods comprising contacting the biological sample, tissue, or cell with an effective amount of a compound or pharmaceutical composition described herein.

In certain embodiments, the activity of an HMT in a subject, biological sample, tissue, or cell is inhibited by a compound, pharmaceutical composition, kit, use, or method described herein by at least 1%, at least 3%, at least 10%, at least 20%, at least 30%, at least 40%, at least 50%, at least 60%, at least 70%, at least 80%, or at least 90%. In certain embodiments, the activity of an HMT in a subject, biological sample, tissue, or cell is inhibited by a compound, pharmaceutical composition, kit, use, or method described herein by not more than 1%, not more than 3%, not more than 10%, not more than 20%, not more than 30%, not more than 40%, not more than 50%, not more than 60%, not more than 70%, not more than 80%, or not more than 90%. In some embodiments, the activity of an HMT in a subject, biological sample, tissue, or cell is selectively inhibited by the compound, pharmaceutical composition, kit, use, or method. In some embodiments, the activity of EZH2 in a subject, biological sample, tissue, or cell is selectively inhibited by the compound, pharmaceutical composition, kit, use, or method, compared to a different HMT (e.g., EZH1). In some embodiments, the activity of EZH1 in a subject, biological sample, tissue, or cell is selectively inhibited by the compound, pharmaceutical composition, kit, use, or method, compared to a different HMT (e.g., EZH2). In some embodiments, the activity of an HMT described herein in a subject, biological sample, tissue, or cell is reversibly inhibited by the compound, pharmaceutical composition, kit, use, or method. In some embodiments, the activity of an HMT described herein in a subject, biological sample, tissue, or cell is irreversibly inhibited by the compound, pharmaceutical composition, kit, use, or method. In certain embodiments, the compound, pharmaceutical composition, kit, use, or method inhibits the activity of a mutant form of an HMT (e.g., mutant form of EZH1, or mutant form of EZH2). In certain embodiments, the compound, pharmaceutical composition, kit, use, or method decreases the methylation of a histone.

Another aspect of the present disclosure relates to methods of decreasing the methylation of a histone in a subject in need thereof, the methods comprising administering to the subject an effective amount of a compound or pharmaceutical composition described herein.

Another aspect of the present disclosure relates to methods of decreasing the methylation of a histone in a biological sample, tissue, or cell, the methods comprising contacting the biological sample, tissue, or cell with an effective amount of a compound or pharmaceutical composition described herein.

Another aspect of the present disclosure relates to methods of modulating (e.g., down-regulating or up-regulating) the expression of a gene in a subject in need thereof, the methods comprising administering to the subject an effective amount of a compound or pharmaceutical composition described herein.

Another aspect of the present disclosure relates to methods of modulating (e.g., down-regulating or up-regulating) the expression of a gene in a biological sample, tissue, or cell, the methods comprising contacting the biological sample, tissue, or cell with an effective amount of a compound or pharmaceutical composition described herein.

In certain embodiments, a gene described herein is a gene that encodes an HMT described herein (e.g., a gene that encodes EZH1, EZH2, or DOT1).

Another aspect of the present disclosure relates to methods of treating a disease in a subject in need thereof, the methods comprising administering to the subject a therapeutically effective amount of a compound or pharmaceutical composition described herein.

HMTs are implicated in a wide range of diseases. For example, changes in the EZH2 gene have been associated with various types of cancers. Mutations of this gene have been identified in hematological malignancies (e.g., lymphoma, leukemia). These mutations may be described as "gain-of-function" because they appear to enhance the activity of the EZH2 enzyme and/or give the enzyme a new, atypical function. In addition, increased activity (overexpression) of the EZH2 gene has been identified in cancerous tumors of the prostate, breast, and other organs. Changes involving the EZH2 gene likely impair normal control of cell division (proliferation), allowing cells to grow and divide too fast or in an uncontrolled way and leading to the development of cancer. Moreover, at least 20 EZH2 gene mutations have been identified in people with Weaver syndrome. Signs and symptoms of this condition include bone overgrowth, a distinctive facial appearance, and joint problems. People with Weaver syndrome have an increased risk of developing cancer. EZH2 gene mutations may disrupt methylation and impair regulation of certain genes in many of the subject's organs and tissues, resulting in the abnormalities characteristic of Weaver syndrome. Weaver syndrome is also associated with aberrant activity of EZH1. It has also been reported that DOT1 was implicated in leukemia (e.g., AML, ALL). In a subject with leukemia, DOT1 may be mis-localized on the chromatin, affecting local H3K79 methylation status. The global levels of H3K79 methylation were not affected, but the local levels of H3K79 methylation at specific regions were aberrantly altered, resulting in the dysregulated transcription of what is likely to be the important players in leukemia.

Mutations at tyrosine 641 (e.g., Y641F, Y641N, Y641S, Y641H) in the SET domain of EZH2 have been found to be associated with certain types of cancer (e.g., non-Hodgkin lymphoma). These mutations have been shown to affect substrate specificity of EZH2 for certain methylation states of lysine 27 on histone H3. A subject may be selected for treatment with an EZH2 inhibitor based on the presence or absence of a mutation in EZH2 in the subject. For example, in some embodiments, a subject is selected for treatment with an EZH2 inhibitor if the subject has a mutation at tyrosine 641 in the SET domain of EZH2.

In certain embodiments, a disease described herein is a disease associated with an HMT. In certain embodiments, a disease described herein is a disease associated with aberrant activity (e.g., increased activity) of an HMT. In certain embodiments, a disease described herein is a proliferative disease. In certain embodiments, a disease described herein is cancer. In certain embodiments, a disease described herein is hyperplasia (e.g., germinal center (GC) hyperplasia). In certain embodiments, a disease described herein is brain cancer, breast cancer, or prostate cancer. In certain embodiments, a disease described herein is a benign neoplasm. In certain embodiments, a disease described herein is or is associated with pathological angiogenesis. In certain embodiments, a disease described herein is an inflammatory disease. In certain embodiments, a disease described herein is an autoimmune disease. In certain embodiments, a disease described herein is a genetic disease. In certain embodiments, a disease described herein is Weaver syndrome. In certain embodiments, a disease described herein is a hematological disease. In certain embodiments, a disease described herein is lymphoma (e.g., follicular large B-cell lymphoma, diffuse large B-cell lymphoma). In certain embodiments, a disease described herein is leukemia (e.g., CML). In certain embodiments, a disease described herein is a neurological disease. In certain embodiments, a disease described herein is a painful condition. In certain embodiments, a disease described herein is a psychiatric disorder. In certain embodiments, a disease described herein is a metabolic disorder.

In still another aspect, the present disclosure provides methods of preventing a disease described herein in a subject in need thereof, the methods comprising administering to the subject a prophylactically effective amount of a compound or pharmaceutical composition described herein.

In another aspect, the present disclosure provides the compounds described herein for use in a method described herein (e.g., a method of inhibiting the activity of an HMT, a method of treating a disease (e.g., a proliferative disease), a method of preventing a disease (e.g., a proliferative disease), a method of inducing apoptosis, or a method of screening a library of compounds).

In still another aspect, the present disclosure provides the pharmaceutical compositions described herein for use in a method described herein (e.g., a method of inhibiting the activity of an HMT, a method of treating a disease (e.g., a proliferative disease), a method of preventing a disease (e.g., a proliferative disease), a method of inducing apoptosis, or a method of screening a library of compounds).

Methods of Screening a Library of Compounds

Another aspect of the disclosure relates to methods of screening a library of compounds, and pharmaceutical acceptable salts thereof, to identify a compound, or a pharmaceutical acceptable salt thereof, that is useful in a method described herein. In certain embodiments, the methods of screening a library include obtaining at least two different compounds described herein; and performing at least one assay using the different compounds described herein. In certain embodiments, at least one assay is useful in identifying a compound that is useful in a method described herein.

Typically, the methods of screening a library of compounds involve at least one assay. In certain embodiments, the assay is performed to detect one or more characteristics associated with the treatment and/or prevention of a disease described herein or with the modulation (e.g., inhibition) of the activity of an HMT. The characteristics may be desired characteristics (e.g., a disease having been treated, a disease having been prevented, the activity of an HMT having been modulated, and/or apoptosis having been induced). The characteristics may be undesired characteristics (e.g., a disease having not been treated, a disease having not been prevented, the activity of an HMT having not been modulated, and/or apoptosis having not been induced). The assay may be an immunoassay, such as a sandwich-type assay, competitive binding assay, one-step direct test, two-step test, or blot assay. The step of performing at least one assay may be performed robotically or manually. In certain embodiments, the assay comprises (a) contacting a library of compounds with an HMT; and (b) detecting the binding of the library of compounds to the HMT. In certain embodiments, the assay comprises detecting the specific binding of the library of compounds to the HMT. In certain embodiments, the detected binding of the library of compounds to the HMT is useful in identifying the compound that is useful in a method described herein. In certain embodiments, the step of detecting the binding comprises using differential scanning fluorimetry (DSF), isothermal titration calorimetry (ITC), and/or an amplified luminescence proximity homogeneous assay (ALPHA). The step of performing at least one assay may be performed in a cell in vitro or in vivo.

Assays

Enhancer of zeste homolog 2 (EZH2) is core component of PRC2 that catalyzes the di- and tri-methylation at histone H3 lysine 27 (H3K27me2/3). Somatic mutations in the SET domain of EZH2 (e.g., Y641N) resulting hyperactivity of the enzyme have been identified in a large portion of follicular and diffuse large B-cell lymphomas, implicating a driver function of EZH2 in cancer formation (Beguelin et al., 2013; Morin et al., 2010).

The compounds described herein are inhibitors of histone methyltransferases (HMTs, e.g., enhancer of zeste homolog 1 (EZH1), enhancer of zeste homolog 2 (EZH2)).

The compounds are useful in treating and/or preventing diseases associated with aberrant or increased activity of an HMT, e.g., a proliferative disease, inflammatory disease, autoimmune disease, genetic disease, hematological disease, neurological disease, painful condition, psychiatric disorder, or metabolic disorder, in a subject in need thereof.

In certain embodiments, compounds of the present invention or those identified by the inventive methods and systems include those which:
  exhibit the ability to inhibit EZH1 binding and/or activity,
  exhibit the ability to inhibit EZH2 binding and/or activity,
  exhibit the ability to compete for binding to EZH1 with a compound that is known to bind to EZH1,
  exhibit the ability to compete for binding to EZH2 with a compound that is known to bind to EZH2,
  exhibit the ability to bind PRC2 and disrupt binding of EZH1 binding site,
  exhibit the ability to bind PRC2 and disrupt binding of EZH2 binding site,
  exhibit the ability to bind PRC2 and displace a compound that is known to bind to EZH1 within a cell, e.g., displace the compound from nuclear localization, or
  exhibit the ability to bind PRC2 and displace a compound that is known to bind to EZH2 within a cell, e.g., displace the compound from nuclear localization According to one aspect of the invention, methods for identifying EZH1 and/or EZH2 binding compounds are provided. In some embodiments, the method comprises an ALPHA assay. The method is based on the detection of EZH1 and/or EZH2-compound complex formation which is accomplished by labeling EZH1 and/or EZH2 and the compound with luminescent probes, including fluorophores, and chemiluminescent substrates. The physical proximity between the EZH1 and/or EZH2 and labeled compound in the protein-compound complex provides for a change in fluorescence signal or formation of a chemiluminescent product associated with protein-labeled compound complex formation, specifically proximity of EZH1 and/or EZH2 and the labeled compound. In the presence of a competitor compound which binds to EZH1 and/or EZH2, protein-labeled compound complex formation is disrupted leading to a corresponding decrease in the expected luminescence detection signal.

The method typically comprises providing an EZH1 and/or EZH2 binding compound labeled with a fluorescence donor and EZH1 and/or EZH2 labeled with a fluorescence acceptor, wherein binding of the labeled compound to EZH1 and/or EZH2 is detected by proximity-based luminescence detection; combining the labeled compound and EZH1 and/or EZH2 in presence of a test compound; and identifying the test compound as an EZH1 and/or EZH2 inhibitor when the proximity-based luminescence detection signal is decreased in the presence of the test compound relative to the signal in the absence of the test compound. The amount of decrease in measured detection signal necessary for a test compound to be identified as an EZH1 and/or EZH2 inhibitor depends upon the type of proximity-based luminescence detection assay used. Generally a 5% or greater decrease relative to an assay performed in the absence of the test compound indicates that the test compound is an EZH1 and/or EZH2 inhibitor. In certain embodiments, the test compound stimulates at least a 10%, 25%, 50%, 75% or 100% decrease in detection signal.

Any method of proximity-based luminescence detection can be used in the present invention. Embodiments of proximity based luminescence detection methods include, but are not limited to, fluorescence resonance energy transfer ("FRET") (Stryer, L. Ann. Rev. Biochem. 47, 819-846, 1978), luminescence resonance energy transfer ("LRET") (Mathis, G. Clin. Chem. 41, 1391-1397, 1995), fluorescence cross-correlation spectroscopy ("FCCS") (Maiti et al. Proc. Nat'l Acad Sci USA 94, 11753-11757, 1997), scintillation proximity ("SPA") (Hart and Greenwald, Molecular Immunology 16:265-267, 1979; U.S. Pat. No. 4,658,649), direct quenching (Tyagi et al., Nature Biotechnology 16, 49-53, 1998), chemiluminescence energy transfer ("CRET") (Campbell, A. K., and Patel, A. Biochem. J. 216, 185-194, 1983), bioluminescence energy transfer ("BRET") (Xu, Y., Piston, D. W., Johnson, Proc. Natl. Acad. Sci., 96, 151-156, 1999) and excimer formation (Lakowicz, J. R. Principles of Fluorescence Spectroscopy, Kluwer Academic/Plenum Press, New York, 1999). It is understood that the skilled artisan would recognize alternative proximity-based luminescence detection methods that are applicable to the present invention and are useful in the present invention.

The term "luminescence" or "luminescent" means any process of light emission including fluorescence, phosphorescence, scintillation, chemiluminescence, and bioluminescence.

The term fluorescent donor or fluorescence donor refers to a luminescent molecule which emits light that is absorbed by a fluorescence acceptor. The term fluorescent acceptor or fluorescence acceptor refers to either a second luminescent molecule or a quenching molecule which absorbs light emitted from the fluorescence donor. The second fluorophore absorbs the light that is emitted from the fluorescence donor and emits light of different wavelength than the light emitted by the fluorescence donor. The quenching molecule absorbs light emitted by the fluorescence donor. It is envisioned that any luminescent molecule may be used in the practice of this invention.

Examples of fluorophores and quenchers include, but are not limited to, Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, 7-diethylaminocoumarin-3-carboxylic acid, Fluorescein, Oregon Green 488, Oregon Green 514, Tetramethylrhodamine, Rhodamine X, Texas Red dye, QSY 7, QSY33, Dabcyl, BODIPY FL, BODIPY 630/650, BODIPY 650/665, BODIPY TMR-X, BODIPY TR-X, Dialkylaminocoumarin, Cy5.5, Cy5, Cy3.5, Cy3, DTPA (Eu3+)-AMCA and TTHA (Eu3+)-AMCA.

The term "chemiluminescence," "chemiluminescent," or "chemiluminescent substrate" refers to a chemical that produces light as a result of a chemical reaction. Commonly used chemiluminescent substrates include, but are not limited to, luminol (5-amino-2,3-dihydro-1, 4-phthalazinedione), lophine (2, 4, 5-triphenylimidazole), lucigenin (bis-N-methylacridinium), other acridinium esters, luciferin-luciferase, and thioxene derivatives. For example, in the art-recognized ECL™ detection system of Amersham, an acridinium substrate is oxidized by horse radish peroxidase to produce acridinium esters, which react with excess peroxide at an alkaline pH to produce visible chemiluminescence at 430 nm.

In some embodiments, the art-recognized AlphaLISA TruHits Kit of PerkinElmer is used. This kit includes AlphaLISA BSA-biotin Acceptor beads and Streptavidin Alpha Donor beads which interact together to generate an AlphaLISA signal. The excitation of the Donor beads provokes the release of singlet oxygen molecules that triggers a cascade of energy transfer in the Acceptor beads, resulting in a sharp peak of light emission at 615 nm.

It is understood that the skilled artisan would recognize that any compatible fluorescence donor-acceptor pair will work in the present invention and that the aforementioned fluorophores and quenchers are exemplary and not limiting.

In one embodiment, the labeled compound and/or EZH1 and/or EZH2 are in solution and free to diffuse in all directions. In another embodiment, the labeled compound and/or EZH1 and/or EZH2 are affixed to a solid phase substrate, such as, a microtiter plate, microarray slide, membrane or microsphere. In some embodiments, labeled compound and/or EZH1 and/or EZH2 are linked to the solid substrate via a covalent or non-covalent interaction, e.g., biotin/avidin interaction.

In some embodiments, the method comprises a fluorescence polarization (FP) assay. Fluorescence polarization (FP) assays can be used to study molecular interactions (e.g., Lea, W. A., Simeonov, A. *Expert Opin. Drug Discov.*, 6, 17-32, 2011). Generally in an FP assay, a fluorescently labeled molecule, when excited by plane polarized light, will emit fluorescence having a degree of polarization that is inversely related to its rate of rotation. In solution, numerous phenomena (e.g., drag, diffusion, Brownian motion) dictate that smaller particles will have a greater rate of rotation than larger particles. Thus, when a complex comprising a protein (e.g., EZH1 and/or EZH2) and a fluorescently labeled compound (e.g., a compound described herein) is excited with plane polarized light, the emitted light remains highly polarized because the fluorophore is constrained from rotating between the time that light is absorbed and emitted. When the unbound fluorescently labeled compound is excited by plane polarized light, its rate of rotation is faster than that of the corresponding complex. As a result, the light emitted from the unbound fluorescently labeled compound is depolarized to a greater extent than the same molecule constrained by complexation. In the context of a small molecule compound screening, a fluorescent label may be attached to a compound that is known to form binding interactions with a protein (e.g., EZH1 and/or EZH2). The binding of the labeled compound to the protein can be monitored via FP. In the presence of an unlabeled compound that binds to the protein, the complex comprising the labeled compound and the protein is displaced. As a result, the concentration of unbound labeled compound is increased and the FP signal reflects the subsequent increase in depolarized light.

In some embodiments, the method comprises an intracellular competitive binding assay, e.g., an intracellular competitive EZH2 binding assay. For example, cells in culture may be incubated with labeled EZH2 binding compound, which may localize to the nucleus to bind endogenous EZH2. The cells can be incubated in the presence of an unlabeled test compound (e.g., candidate EZH2 inhibitor compound). If the test compound binds to exogenous EZH2, it can compete for binding with the labeled EZH2 binding compound, thereby causing the labeled EZH2 binding compound to localize to a location other than the cell nucleus. Such binding and localization can be detected, e.g., by detection of the label. Thus, in the presence of an unlabeled compound that binds to the EZH2, the complex comprising the labeled compound and the endogenous EZH2 is displaced. As a result, the labeled compound will localize to the nucleus of the cell to a lower level as compared to the labeled compound localization in absence of the unlabeled compound.

Candidate test compounds useful in accordance with the invention encompass numerous chemical classes, although typically they are small organic compounds. The term "small molecule" is used to refer to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, heterocyclic rings, etc.). In some embodiments, small molecules are monomeric and have a molecular weight of less than about 1500 g/mol. In certain embodiments, the molecular weight of the small molecule is less than about 1000 g/mol or less than about 500 g/mol. In certain embodiments, small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

Candidate test compounds comprise functional chemical groups necessary for structural interactions with proteins and/or nucleic acids, and typically include at least an amine, carbonyl, hydroxyl or carboxyl group, preferably at least two of the functional chemical groups and more preferably at least three of the functional chemical groups. The candidate test compounds can comprise cyclic carbon or heterocyclic structure and/or aromatic or polyaromatic structures substituted with one or more of the above-identified functional groups. Candidate test compounds also can be biomolecules such as peptides, saccharides, fatty acids, sterols, isoprenoids, purines, pyrimidines, and derivatives or structural analogs of the above, or combinations thereof and the like.

Candidate test compounds are obtained from a wide variety of sources including libraries, (such as, but not limited to, commercial libraries, historical libraries/collections) of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the reaction mixture. These include reagents such as salts, buffers, proteins (e.g., albumin), detergents, and polymers, which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

The order of addition of components, incubation temperature, time of incubation, and other parameters of the assay may be determined by one of skill in the art. Such experimentation typically involves optimization of the assay parameters, not the fundamental composition of the assay. Incubation temperatures typically are between 4° C. and 40° C. Incubation times preferably are minimized to facilitate rapid, high throughput screening, and can be between 0.1 and 10 hours.

The instant invention is also directed to kits and compositions comprising labeled compound and/or EZH1 and/or EZH2. The kit can contain other compounds, such as enzymes, and/or buffers, for performing the methods of the present invention. The kit can also include instructions for performing the inventive methods to identify EZH1 and/or EZH2 inhibitors as described here. Kits may also include a package housing one or more containers comprising one or more reagents for performing the method(s) of the present invention.

In certain embodiments, the method to identify EZH1 and/or EZH2 inhibitors comprises performing a high-throughput proximity-based luminescence detection assay to identify compounds having potential EZH1 and/or EZH2 inhibitory activity; re-testing the identified potential EZH1 and/or EZH2 inhibitor compounds by proximity-based luminescence detection assay using different concentrations of the potential EZH1 and/or EZH2 inhibitors, thereby identifying at least a subset of compounds having potential EZH1 and/or EZH2 inhibitory activity; and performing secondary and tertiary assays to confirm the ability of the identified compounds to inhibit EZH1 and/or EZH2 and optionally to determine the mode of action of the identified compounds. In certain embodiments, the secondary assays are cell-based and/or biochemical assays.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Preparation of the Compounds Described Herein

The compounds provided herein can be prepared from readily available starting materials using the following general methods and procedures. For example, compounds of Formula (I) can be prepared according to any one of Schemes 1 to 3, and compounds of Formula (II) can be prepared according to methods similar to the methods shown in any one of Schemes 1 to 3. Alternatively, the compounds described herein may be prepared using methods similar to the methods described in U.S. Patent Application Publication, US 2013/0040906, and in International PCT Application Publications, WO 2013/067302, WO 2013/039988, WO 2012/118812, WO 2012/005805, WO 2014/100665, WO 2013/138361, WO 2013/067300, WO 2013/067296, WO 2013/049770, and WO 2011/140324. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

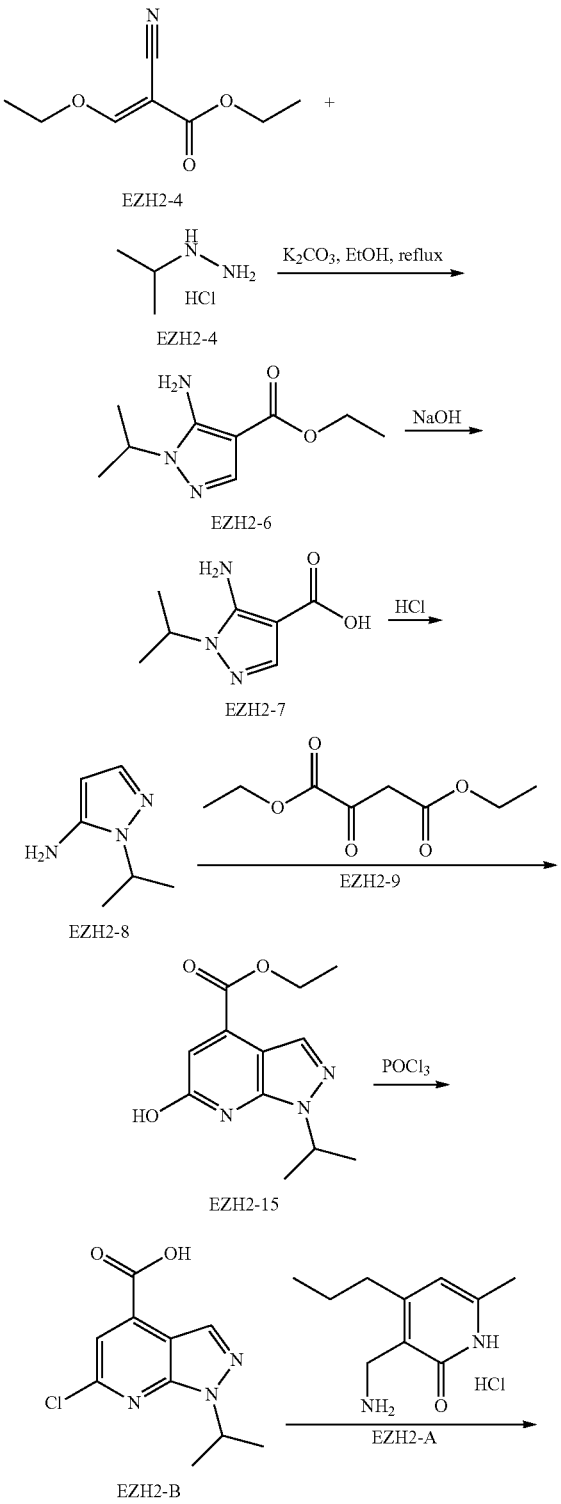

Scheme 1. An exemplary preparation of compound EZ-005

217
-continued
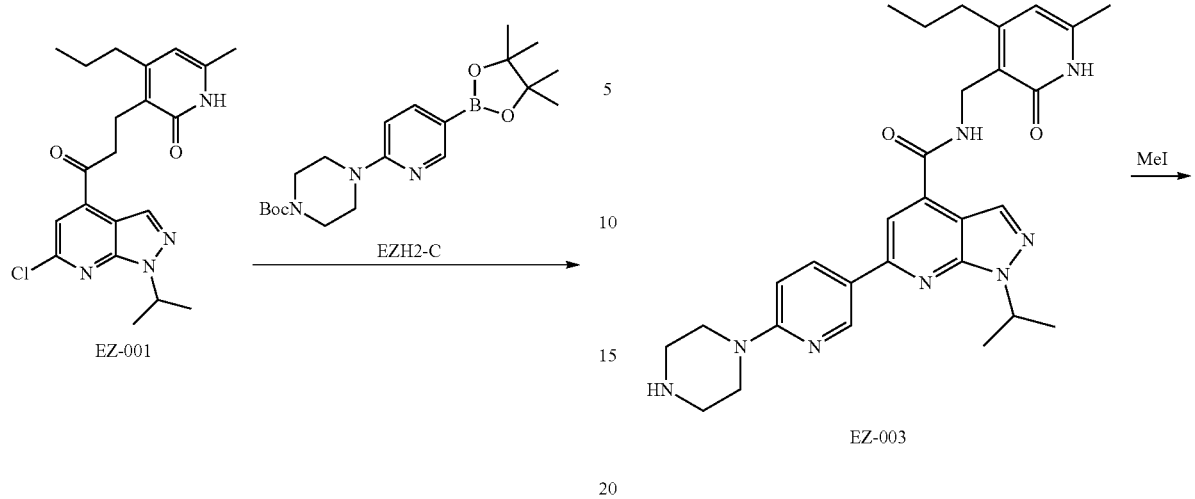
218
-continued
Scheme 2. An exemplary preparation of compound JQEZ6 and AVC-1-018
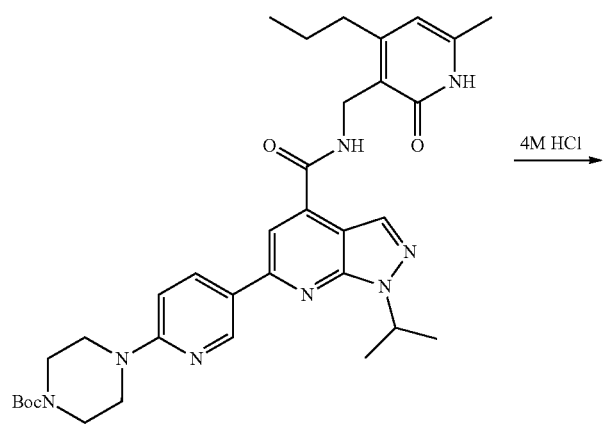

-continued
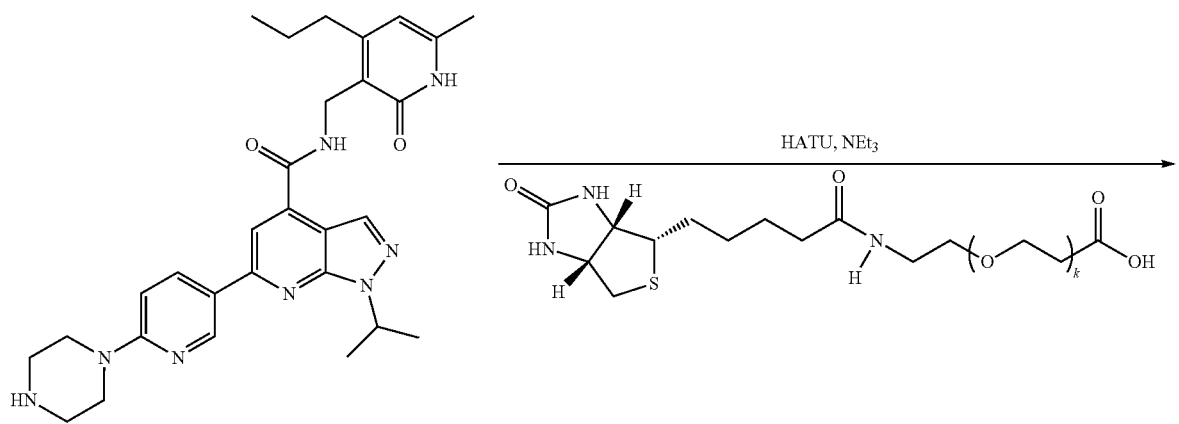
JQEZ6 (k is 3)
or
AVC-1-018 (k is 12)
Scheme 3. An exemplary preparation of additional compounds described herein
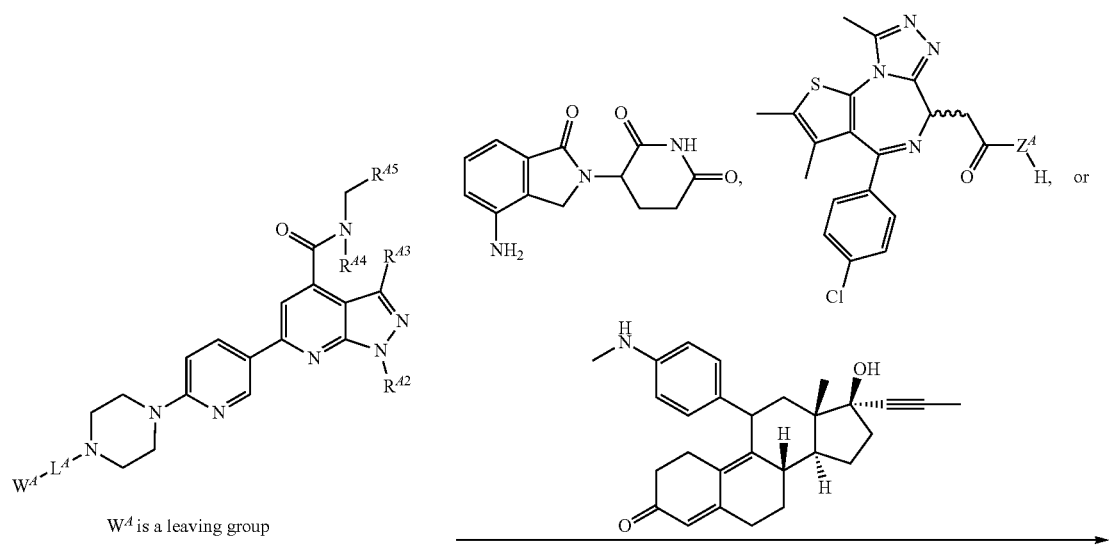
$W^A$ is a leaving group

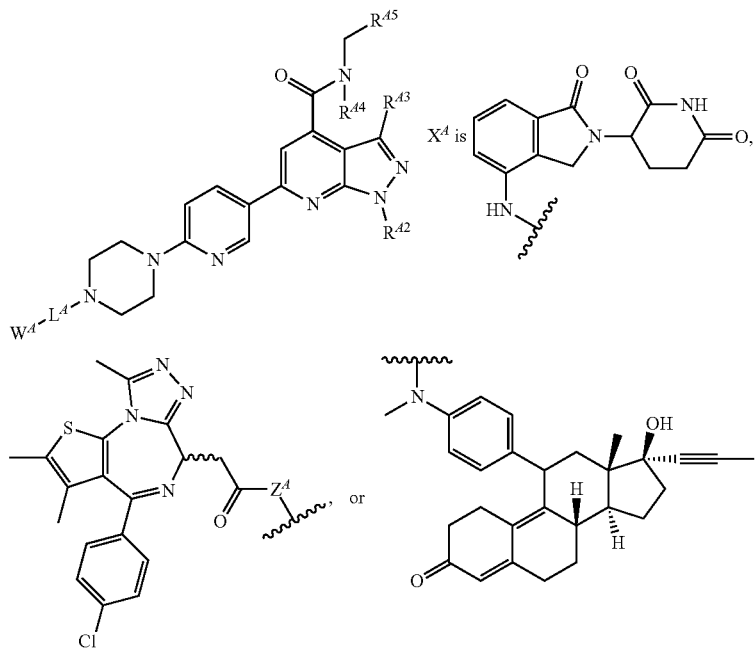

In certain embodiments, the hydrazides described herein are prepared pursuant to the methods described in international PCT application, PCT/US2015/044303, incorporated herein by reference. In certain embodiments, the hydrazides described herein are prepared pursuant to the methods shown in Scheme 4 or 5.

Scheme 4. An exemplary preparation of compounds described herein that are hydrazides

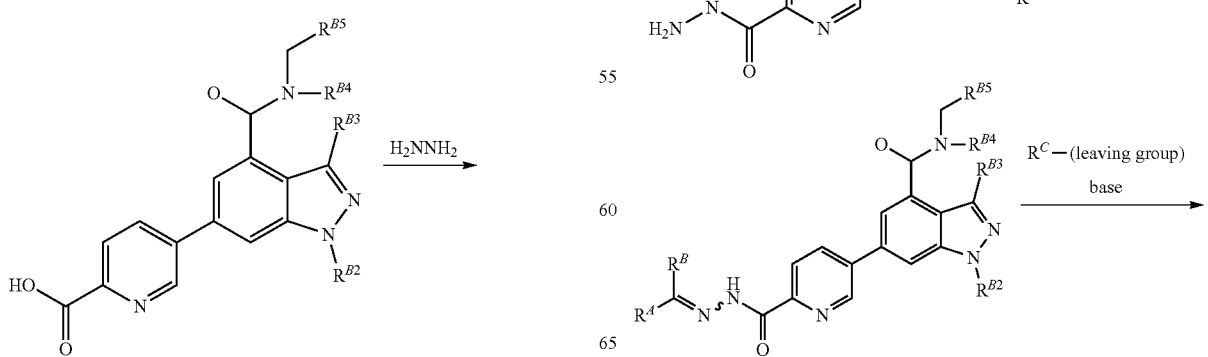

-continued

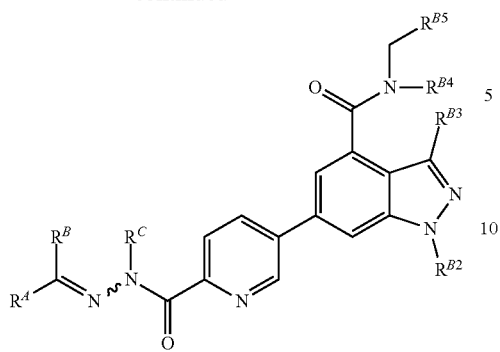

Scheme 5. An exemplary preparation of compounds described herein that are hydrazides

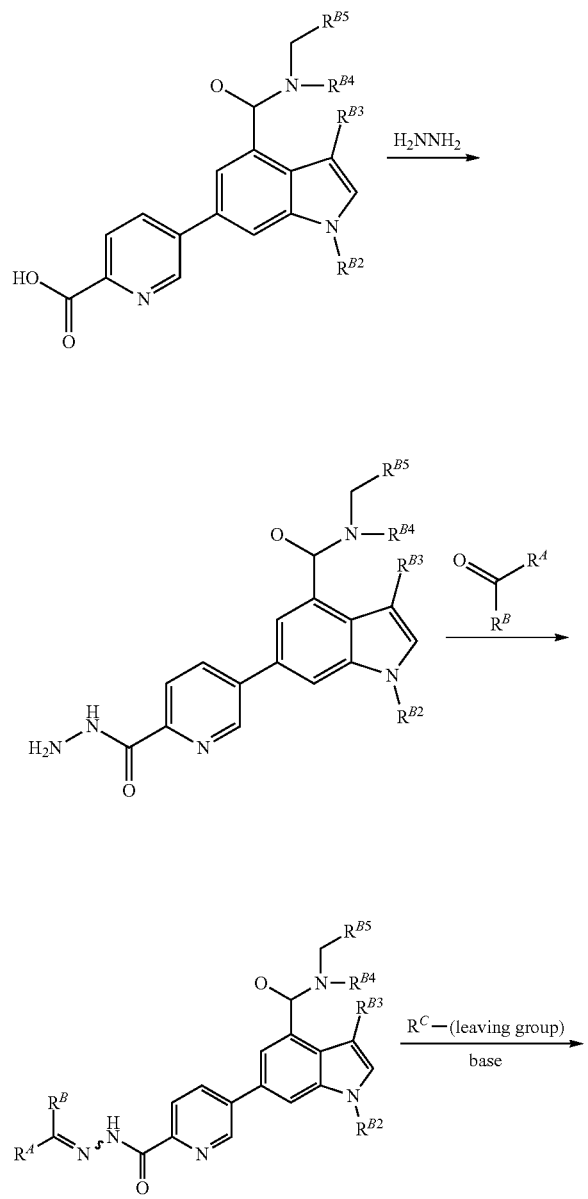

-continued

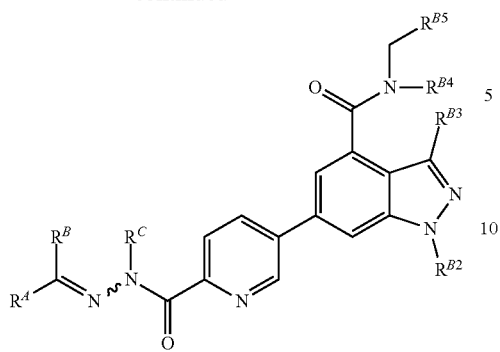

In certain embodiments, $$\underset{R^B}{\overset{O}{\|}}\!\!\!\!\!\diagup\!\!R^A$$

is an aldehyde or ketone shown in FIG. 21.

GSK126 and UNC1999 were directly purchased from Sigma-Aldrich, Inc. The structure and purity of these two compounds were further confirmed by NMR and LCMS. The detail syntheses of compound JQEZ5 and JQEZ23 were described in detail below. Reactions were run as described in the individual procedures using standard double manifold and syringe techniques; glassware was dried by baking in an oven at 130° C. for 12h prior to use. Solvents for reactions were purchased anhydrous from Sigma-Aldrich and used as received; the only exception being EtOH, which was stored over 4 Å molecular sieves. HPLC grade solvents were used for aqueous work ups and chromatography. Reagents were used as received. Reactions were monitored by thin-layer chromatography using EMD silica gel 60 F254 (250-micron) glassbacked plates (visualized by UV fluorescence quenching and staining with KMnO4) and by LCMS using a Waters Aquity BEH C18 2×50 mm 1.7 μm particle column (50° C.) eluting at 1 mL/min with H2O/acetonitrile [0.2% v/v added formic acid or concentrated NH4OH(aq) solution; 95:5(0 min)→1:99(3.60 min)→1:99(4.00 min)] using alternating positive/negative electrospray ionization (125-1000 amu) and UV detection (210-350 nm). Flash column chromatography was carried out using Merck grade 9385 silica gel 60 Å pore size (230-400 mesh). Melting points were obtained using a capillary melting point apparatus and are uncorrected. 1H NMR spectra were recorded at 400 MHz on a Bruker spectrometer and are reported in ppm using the residual solvent signal (dimethylsulfoxide-d6=2.50 ppm; chloroform-d=7.27 ppm; methanol-d4=3.31 ppm; dichloromethane-d2=5.32 ppm) as an internal standard. Data are reported as: {(δ shift), [(s=singlet, d=doublet, dd, doublet of doublets, ddd=doublet of a dd, t=triplet, quin=quintet, sept=septet, br=broad, ap=apparent), (J=coupling constant in Hz) and (integration)]}. Proton-decoupled 13C NMR specta were recorded at 100 MHz on a Bruker spectrometer and are reported in ppm using the residual solvent signal (chloroform-d=77.0 ppm; dimethylsulfoxide-d6=39.51 ppm; methanol-d4=49.15 ppm) as an internal standard. Infrared spectra were recorded using an ATR-FTIR instrument. High resolution mass spectra were acquired by flow injection on a qTOF Premiere Mass Spectrometer operating in ES+ ionization with resolution ~15,000.

225

Scheme 6. Synthesis of intermediate 4.

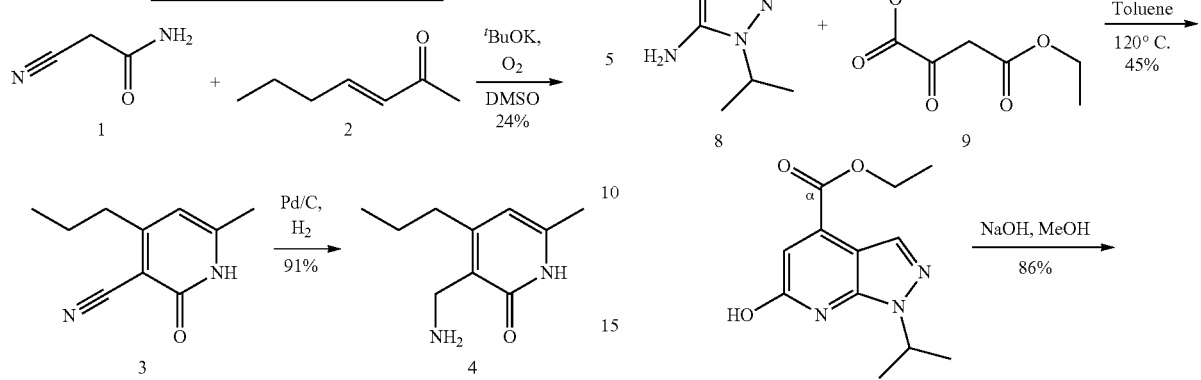

A mixture of potassium t-butyloxide (BuOK, 4 g, 35.7 mmol), 2-cyanoacetamide (1) (3.3 g, 39.2 mmol) and 3-hepten-2-one (2) (4 g, 35.7 mmol) in DMSO (60 mL) was stirred at room temperature for 30 min. Then additional t-BuOK (12 g, 107 mmol) was added and the reaction mixture was stirred under an atmosphere of oxygen for 1 h. The reaction mixture was purged with nitrogen, and diluted slowly with water (250 mL) and aq. HCl (4 N, 300 mL). The reaction mixture was filtered to collect the yellow precipitate, which was washed with water and dried to give 1.5 g of 3 (24% yield) as a yellow solid. MS: m/z 177 (M+H)+.

A mixture of the above 3 (1.5 g) in THF (20 mL) was added Pd/C (10%, 1.5 g) and conc. HCl (1 mL). The mixture was stirred at room temperature overnight under an atmosphere of hydrogen. The mixture was filtered through Celite and the filtration was concentrated in vacuo. the residue was recrystallized from PE/EA (v/v=10) to give 1.4 g of 4 (91% yield) as a tan-yellow solid. MS: m/z 181.1 (M+H)+; 164.1 (M−NH$_3$+H)+; $^1$H NMR (500 MHz, DMSO$_{d6}$) δ 11.87 (br s, 1H), 8.12 (s, 3H), 6.49 (br s, 1H), 6.00 (s, 1H), 3.78 (m, 2H), 2.18 (s, 3H), 1.50 (m, 2H), 0.92 (t, J=7.0 Hz, 3H) ppm.

Scheme 7. Synthesis of intermediate 12

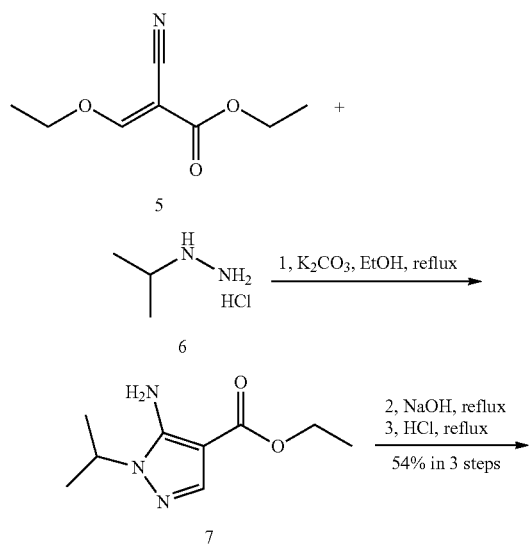

226

-continued

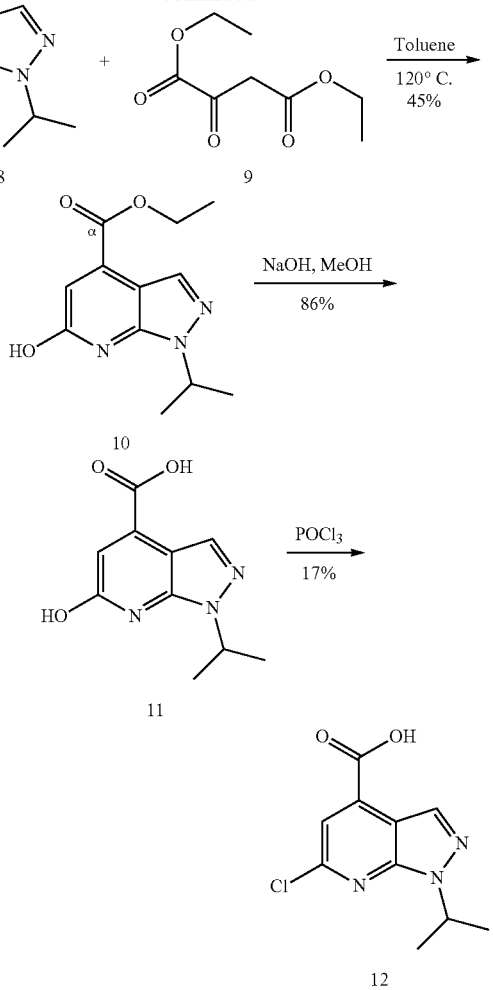

A mixture of ethyl (ethoxymethylene)cyanoacetate (5) (5 g, 29.6 mmol), isopropylhydrazine hydrochloride (6) (3.9 g, 35.5 mmol) and potassium carbonate (8.2 g, 59.2 mmol) in ethanol (100 mL) was refluxed for 16 h. The volatiles were removed in vacuo to give crude 7 as a yellow solid containing inorganic salt, which was used for the next step without further purification. MS: m/z 198.1 (M+H)+.

A suspension of the above crude 7 in aq. sodium hydroxide (4 N, 50 mL) was refluxed for 16 h. The mixture was cooled and acidified with conc. HCl to pH~3.5. HCl in dioxane (4 N, 2 mL to pH<1) was added to the reaction mixture and was refluxed for 16 h. The organic layer was separated off and the aqueous solution was neutralized with aq. sodium hydroxide (4 N, to pH >10). Then the mixture was extracted with methylene chloride. The combined organic solution was washed with brine, dried over sodium sulfate and concentrated to give about 2 g of 8 as orange oil (54% yield in 3 steps), and was used for the next step without further purification. MS: m/z 126.1 (M+H)+.

A mixture of 8 (1.00 g, 7.99 mmol) and diethyl oxalacetate (9) (2.26 g, 12.0 mmol) in toluene (20 mL) was refluxed for 16 h. The volatiles were removed in vacuo and the residue was dissolved in acetic acid (10 mL) and refluxed for 4 hours. Then the mixture was diluted with water (20 mL) and extracted with ethyl acetate. The combined organic solution was washed with water and brine, dried over sodium sulfate and concentrated. The crude product was recrystallized from methylene chloride to give 0.9 g of 10 (45% yield) as a white solid. MS: m/z 250 (M+H)+.

A solution of 10 (0.90 g, 3.61 mmol) in THF (10 mL) was added aq. sodium hydroxide (4 N, 5 mL), and was stirred at room temperature overnight. The resulting mixture was then acidified with conc. HCl to pH~2 and was extracted with methylene chloride. The organic solution was washed with brine, dried over sodium sulfate and concentrated in vacuo. The crude product was recrystallized from methylene chloride to give 0.7 g of 11 (88% yield) as a yellow solid. MS: m/z 222 (M+H)+.

A mixture of 11 (600 mg, 2.71 mmol) in phosphorus oxychloride (15 mL) was stirred at 120° C. in a sealed tube overnight. Most of the phosphorus oxychloride was removed in vacuo and the residue was quenched with water at 0° C. The mixture was extracted with methylene chloride. The combined organic solution was washed with water, dried over sodium sulfate and concentrated in vacuo. The residue was purified by silica gel column chromatography (PE/EA, v/v=1) to give 110 mg of 12 (17% yield) as a white solid. MS: m/z 240 (M+H)+. MS: m/z 240.0 (M+H)+; 1H NMR (500 MHz, CDCl3) δ 8.51 (s, 1H), 7.83 (s, 1H), 5.34 (m, 1H), 1.64 (d, J=6.5 Hz, 6H) ppm.

Scheme 8. Synthesis of compound JQEZ5

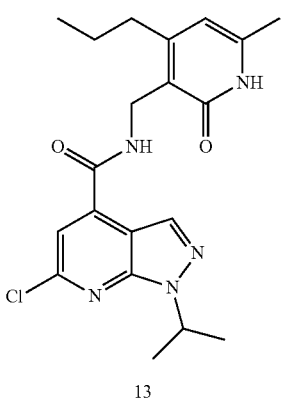

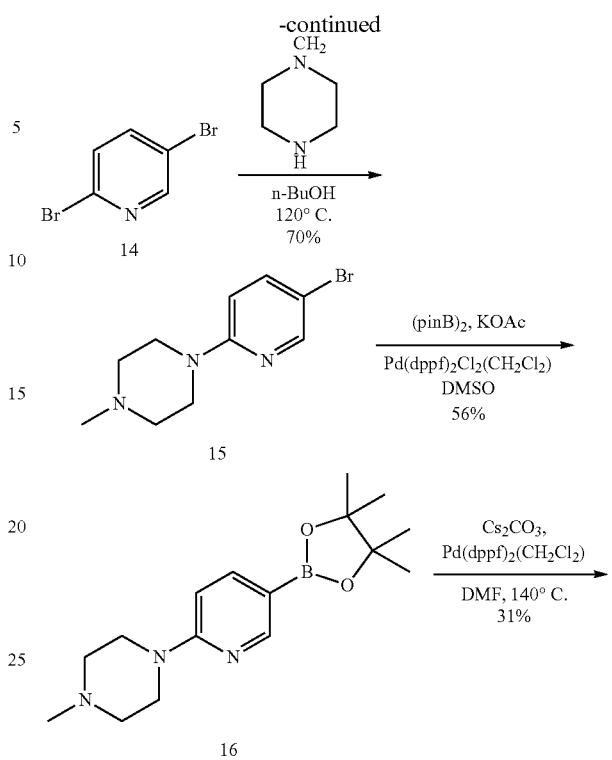

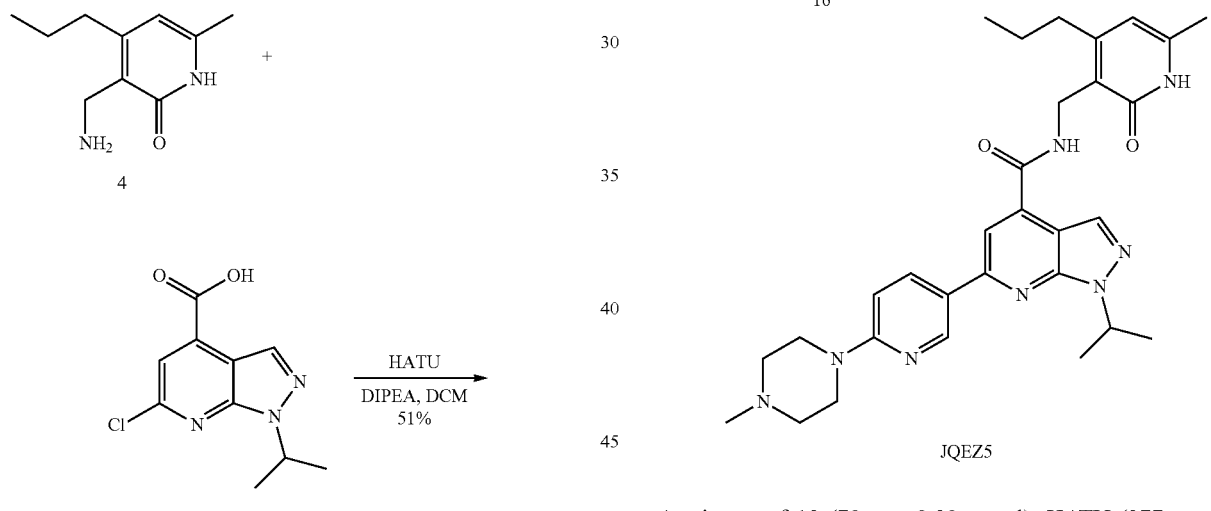

JQEZ5

A mixture of 12 (70 mg, 0.29 mmol), HATU (277 mg, 0.73 mmol) and diethylpropyl ethyl amine (DIPEA) (1 mL) in methylene chloride (10 mL) was stirred for 10 min and then was added 4 (127 mg, 0.58 mmol). The reaction mixture was stirred at room temperature for 3 hours. The mixture was diluted with methylene chloride (50 mL) and washed with water and brine, dried over sodium sulfate and concentrated in vacuo. The residue was purified by flash chromatography (50% EA in PE) to give 60 mg of 13 (51% yield) as a white solid. MS: m/z 402.1 (M+H)+; 1H NMR (500 MHz, CDCl3) δ 11.91 (br s, 1H), 8.38 (s, 1H), 8.24 (t, J=5.0 Hz, 1H), 7.43 (s, 1H), 6.00 (s, 1H), 5.26 (m, 1H), 4.65 (d, J=5.5 Hz, 2H), 2.69 (t, J=7.5 Hz, 2H), 2.28 (s, 3H), 1.64 (m, 2H), 1.55 (d, J=6.5 Hz, 6H), 1.02 (t, J=7.0 Hz, 3H) ppm.

A mixture of 14 (2.37 g, 10 mmol) and N-methylpiperazine (4 g, 40 mmol) in n-BuOH (25 mL) was refluxed for 96 h. The volatiles were removed in vacuo and the crude product was purified by silica gel column chromatography (PE/EA, v/v=3 to EA) to give 1.8 g of 15 (70% yield) as a yellow semi-solid. MS: m/z 256.0 (M+H)+, 258.0 (M+H, Br)+.

A mixture of 15 (1.5 g, 5.9 mmol), bis(pinacolato)diboron (1.6 g, 6.5 mmol), potassium acetate(1.8 g, 18 mmol) and Pd(dppf)$_2$Cl$_2$[CH$_2$Cl$_1$] (0.73 g, 0.89 mmol) in DMSO (20 mL) was protected with nitrogen and stirred at 80° C. overnight. The mixture was diluted with water and extracted with EA. The organic solution was concentrated in vacuo and the residue was purified by silica gel column chromatography (PE/EA, v/v=3 to EA) to give 1.0 g of 16 (56% yield) as a brown solid. MS: m/z 304 (M+H)$^+$.

A mixture of 13 (133 mg, 0.33 mmol), 16 (200 mg, 0.66 mmol), Pd(dppf)$_2$Cl$_2$[CH$_2$Cl]$_2$ (41 mg, 0.050 mmol) and Cs$_2$CO$_3$ (215 mg, 0.66 mmol) in DMF (5 mL) was protected with argon and irradiated with microwave at 140° C. for 30 minutes. The mixture was diluted with ethyl acetate and filtered through Celite. The filtrate was concentrated and the residue was purified by flash chromatography and prep-HPLC (HCOOH system) to give 55 mg of JQEZ5 (31% yield) as a dark solid. MS: m/z 543.4 (M+H)+; 1H NMR (500 MHz, CDCl3) δ 9.00 (d, J=2.5 Hz, 1H), 8.33 (s, 1H), 8.31 (dd, J=9.0 and 2.5 Hz, 1H), 8.14 (t, J=6.0 Hz, 1H), 7.87 (s, 1H), 6.75 (d, J=9.0 Hz, 1H), 6.02 (s, 1H), 5.38 (m, 1H), 4.69 (d, J=6.0 Hz, 2H), 3.88 (m, 4H), 2.92 (m, 4H), 2.75 (m, 2H), 2.62 (s, 3H), 2.27 (s, 3H), 1.67 (m, 2H), 1.62 (d, J=6.5 Hz, 6H), 1.05 (t, J=7.0 Hz, 3H) ppm.

Biological Assays of the Compounds Described Herein

Example 1. Inhibitory Activities of Compound 5 Against Select HMTs

Compound 5 was profiled with a panel of 22 HMTs (the list of the methyltranferase in Table 1) and exhibited not only activity against EZH2 but also a 10-fold selectivity for EZH2 over EZH1 or DOT1 (Table 1). Compound 5 inhibited EZH2 at 1 µM after a 72-hour treatment, which caused the reduction of trimethylation of H3K27 at 1 µM in EZH2 mutation line.

TABLE 1

Inhibitory activities of compound 5 against select HMTs.

| HMT | IC$_{50}$ (M) Compound 5 | SAH |
|---|---|---|
| DOT1 | 8.32E−06 | 1.41E−07 |
| EZH1 | 1.30E−06 | 2.15E−05 |
| EZH2 | 1.72E−07 | 1.52E−05 |
| G9a |  | 6.67E−06 |
| GLP |  | 3.19E−07 |
| MLL1 |  | 3.28E−06 |
| MLL2 |  | 1.79E−05 |
| MLL3 |  | 4.27E−05 |
| MLL4 |  | 1.20E−05 |
| NSD2 |  | 7.49E−06 |
| PRMT1 |  | 7.23E−07 |
| PRMT3 |  | 1.77E−06 |
| PRMT4 |  | 2.16E−07 |
| PRMT5 |  | 1.91E−07 |
| PRMT6 |  | 2.52E−07 |
| SET1B |  | 6.69E−06 |
| SET7/9 |  | 1.21E−04 |
| SET8 |  | 1.40E−04 |
| SETMAR |  | 5.61E−07 |
| SMYD2 |  | 8.24E−07 |
| SUV39H1 |  | 1.06E−04 |
| SUV39H2 |  | 2.11E−05 |

Example 2. Surface Plasma Resonance Experiments of Compound JQEZ6 for Identifying the Binding of the Compound with PRC2

Figure 6:
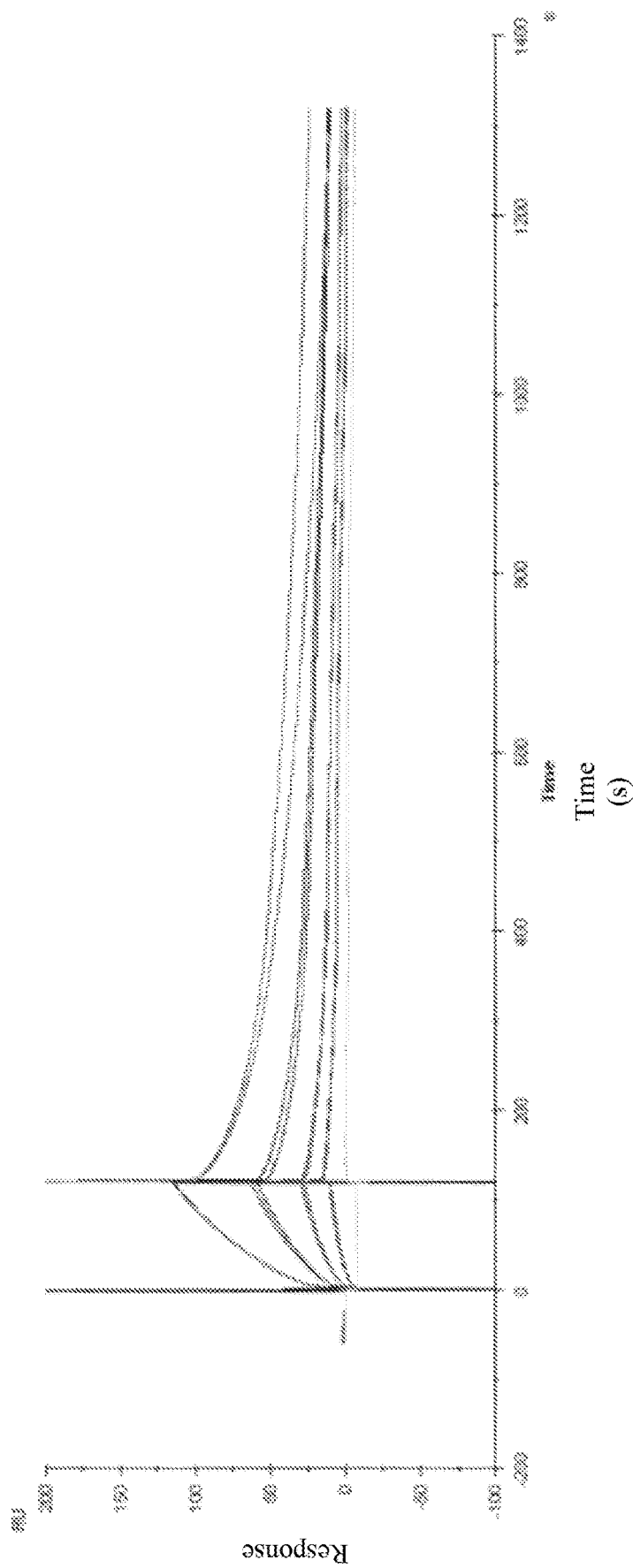
FIG. 6 shows exemplary surface plasmon resonance (SPR) results of compound JQEZ6 by mobilizing compound JQEZ6 on a surface to capture PRC2 five component complex.
Figure 7:
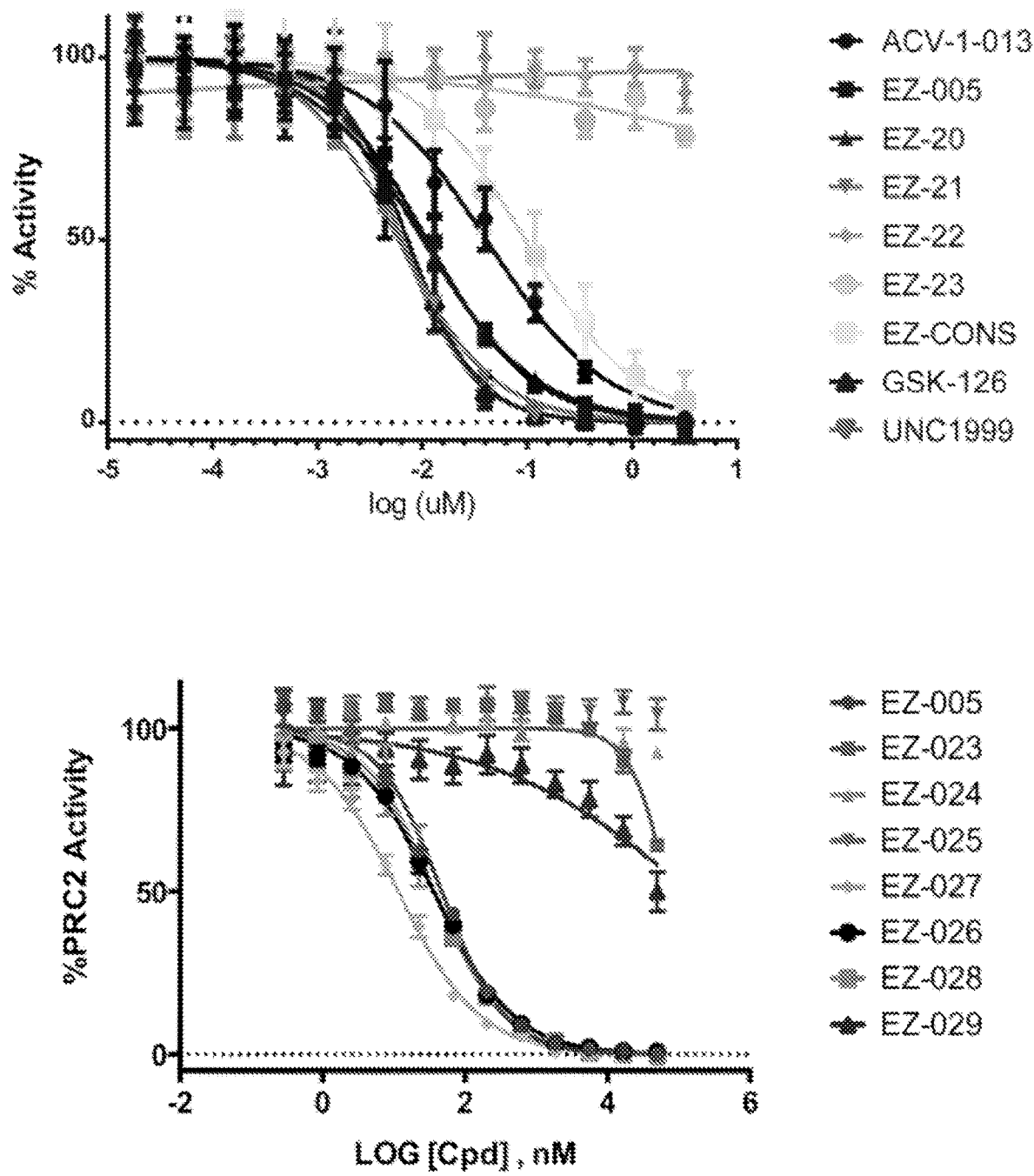
FIG. 7 shows exemplary inhibitory activities of one set of compounds described herein (top panel) and another set of compounds described herein (bottom panel) against PRC2 5 component complex. Log (uM): log(concentration of a compound in micromolar). Log [Cpd], nM: log(concentration of a compound in nanomolar). % Activity: % PRC2 activity.
Figure 8:
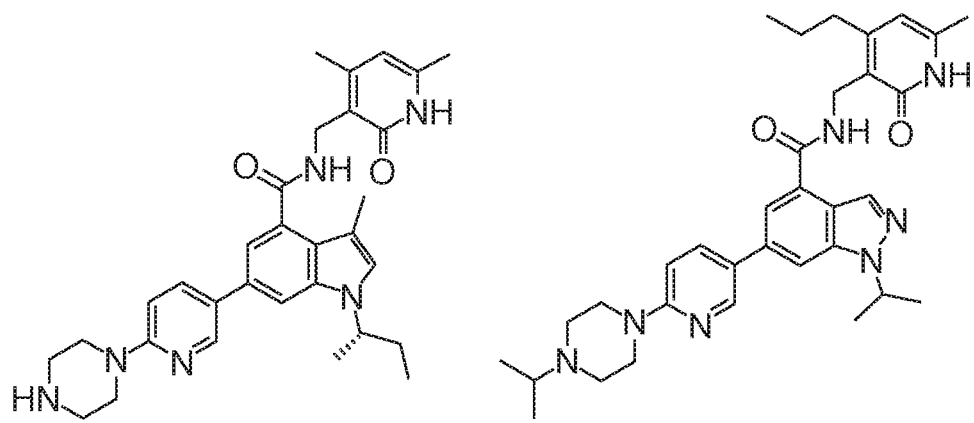
FIG. 8 shows the chemical structures of select compounds.
Figure 8:
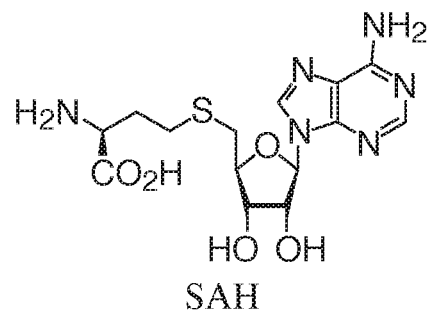
Figure 8:
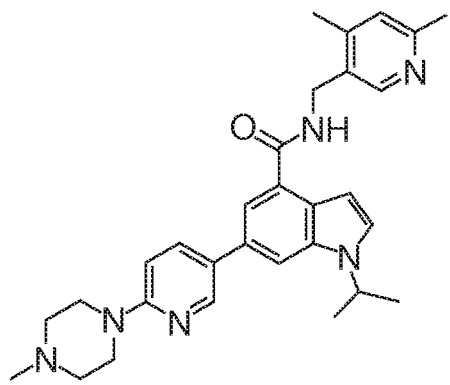

Compound EZ06 was immobilized on the SPR chip via biotin-strapavidin interaction. The PRC2 five component complex solution was then flow through the chip slowly, and the binding between EZ06 and 5 component complex was then detected by SPR. Exemplary results are shown in FIG. 6. The data show that compound JQEZ6 bound to PRC2 complex. Compound JQEZ6 was also employed for developing the ALPHA assay that was useful in evaluating the activity of small molecule inhibitors of EZH2. This ALPHA assay was advantageous over known assays for HMTs because this ALPHA assay was a non-radiometric assay, whereas the known assays for HMTs were radiometric assays, which required special radiometric reagents and produced a low throughput. The ALPHA assay described herein allowed for high through-put screening. For the alpha assay, JQEZ6 immoblized on the surface of donor beads, and PRC2 5 component complex with Flag tag was immobilized on acceptor bead via Flag anti-Flag tag interaction. Mixture of these two beads generate signal upon excitation. The potent inhibitors would break the interaction, and cause the signal decrease, which used for evaluating all compounds.

Example 3. Oncogenic Deregulation of EZH2 as an Opportunity for Targeted Therapy in Lung Cancer Summary As a master regulator of chromatin structure and function, the EZH2 lysine methyltransferase orchestrates transcriptional silencing of developmental gene networks. Overexpression of EZH2 is commonly observed in human epithelial cancers, such as non-small cell lung carcinoma (NSCLC), yet definitive demonstration of malignant transformation by deregulated EZH2 has proven elusive. The causal role of EZH2 overexpression in NSCLC is demonstrated herein with a new genetically-engineered mouse model of lung adenocarcinoma. Deregulated EZH2 silences normal developmental pathways leading to epigenetic transformation independent from canonical growth factor pathway activation. As such, tumors feature a transcriptional program distinct from KRAS- and EGFR-mutant mouse lung cancers, but shared with human lung adenocarcinomas exhibiting high EZH2 expression. To target EZH2-dependent cancers, a novel and potent EZH2 inhibitor that arises from a facile synthesis and possesses improved pharmacologic properties was developed. JQEZ5 promoted the regression of EZH2-driven tumors in vivo, confirming oncogenic addiction to EZH2 in established tumors and providing the rationale for epigenetic therapy in a defined subset of lung cancer.

Targeted therapies for the treatment of lung cancer have significantly improved overall survival of defined patient subsets; however, many oncogenic drivers of lung cancer are still unknown. Deregulation of chromatin-associated enzymes is pathogenic in many cancers and, because they are reversible, represent potential therapeutic targets. Here, it is shown that overexpression of EZH2 can induce lung cancers in mice that are phenotypically similar to human lung cancers with high EZH2 expression. Murine and human lung cancers with EZH2 overexpression displayed low levels of phosphorylated AKT and ERK, suggesting additional biomarkers for tumors that may be sensitive to EZH2 inhibitors. Finally, a novel small-molecule inhibitor, JQEZ5, that selectively inhibits EZH2 and promotes the regression of these tumors was developed, revealing a potential role for anti-EZH2 therapy in lung cancer.

Introduction

Lung cancer is the most common and one of the most deadly cancers worldwide (Jemal et al., 2011). Non-small cell lung cancers (NSCLC) are the most prevalent type of lung cancer, comprising a heterogeneous set of diseases (Chen et al., 2014). The identification of recurrent mutations and amplifications in many potentially targetable oncogenes has significantly improved overall survival of subsets of NSCLC patients. Activating mutations in BRAF, KRAS and the epidermal growth factor receptor (EGFR), as well as fusions involving anaplastic lymphoma kinase (ALK), have been associated with response to kinase inhibition (Lynch et al., 2004; Paez et al., 2004; Pao et al., 2004; Soda et al., 2007). Furthermore, with the advent of improved genomic profiling and next-generation sequencing, recurrent mutations and amplifications have been identified in HER2, MET, fibroblast growth factor receptor 1 (FGFR1) and FGFR2, the ROS1 receptor tyrosine kinase, neuregulin 1 (NRG1), neurotrophic tyrosine kinase receptor type 1 (NTRK1) and RET (reviewed in (Chen et al., 2014). While together these alterations account for most cases of lung adenocarcinoma, a considerable population of NSCLC patients lacks identifiable genetic lesions in therapeutically tractable targets.

Beyond growth factor signaling pathways, chromatin-associated complexes have recently been identified as recurrently altered or transcriptionally deregulated in NSCLC, including TET methylcytosine dioxygenase 2 (TET2), DNA methyltransferase 3A (DNMT3A) and enhancer of zeste homologue 2 (EZH2) (Kandoth et al., 2013). Notably, each of these factors influences heterochromatin structure, and each has been linked to coordinated regulation of normal developmental transcriptional pathways (Chen and Chan, 2014; Hamidi et al., 2015; Simon and Kingston, 2009; Wu and Zhang, 2011). These data illustrate that disruption of chromatin architecture is a common event in lung cancer pathogenesis, either permissive with or distinct from oncogenic signaling pathways, functioning to deregulate transcriptional programs associated with cellular differentiation.

The dynamic structure of chromatin is influenced by post-translational modifications (PTMs) to DNA and to the unstructured amino-terminal tails of histone proteins within nucleosomal particles. Control of gene expression pathways by DNA-binding transcriptional activators and repressors influences the recruitment of chromatin-associated enzyme complexes that confer covalent PTMs to chromatin. In general, side-chain acetylation of lysine residues on histone tails is associated with active, euchromatin, notably at histone 3 lysine 27 as associated with active cis-regulatory enhancer elements (H3K27ac) (Zhou et al., 2011). Modification of H3K27 exhibits switch-like behavior, as mono-, di- and tri-methylation of H3K27 (H3K27me1, -me2, -me3) is associated with repressive, facultative heterochromatin (Margueron and Reinberg, 2011). H3K27 methylation is principally mediated by the polycomb group repressive complex 2 (PRC2), a multi-protein assembly that activates and directs the function of a core catalytic enzyme mediating S-adenosyl methionine dependent lysine methylation: EZH2.

Recurrent alteration of EZH2 is observed in solid and hematologic malignancies, underscoring the unexpected centrality of chromatin structure in the pathogenesis of cancer. Both activating (recurrent mutation) and inactivating (deletions, inactivating mutations) of EZH2 have been characterized, supporting a tissue-specific role for EZH2 as either oncogene or tumor suppressor. Activating mutations promoting efficient H3K27 trimethylation have been characterized in B-cell lymphoma (Morin et al., 2010; Sneeringer et al., 2010). Inactivating alterations have been identified in T-cell acute lymphoblastic leukemia and malignant myeloid diseases (Ernst et al., 2010; Nikoloski et al., 2010; Ntziachristos et al., 2012). More broadly than these focused genetic events, overexpression of EZH2 is found in a wide range of cancers (Bracken et al., 2003; Simon and Lange, 2008; Varambally et al., 2002). Like gain-of-function mutation, overexpression is associated with increased global H3K27me3, prompts silencing of tumor suppressors and developmental regulators and often confers a poor prognosis (Alford et al., 2012; Bachmann et al., 2006; Gong et al., 2011; Kleer et al., 2003; Varambally et al., 2002). Of relevance to lung adenocarcinoma, several recently studies reproducibly demonstrated a correlation between increased EZH2 expression and poor outcome (Behrens et al., 2013; Kikuchi et al., 2010; Lv et al., 2012).

EZH2 has thus emerged as a pressing target for cancer therapeutic development. Strategies have been undertaken to develop disruptors of complex assembly (Kim et al., 2013), as well as SAM-competitive inhibitors of the canonical SET lysine methyltransferase domain (Knutson et al., 2012; McCabe et al., 2012; Qi et al., 2012). Selective EZH2 inhibition using these chemical probes has established EZH2 as a context-specific tumor dependency while providing pharmacologic target validation in B-cell lymphoma (Knutson et al., 2012; McCabe et al., 2012; Qi et al., 2012; Zhao et al., 2013) and defined soft-tissue sarcomas (Ciarapica et al., 2014; Knutson et al., 2013; Li et al., 2013). Accordingly, human clinical investigation has been initiated using drug-like EZH2 inhibitors administered by oral and intravenous administration (ClinicalTrial.gov identifier: NCT01897571, NCT02082977, NCT02395601).

The evident overexpression of EZH2 in lung adenocarcinoma and the feasibility of clinical investigation motivated the present effort to characterize the effect of transcriptional deregulation of EZH2 on lung cancer pathogenesis. Using genetic and chemical genetic approaches, an oncogenic role for wild-type EZH2 overexpression in lung cancer and the opportunity for epigenomic therapy in this disease were demonstrated. Specifically, genetically-engineered mouse models (GEMM) overexpressing wild-type EZH2 systemically and specifically in lung were generated. Both systemic and lung-specific EZH2 overexpression promotes the formation of lung tumors that exhibit biochemical and transcriptional features akin to the subset of human tumors that express high levels of EZH2. Analysis of chromatin state in EZH2 overexpressing lung tumors revealed the aberrant spread of H3K27me3 notably at developmental regulator gene loci, many of which are known tumor suppressors in lung cancer. To overcome limitations in potency, availability and in vivo utility of current EZH2 inhibitors, a novel and open-source EZH2 chemical probe, JQEZ5 was developed and characterized. In GEMM and human NSCLC models, JQEZ5 exhibits excellent exposure and pharmacodynamic target modulation. Long-term treatment of EZH2-addicted, tumor-bearing mice with JQEZ5 uniformly led to decreases in tumor burden. Together, these studies reveal a role for EZH2 as a NSCLC driver gene and an opportunity for targeted epigenomic therapy.

EZH2 Overexpression Causes Murine Lung Cancer

Figure 9A:
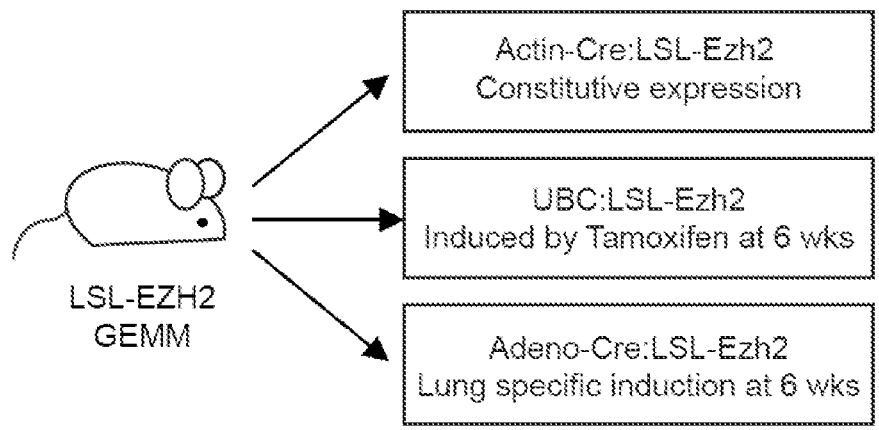
FIGS. 9A-9E. EZH2 Overexpression Induces Murine Lung Cancer.
Figure 15A:
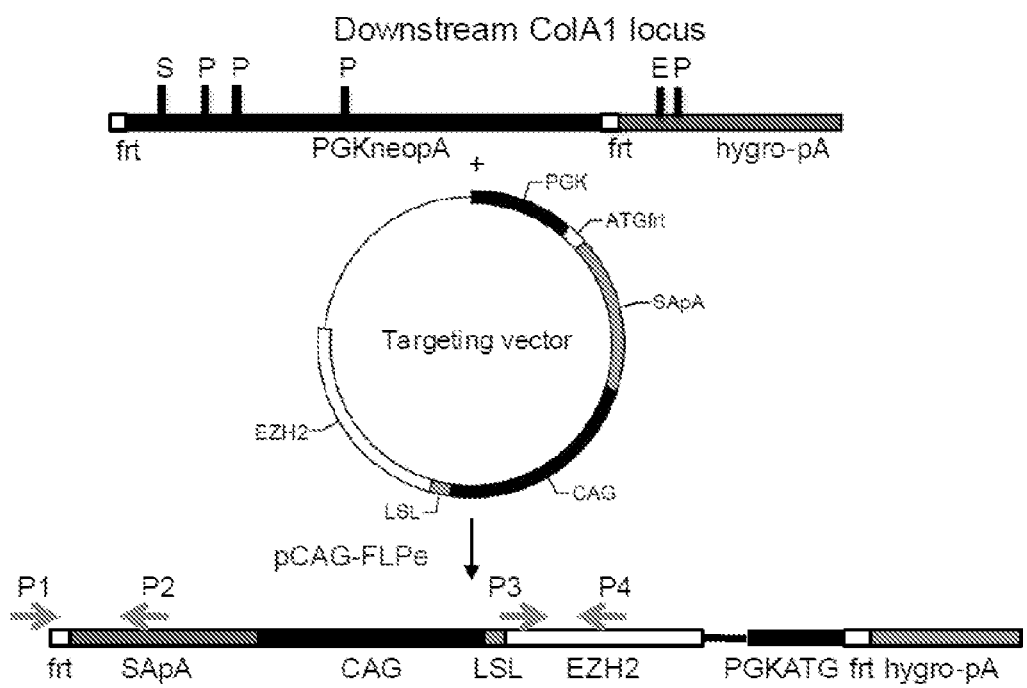
FIGS. 15A-15E, related to FIG. 9. Generation of LSL-Ezh2 conditional transgenic mice.
Figure 15B:
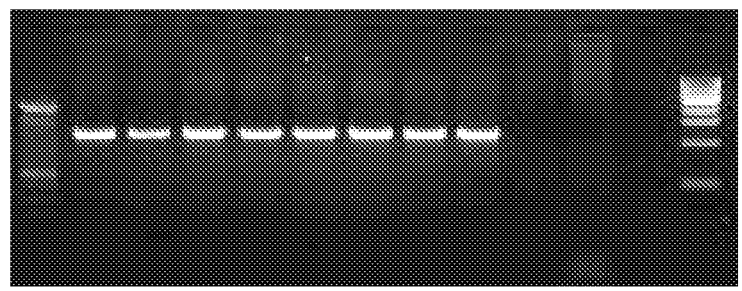
Figure 15B:
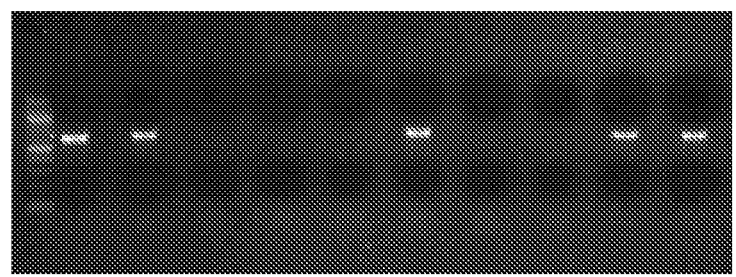
Figure 15C:
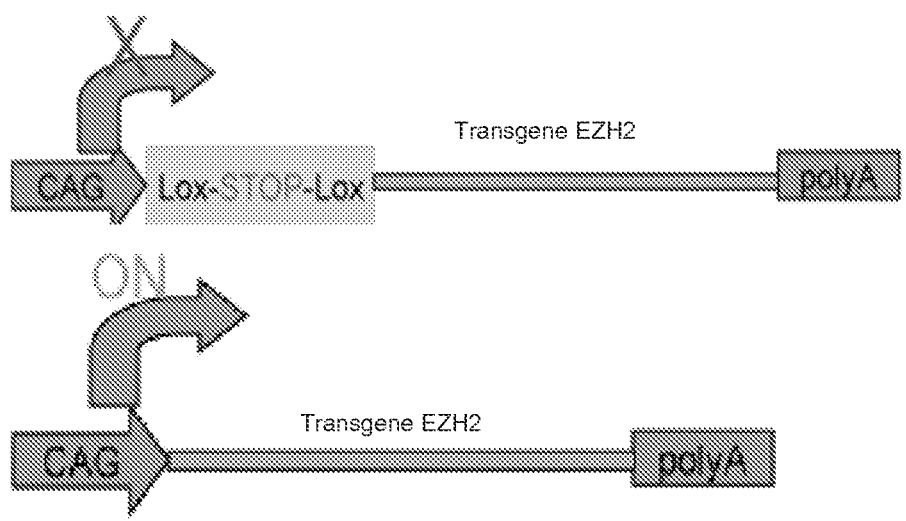

To investigate the causal role of EZH2 overexpression in cancer, human EZH2 expression in the mouse was ubiquitously enforced using two different strategies to control for temporal specificity, as EZH2 is critical to embryogenesis and early development. All mice were engineered to carry one copy of a transgene expressing full-length murine EZH2 containing a STOP cassette flanked by loxP sites between the CAG promoter and the EZH2 gene (LSL-Ezh2) (FIGS. 15A-15C). Two different strategies were used to induce EZH2 overexpression using Cre recombinase (FIG. 9A).

First, Actin-Cre was used to constitutively overexpress EZH2 in all tissues of the mouse (Actin-Cre:LSL-EZH2). Secondly, Ubiquitin-Cre-ERT2 (UBC:LSL-EZH2) was used to ubiquitously overexpress Ezh2 upon treatment with tamoxifen at 6 weeks of age. This approach was devised to circumvent any lethality due to overexpressing EZH2 at critical stages of embryogenesis and early development.

Figure 15D:
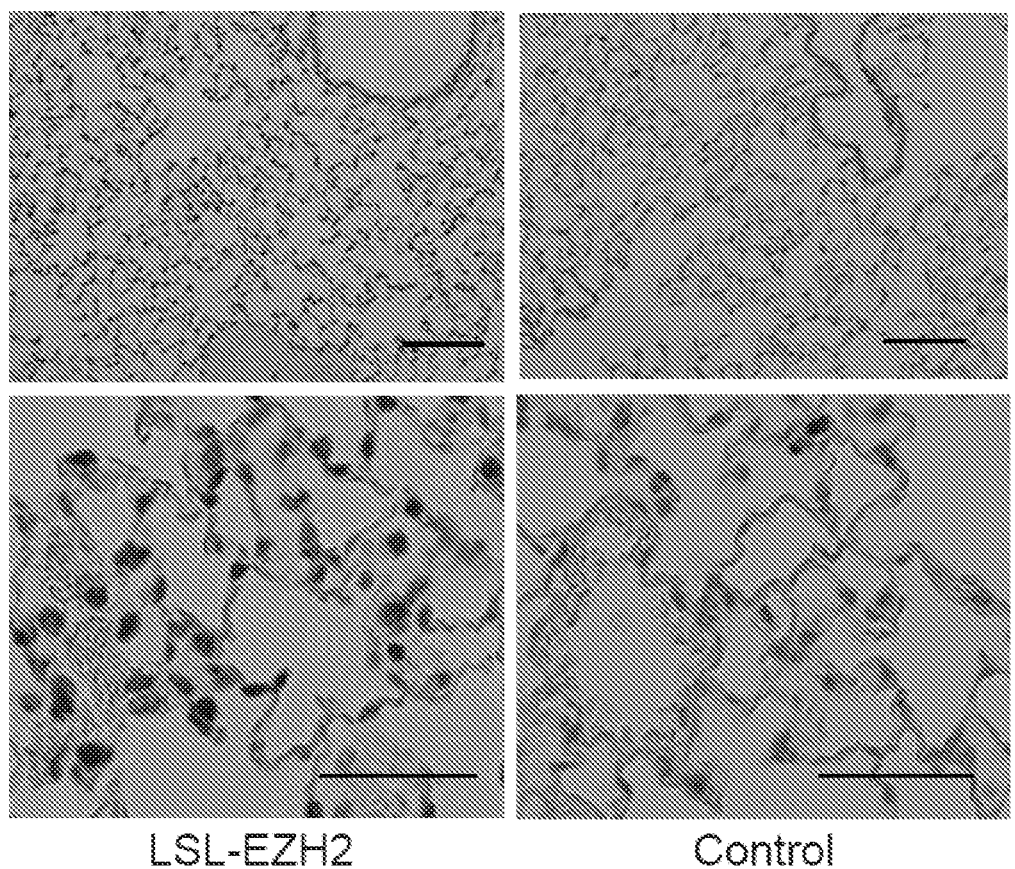
Figure 15E:
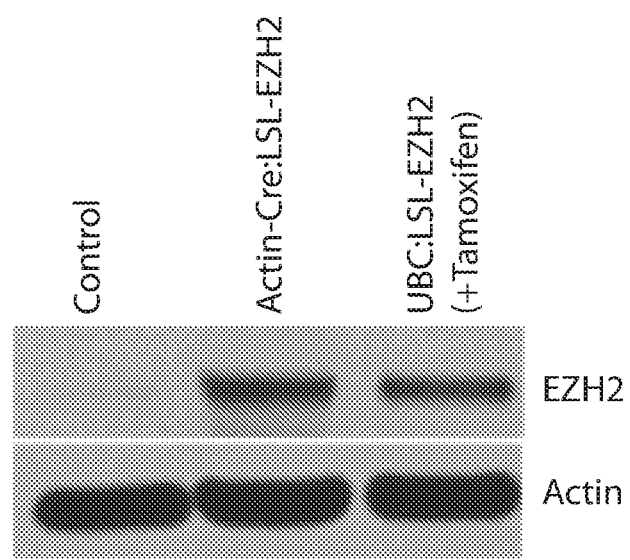

Actin-Cre:LSL-Ezh2 mice overexpressed EZH2 as demonstrated by both immunohistochemistry (IHC) and Western blotting (FIGS. 15D and 15E). The animals were viable, fertile, developmentally normal, and indistinguishable from their littermates that did not express Cre recombinase through adulthood. These results demonstrate that overexpression of EZH2 is tolerable during embryonic and developmental growth. As the Actin-Cre:LSL-EZH2 mice entered adulthood, multiple tumor types were observed including lymphoma and histiocytic sarcoma of the liver. The majority of mice (6/11 mice; 55%); however, developed lung adenomas/adenocarcinomas without apparent metastases at an average of 64.8±3.3 weeks of age (Table 2 and FIG. 9B). Additionally, UBC:LSL-Ezh2 mice that were administered tamoxifen at 6 weeks of age also developed lung adenocarcinomas with 40% penetrance (4/10 mice) at 84.8±10.1 weeks, on average. In contrast, wild-type mice had no evident phenotype and all harvested lungs were normal at 80 weeks, suggesting a causal role of EZH2 overexpression in lung tumorigenesis (Table 3 and FIG. 9B).

TABLE 2

Summary of LSL-EZH2 Mouse Models

| Mouse Model LSL-EZH2 | Lung Adenocarcinoma | Histiocytic Sarcoma (Liver) | Lymphoma | Mice with Tumors/Total Mice |
|---|---|---|---|---|
| Actin-Cre | 6 | 2 | 1 | 8/11[a] |
| UBC-Cre | 4 | 2 | 1 | 5/10[b] |
| Adeno-Cre | 5 | 1 | 0 | 5/12[a] |

[a]One mouse had both lung adenocarcinoma and histiocytic sarcoma in the liver.
[b]Two mice had both lung adenocarcinoma and histiocytic sarcoma in the liver.

TABLE 3

Summary of Lung Adenocarcinoma in LSL-EZH2 Mouse Models

| Mouse Model LSL-EZH2 | Lung Adenocarcinoma | Penetrance (n) | Avg Latency (wks ± SEM) | Range (wks) |
|---|---|---|---|---|
| Actin-Cre | 6 | 55% (11) | 64.8 ± 3.3 | 51.4-74.1 |
| UBC-Cre | 4 | 40% (10) | 84.8 ± 10.1 | 70.7-114.9 |
| Adeno-Cre | 5 | 42% (12) | 88.2 ± 14.6 | 53.0-122.9 |

Figure 9B:
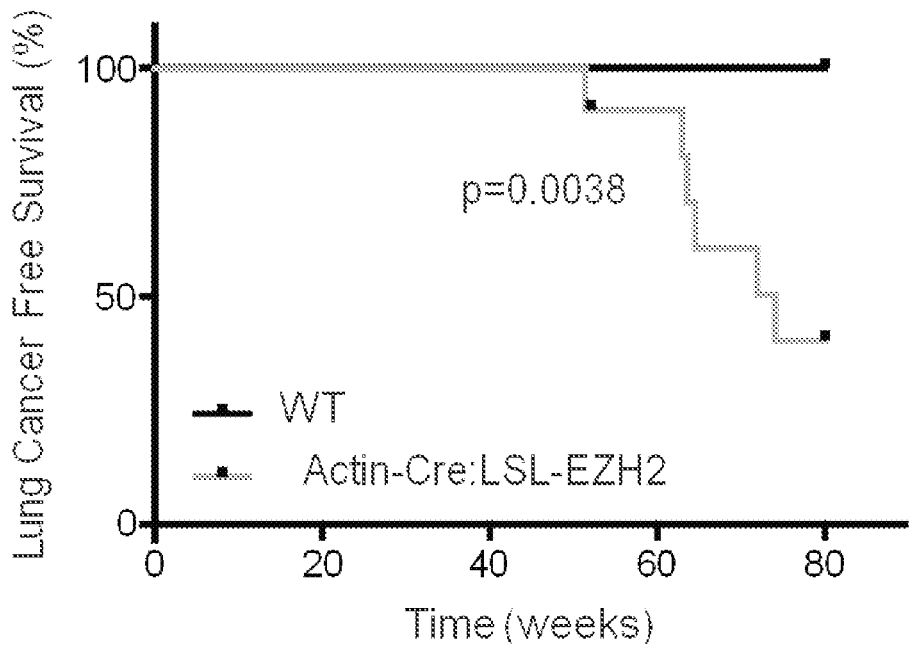

To extend these findings, EZH2 overexpression was restricted to lung in a third GEMM using inhaled Adeno-Cre virus to direct Cre expression to the pulmonary epithelium of LSL-EZH2 mice (FIG. 9A) (DuPage et al., 2009). Viral Adeno-Cre was administered to animals by inhalation at 6-weeks of age and 42% (5/12) of these animals developed lung adenocarcinoma at 88.2±14.6 weeks, demonstrating that EZH2 overexpression in lung epithelial cells is sufficient to induce cancer. In sum, the data demonstrate that 45% of EZH2 overexpressing mice develop lung adenocarcinomas with an average survival to 73.6 weeks of age (FIG. 9B).

Figure 9C:
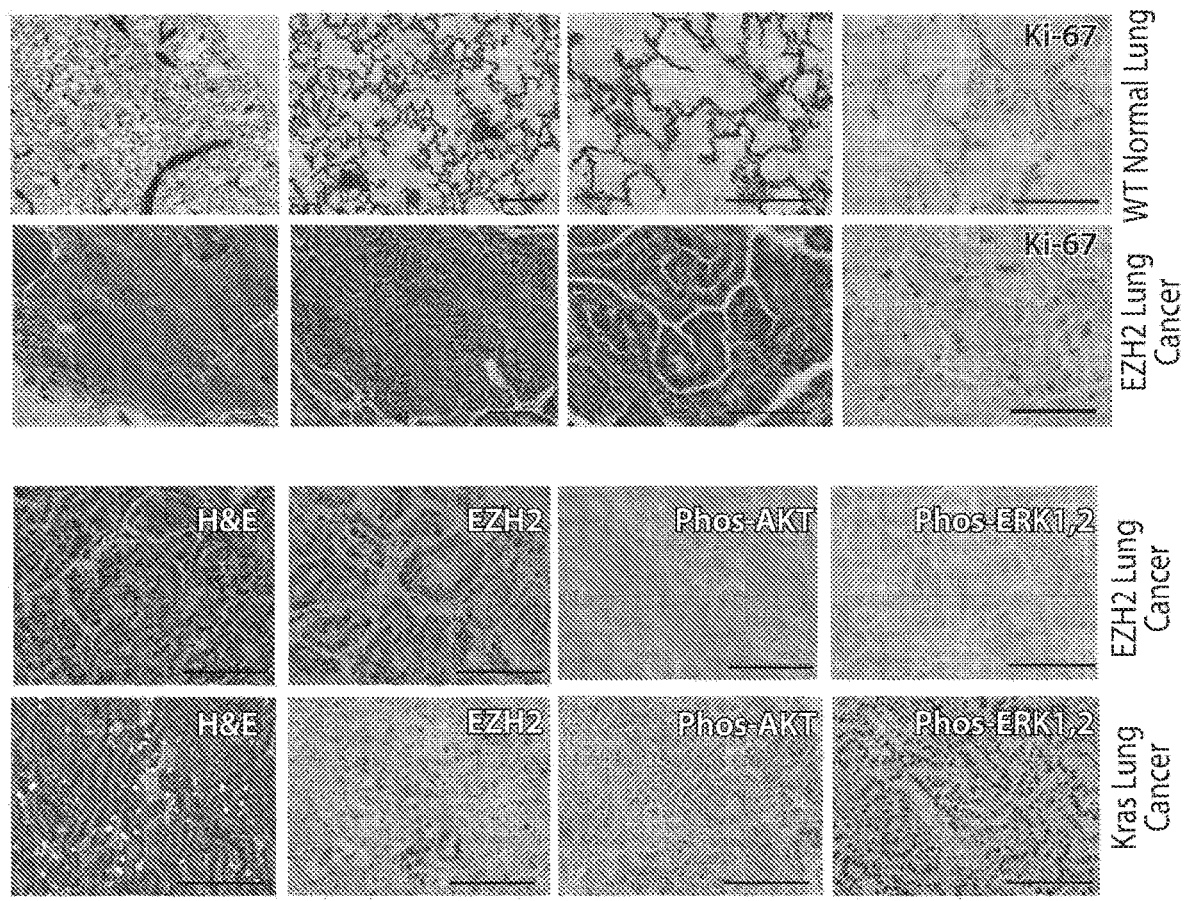
Figure 9D:
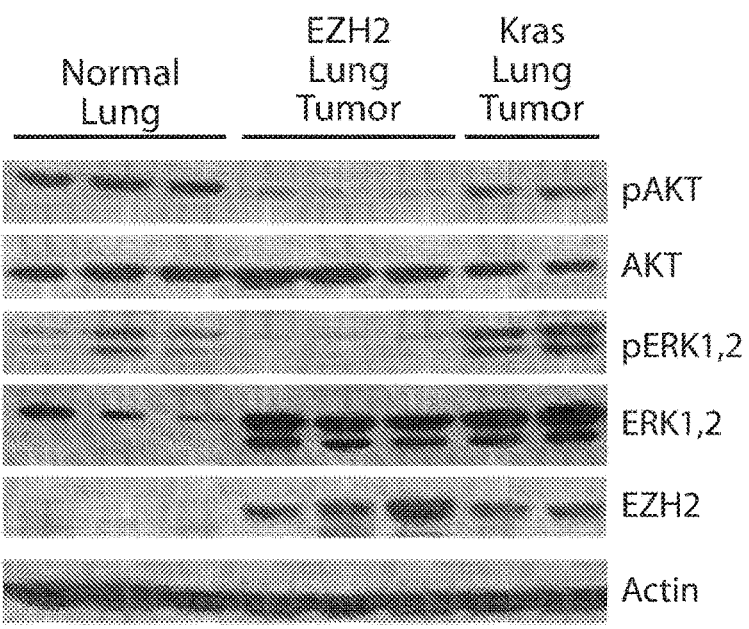
Figure 9E:
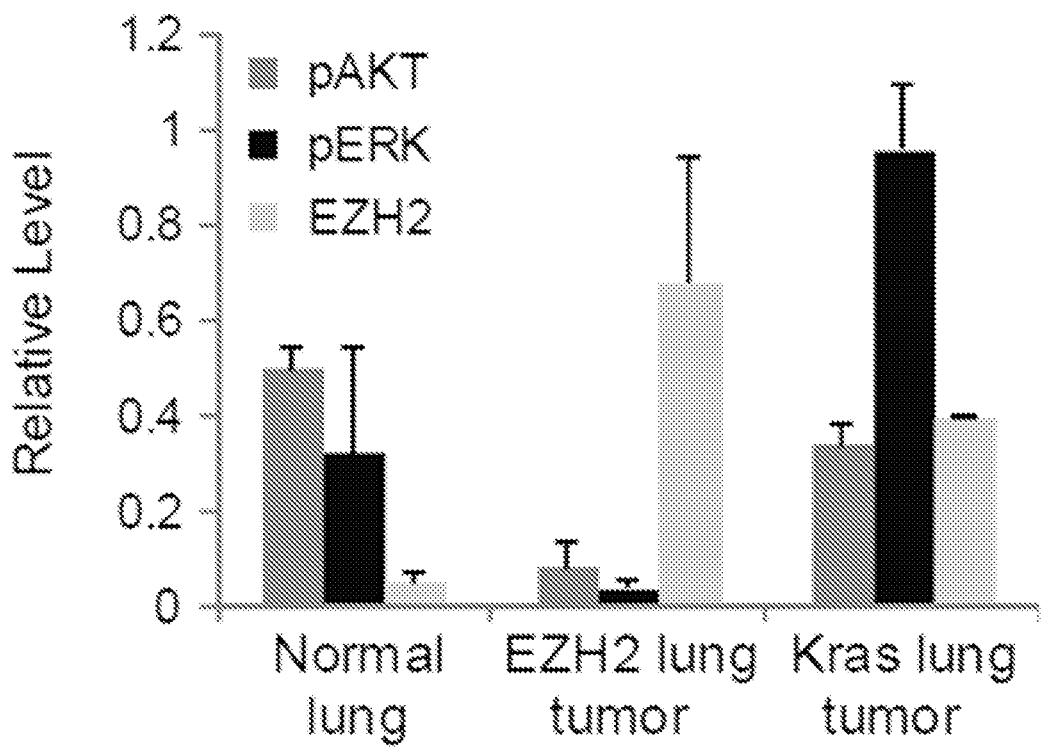
Figure 9E:
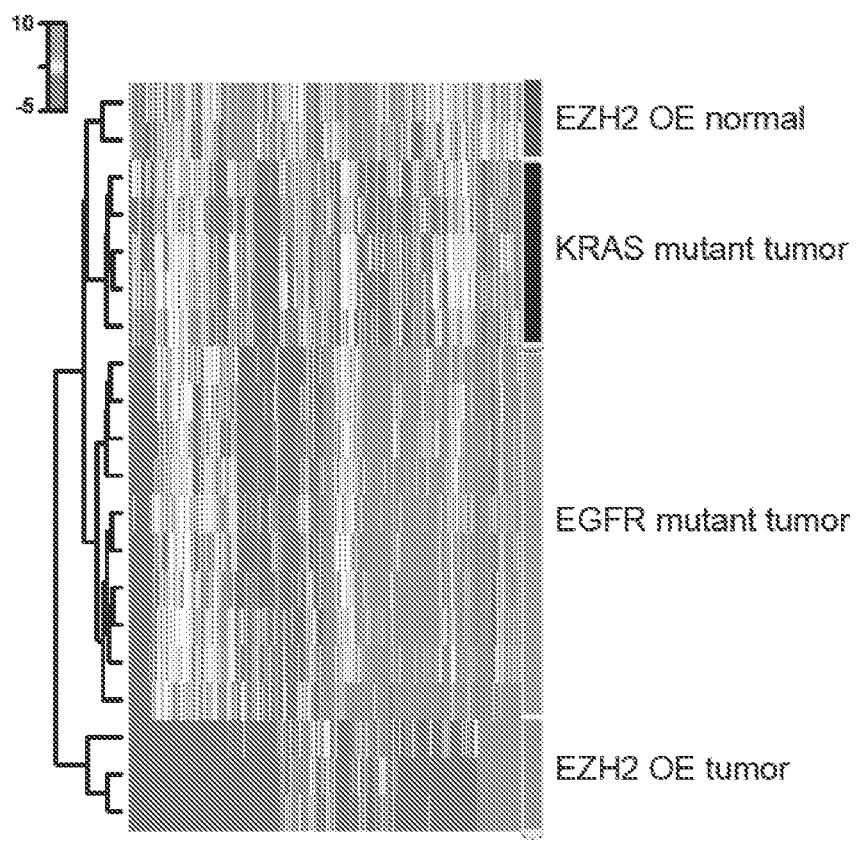

The histology of all resultant mouse lung tumors demonstrated features of human grade 1-2 lung adenoma/adenocarcinoma. As compared to staining of normal mouse lung (FIG. 9C, top panels) EZH2-overexpressing lung adenocarcinomas showed high cellularity and less differentiation, all consistent with low- and intermediate-grade adenocarcinoma. Immunohistochemical (IHC) analysis of tumors arising from Ezh2 overexpression demonstrated an increase in the proliferative marker, Ki67, as compared to normal lung tissue (FIG. 9C). In a comparison to murine lung cancers driven by expression of Kras, Ezh2 expression was markedly higher in the EZH2-driven lung tumors (FIG. 9D). Analysis for the expression of pathway markers typically identified in Kras-driven lung cancer, such as phosphorylated AKT (p-AKT) and phosphorylated ERK (p-ERK), revealed low p-AKT and p-ERK expression in EZH2-induced mouse lung tumors (FIG. 9D). Western blot analysis further confirmed that EZH2 mouse lung tumors have significantly less p-AKT and p-ERK than both KRAS-induced mouse lung tumors and normal mouse lung (FIG. 9E). Taken together, these data suggest that lung tumors driven by EZH2-mediated epigenomic dysregulation are histologically similar but molecularly distinct from lung tumors driven by KRAS-dependent oncogenic signaling.

EZH2-Driven Lung Cancer as a Molecularly Distinct Entity

Figures 10A, 10B:
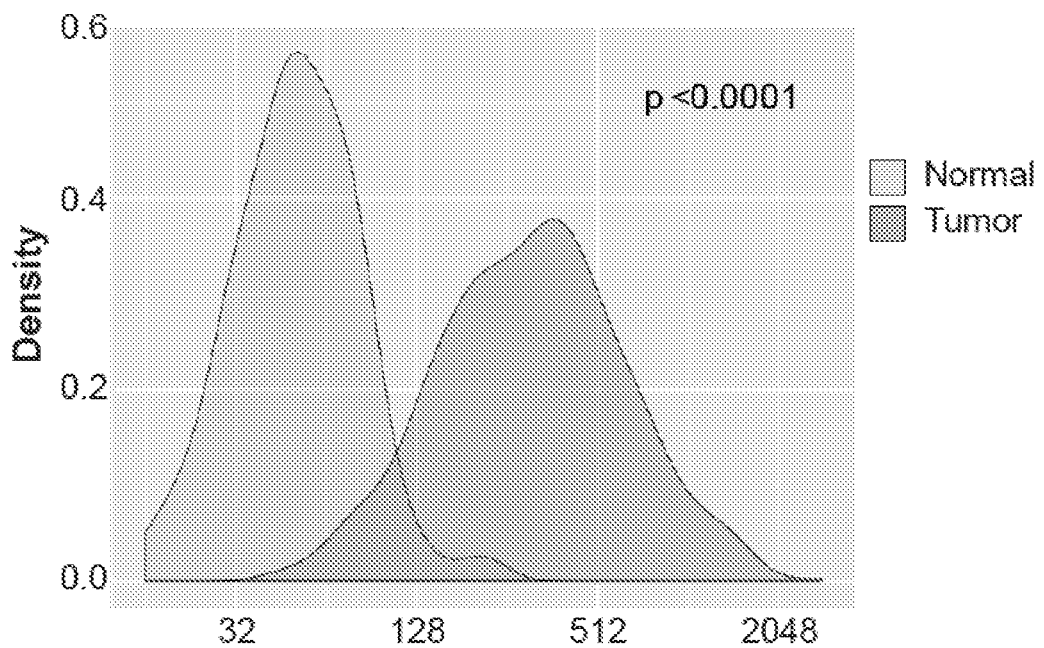
FIGS. 10A-10C. EZH2-Driven Lung Cancer as a Molecularly Distinct Entity.

To determine whether EZH2-induced mouse lung cancer reflects the molecular features of the human disease, unsupervised comparative gene expression profiling of murine lung, GEMM tumors and human cancers were performed. First, RNA sequencing (RNA-seq) was performed to compare the gene expression profiles of EZH2-overexpressing pre-cancerous normal lung tissue and EZH2-overexpressing lung adenocarcinoma tumors from mice. Using unsupervised hierarchical clustering, gene expression profiles from these samples were compared to expression profiles of EGFR-mutated and KRAS-mutated lung adenocarcinoma mouse tumors (FIG. 10A). EZH2-overexpressing tumors segregated as transcriptionally distinct from EZH2-overexpressing normal lung, EGFR- and KRAS-mutated lung tumors. These data demonstrate that EZH2 modulation of chromatin leads to activation/repression of transcriptional pathways distinct from canonical lung adenocarcinomas driven by EGFR and KRAS hyperactivating mutations, providing further transcriptional evidence for the above measures of divergent upstream signaling pathway activation state.

Figure 10C:
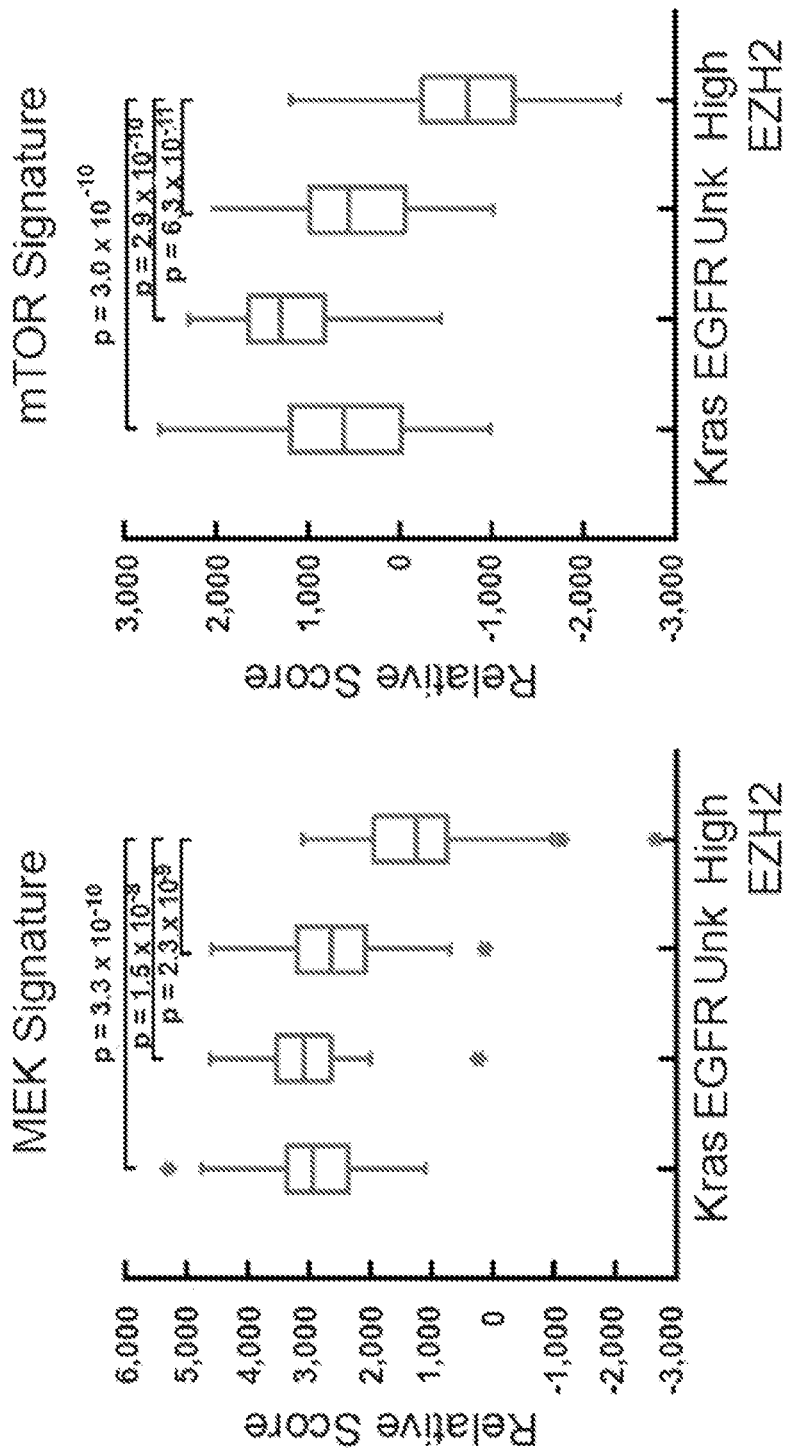

Having defined an EZH2-dependent and tumor-specific transcriptional state in murine lung adenocarcinoma, whether a comparable subset of human NSCLC exists was assessed next. Using publicly available data from The Cancer Genome Atlas (TCGA), a cohort of lung adenocarcinoma patients with elevated tumor EZH2 expression were identified (FIG. 10B). EZH2 expression in human lung cancer was found to be broadly distributed over a >50-fold range and high EZH2 levels were not mutually exclusive with KRAS or EGFR mutations. Highly EZH2-overexpressing tumors (top 20%) with wild-type KRAS and EGFR to emulate the genetics of the murine models were further selected. Pathway enrichment was assessed by Gene Set Enrichment Analysis (GSEA) (Subramanian et al., 2005). Transcriptional signatures associated with MEK and mTOR activation were repressed in EZH2-overexpressing tumors as compared to tumors with low EZH2 expression regardless of the presence or absence of oncogenic KRAS or EGFR mutations (FIG. 10C), corroborating again that EZH2 driven tumors are molecularly distinct from tumors driven by canonical signaling pathways.

Influence of EZH2 Overexpression on Chromatin Structure in Lung Cancer

The polycomb repressive complex exerts broad effects on cis-regulatory chromatin domains, thereby influencing epigenomic cell state (Ku et al., 2008). H3K27 acetylation and trimethylation are mutually exclusive biochemical events, in keeping with the fulcrum of transcriptional activation (H3K27ac) and repression (H3K27me3) observed in developmental transitions (Riising et al., 2014). Genome-wide assessment of enhancer-promoter activity, measured by H3K27ac chromatin immunoprecipitation with massively parallel DNA sequencing (ChIP-seq), have been used to comparatively study malignant and inflammatory cell states (Brown et al., 2014; Chapuy et al., 2013). Focusing epigenomic analysis on regions of massive H3K27ac enrichment, so-called super enhancers (SEs), has afforded inferences into oncogenic signaling (Hnisz et al., 2015) and the sub-classification of human tumors (Chapuy et al., 2013). It was thought that EZH2 overexpression in pulmonary epithelium, over time, leads to stable trimethylation and silencing of developmental transcription factors.

Figure 11A:
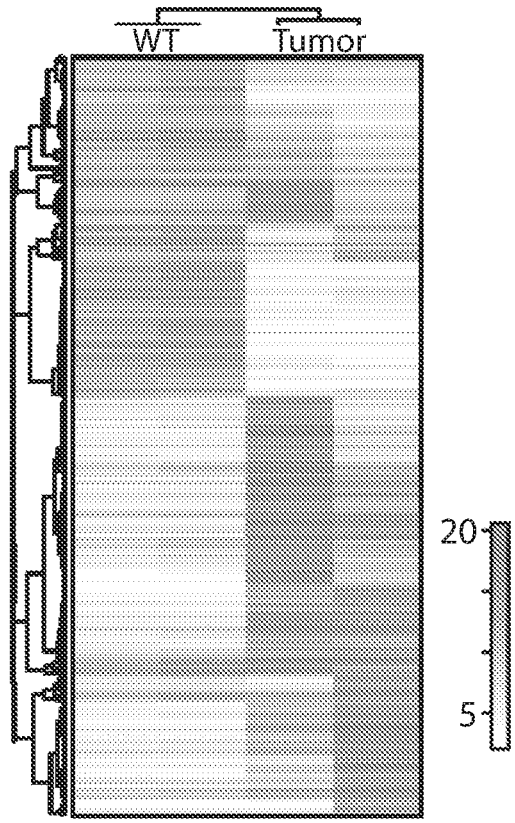
FIGS. 11A-11I. EZH2 Overexpression Modulates the Super Enhancer-Associated Transcriptional Landscape in Mouse Lung.
Figure 11B:
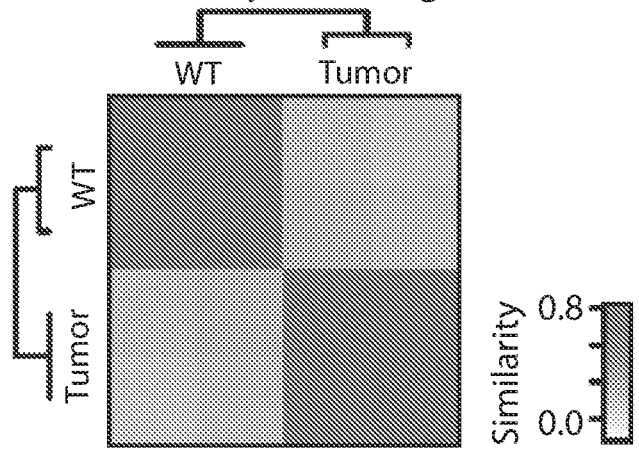
Figure 11C:
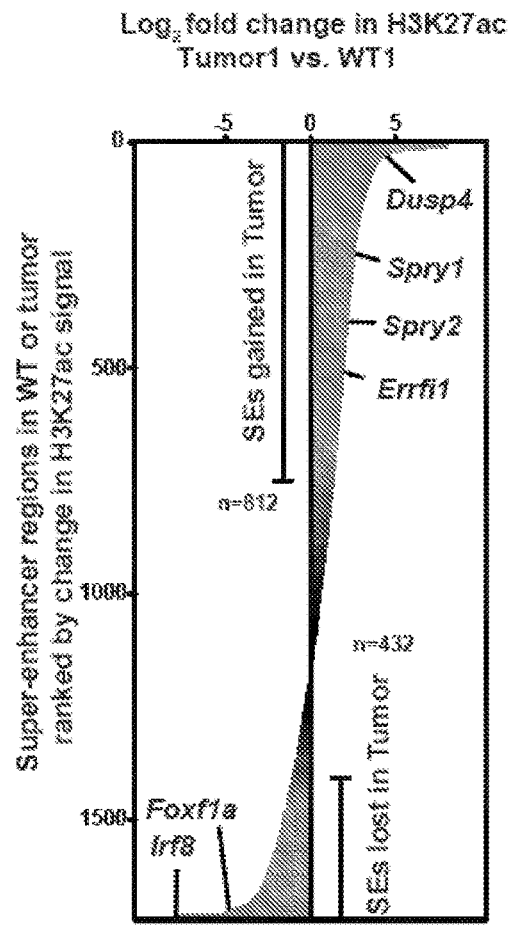
Figure 11D:
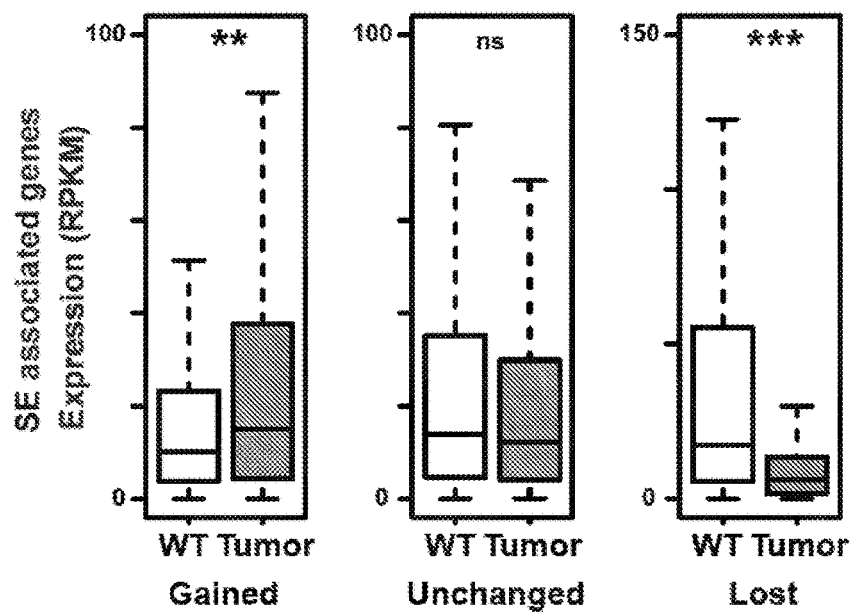
Figure 11E:
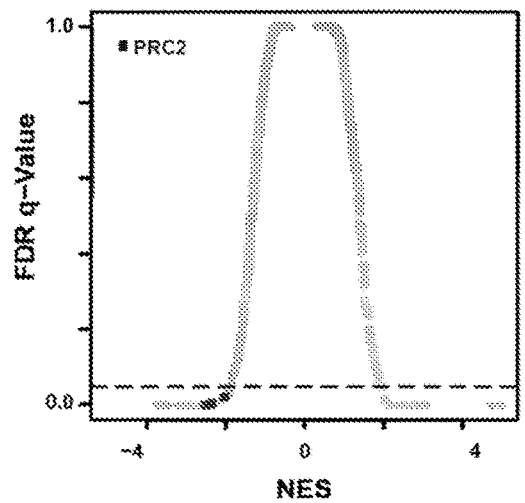
Figure 11F:
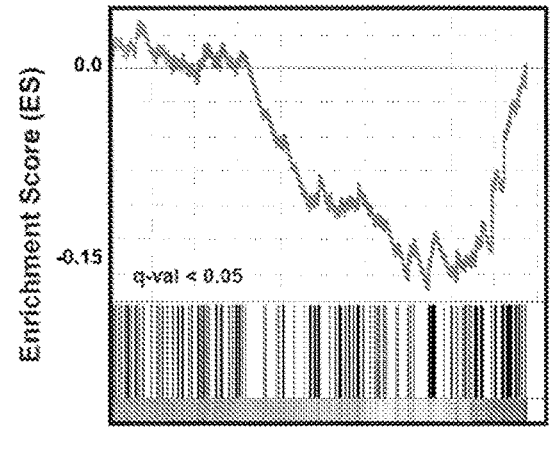

To understand the dynamic effects of EZH2 overexpression on chromatin structure in the context of malignant transformation, comparative epigenomic analysis of EZH2-overexpressing normal and malignant lung tissue was performed. First, active enhancers in two sets of tumor-normal pairs by H3K27ac ChIP-seq were mapped, and identified regions of asymmetric hyperacetylation (SEs), as was previously reported (Chapuy et al., 2013; Loven et al., 2013). Unsupervised hierarchical clustering segregated EZH2-overexpressing tumor and pulmonary epithelium (WT), belying an apparent distinct euchromatin epigenome structure (FIGS. 11A, 11B). Differential analysis of highly occupied H3K27ac regions in EZH2-overexpressing tumors and normal lung revealed global redistribution of H3K27ac, with 1244 individual loci exhibiting a greater than $\log_2$ 1.5-fold change in H3K27ac (432 lost, 812 gained, FIG. 11C). Changes in H3K27ac at SEs resulted in reciprocal changes in gene expression at adjacent expressed genes (measured by RNA-seq), suggesting that modulation of chromatin impacted gene expression in these tumors (FIG. 11D). Unbiased leading edge analysis of genes proximal to regions of lost H3K27ac in tumors identified polycomb repressive target gene signatures, implicating PRC2-mediated repression of these regulatory elements (FIG. 11E, 11F).

Figure 11G:
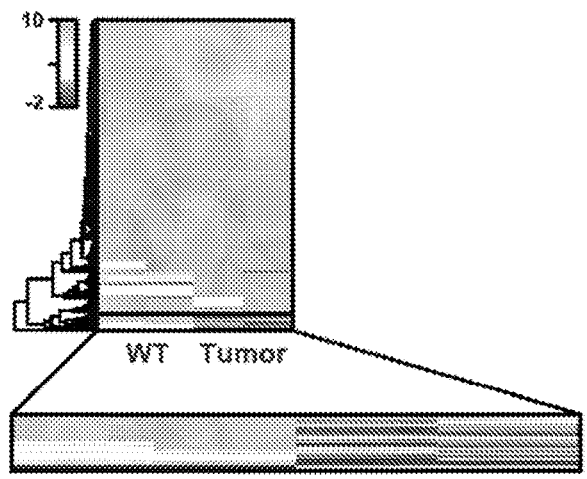
Figure 11H:
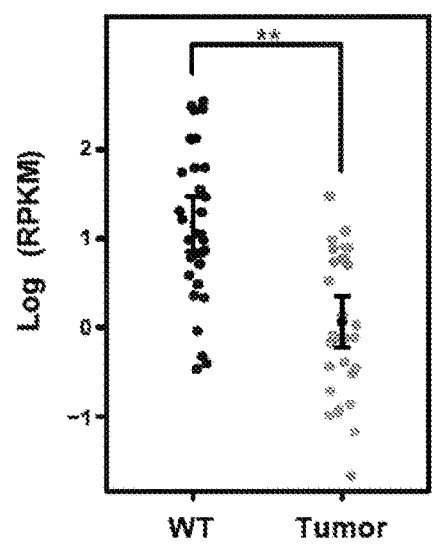
Figures 16A, 16B:
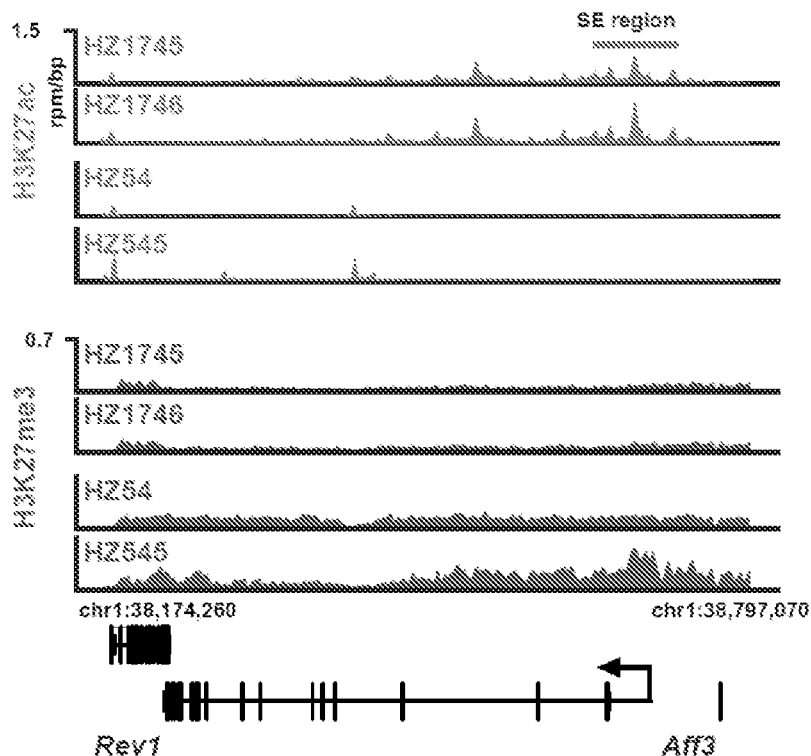
FIGS. 16A-16F, related to FIG. 11. H3K27ac super enhancer (SE) analysis in EZH2 mouse lung tumors.
Figure 16C:
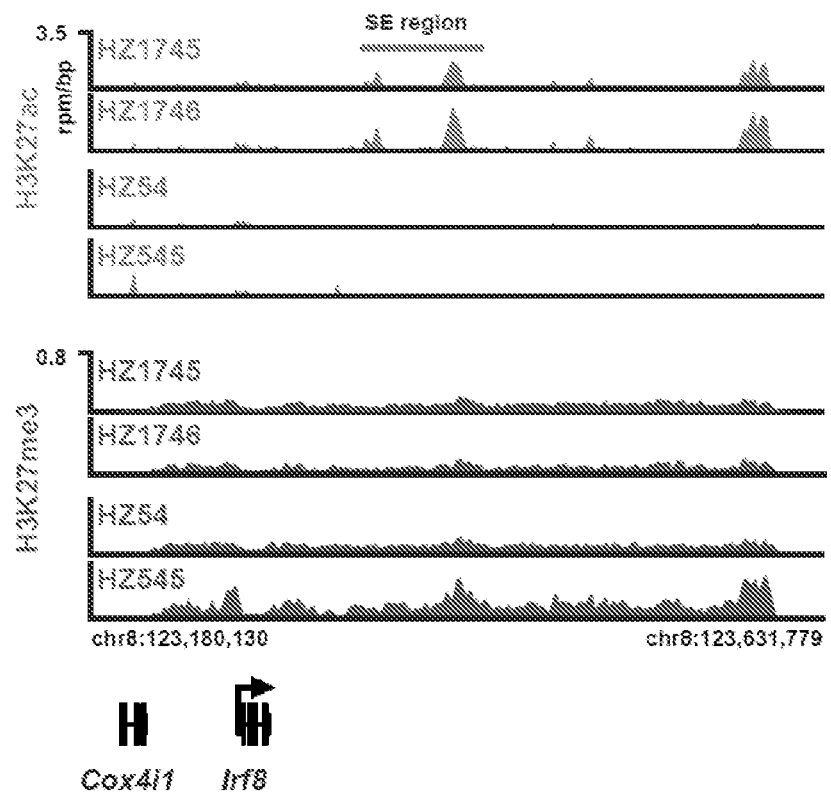
Figure 16D:
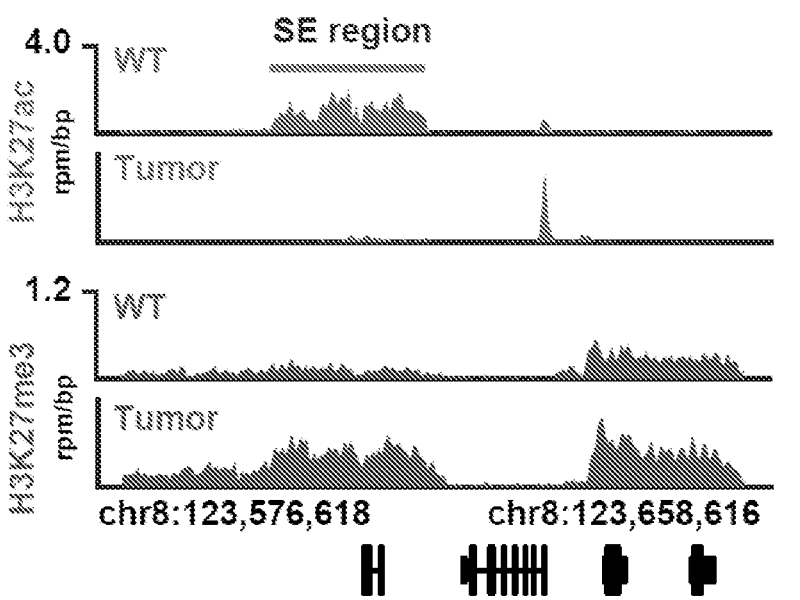

To link EZH2 function to lost SEs, H3K27me3 ChIP-seq on all samples was next performed. Among regions of lost H3K27ac SEs, a distinct subgroup of 33 cis-regulatory regions where loss of H3K27ac was accompanied by strong gain of the polycomb H3K27me3 mark were identified (FIG. 11G). Functionally, genes associated with these 33 regulatory regions showed decreased gene expression in tumors by RNA-seq (FIG. 11H), and were comprised of numerous developmental transcriptional regulators, including Foxf1a, Irf8, Hoxa9, and Meis1, as well as other chromatin factors such as Aff3 (Figure S2A). Repression of Hoxa9, Meis1, Irf8, and Foxf1 have been observed in NSCLC, and their activity has been functionally linked to decreased tumorigenesis, suggesting a tumor suppressive role for these gene regulators (Hwang et al., 2014; Li et al., 2014; Suzuki et al., 2014). Visual inspection of master developmental TFs repressed in tumor samples confirmed an epigenomic switch from large hyperacetylated enhancer elements to broad regions of H3K27 trimethylation, (FIG. 16B-16D).

Figure 16E:
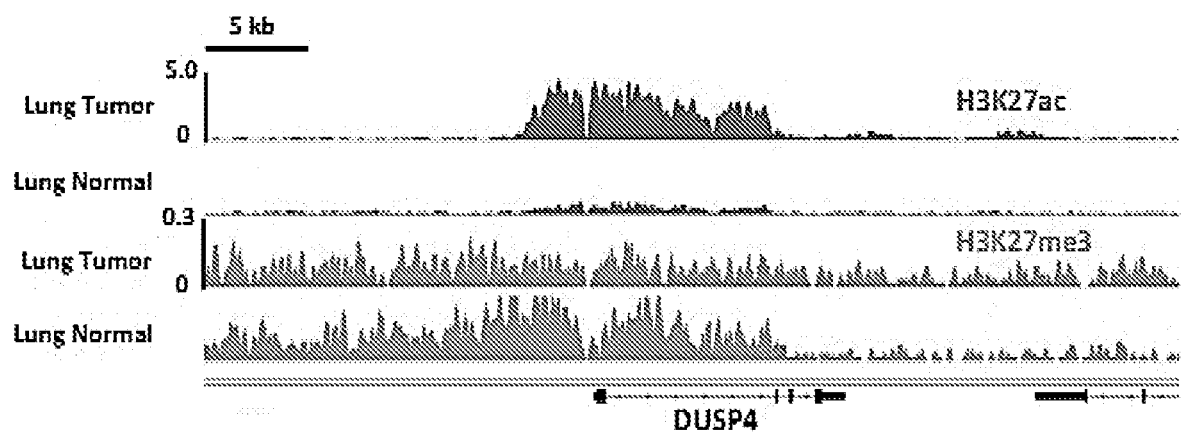
Figure 16F:
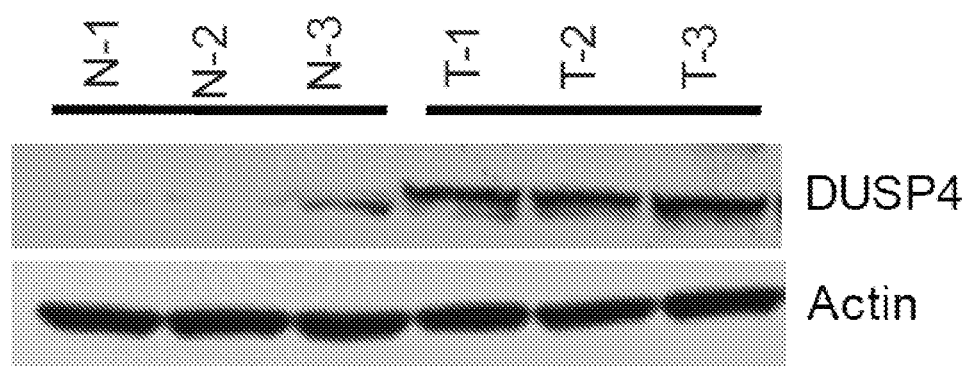

Among the gained SE-associated regions in tumor samples, notably, were genes encoding well-characterized, negative regulators of the MAPK-ERK pathway: Dusp4, Spry1, Spry2 and Errfi1 (FIG. 11C). Visual inspection corroborated that all four genes featured robust gain in H3K27ac at cis-regulatory elements (FIGS. 16E, 16F), and RNA-seq confirmed elevated expression in tumors. These data identify enhancer remodeling attributable to overexpressed EZH2 in the progression to lung adenocarcinoma, specifically silencing normal differentiation genes and activating negative regulators of MAPK-ERK signaling consistent with the signal transduction immunophenotyping of the EZH2-driven GEMMs.

Figure 11I:
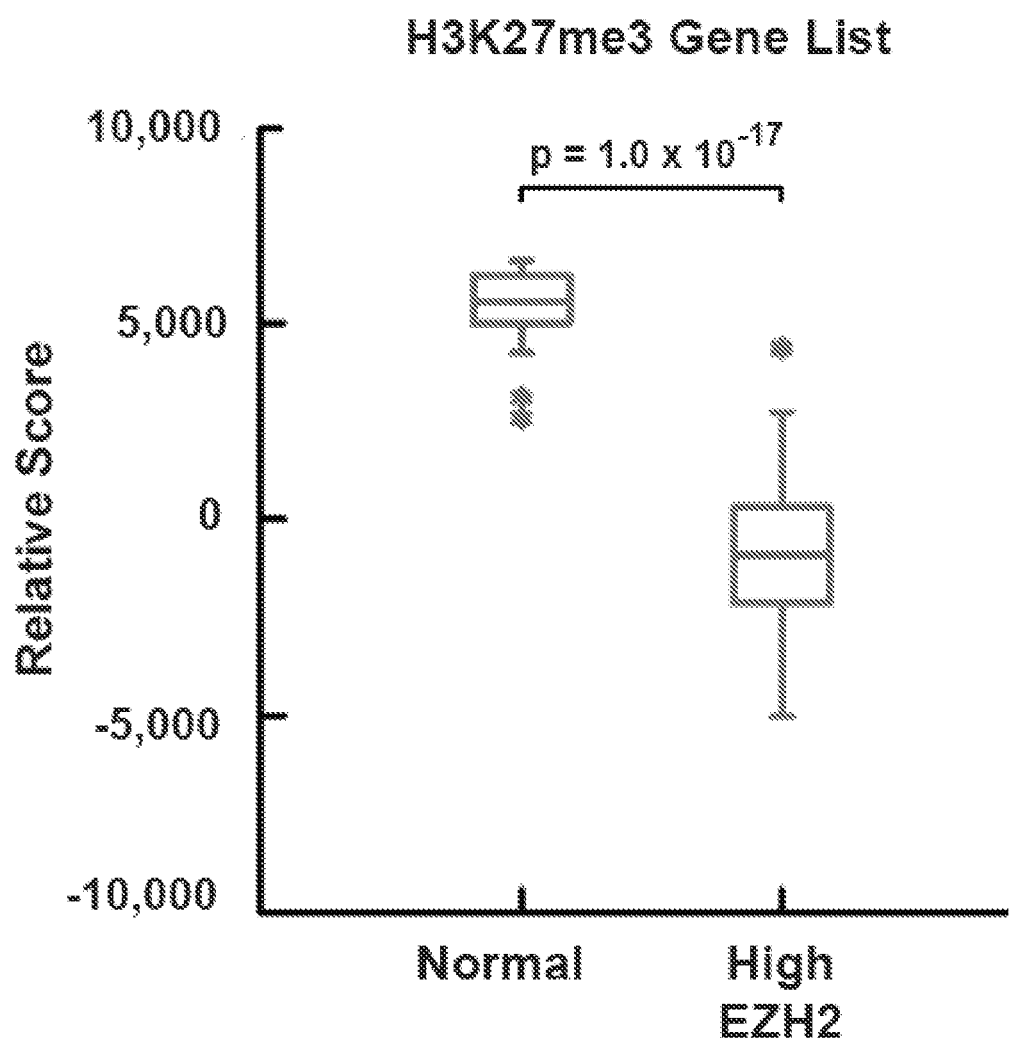

To explore the relevance of these findings to human lung cancer pathophysiology, we next asked whether downregulation of the PRC2 hypermethylated, SE-associated genes identified in murine tumors is observed in EZH2 overexpressing human lung adenocarcinoma. Strong downregulation of the functional, 32 gene set is observed in human lung cancers with the highest (top 20%) expression of EZH2 (FIG. 11I). Taken together, integrated epigenomic analysis argues that there is a distinct subset of human lung cancers that are characterized by 1) high levels of EZH2, 2) low activation of Ras effectors, and 3) suppression of a distinct set of EZH2 target genes.

EZH2 Overexpression Facilitates Cellular Transformation in Human Cells

Figures 12A, 12B:
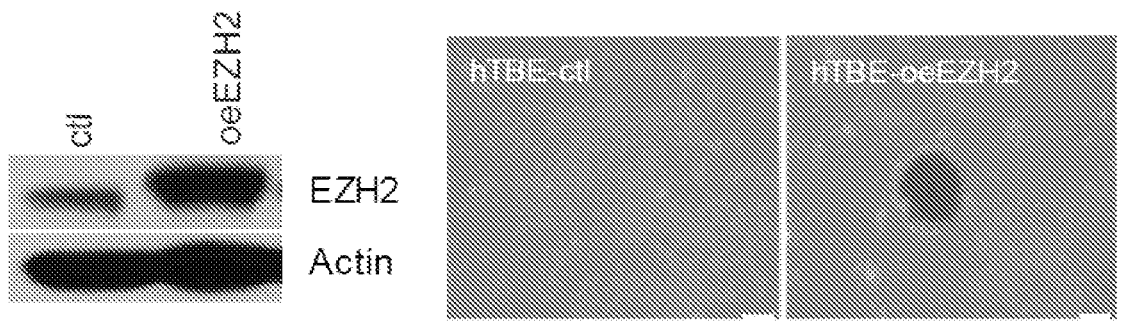
FIGS. 12A-12G. EZH2 Overexpression Transforms Human Lung Epithelial Cells.
Figure 12C:
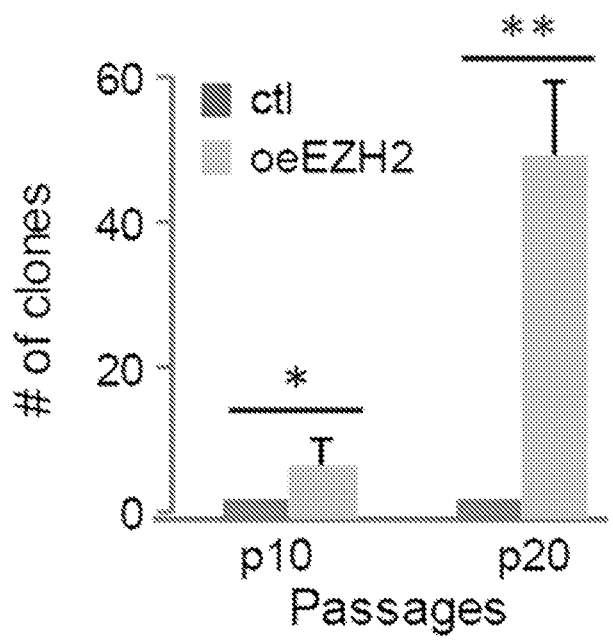

To examine the oncogenic potential of EZH2 in human cells, EZH2 was overexpressed in an immortalized normal human lung epithelial cell line, human tracheobronchial epithelial (hTBE) cells and monitored their oncogenic potential (FIG. 12A). To monitor transformation, we performed soft agar colony formation assays. As compared to cells expressing a control vector (hTBE-ctl), EZH2-overexpressing hTBE cells (hTBE-EZH2) formed colonies on soft agar four weeks after seeding (FIG. 12B). Since many transformed cell lines can form colonies on soft agar plates with shorter latencies, and given the epigenetic mechanism of EZH2-driven transformation, it was considered that hTBE-EZH2 cells might acquire higher transformation capacity over time. Therefore, hTBE-EZH2 cells were serially passaged for 20 doublings (p20) prior to seeding on soft agar. hTBE-oeEZH2 cells at p20 formed colonies in two weeks and had greater transformation potential than cells at p10 (FIG. 12C). Additionally, hTBE-ctl cells, passage for 10 or 20 doublings, were not able to form colonies on soft agar (FIG. 12C). Thus, the data suggest that constitutive overexpression of EZH2 facilitates cellular transformation of human cells over time, consistent with the long latency of lung cancer formation in EZH2 transgenic mice (FIG. 9C).

Human NSCLC with High EZH2 Expression is Sensitive to EZH2 Depletion

Figure 12D:
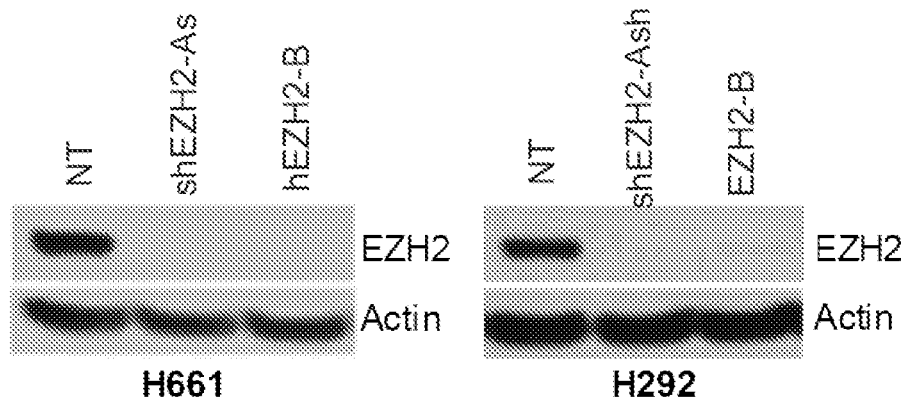
Figure 12E:
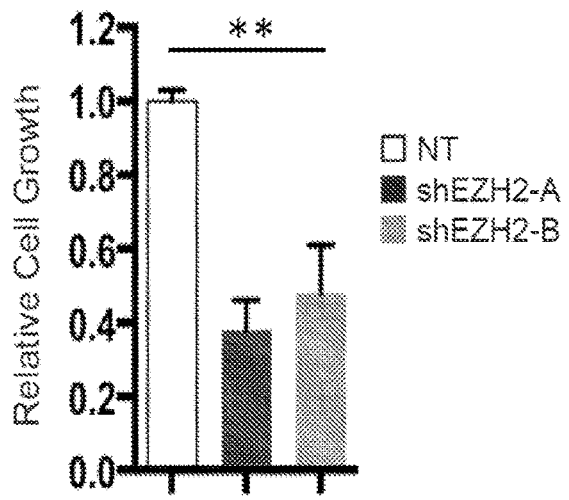
Figure 12F:
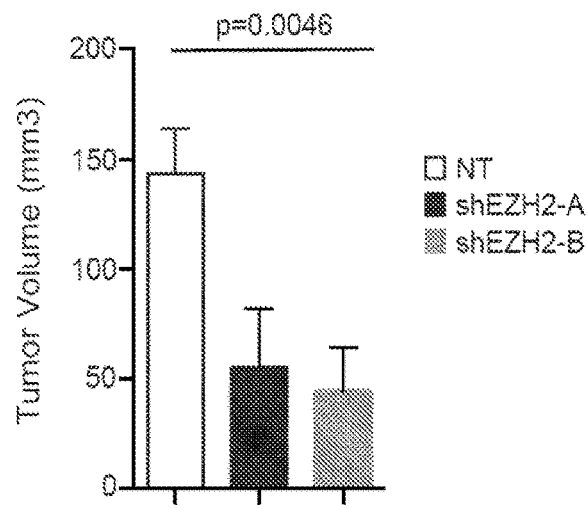
Figure 12G:
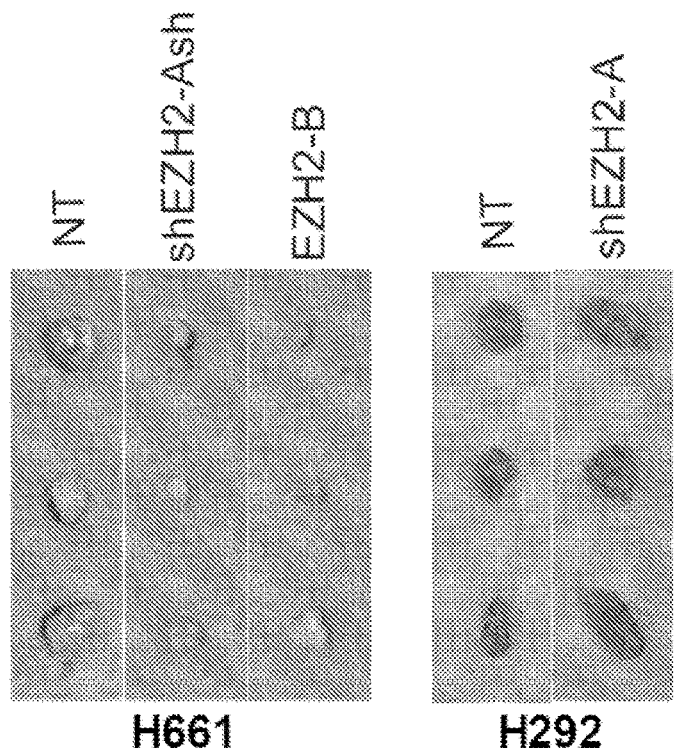
Figure 17A:
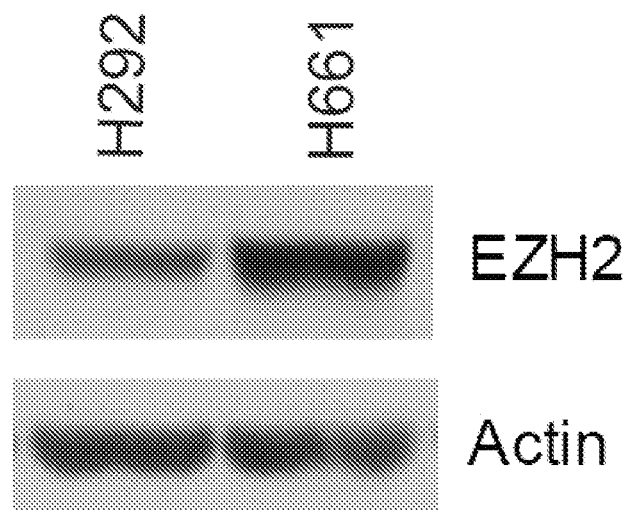
FIGS. 17A-17B, related to FIG. 12. Cells with low levels of EZH2 are not sensitive to disruption of EZH2.
Figure 17B:
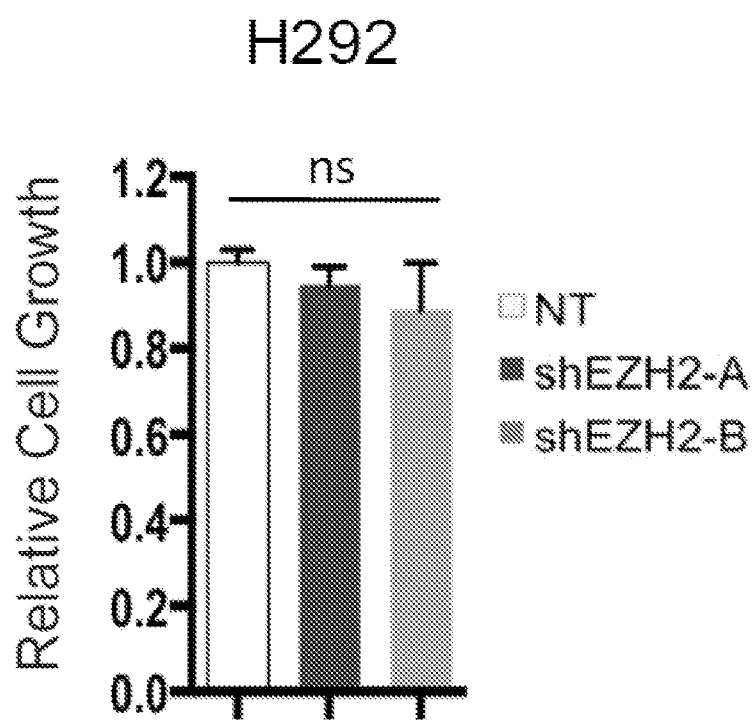

The observation that EZH2 overexpression produces lung cancer in mice and transforms normal human lung epithelial cells suggests that EZH2 may play an essential role in a subset of human NSCLCs. Using two previously verified EZH2 shRNAs (shEZH2-A and shEZH2-B), EZH2 expression was knocked down in human NSCLC cells that express high levels of EZH2 with no other known oncogenic mutations (H661) (Fillmore et al., 2015; Tzatsos et al., 2013; Xu et al., 2012). Both shRNAs showed nearly complete inhibition of EZH2 protein expression as compared to cells with a non-targeting shRNA (shNT) control (FIG. 12D). Cell proliferation assays revealed that H661 cells displayed more than 50% growth inhibition in response to shEZH2 knockdown compared to control cells (FIG. 12E). Finally, whether EZH2 expression was required for tumor formation in mouse xenograft models of human NSCLC was tested. H661 cells expressing either control or shEZH2 vectors were injected subcutaneously into mice and tumor formation was monitored bi-weekly. EZH2 knockdown significantly inhibited growth of H661 tumors in vivo (FIG. 12F, 12G). In contrast to H661 cells that express high levels of EZH2 protein, human H292 lung cancer cells express lower levels of EZH2 (FIG. 17A). In agreement with this, H292 cell growth was not affected by knockdown of EZH2 (FIGS. 12D and 17B). Likewise, EZH2 knockdown also did not affect the growth of these cells in xenograft models of NSCLC in mice (FIG. 12G).

Dependency of EZH2—Overexpressing Lung Cancer on Catalytically Active EZH2

To assess the dependency of EZH2-overexpressing lung tumors on sustained EZH2 enzymatic activity, a chemical genetic approach was employed. Recently, several pyridinone-based small molecule inhibitors of EZH2 were reported as chemical probes (e.g. GSK-126 and UNC1999; FIG. 18A) (Konze et al., 2013; McCabe et al., 2012). Both of these near structural analogues are potent and selective inhibitors of EZH2, however the broader utility of these probes in biological research in vivo may be limited by low potency (high dose administration), limited bioavailability (twice daily dosing), and uncertain availability (cost of synthesis, pharmaceutical material transfer). The development of a novel EZH2 inhibitor as an open-source chemical probe for the scientific community was undertaken. Lacking the guidance of crystallographic data, structure-activity relationships were deduced empirically from iterative analogue synthesis and biochemical testing.

Figure 1:
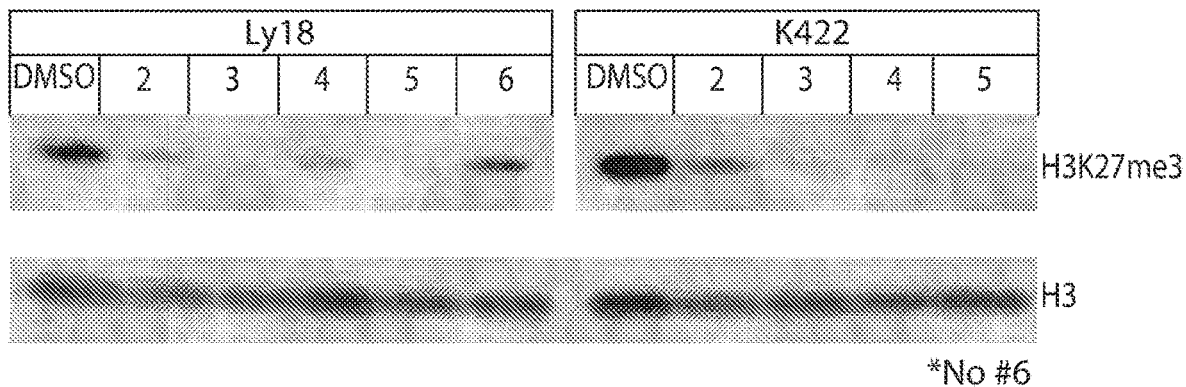
FIG. 1 shows exemplary Western blotting results of H3K27me3 treated for 72 hours with compound 5 at 1 μM (top panel) and 0.1 μM (bottom panel). uM: μM.
Figure 2:
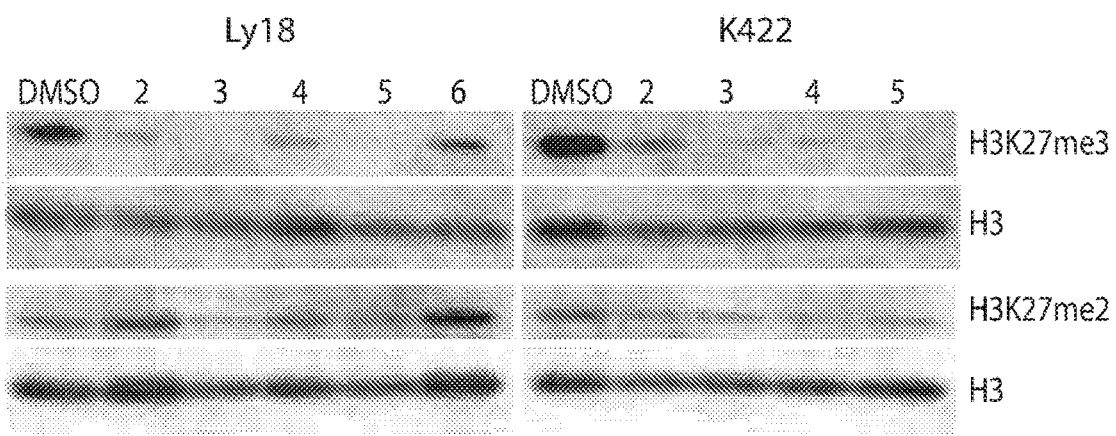
FIG. 2 shows exemplary dimethylation and trimethylation of H3K27 with a treatment of compound 5 at 1 μM for 72 hours.
Figure 3:
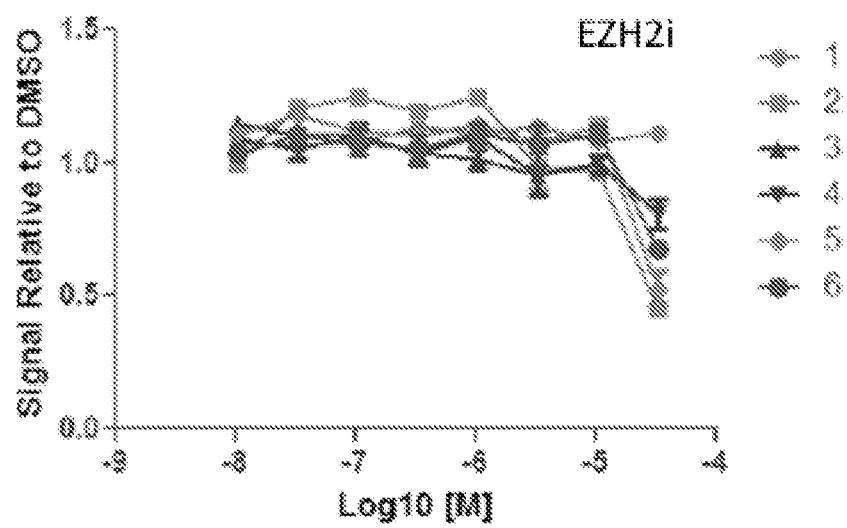
FIG. 3 shows exemplary cell viability results of select cell lines treated with compound 5 for 72 hours. Top panel: Ly18 (EZH2 wt (wild type)) cell line. Bottom panel: K422 (EZH2 mutant) cell line. Log 10 [M]: log(concentration of compound 5 in molar).
Figure 3:
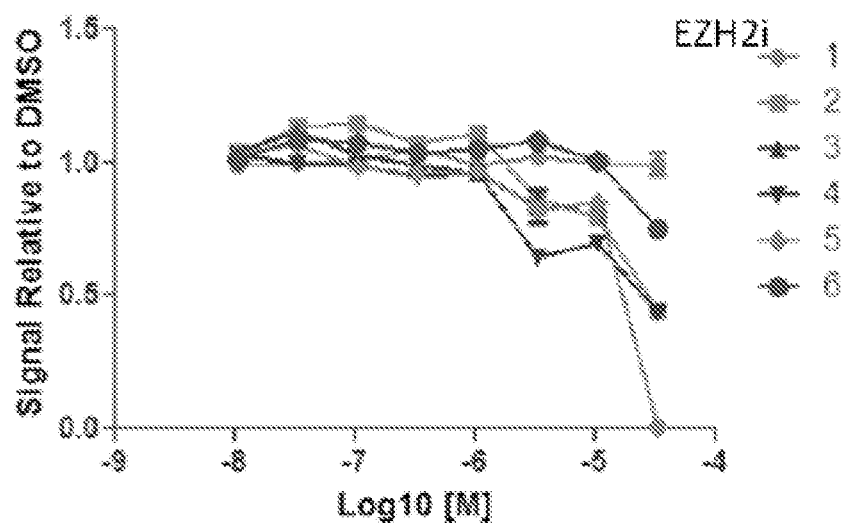
Figure 4:
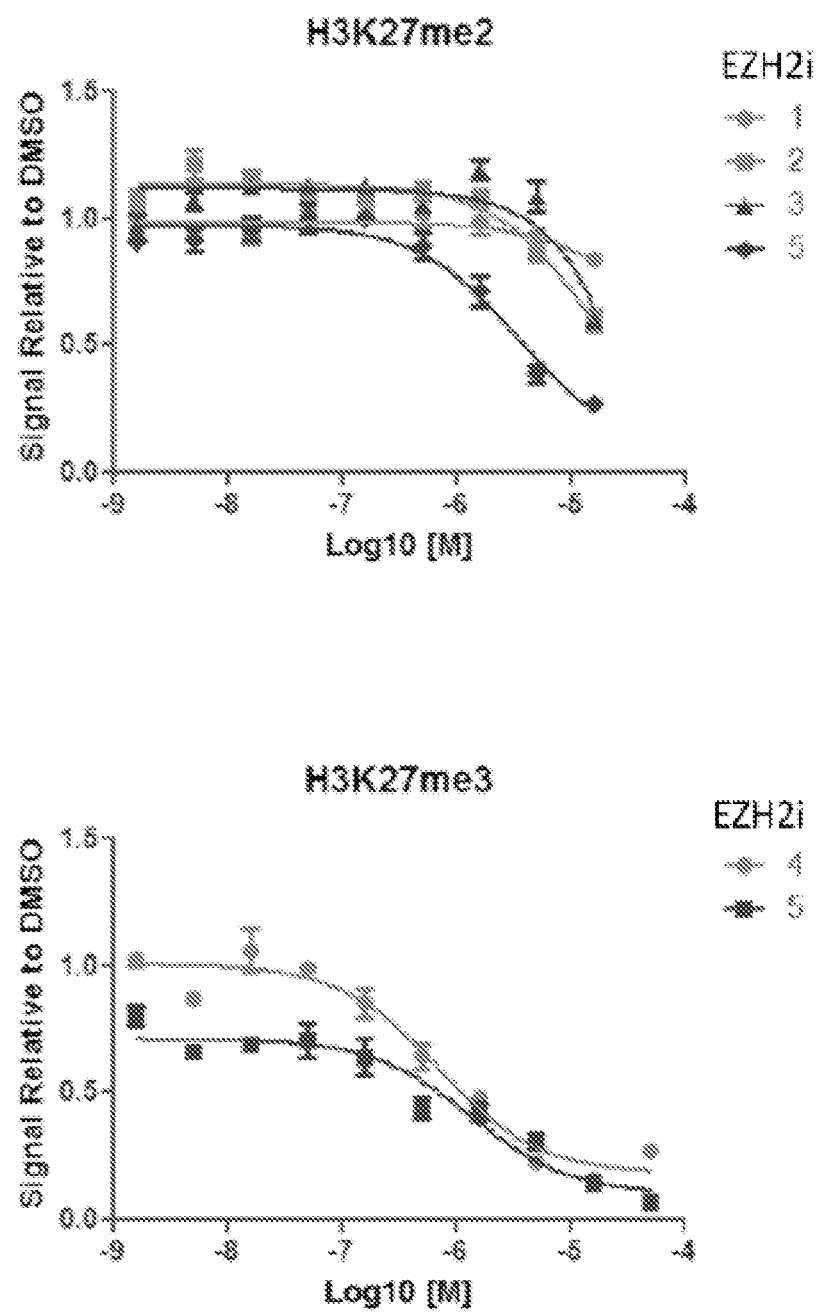
FIG. 4 shows exemplary dimethylation and trimethylation of H3K27 with a treatment of compound 5 measured using an ALPHALISA assay. Top panel: H3K27me2. Bottom panel: H3K27me3. Log 10 [M]: log(concentration of compound 5 in molar).
Figure 5:
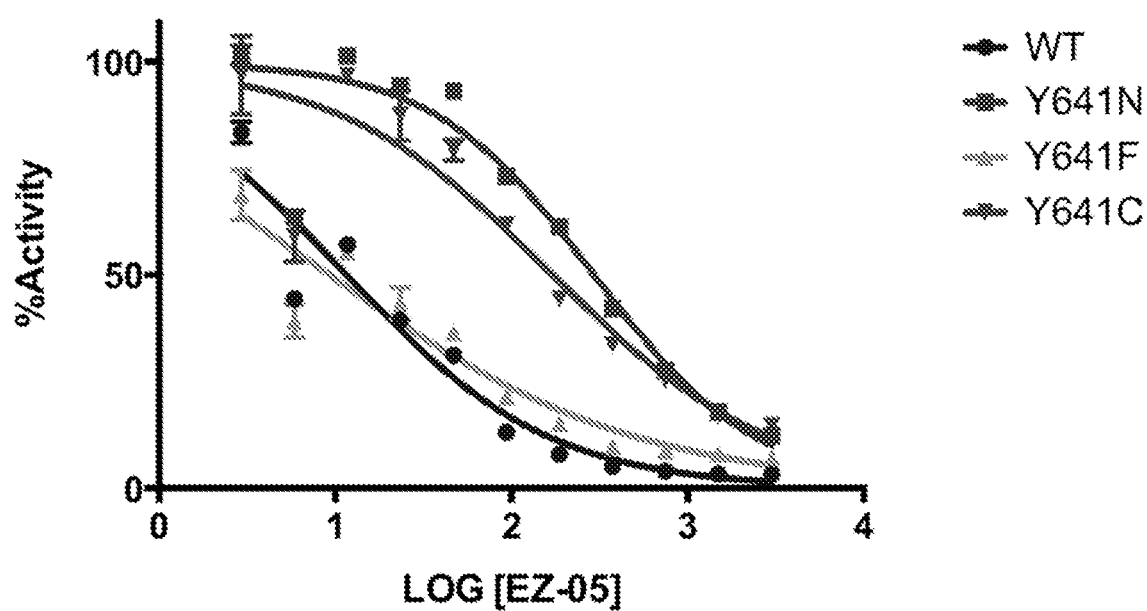
FIG. 5 shows exemplary activities of compound EZ-05 against WT (wild type) and mutant EZH2 PRC2 complexes. Log [EZ-05]: log(concentration of compound EZ-05 in molar).
Figure 13A:
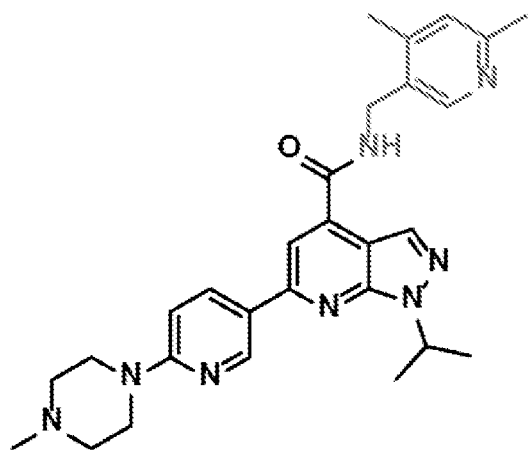
FIGS. 13A-13C. Small Molecule EZH2 Inhibitor Development.
Figure 13B:
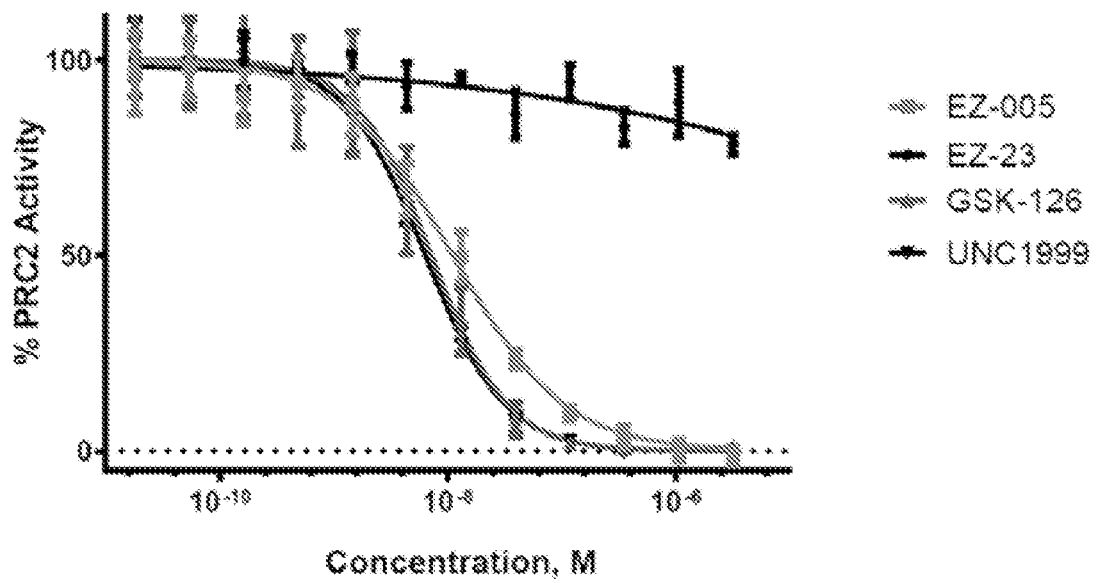
Figure 13C:
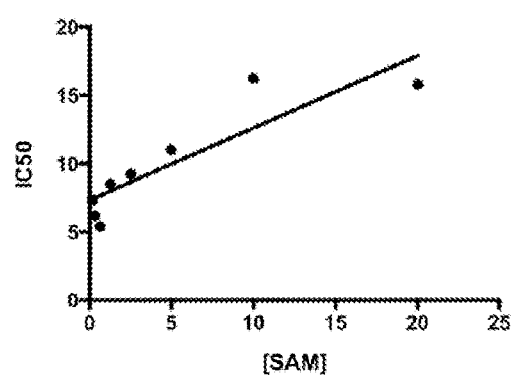
Figure 13D:
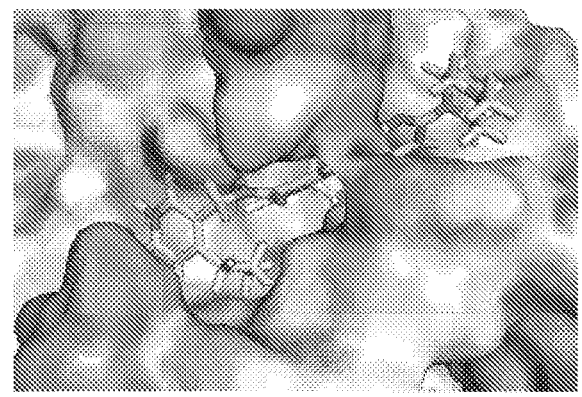
(FIG. 13D) Computational docking model of JQEZ5 binding to EZH2.
Figure 13E:
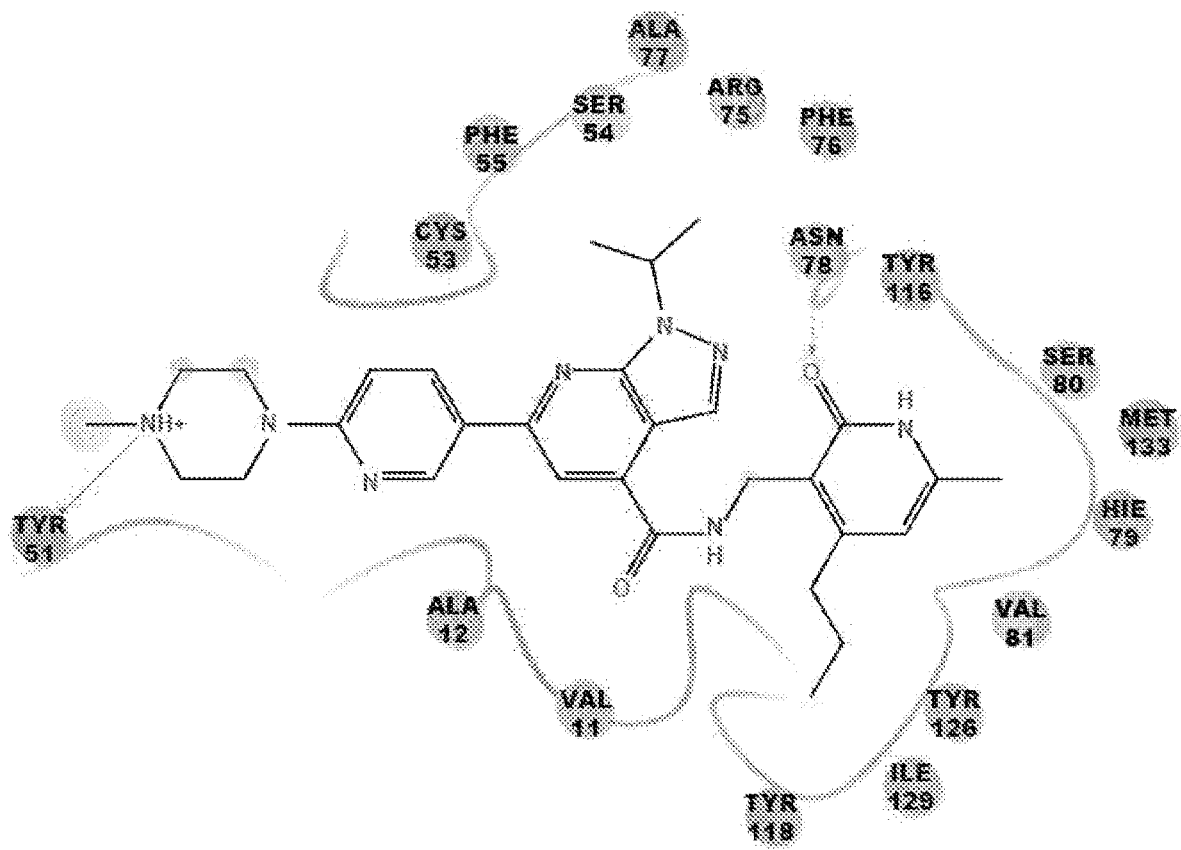
(FIG. 13E) Ligand interaction diagram (LID) depicts how JQEZ5 interacts with EZH2 residues.
Figure 13F:
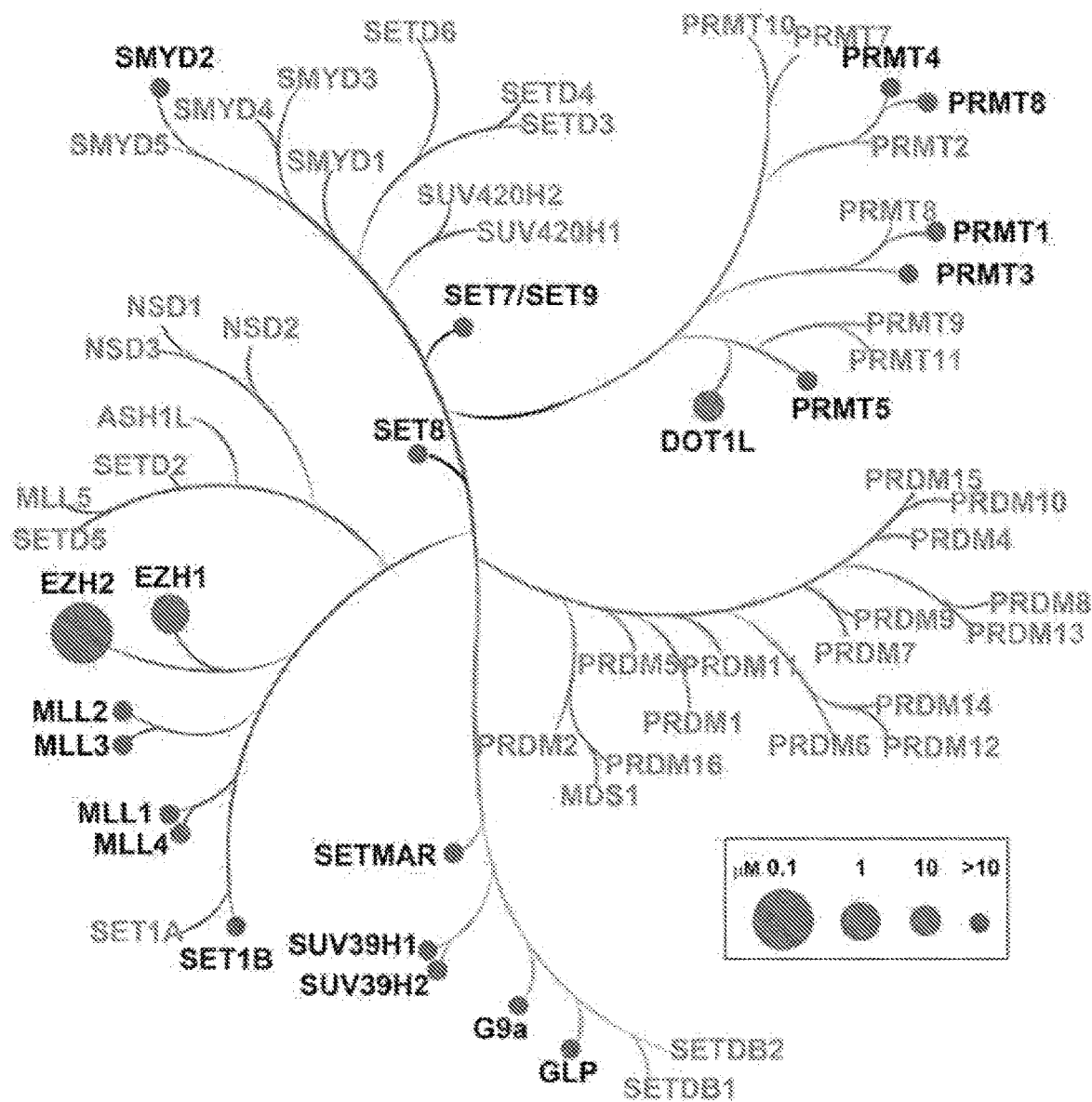
(FIG. 13F) Selectivity profiling with a methyltransferase panel showed that JQEZ5 selectively binds EZH2 in a panel of 22 methyltransferase assays. See also FIG. 18.

Emerging from follow-up chemistry is JQEZ5, which features a pyrazolo-pyridine core displaying a 6-substituted solubilizing feature and a preserved pyridinone warhead (highlighted in grey; FIG. 13A). The synthesis of JQEZ5 is nine linear steps, high-yielding and scalable (see below), to support broad distribution. As a paired control, JQEZ23, that substitutes the active pyridinone with a predicted inactive pyridinium ring (highlighted in grey; FIG. 5A) was developed. Both compounds were evaluated in enzymatic assays with a five-component PRC2 complex with radiometric labeled S-adenosyl methionine (SAM). JQEZ5 inhibited enzymatic functionality of PRC2 with a biochemical IC50 of 80 nM, similar to GSK-126 and UNC1999, while JQEZ23 had little inhibitory activity towards purified PRC2 (FIG. 5B, S4B). JQEZ5 exhibited SAM-competitive inhibition of PRC2, as determined by biochemical inhibition assessed in the presence of escalating unlabeled SAM co-factor concentration (FIGS. 13C, 18C). To understand the putative mode of molecular recognition of EZH2 by the inhibitor, binding of JQEZ5 to EZH2 was modeled using a recently reported computational model (FIG. 13D) (Kalinic et al., 2014). The binding model we established indicates that the pyridinone ring of JQEZ5 binds to Asn78 on EZH2, and that the pyrazolo pyridine ring is also deeply buried in the SAM-binding pocket of EZH2. The ligand interaction diagram (LID) of JQEZ5 and EZH2 also predicts that the piperazine ring on JQEZ5 extends out of the SAM-binding pocket of EZH2 and is thus, amenable to further modification, as needed (FIG. 13E). Specificity of JQEZ5 for EZH2 was assessed and confirmed by parallel study of a panel of recombinant, purified lysine methyltransferases (FIG. 13F, 18D) (Horiuchi et al., 2013).

Figure 14A:
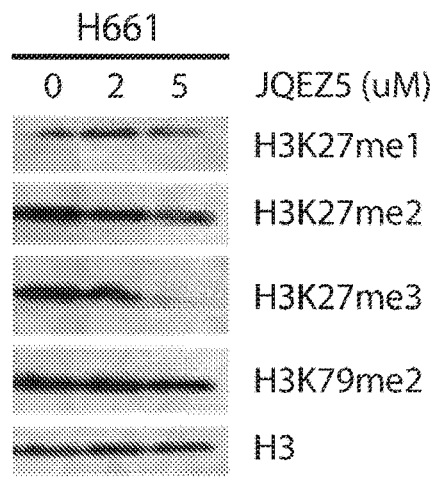
FIGS. 14A-14G. JQEZ5 Inhibits Lung Cancer Growth In Vitro and In Vivo.
Figure 14B:
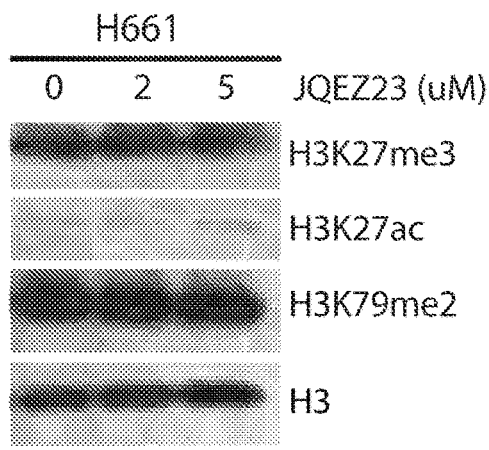
Figure 14C:
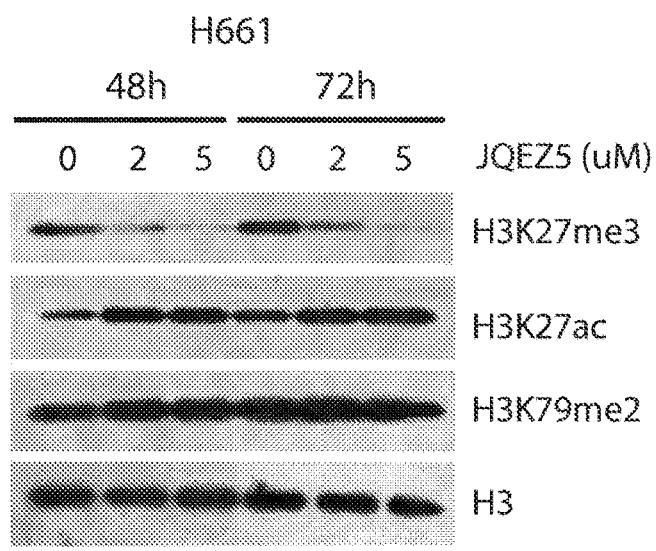
Figure 14D:
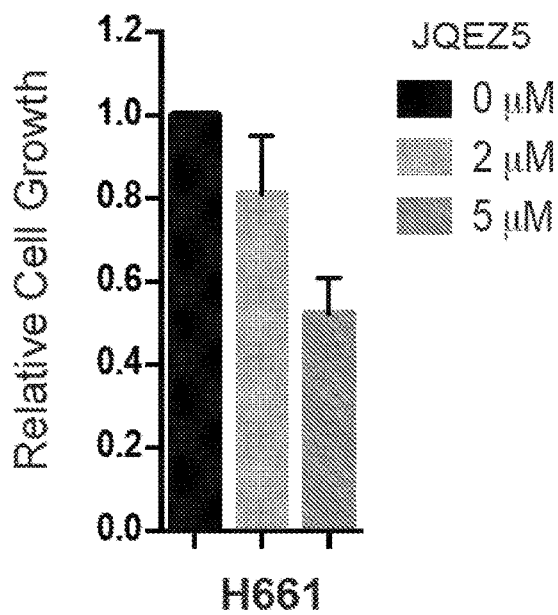
Figure 14E:
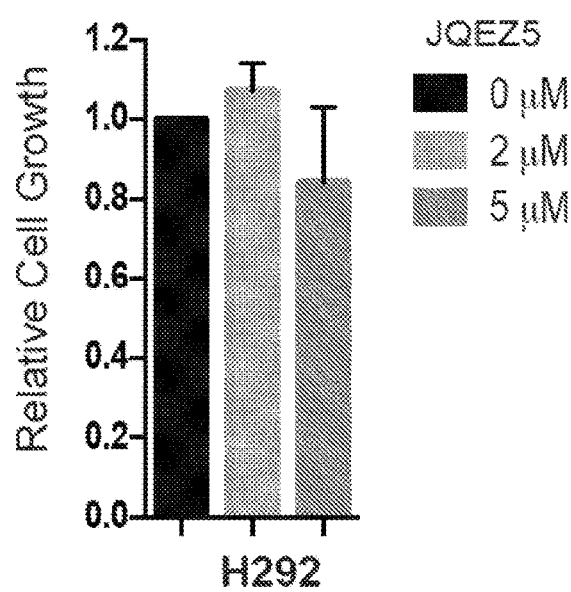
Figure 14F:
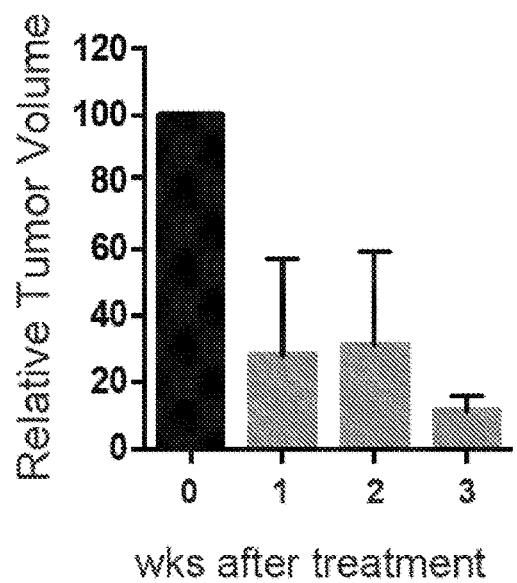
Figure 14G:
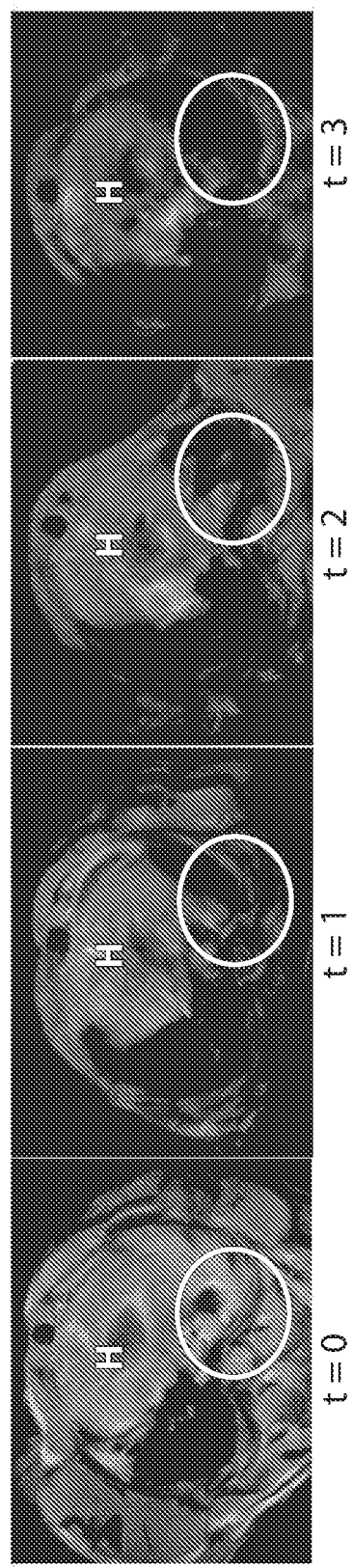

After biochemically validating the specificity and potency of JQEZ5, human NSCLC cells were treated in dose-ranging biochemical and cellular studies (H661). Cells treated with increasing concentrations of JQEZ5 demonstrated acutely reduced levels of H3K27me3 without affecting H3K27 mono- or di-methylation, as assessed by Western blotting (FIG. 14A). Treatment with the negative control compound, JQEZ23, did not have any affect on H3K27 methylation status (FIG. 14B). H3K27me3 reduction correlated with compound concentration as well as length of treatment (FIG. 14C). Similar to the EZH2 shRNA studies, JQEZ5 suppressed the proliferation of EZH2-overexpressing H661 cells after treatment for 4 days without affecting the proliferation of H292 cells that feature lower EZH2 expression (FIGS. 14D-14E).

Figure 19A:
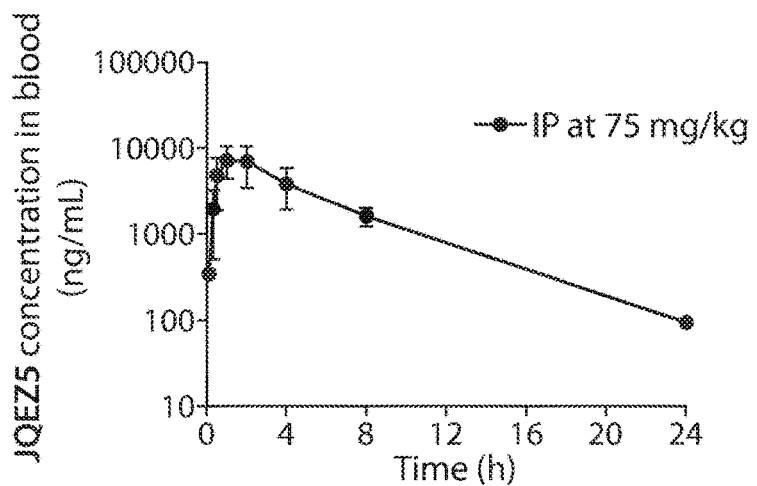
FIGS. 19A-19C, related to FIG. 14. In vivo properties of JQEZ5 (FIG. 19A) JQEZ5 half-life in mice as revealed by pharmacokinetic analyses of mean whole blood concentration with time after intraperitoneal injection at 75 mg/kg in male CD1 mice (n=3).
Figure 19B:
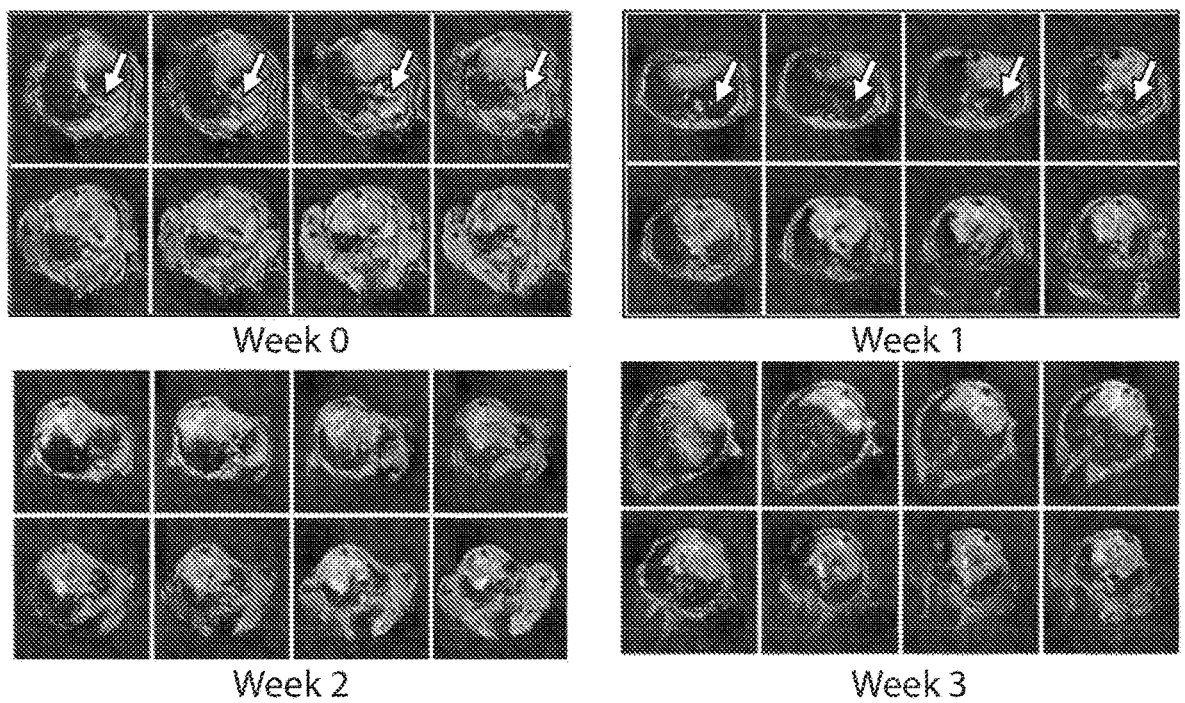
Figure 19C:
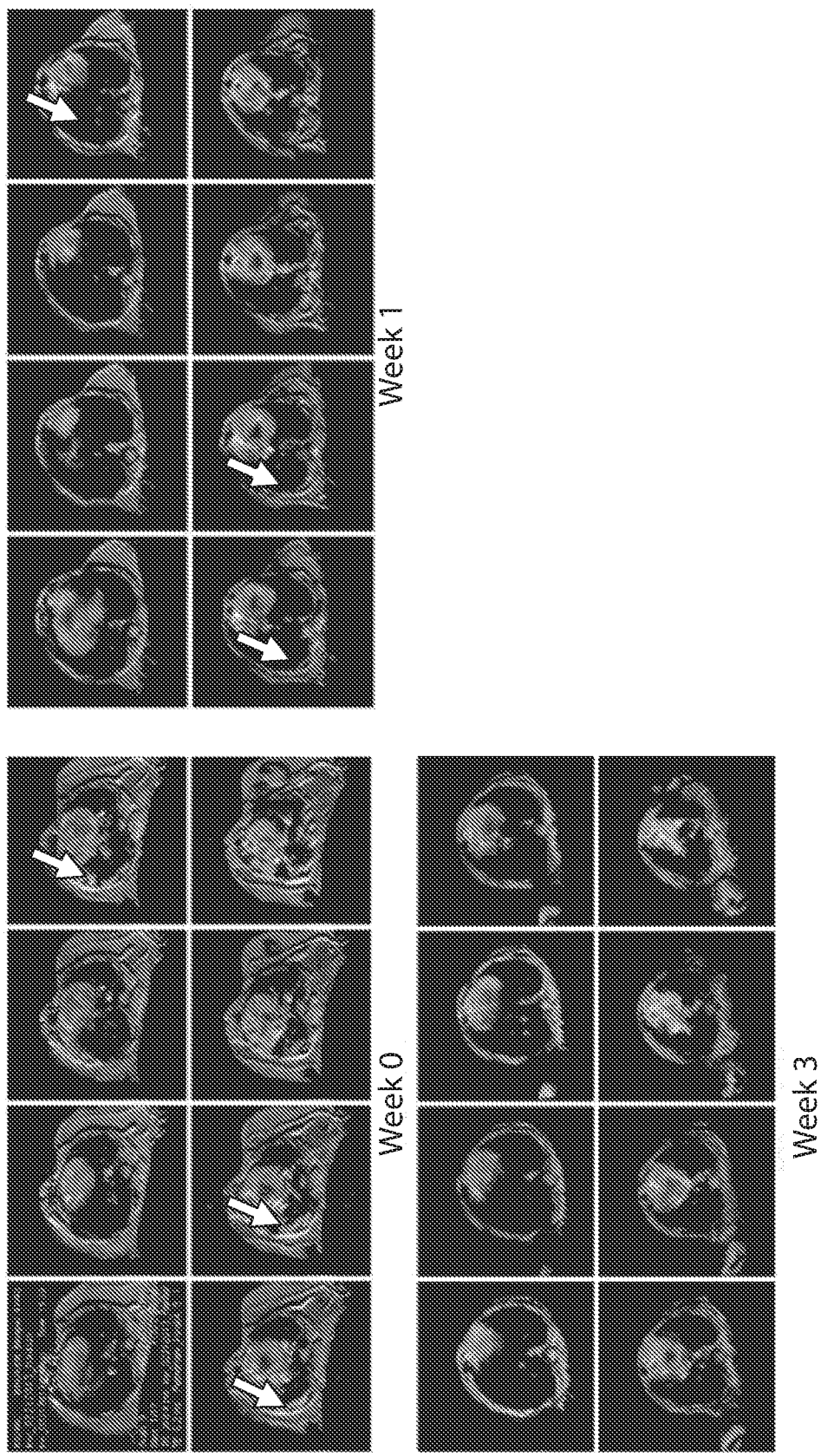
Figure 20:
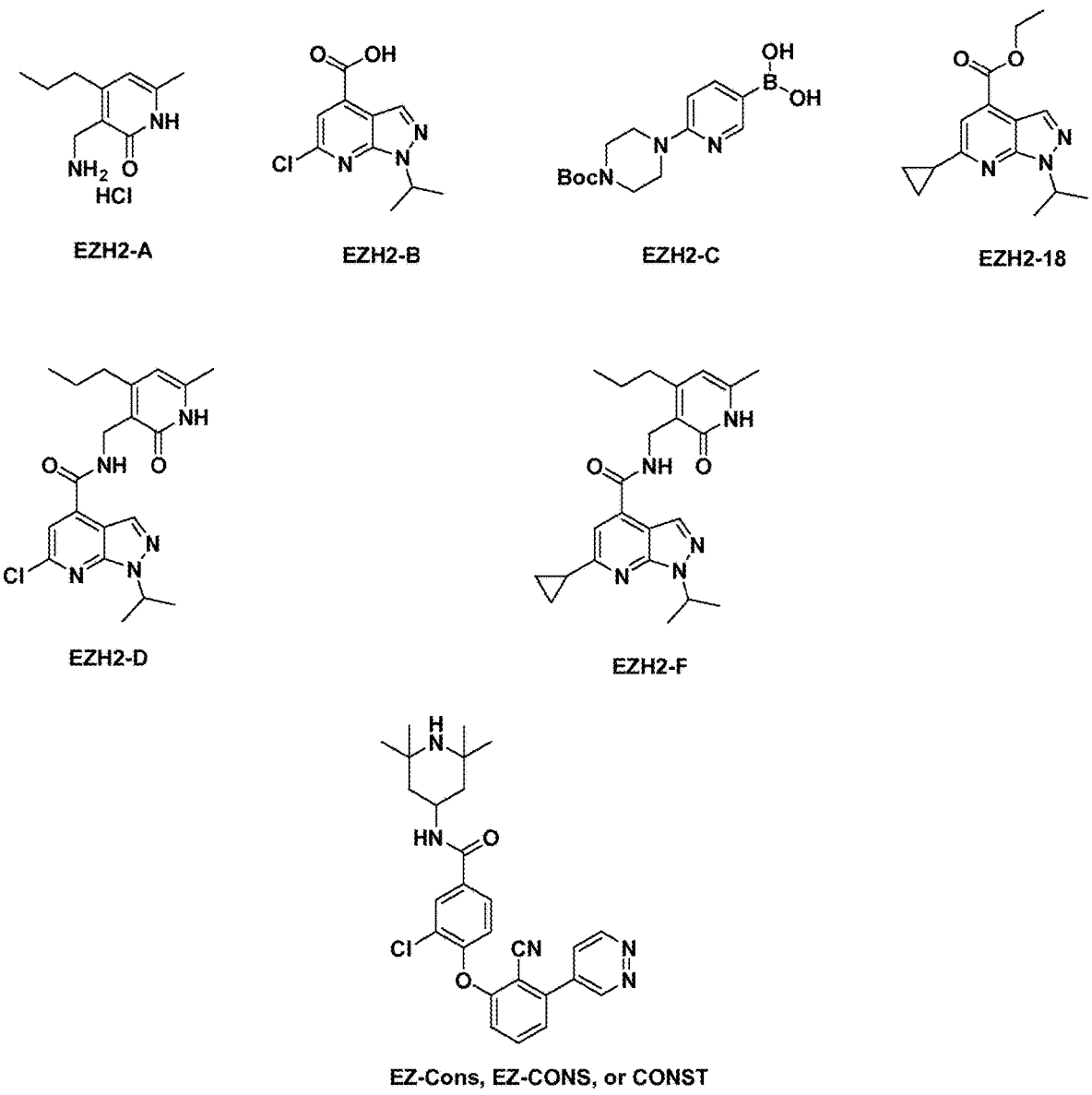
FIG. 20 shows the chemical structures of select comparative compounds. "EZH2-F" is the same as "EZ-F".

To explore the translational relevance of this research, therapeutic trials of JQEZ5 in tumor-bearing GEMMs were performed. JQEZ5 was formulated for intraperitoneal (IP) administration, and repeat dosing studies established 75 mg/kg IP daily as a tolerated dose and schedule. Pharmacokinetic studies confirmed excellent exposure to JQEZ5 without the need for twice weekly dosing (FIG. 19A). To prepare for therapeutic studies, Actin-Cre:LSL-EZH2 mice and UBC:LSL-Ezh2 mice (treated with tamoxifen at 6 weeks of age) were monitored weekly for the onset of symptoms of lung adenocarcinoma (breath distress). At that time (t=0), lung cancers were visualized and confirmed by MRI (FIGS. 19B-19C). Tumor-bearing mice were then treated with JQEZ5 for three weeks (75 mg/kg IP daily) and tumors were comparatively visualized by MRI. Animals treated with JQEZ5 exhibited rapid and pronounced tumor regression over the three week treatment course, as demonstrated by two-dimensional MRI and volumetric measurements (FIGS. 14F-14G, 19B-19C).

Discussion

As the leading cause of death from cancer, lung cancer comprises a profound unmet medical need. A subset of lung cancer patients have benefited from targeted therapies in the past decade, yet the majority of patients will not benefit from these approaches and all metastatic disease remains incurable. There exist a large number of patients who cannot be effectively treated due to the lack of druggable oncogenic drivers (e.g. KRAS). As such, discovering new actionable drivers and tumor dependencies in these remaining tumors is an urgent and important endeavor.

Though not affected by somatic alteration, deregulated overexpression of EZH2 is observed in a subset of human lung cancers (Behrens et al., 2013; Kikuchi et al., 2010; Lv et al., 2012). To date, a causal role in lung tumor development has not been established. Above, the oncogenic potential of EZH2 deregulation was explored by generating a series of genetically engineered mouse models (GEMMs) with conditional EZH2 overexpression. Three GEMMs establish strong oncogenic activity for EZH2 in NSCLC formation. Indeed, 45% of mice engineered to overexpress EZH2 developed lung adenocarcinomas. These data resonate with prior studies that exemplified the transforming activity of mutant EZH2 in B-cell lymphoma (Morin et al., 2010; Sneeringer et al., 2010). A prior study showed that EZH2 overexpression in the myeloid compartment elaborated a myeloproliferative disorder, but to date firm evidence of neoplastic transformation by EZH2 overexpression has been elusive (Herrera-Merchan et al., 2012). This work is a demonstration of cancer resulting from wild-type EZH2 overexpression in vivo. Overexpression of EZH2 is, a common feature of numerous solid tumors, and the reagents created in this study will be helpful to further define the role of EZH2 in the pathogenesis of cancer more broadly.

Cell biology studies and integrated epigenomic analysis of the resultant EZH2-driven murine tumors emulate the cytosolic and transcriptional signaling of a defined subset of the human disease. Lung adenocarcinomas induced by EZH2 overexpression displayed low levels of p-AKT and p-ERK, which are accompanied by elevated expressions of known negative regulators of the MAPK-ERK pathway such as dual-specificity protein phosphatase 4 (DUSP4) and sprouty homologs 1 and 2 (SPRY1 & SPRY2). Consistent with these findings, transcriptional signatures associated with MEK and mTOR activation are repressed in human tumors that expressed high levels of EZH2. Given that many of the known oncogenes in lung cancer activate these pathways, EZH2 appears to promote tumorigenesis through mechanisms that do not involve these canonical pathways, which has important mechanistic and therapeutic implications. However some EGFR and KRAS mutant human cancers also express high levels of EZH2, suggesting that in some settings these pathways may cooperate. Consistent with this concept, DUSP4 has been implicated as a growth suppressor in EGFR-mutant lung adenocarcinoma (Chitale et al., 2009) and as a positive activator of ERK in EGFR-mutant lung cancer cell lines (Britson et al., 2009). A unifying model for EZH2-mediated malignant transformation based on these findings could be the remodeling of chromatin architecture toward a de-differentiated cell state that facilitates proliferative transformation by additional genetic drivers.

Using functional genetic (shRNA) and chemical genetic approaches, the dependency of EZH2 overexpressing human and murine lung cancer models on EZH2 was demonstrated. Toward pharmacologic target validation, a novel, SAM-competitive inhibitor that establishes an evident therapeutic index for targeting EZH2 overexpressing tumors in vivo was created. Successful clinical translation of targeted lung cancer therapeutics has been facilitated by genomic or immunohistochemical biomarkers. Here, it is shown that EZH2 is important for the growth of human lung cancer cell lines that express high levels of EZH2, while being dispensable for cell lines with lower levels of EZH2. As such, EZH2 expression may be a useful biomarker for patient selection or planned stratification in downstream clinical trials. These findings support prior work in prostate cancer, where EZH2 was found to be indispensable for cell growth in LNCaP-abl cells with higher EZH2 levels, but not in LNCaP cells with lower EZH2 levels (Xu et al., 2012).

EZH2 inhibition has previously been proposed as a therapeutic strategy in NSCLC in the context of BRG1 or EGFR mutations (Fillmore et al., 2015). The instant study found that EZH2 inhibitors can sensitize NSCLC cells with EGFR or BRG1 mutations to chemotherapy and a combination of EZH2 inhibition with Topo II inhibition was proposed. Here, it was established that EZH2 inhibition is an effective single-agent therapy in the defined subset of NSCLC that overexpress EZH2 without other known concurrent oncogenic mutations. In sum, this work establishes an oncogenic role for EZH2 deregulation in lung adenocarcinoma, creates faithful models of a subset of human disease, describes and characterizes a novel chemical probe for studying EZH2 function in vivo, and provides the rationale for human clinical investigation.

Experimental Procedures

Mice were housed in pathogen-free animal facilities, and all experiments were performed with the approval of the Animal Care and Use Committee at Harvard Medical School and Dana-Farber Cancer Institute.

Human EZH2 cDNA was cloned into transgenic targeting vectors and co-electroporated into v6.5 C57BL/6(F)×129/sv(M) embryonic stem cells (Open Biosystems, #MES 1402) with plasmid expressing FLP recombinase as described (Beard et al., 2006). Embryonic stem cells were screened for integration of the transgene by PCR. Correctly targeted embryonic stem cells were injected into Black 6 blastocysts, and the resulting chimeras were bred with BALB/c strain wildtype mice for germline transmission of the transgenes. EZH2 transgenic mice were crossed with ubiquitin-Cre-ERT2 (Ruzankina et al., 2007) or actin-Cre mice (Jackson Laboratories). Mice were maintained in a mixed background strain, and bitransgenic mice were given 2 mg of 4-hydroxytamoxifen (4-OHT) (Sigma, #1054029-01) at 6 weeks of age for 4 consecutive days.

Immunohistochemistry

Tissues were fixed overnight in 10% buffered formalin and paraffin-embedded (FFPE) overnight to two days. Staining was performed as previously described (Xu et al., 2014).

Gene Expression Profiling

Total RNA was extracted using Trizol (Invitrogen) followed by RNA cleanup (Qiagen, #74204). Due to the difference in platform (the gene expression levels in EZH2-OE tumors and control lungs came from RNA-seq, whereas the gene expression levels in KRAS-mutant tumors and EGFR-mutant tumors were obtained from microarray (Carretero et al., 2010)), log 2 fold-change of gene expression was calculated using expression value from tumor divided by average expression value from the corresponding normal. The top 500 most variable genes were selected across all samples for clustering.

Single Sample Gene Set Enrichment Analysis

The expression profiles of TCGA lung adenocarcinoma tumors and normal lung were used to perform ssGSEA (cancergenome.nih.gov/). For each tumor, the driver mutation was determined based on TCGA mutation analysis. All ALK and NF1 mutant tumors were removed from the analysis. EZH2 high tumors were defined as the top 20% of tumors with highest EZH2 expression and lacking any mutation in KRAS, EGFR, ALK, or NF1. The KRAS and EGFR mutant categories were defined as being mutant in KRAS or EGFR and having low EZH2 expression (tumors with 20% lowest EZH2 expression). Analysis was performed with the MEK (MEK_UP.V1_UP) and mTOR (mTOR_UP.N4.V1_DN) gene lists and our own gene list of H3K27Me3 bound genes.

Chromatin Immunoprecipitation (ChIP)

Chromatin libraries were prepared with 10-20ng of Input or ChIP'd DNA according to the ThruPLEX-FD Prep Kit (Rubicon #R40048) and sequenced by SE75 Next-Seq.

Chromatin Preparation:

Mouse lung tissue was pulverized using Covaris Tissue Smasher model CP02 by following the CryoPrep Dry Pulverization Manuel. Lung tissue was smashed 1-2 times on setting 4 in the tissueTUBE (Covaris #520071). Approximately 50 mg of pulverized lung tissue was cross-linked with prewarmed 1% formaldehyde (ThermoScientific #28906 diluted in PBS) for 20 minutes at 37° C. The tissue was spun down at 1,000 rpm for 2 minutes and quenched with 0.125M glycine in PBS+0.5% BSA for 20 minutes at room temperature, spun down at 1,000 rpm for 2 minutes and washed with PBS+2× Protease Inhibitor Cocktail (PIC) (Roche #11873580001)+5 mM Sodium Butyrate (Millipore #19-137) then spun down at 1,000 rpm for 2 minutes. The crosslinked tissue was then lysed with 390 uL ChIP Lysis Buffer (1% SDS, 10 nM EDTA pH8.0, 50 mM Tris-HCl pH 8.0, 2×PIC and 5 mM Sodium Butyrate) on ice for one hour. The lysate was split into 3 microTUBEs (Covaris #520045) and sheared on the Covaris E210 Series with 5% Duty Cycle, 5 Intensity, 200 Cycles per Burst for a total of 27 minutes. The sheared chromatin was spun down at 14,000 rpm for 15 minutes at 4° C. An aliquot of input was saved while the remaining chromatin was snap frozen and stored at −80° C. Input was brought up to 100ul with TE, 10 ug of RNAseA (Roche) added and incubated for 30 minutes at 37° C. followed by addition of 100ug of Proteinase K (Roche) and incubation at 65° C. overnight. Input was purified with Qiagen PCR Purification Kit (#28104) and quantified.

Library Preparation and CHIP:

The prepared chromatin was thawed on ice while 10 ug of antibodies against either H3K27ac (Abcam #Ab4729) or H3K27me3 (Cell Signaling #CS9733S) were conjugated to a mix of magnetic Protein A and Protein G coupled beads (Invitrogen #100.02D and #100.04D respectively) in the presence of 0.5% BSA in PBS with rotation at 4° C. for 2 hours. Beads were washed 3 times with 0.5% BSA in PBS and either 5ug of chromatin was added to the H3K27ac ChIP or 10 ug of chromatin was added to the H3K27me3 ChIP and rotated overnight at 4° C. The beads were washed 2 times with Tris based RIPA buffer (0.1% SDS, 1% Triton X-100, 10 mM Tris-HCl pH 7.4, 1 mM EDTA pH 8.0, 0.1% Sodium Deoxycholate), 2 times with 0.3M NaCl RIPA (0.1% SDS, 1% Triton X-100, 10 mM Tris-HCl pH 7.4, 1 mM EDTA pH 8.0, 0.1% Sodium Deoxycholate, 0.3M NaCl), 2 times with LiCl Buffer (250 mM LiCl, 0.5% NP-40, 0.5% Sodium Deoxycholate, 1 mM EDTA pH 8.0, 10 mM Tris-HCl pH 8.0) and 2 times with TE buffer pH 7.6 (Fisher Scientific cat. no. BP2474-1). The beads were resuspended in 100 uL of TE and RNAseA and PK digested/reverse crosslinked and purified as described in the chromatin prep.

Docking and Ligand-Interaction Determination

All structural modeling was conducted using the Schrodinger computational suite through the SBgrid. Ligands of interest were imported into Maestro and an exhaustive conformational search was preformed through Monte-Carlo simulation using the MM5 force field. The resulting conformations were clustered by 3D similarity and an exemplar structure was chosen from each structure for subsequent docking. The docking was performed on a previously reported published binding model with the ligand-binding site used to define the receptor grid (Kalinic et al., 2014). The protein was preprocessed with Maestro and grid generation and docking was preformed with Glide using standard input parameters. All docking was performed using the XP level of precision and results were ranked using the Glide Score. Ligand-interaction diagrams were generated with Maestro for the top docking poses.

General Synthetic Procedure and Biochemical Assay Measurement

All reactions were performed in oven-dried or flame-dried round-bottomed flasks. The flasks were fitted with rubber septa and reactions were conducted under a positive pressure of nitrogen. Flash column chromatography was performed as described by Still et al. using silica gel (60 Å pore size, 40-63 µm, 4-6% $H_2O$ content, Zeochem). Analytical thin-layer chromatography was performed use glass plates, pre-coated with 0.25 mm 230-400 mesh silica gel impregnated with a fluorescent indicator (254 nm). Thin layer chromatography plates were visualized by exposure to iodine vapor. All the intermediates and final product were fully characterized with proton and carbon-13 nuclear magnetic resonance (1H NMR and $^{13}$C NMR) spectra and mass spectra (MS).

PRC2 Methyltransferase Assay:

Recombinant five-component PRC2 (EZH2/EED/SUZ12/RBBP4/AEBP2) was co-expressed in Sf9 and purified as described (Cao and Zhang, 2004). PRC2 activity was measured using a radiometric Scintillation Proximity Assay (SPA) performed in 384-well OptiPlates (Perkin Elmer). For IC50 determination, 2.3 nM PRC2 was incubated for 90 min at RT with 1 uM histone H3 (21-44)-lys(biotin) (Anaspec), 1.5 uM SAM (NEB), and 500 nM 3H-SAM in 20 uL reaction buffer (50 mM Tris pH 8.5, 5 mM DTT, and 0.01% Tween-20) containing compound or DMSO. Reactions were quenched with TCA and, following the addition of PVT streptavidin-coated SPA beads (Perkin Elmer; 40 uL of 140 ng diluted in PBS), incubated for 1 hr at RT. CPM values were measured using the TopCount NXT plate reader. Percent activity values were calculated by setting the average background (no-enzyme wells) to 0% and the average DMSO wells to 100% activity. Standard deviations were determined from four replicate measurements for each compound concentration. Data were analyzed and plotted using GraphPad PRISM v6, using the 'log(inhibitor) vs normalized response—variable slope' analysis module to calculate $IC_{50}$.

For determination of JQEZ5 mechanism of action and Ki values, reactions were carried out as described above in the presence of varying concentrations SAM/3H-SAM (at a 1:20 ratio) with a fixed concentration of 1 uM histone H3 peptide. Data were analyzed and plotted using 'Enzyme Kinetics—inhibition' and 'Enzyme Kinetics—substrate versus velocity' analysis modules in GraphPad PRISM v6.

Exemplary results regarding the EZH2 vs. EZH1 biochemical selectivity of select compounds described herein are shown in FIG. 22. Compounds EZH2-16, EZ-27, and EZ-005 showed about 10-fold selectivity for EZH2 over EZH1. Compounds EZ-26 and EZ-20 showed about 20- to about 40-fold selectivity for EZH2 over EZH1.

Docking experiments were performed using compound EZ-41 and EZH2. See, McCabe et. al., *Nature,* 492, 108-112 (2012). The docking results show that EZ-41 and EZH2 may form a covalent bond.

EZH1/2 Radiometric Methyltransferase Assay

Recombinant five-component PRC2-EZH2 (EZH2/EED/SUZ12/RBBP4/AEBP2) and PRC2-EZH1 complex (EZH1/EED/SUZ12/RBBP4/AEBP2) were co-expressed in Sf9 and purified as described in (Cao and Zhang, 2004). Methyltransferase activity was measured using a radiometric Scintillation Proximity Assay (SPA) performed in 384-well OptiPlates (Perkin Elmer). For IC50 determination, 2.3 nM PRC2-EZH1/2 was incubated for 90 min at RT with 1 uM histone H3 (21-44)-lys(biotin) (Anaspec), 1.5 uM SAM (NEB), and 500 nM 3H-SAM in 20 uL reaction buffer (50 mM Tris pH 8.5, 5 mM DTT, and 0.01% Tween-20) containing compound or DMSO. Reactions were quenched with TCA and, following the addition of PVT streptavidin-coated SPA beads (Perkin Elmer; 40 uL of 140 ng diluted in PBS), incubated for 1 hr at RT. CPM values were measured using the TopCount NXT plate reader. Percent activity values were calculated by setting the average background (no-enzyme wells) to 0% and the average DMSO wells to 100% activity. Standard deviations were determined from four replicate measurements for each compound concentration. Data were analyzed and plotted using GraphPad PRISM v6, using the 'log(inhibitor) vs normalized response—variable slope' analysis module to calculate IC50 (FIG. 32 and FIG. 33).

For determination of MOA and Ki values, reactions were carried out as described above in the presence of varying concentrations SAM/3H-SAM (at a 1:20 ratio) with a fixed concentration of 1 uM histone H3 peptide. Data were analyzed and plotted using 'Enzyme Kinetics—inhibition' analysis module in GraphPad PRISM v6.

EZH2 Ligand-Displacement AlphaScreen Assay

Figure 31:
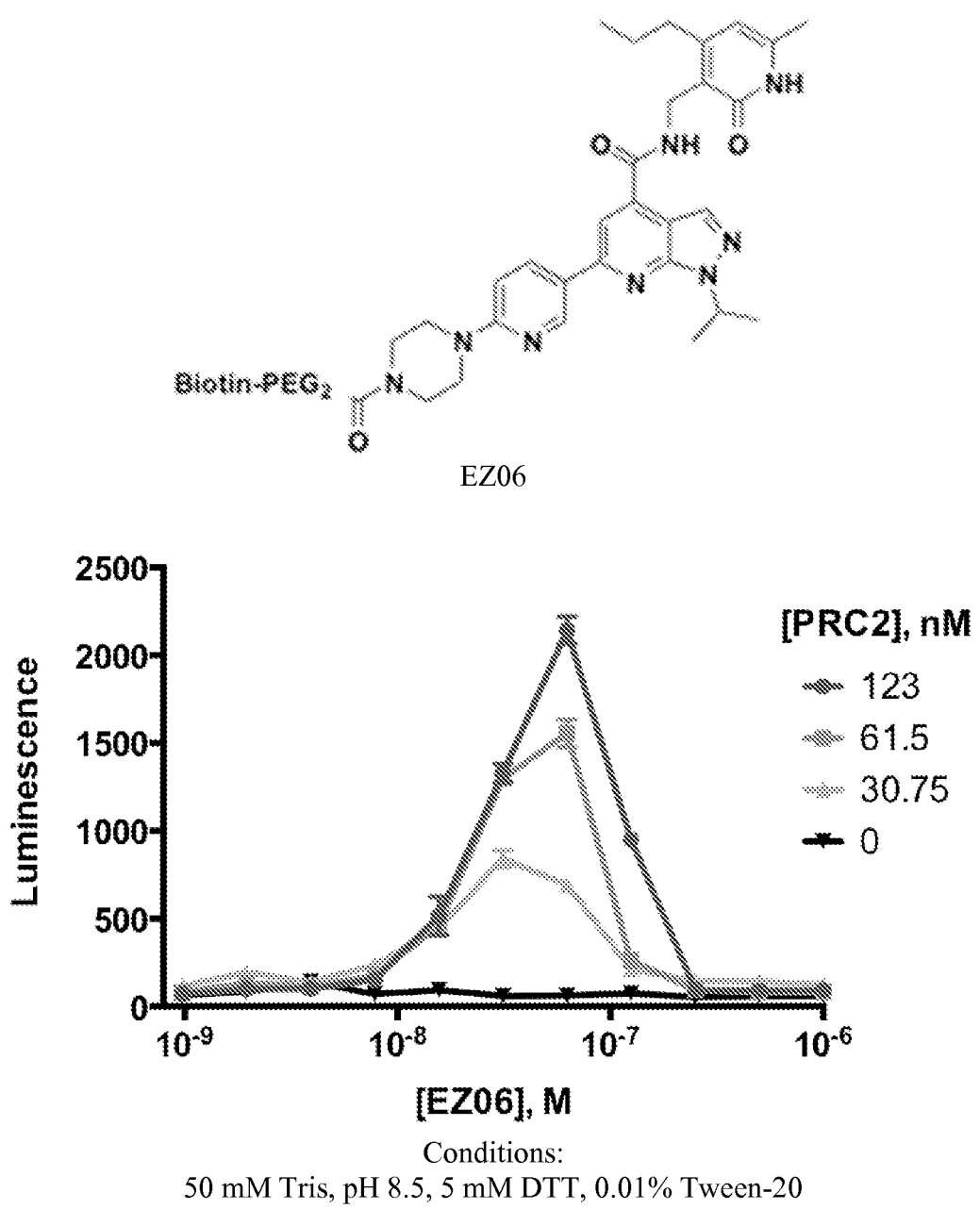
FIG. 31 depicts the binding of EZ06 to PRC2 using an AlphaAssay.
Figure 32:
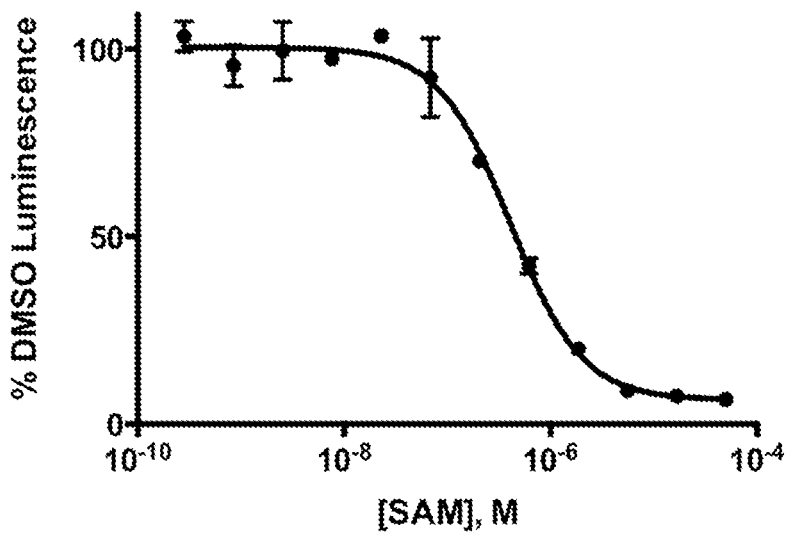
FIG. 32 depicts a competitive AlphaScreen for PRC2 SAM-competitive inhibitors.
Figure 32:
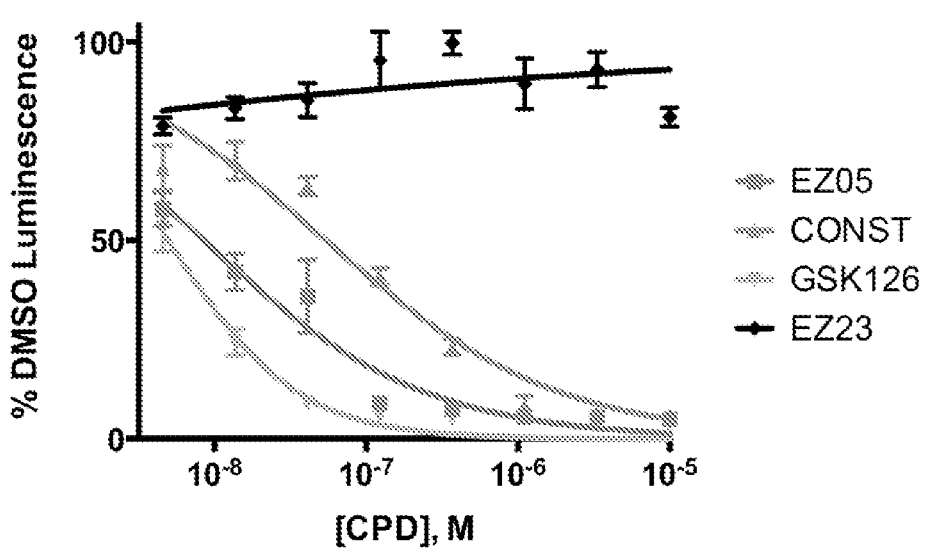
Figure 33:
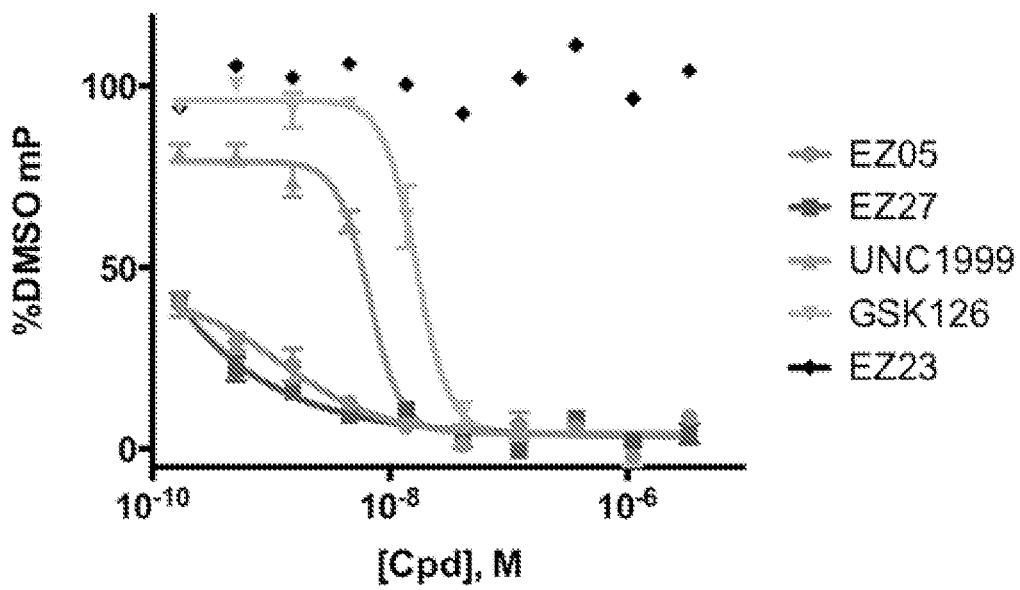
FIG. 33 depicts a PRC2-EZH2 competitive fluorescence polarization assay using EZ05-FITC.

We employed a novel ligand competition AlphaScreen assay in to estimate the binding affinity of SAM for EZH2 as well as determine compound IC50 in a non-radiometric format (FIG. 31 and FIG. 32). In 384-well AlphaPlates (Perkin Elmer), 61.5 nM PRC2-EZH2 and 62.5 nM EZ-06 were diluted in 20 uL reaction buffer (50 mM Tris pH 8.5, 5 mM DTT, and 0.01% Tween-20) containing competitor compound or DMSO. Following a 30 min incubation, 20 uL detection solution containing Streptavidin Donor Beads and AlphaLISA® Anti-FLAG Acceptor Beads diluted to 20 ng/uL in 1× Epigenetics Buffer (Perkin Elmer) was added to each well. After 1 hr incubation at RT, luminescence was measured on the Envision 2104 plate reader. Percent activity values were calculated by setting the average background (no enzyme wells) to 0% the average DMSO wells to 100% activity. Standard deviations were determined from four replicate measurements for compound concentration (FIG. 32). Data were analyzed and plotted using GraphPad PRISM v6 and IC50 values were determined using the 'log(inhibitor) vs normalized response—variable slope' analysis module (FIG. 32).

EZH2 Ligand-Displacement FP Assay

Figure 34:
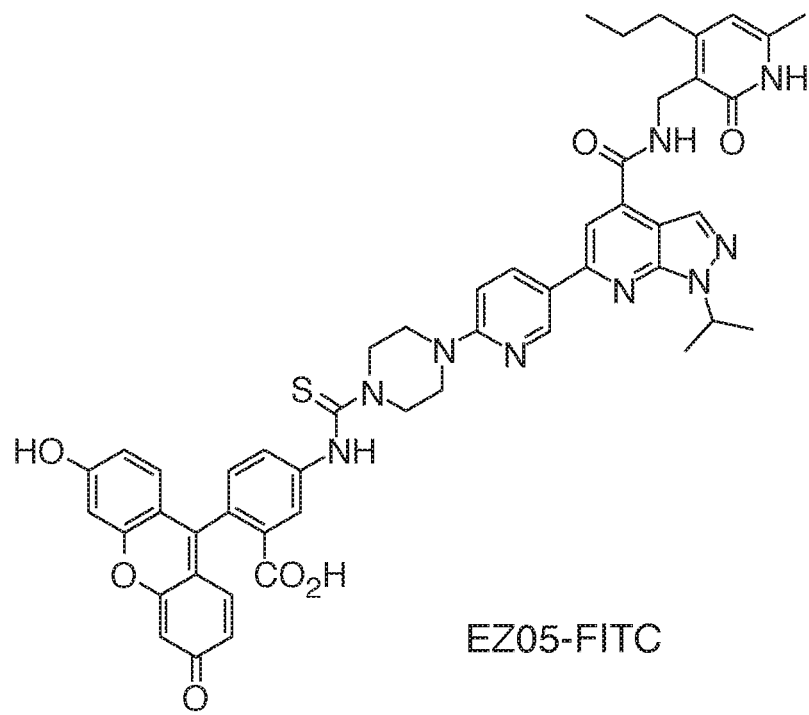
FIG. 34 depicts a PRC2-EZH2 fluorescence polarization assay using EZ05-FITC.
Figure 34:
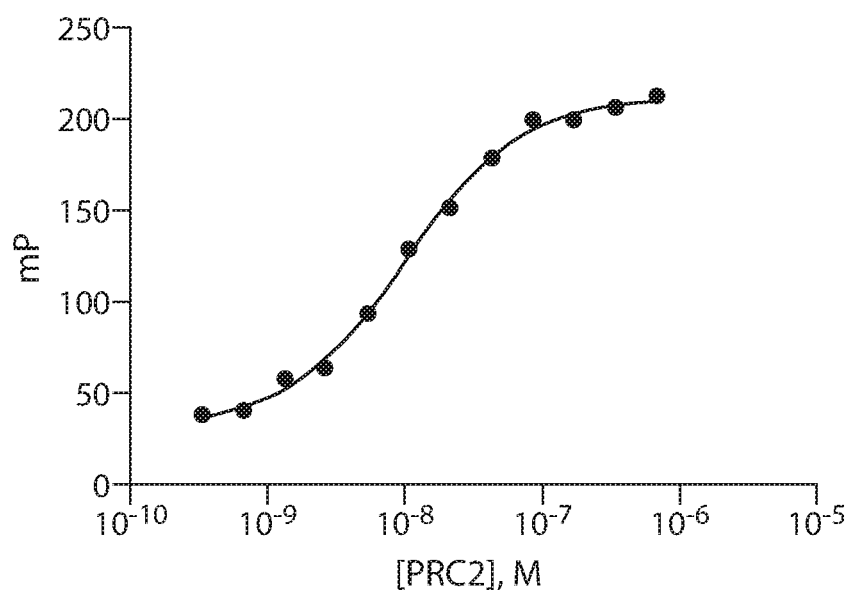
Figure 35:
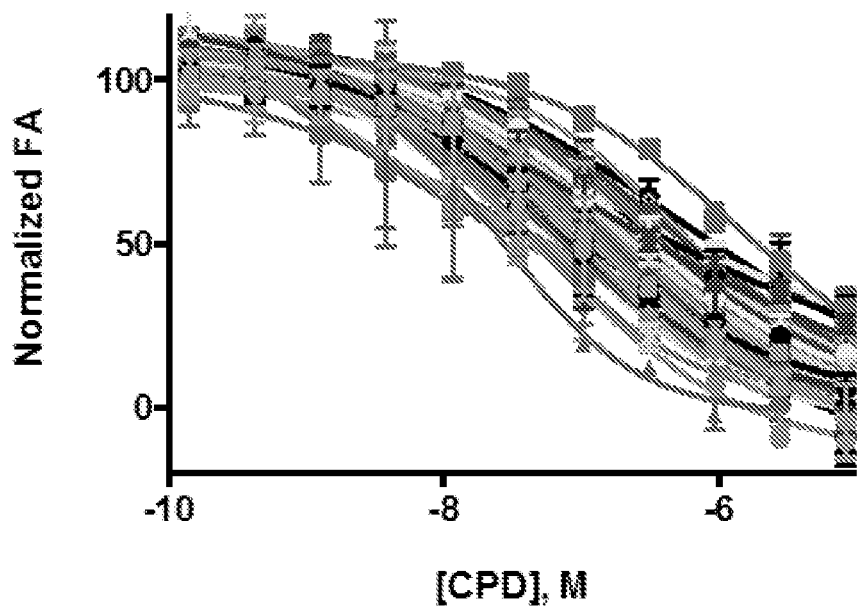
FIG. 35 depicts the binding isotherms of all compounds screened in the EZH2 ligand-displacement fluorescence polarization assays.
Figure 36:
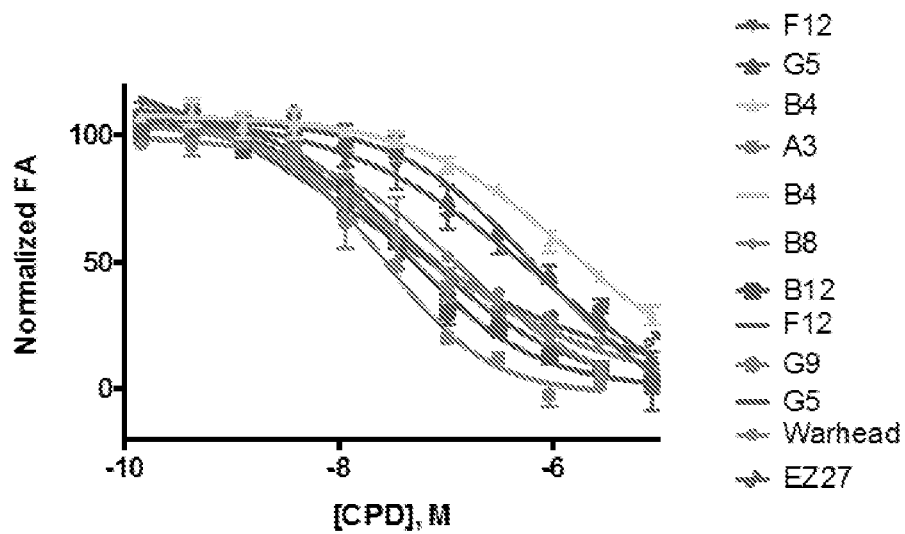
FIG. 36 depicts the binding isotherms of the most effective and least effective compounds screened in the EZH2 ligand-displacement fluorescence polarization assays. Compound "X#", wherein X is one letter, and # is one integer between 1 and 12, inclusive, denotes a compound prepared by the method shown below.

In 384-well black plates (Nunc), 43 nM PRC2-EZH2 and 32 nM EZ05-FITC were diluted in 20 uL reaction buffer (50 mM Tris pH 8.5, 5 mM DTT, and 0.01% Tween-20) containing competitor compound or DMSO. Following a 30 min incubation, fluorescence polarization (mP) was measured using Wallac Envision 2104 Multilabel Reader (FP FITC dual optical module; Excitation: 480 nm, Emission: 535 nm for both S- and P-channels) (FIG. 34). Normalized mP values were calculated by setting the average background (no enzyme wells) to 0% the average DMSO wells to 100% activity. Standard deviations were determined from four replicate measurements for compound concentration (FIG. 35, FIG. 36, FIG. 33). Data were analyzed and plotted using GraphPad PRISM v6 and IC50 values were determined using the 'log(inhibitor) vs normalized response—variable slope' analysis module (FIG. 37 and FIG. 33).

Intracellular EZH2 Binding Assay

MDA-MB-231 cells (ATCC) were cultured in Ham's F12K media supplemented 10% (v/v) FBS, and 100 U mL-1 penicillin-streptomycin. Cells were diluted in culture medium at 1e5 cells/mL and plated in black, clear-bottom 384-well plates (Aurora IQ-EB 384) at 40 uL/well and incubated at 37° C./5% CO2 for 24 hrs. To assess overall engagement of endogenous EZH2, cells were fixed with 4% paraformaldehyde for 10 min, permeabilized with 0.3% Triton X-100 in PBS for 20 min. Cells were then incubated with 40 uL of 1 nM Hoechst 33342 (Life Technologies), 5 uM TAMRA-EZ05 and varying concentrations of competitor compound. Following a 1 hr incubation at RT, cells were washed 4× with 40 uL PBS and later imaged. To assess cellular permeability and engagement of endogenous EZH2, TAMRA-EZ05 and competitor compounds were pin transferred in media and allowed to incubate with cells at 37° C./5% CO2 for 2 hrs prior to fixation and counterstaining (FIG. 38, FIG. 39, FIG. 40). All plates were imaged on an ImageXpress Micro automated microscope (Molecular Devices) using a 10× objective with laser-based focusing. Image analysis was performed using the Cell Scoring module in MetaXpress (Molecular Devices) to determine average nuclear fluorescence and nuclei counts per well. Mean and standard deviation (STDEV) were calculated for all DMSO wells within each assay plate. Data were analyzed and plotted using GraphPad PRISM v6 and IC50 values were determined using the 'log(inhibitor) vs normalized response—variable slope' analysis module.

REFERENCES

Alford, S., Toy, K., Merajver, S., and Kleer, C. (2012). Increased risk for distant metastasis in patients with familial early-stage breast cancer and high EZH2 expression. Breast Cancer Res Treat 132, 429-437.

Bachmann, I., Halvorsen, O., Collett, K., Stefansson, I., Straume, O., Haukaas, S., Salvesen, H., Otte, A., and Akslen, L. (2006). EZH2 Expression Is Associated With High Proliferation Rate and Aggressive Tumor Subgroups in Cutaneous Melanoma and Cancers of the Endometrium, Prostate, and Breast. J Clin Oncol 24, 268-273.

Beard, C., Hochedlinger, K., Plath, K., Wutz, A., and Jaenisch, R. (2006). Efficient method to generate single-copy transgenic mice by site-specific integration in embryonic stem cells. Genesis 44, 23-28.

Behrens, C., Solis, L. M., Lin, H., Yuan, P., Tang, X., Kadara, H., Riquelme, E., Galindo, H., Moran, C. A., Kalhor, N., et al. (2013). EZH2 Protein Expression Associates with the Early Pathogenesis, Tumor Progression, and Prognosis of Non-Small Cell Lung Carcinoma. Clinical Cancer Research 19, 6556-6565.

Bracken, A. P., Pasini, D., Capra, M., Prosperini, E., Colli, E., and Helin, K. (2003). EZH2 is downstream of the pRB-E2F pathway, essential for proliferation and amplified in cancer. The EMBO journal 22, 5323-5335.

Britson, J. S., Barton, F., Balko, J. M., and Black, E. P. (2009). Deregulation of DUSP activity in EGFR-mutant lung cancer cell lines contributes to sustained ERK1/2 signaling. Biochemical and biophysical research communications 390, 849-854.

Brown, J. D., Lin, C. Y., Duan, Q., Griffin, G., Federation, A. J., Paranal, R. M., Bair, S., Newton, G., Lichtman, A. H., Kung, A. L., et al. (2014). NF-kappaB directs dynamic super enhancer formation in inflammation and atherogenesis. Mol Cell 56, 219-231.

Cao, R., and Zhang, Y. (2004). SUZ12 is required for both the histone methyltransferase activity and the silencing function of the EED-EZH2 complex. Mol Cell 15, 57-67.

Carretero, J., Shimamura, T., Rikova, K., Jackson, A. L., Wilkerson, M. D., Borgman, C. L., Buttarazzi, M. S., Sanofsky, B. A., McNamara, K. L., Brandstetter, K. A., et al. (2010). Integrative Genomic and Proteomic Analyses Identify Targets for Lkb1-Deficient Metastatic Lung Tumors. Cancer Cell 17, 547-559.

Chapuy, B., McKeown, M. R., Lin, C. Y., Monti, S., Roemer, M. G., Qi, J., Rahl, P. B., Sun, H. H., Yeda, K. T., Doench, J. G., et al. (2013). Discovery and characterization of super-enhancer-associated dependencies in diffuse large B cell lymphoma. Cancer Cell 24, 777-790.

Chen, B. F., and Chan, W. Y. (2014). The de novo DNA methyltransferase DNMT3A in development and cancer. Epigenetics: official journal of the DNA Methylation Society 9, 669-677.

Chen, Z., Fillmore, C. M., Hammerman, P. S., Kim, C. F., and Wong, K. K. (2014). Non-small-cell lung cancers: a heterogeneous set of diseases. Nat Rev Cancer 14, 535-546.

Chitale, D., Gong, Y., Taylor, B. S., Broderick, S., Brennan, C., Somwar, R., Golas, B., Wang, L., Motoi, N., Szoke, J., et al. (2009). An integrated genomic analysis of lung cancer reveals loss of DUSP4 in EGFR-mutant tumors. Oncogene 28, 2773-2783.

Ciarapica, R., Carcarino, E., Adesso, L., De Salvo, M., Bracaglia, G., Leoncini, P., Dall'Agnese, A., Verginelli, F., Milano, G., Boldrini, R., et al. (2014). Pharmacological inhibition of EZH2 as a promising differentiation therapy in embryonal RMS. BMC Cancer 14, 139.

DuPage, M., Dooley, A. L., and Jacks, T. (2009). Conditional mouse lung cancer models using adenoviral or lentiviral delivery of Cre recombinase. Nature protocols 4, 1064-1072.

Ernst, T., Chase, A. J., Score, J., Hidalgo-Curtis, C. E., Bryant, C., Jones, A. V., Waghorn, K., Zoi, K., Ross, F. M., Reiter, A., et al. (2010). Inactivating mutations of the histone methyltransferase gene EZH2 in myeloid disorders. Nat Genet 42, 722-726.

Filippakopoulos, P., Qi, J., Picaud, S., Shen, Y., Smith, W. B., Fedorov, O., Morse, E. M., Keates, T., Hickman, T. T., Felletar, I., et al. (2010). Selective inhibition of BET bromodomains. Nature 468, 1067-1073.

Fillmore, C. M., Xu, C., Desai, P. T., Berry, J. M., Rowbotham, S. P., Lin, Y.-J., Zhang, H., Marquez, V. E., Hammerman, P. S., Wong, K.-K., and Kim, C. F. (2015). EZH2 inhibition sensitizes BRG1 and EGFR mutant lung tumours to TopoII inhibitors. Nature advance online publication.

Gong, Y., Huo, L., Liu, P., Sneige, N., Sun, X., Ueno, N. T., Lucci, A., Buchholz, T. A., Valero, V., and Cristofanilli, M. (2011). Polycomb group protein EZH2 is frequently expressed in inflammatory breast cancer and is predictive of worse clinical outcome. Cancer 117, 5476-5484.

Hamidi, T., Singh, A. K., and Chen, T. (2015). Genetic alterations of DNA methylation machinery in human diseases. Epigenomics 7, 247-265.

Herrera-Merchan, A., Arranz, L., Ligos, J. M., de Molina, A., Dominguez, O., and Gonzalez, S. (2012). Ectopic expression of the histone methyltransferase Ezh2 in haematopoietic stem cells causes myeloproliferative disease. Nat Commun 3, 623.

Hnisz, D., Schuijers, J., Lin, C. Y., Weintraub, A. S., Abraham, B. J., Lee, T. I., Bradner, J. E., and Young, R. A. (2015). Convergence of developmental and oncogenic signaling pathways at transcriptional super-enhancers. Mol Cell 58, 362-370.

Horiuchi, K. Y., Eason, M. M., Ferry, J. J., Planck, J. L., Walsh, C. P., Smith, R. F., Howitz, K. T., and Ma, H. (2013). Assay development for histone methyltransferases. Assay and drug development technologies 11, 227-236.

Hwang, J. A., Lee, B. B., Kim, Y., Hong, S. H., Kim, Y. H., Han, J., Shim, Y. M., Yoon, C. Y., Lee, Y. S., and Kim, D. H. (2014). HOXA9 inhibits migration of lung cancer cells and its hypermethylation is associated with recurrence in non-small cell lung cancer. Molecular carcinogenesis.

Jemal, A., Bray, F., Center, M. M., Ferlay, J., Ward, E., and Forman, D. (2011). Global cancer statistics. CA Cancer J Clin 61, 69-90.

Kalinic, M., Zloh, M., and Eric, S. (2014). Structural insights into binding of small molecule inhibitors to Enhancer of Zeste Homolog 2. Journal of computer-aided molecular design 28, 1109-1128.

Kandoth, C., McLellan, M. D., Vandin, F., Ye, K., Niu, B., Lu, C., Xie, M., Zhang, Q., McMichael, J. F., Wyczalkowski, M. A., et al. (2013). Mutational landscape and significance across 12 major cancer types. Nature 502, 333-339.

Kikuchi, J., Kinoshita, I., Shimizu, Y., Kikuchi, E., Konishi, J., Oizumi, S., Kaga, K., Matsuno, Y., Nishimura, M., and Dosaka-Akita, H. (2010). Distinctive expression of the polycomb group proteins Bmi1 polycomb ring finger oncogene and enhancer of zeste homolog 2 in nonsmall cell lung cancers and their clinical and clinicopathologic significance. Cancer 116, 3015-3024.

Kim, W., Bird, G. H., Neff, T., Guo, G., Kerenyi, M. A., Walensky, L. D., and Orkin, S. H. (2013). Targeted disruption of the EZH2-EED complex inhibits EZH2-dependent cancer. Nat Chem Biol 9, 643-650.

Kleer, C. G., Cao, Q., Varambally, S., Shen, R., Ota, I., Tomlins, S. A., Ghosh, D., Sewalt, R. G. A. B., Otte, A. P., Hayes, D. F., et al. (2003). EZH2 is a marker of aggressive breast cancer and promotes neoplastic transformation of breast epithelial cells. Proceedings of the National Academy of Sciences 100, 11606-11611.

Knutson, S. K., Warholic, N. M., Wigle, T. J., Klaus, C. R., Allain, C. J., Raimondi, A., Porter Scott, M., Chesworth, R., Moyer, M. P., Copeland, R. A., et al. (2013). Durable tumor regression in genetically altered malignant rhabdoid tumors by inhibition of methyltransferase EZH2. Proc Natl Acad Sci USA 110, 7922-7927.

Knutson, S. K., Wigle, T. J., Warholic, N. M., Sneeringer, C. J., Allain, C. J., Klaus, C. R., Sacks, J. D., Raimondi, A., Majer, C. R., Song, J., et al. (2012). A selective inhibitor of EZH2 blocks H3K27 methylation and kills mutant lymphoma cells. Nat Chem Biol 8, 890-896.

Konze, K. D., Ma, A., Li, F., Barsyte-Lovejoy, D., Parton, T., Macnevin, C. J., Liu, F., Gao, C., Huang, X. P., Kuznetsova, E., et al. (2013). An orally bioavailable chemical probe of the Lysine Methyltransferases EZH2 and EZH1. ACS chemical biology 8, 1324-1334.

Ku, M., Koche, R. P., Rheinbay, E., Mendenhall, E. M., Endoh, M., Mikkelsen, T. S., Presser, A., Nusbaum, C., Xie, X., Chi, A. S., et al. (2008). Genomewide analysis of PRC1 and PRC2 occupancy identifies two classes of bivalent domains. PLoS genetics 4, e1000242.

Li, W., Huang, K., Guo, H., and Cui, G. (2014). Meis1 regulates proliferation of non-small-cell lung cancer cells. Journal of thoracic disease 6, 850-855.

Li, Z., Wang, Y., Qiu, J., Li, Q., Yuan, C., Zhang, W., Wang, D., Ye, J., Jiang, H., Yang, J., and Cheng, J. (2013). The polycomb group protein EZH2 is a novel therapeutic target in tongue cancer, Vol 4).

Loven, J., Hoke, H. A., Lin, C. Y., Lau, A., Orlando, D. A., Vakoc, C. R., Bradner, J. E., Lee, T. I., and Young, R. A. (2013). Selective inhibition of tumor oncogenes by disruption of super-enhancers. Cell 153, 320-334.

Lv, Y., Yuan, C., Xiao, X., Wang, X., Ji, X., Yu, H., Wu, Z., and Zhang, J. (2012). The expression and significance of the enhancer of zeste homolog 2 in lung adenocarcinoma. Oncol Rep 28, 147-154.

Lynch, T. J., Bell, D. W., Sordella, R., Gurubhagavatula, S., Okimoto, R. A., Brannigan, B. W., Harris, P. L., Haserlat, S. M., Supko, J. G., Haluska, F. G., et al. (2004). Activating mutations in the epidermal growth factor receptor underlying responsiveness of non-small-cell lung cancer to gefitinib. New England Journal of Medicine 350, 2129-2139.

Margueron, R., and Reinberg, D. (2011). The Polycomb complex PRC2 and its mark in life. Nature 469, 343-349.

McCabe, M. T., Ott, H. M., Ganji, G., Korenchuk, S., Thompson, C., Van Aller, G. S., Liu, Y., Graves, A. P., Iii, A. D. P., Diaz, E., et al. (2012). EZH2 inhibition as a therapeutic strategy for lymphoma with EZH2-activating mutations. Nature 492, 108-112.

Morin, R. D., Johnson, N. A., Severson, T. M., Mungall, A. J., An, J., Goya, R., Paul, J. E., Boyle, M., Woolcock, B. W., Kuchenbauer, F., et al. (2010). Somatic mutations altering EZH2 (Tyr641) in follicular and diffuse large B-cell lymphomas of germinal-center origin. Nat Genet 42, 181-185.

Nikoloski, G., Langemeijer, S. M. C., Kuiper, R. P., Knops, R., Massop, M., Tonnissen, E. R. L. T. M., van der Heijden, A., Scheele, T. N., Vandenberghe, P., de Witte, T., et al. (2010). Somatic mutations of the histone methyltransferase gene EZH2 in myelodysplastic syndromes. Nat Genet 42, 665-667.

Ntziachristos, P., Tsirigos, A., Van Vlierberghe, P., Nedjic, J., Trimarchi, T., Flaherty, M. S., Ferres-Marco, D., da Ros, V., Tang, Z., Siegle, J., et al. (2012). Genetic inactivation of the polycomb repressive complex 2 in T cell acute lymphoblastic leukemia. Nat Med 18, 298-301.

Paez, J. G., Janne, P. A., Lee, J. C., Tracy, S., Greulich, H., Gabriel, S., Herman, P., Kaye, F. J., Lindeman, N., Boggon, T. J., et al. (2004). EGFR mutations in lung cancer: Correlation with clinical response to gefitinib therapy. Science 304, 1497-1500.

Pao, W., Miller, V., Zakowski, M., Doherty, J., Politi, K., Sarkaria, I., Singh, B., Heelan, R., Rusch, V., Fulton, L., et al. (2004). EGF receptor gene mutations are common in lung cancers from, Äünever smokers, Äù and are associated with sensitivity of tumors to gefitinib and erlotinib. Proceedings of the National Academy of Sciences of the United States of America 101, 13306-13311.

Qi, W., Chan, H., Teng, L., Li, L., Chuai, S., Zhang, R., Zeng, J., Li, M., Fan, H., Lin, Y., et al. (2012). Selective inhibition of Ezh2 by a small molecule inhibitor blocks tumor cells proliferation. Proceedings of the National Academy of Sciences 109, 21360-21365.

Riising, E. M., Comet, I., Leblanc, B., Wu, X., Johansen, J. V., and Helin, K. (2014). Gene silencing triggers polycomb repressive complex 2 recruitment to CpG islands genome wide. Mol Cell 55, 347-360.

Ruzankina, Y., Pinzon-Guzman, C., Asare, A., Ong, T., Pontano, L., Cotsarelis, G., Zediak, V. P., Velez, M., Bhandoola, A., and Brown, E. J. (2007). Deletion of the developmentally essential gene ATR in adult mice leads to age-related phenotypes and stem cell loss. Cell Stem Cell 1, 113-126.

Simon, J. A., and Kingston, R. E. (2009). Mechanisms of polycomb gene silencing: knowns and unknowns. Nature reviews Molecular cell biology 10, 697-708.

Simon, J. A., and Lange, C. A. (2008). Roles of the EZH2 histone methyltransferase in cancer epigenetics. Mutation research 647, 21-29.

Sneeringer, C. J., Scott, M. P., Kuntz, K. W., Knutson, S. K., Pollock, R. M., Richon, V. M., and Copeland, R. A. (2010). Coordinated activities of wild-type plus mutant EZH2 drive tumor-associated hypertrimethylation of lysine 27 on histone H3 (H3K27) in human B-cell lymphomas. Proc Natl Acad Sci USA 107, 20980-20985.

Soda, M., Choi, Y. L., Enomoto, M., Takada, S., Yamashita, Y., Ishikawa, S., Fujiwara, S. I., Watanabe, H., Kurashina, K., Hatanaka, H., et al. (2007). Identification of the transforming EML4-ALK fusion gene in non-small-cell lung cancer. Nature 448, 561-U563.

Subramanian, A., Tamayo, P., Mootha, V. K., Mukherjee, S., Ebert, B. L., Gillette, M. A., Paulovich, A., Pomeroy, S. L., Golub, T. R., Lander, E. S., and Mesirov, J. P. (2005). Gene set enrichment analysis: A knowledge-based approach for interpreting genome-wide expression profiles. Proceedings of the National Academy of Sciences 102, 15545-15550.

Suzuki, M., Ikeda, K., Shiraishi, K., Eguchi, A., Mori, T., Yoshimoto, K., Shibata, H., Ito, T., Baba, Y., and Baba, H. (2014). Aberrant methylation and silencing of expression in non-small cell lung cancer. Oncology letters 8, 1025-1030.

Tzatsos, A., Paskaleva, P., Ferrari, F., Deshpande, V., Stoykova, S., Contino, G., Wong, K.-K., Lan, F., Trojer, P., Park, P. J., and Bardeesy, N. (2013). KDM2B promotes pancreatic cancer via Polycomb-dependent and -independent transcriptional programs. The Journal of Clinical Investigation 123, 727-739.

Varambally, S., Dhanasekaran, S. M., Zhou, M., Barrette, T. R., Kumar-Sinha, C., Sanda, M. G., Ghosh, D., Pienta, K. J., Sewalt, R. G. A. B., Otte, A. P., et al. (2002). The polycomb group protein EZH2 is involved in progression of prostate cancer. Nature 419, 624-629.

Wu, H., and Zhang, Y. (2011). Mechanisms and functions of Tet protein-mediated 5-methylcytosine oxidation. Genes & development 25, 2436-2452.

Xu, C., Fillmore, C. M., Koyama, S., Wu, H., Zhao, Y., Chen, Z., Herter-Sprie, G. S., Akbay, E. A., Tchaicha, J. H., Altabef, A., et al. (2014). Loss of Lkb1 and Pten leads to lung squamous cell carcinoma with elevated PD-L1 expression. Cancer Cell 25, 590-604.

Xu, K., Wu, Z. J., Groner, A. C., He, H. H., Cai, C., Lis, R. T., Wu, X., Stack, E. C., Loda, M., Liu, T., et al. (2012). EZH2 Oncogenic Activity in Castration-Resistant Prostate Cancer Cells Is Polycomb-Independent. Science 338, 1465-1469.

Zhao, X., Lwin, T., Zhang, X., Huang, A., Wang, J., Marquez, V. E., Chen-Kiang, S., Dalton, W. S., Sotomayor, E., and Tao, J. (2013). Disruption of the MYC-miRNA-EZH2 loop to suppress aggressive B-cell lymphoma survival and clonogenicity. Leukemia 27, 2341-2350.

Zhou, V. W., Goren, A., and Bernstein, B. E. (2011). Charting histone modifications and the functional organization of mammalian genomes. Nat Rev Genet 12, 7-18.

Cao, R., and Zhang, Y. (2004). SUZ12 is required for both the histone methyltransferase activity and the silencing function of the EED-EZH2 complex. Molecular Cell 15, 57-67.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control.

In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of the formula:

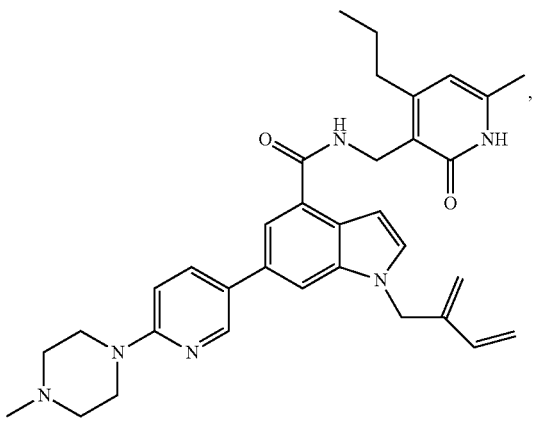

or a pharmaceutically acceptable salt thereof.

2. A pharmaceutical composition comprising the compound of claim 1, or a pharmaceutically acceptable salt thereof, and a pharmaceutically acceptable excipient.

3. A method of inhibiting the activity of an enhancer of zeste homolog 1 (EZH1) or an enhancer of zeste homolog 2 (EZH2) in a subject in need thereof, the method comprising administering to the subject an effective amount of the compound of claim 1, or a pharmaceutically acceptable salt thereof.

4. A method of inhibiting the activity of an enhancer of zeste homolog 1 (EZH1) or an enhancer of zeste homolog 2 (EZH2) in a cell, the method comprising contacting the cell with an effective amount of the compound of claim 1, or a pharmaceutically acceptable salt thereof.

5. A kit comprising the compound of claim 1 or a pharmaceutically acceptable salt thereof and instructions for using the compound or a pharmaceutically acceptable salt thereof.

6. The method of claim 3, wherein the subject is a human.

7. A method of treating cancer in a subject in need thereof, the method comprising administering to the subject a therapeutically effective amount of the compound of claim 1 or a pharmaceutically acceptable salt thereof.

8. The method of claim 7, wherein the cancer is lung cancer.

9. The method of claim 8, wherein the lung cancer is non-small cell lung cancer.

10. The method of claim 7, wherein the cancer is brain cancer.

11. The method of claim 7, wherein the cancer is breast cancer.

12. The method of claim 7, wherein the cancer is prostate cancer.

13. The method of claim 7, wherein the cancer is lymphoma.

14. The method of claim 7, wherein the cancer is leukemia.

15. A method of treating hyperplasia in a subject in need thereof, the method comprising administering to the subject a therapeutically effective amount of the compound of claim 1 or a pharmaceutically acceptable salt thereof.

16. A method of treating a benign neoplasm in a subject in need thereof, the method comprising administering to the subject a therapeutically effective amount of the compound of claim 1 or a pharmaceutically acceptable salt thereof.

17. The method of claim 7, wherein the subject is a human.

18. The method of claim 8, wherein the subject is a human.

19. The method of claim 9, wherein the subject is a human.

20. The method of claim 10, wherein the subject is a human.

21. The method of claim 11, wherein the subject is a human.

22. The method of claim 12, wherein the subject is a human.

23. The method of claim 13, wherein the subject is a human.

24. The method of claim 14, wherein the subject is a human.

* * * * *

UNITED STATES PATENT AND TRADEMARK OFFICE
CERTIFICATE OF CORRECTION

PATENT NO. : 11,236,082 B2
APPLICATION NO. : 15/524679
DATED : February 1, 2022
INVENTOR(S) : James E. Bradner et al.

Page 1 of 1

It is certified that error appears in the above-identified patent and that said Letters Patent is hereby corrected as shown below:

In the Claims

In Claim 1, at Column 251, Lines 21-39, formula:

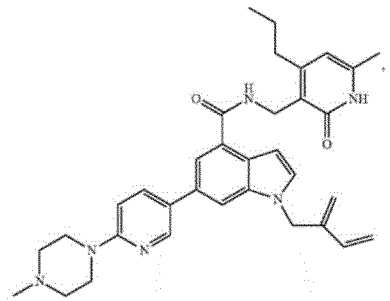

Should be replaced with the formula:

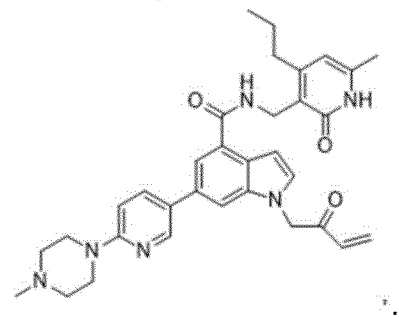

Signed and Sealed this
Twenty-seventh Day of September, 2022

Katherine Kelly Vidal
*Director of the United States Patent and Trademark Office*